US009662310B2

(12) United States Patent
Nagata et al.

(10) Patent No.: US 9,662,310 B2
(45) Date of Patent: *May 30, 2017

(54) CYCLOPROPANECARBOXYLIC ACID DERIVATIVE

(71) Applicant: DAIICHI SANKYO COMPANY, LIMITED, Tokyo (JP)

(72) Inventors: Tsutomu Nagata, Tokyo (JP); Jun Kobayashi, Tokyo (JP); Yoshiyuki Onishi, Tokyo (JP); Masamichi Kishida, Tokyo (JP); Kengo Noguchi, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 16 days.

This patent is subject to a terminal disclaimer.

(21) Appl. No.: 14/613,145

(22) Filed: Feb. 3, 2015

(65) Prior Publication Data

US 2015/0216847 A1 Aug. 6, 2015

Related U.S. Application Data

(63) Continuation of application No. 13/634,678, filed as application No. PCT/JP2011/055954 on Mar. 14, 2011, now Pat. No. 8,946,443.

(30) Foreign Application Priority Data

Mar. 18, 2010 (JP) ................................. 2010-062156

(51) Int. Cl.
| | | |
|---|---|---|
| A61K 31/4164 | (2006.01) | |
| A61K 31/4178 | (2006.01) | |
| A61K 31/4725 | (2006.01) | |
| A61K 31/506 | (2006.01) | |
| A61K 31/4709 | (2006.01) | |
| A61K 31/4439 | (2006.01) | |
| A61K 31/427 | (2006.01) | |
| C07D 233/64 | (2006.01) | |
| C07D 401/04 | (2006.01) | |

(52) U.S. Cl.
CPC ...... *A61K 31/4164* (2013.01); *A61K 31/4178* (2013.01); *A61K 31/427* (2013.01); *A61K 31/4439* (2013.01); *A61K 31/4709* (2013.01); *A61K 31/4725* (2013.01); *A61K 31/506* (2013.01); *C07D 233/64* (2013.01); *C07D 401/04* (2013.01)

(58) Field of Classification Search
CPC ............ A61K 31/4164; A61K 31/4709; A61K 31/427; A61K 31/4725; A61K 31/506; A61K 31/4178; A61K 31/4439; C07D 401/04; C07D 233/64
See application file for complete search history.

(56) References Cited

U.S. PATENT DOCUMENTS

| | | | |
|---|---|---|---|
| 6,713,496 | B2 | 3/2004 | Allerton et al. |
| 6,897,208 | B2 | 5/2005 | Edwards et al. |
| 6,949,577 | B2 | 9/2005 | Allerton et al. |
| 6,958,402 | B2 | 10/2005 | Allerton et al. |
| 8,288,425 | B2 | 10/2012 | Edwards et al. |
| 8,609,710 | B2 | 12/2013 | Nagata et al. |
| 8,946,443 | B2 | 2/2015 | Nagata et al. |
| 9,340,531 | B2 | 5/2016 | Nagata et al. |
| 2003/0191107 | A1 | 10/2003 | Allerton et al. |
| 2003/0199522 | A1 | 10/2003 | Allerton et al. |
| 2007/0129341 | A1 | 6/2007 | Kallus et al. |
| 2008/0262028 | A1 | 10/2008 | Kallus et al. |
| 2011/0213143 | A1 | 9/2011 | Amada et al. |
| 2013/0012532 | A1 | 1/2013 | Nagata et al. |

FOREIGN PATENT DOCUMENTS

| | | |
|---|---|---|
| CA | 2 563 401 | 8/2012 |
| CN | 100572376 C | 12/2009 |
| ES | 2 299 026 | 1/2007 |
| JP | 2004-506044 A | 2/2004 |

(Continued)

OTHER PUBLICATIONS

Bunnage, Mark E., et al., "Discovery of Potent & Selective Inhibitors of Activated Thrombin-Activatable Fibrinolysis Inhibitor for the Treatment of Thrombosis," *Journal of Medicinal Chemistry*, vol. 50, pp. 6095-6103 (2007).
Muto, Yuko, et al., "EF6265, a novel inibitor of activated thrombin-activatable fibrinolysis inhibitor, protects against sepsis-induced organ dysfunction in rats," *Critical Care Medicine*, vol. 37, No. 5, pp. 1744-1749 (2009).
Nantermet et al., "Imidazole acetic acid TAFIa inhibitors; SAR studies centered around the basic P'$_1$ group," *Bioorganic & Medicinal Chemistry Letters*, (2004), 14(9):2141-2145.
Suzuki, Kokichi, et al., "Enhancement of Fibrinolysis by EF6265 [(S)-7-Amino-2-[[[(R)-2-methyl-1-(3-phenylpropanoylamino) propyl]hydroxyphosphinoyl]methyl]heptanoic Acid], a Specific Inhibitor of Plasma Carboxypeptidase B," *Journal of Pharmacology and Experimental Therapeutics*, vol. 309, No. 2, pp. 607-615 (2004).

(Continued)

*Primary Examiner* — Sarah Pihonak
*Assistant Examiner* — Jason A Deck
(74) *Attorney, Agent, or Firm* — Dorsey & Whitney LLP

(57) ABSTRACT

A compound represented by the following general formula (I) or a pharmacologically acceptable salt thereof, wherein $R^1$ represents a C1 to C6 alkyl group which may be substituted by one to three groups selected from substituent group A, or the like (substituent group A: a hydroxy group, a halogeno group, a cyano group, a nitro group, an amino group, a carboxy group, a C1 to C3 alkyl group, etc.); $R^2$, $R^3$, and $R^8$ each independently represent a hydrogen atom or a C1 to C3 alkyl group; $R^4$, $R^5$, $R^6$, $R^7$, $R^9$, and $R^{10}$ each independently represent a hydrogen atom or the like; and $R^{11}$ represents a hydrogen atom or the like, has TAFIa enzyme inhibitory activity and is useful as a therapeutic drug for myocardial infarction, angina pectoris, acute coronary syndrome, cerebral infarction, deep vein thrombosis, pulmonary embolism, or the like.

17 Claims, No Drawings

(56) References Cited

FOREIGN PATENT DOCUMENTS

| JP | 2005-516972 A | 6/2005 |
|---|---|---|
| JP | 2005-520811 A | 7/2005 |
| RU | 2 140 901 C1 | 11/1999 |
| WO | WO 93/023383 A1 | 11/1993 |
| WO | WO 02/14285 A1 | 2/2002 |
| WO | WO 03/013526 A1 | 2/2003 |
| WO | WO 03/061652 A1 | 7/2003 |
| WO | WO 03/061653 A1 | 7/2003 |
| WO | WO 2005/105781 A1 | 11/2005 |
| WO | WO 2007/045339 A1 | 4/2007 |

OTHER PUBLICATIONS

Wang, X., et al., "Murine model of ferric chloride-induced vena cava thrombosis: evidence for effect of potato carboxypeptidase inhibitor," *Journal of Thrombosis and Haemostasis*, vol. 4, pp. 403-410 (2006).

Willemse, J. L., et al., "Carboxypeptidase U (TAFIa): a new drug target for fibrinolytic therapy?," *Journal of Thrombosis and Haemostasis*, vol. 7, pp. 1962-1971 (2009).

English translation of International Search Report, Application No. PCT/JP2011/055953, Filed Mar. 14, 2011, Mailed May 10, 2011, 5 pages.

English translation of International Preliminary Report on Patentability, Application No. PCT/JP2011/055953, Filed Mar. 14, 2011, Mailed May 10, 2011, 9 pages.

English translation of International Search Report, Application No. PCT/JP2011/055954, Filed Mar. 14, 2011, Mailed May 10, 2011, 3 pages.

English translation of International Preliminary Report on Patentability, Application No. PCT/JP2011/055954, Filed Mar. 14, 2011, Mailed May 10, 2011, 7 pages.

Extended European Search Report issued in European Patent Application No. 11 756 249 on Jun. 28, 2013, 8 pages.

CYCLOPROPANECARBOXYLIC ACID DERIVATIVE

This application is a continuation application of application Ser. No. 13/634,678, filed Sep. 13, 2012, entitled "Cyclopropanecarboxylic Acid Derivative," which is a national stage application under 35 U.S.C. §371 of International Application No. PCT/JP2011/055954, filed Mar. 14, 2011, entitled "Cyclopropanecarboxylic Acid Derivative," which claims priority to Japanese Patent Application No. 2010-062156, filed Mar. 18, 2010.

TECHNICAL FIELD

The present invention relates to a novel cyclopropanecarboxylic acid derivative having excellent TAFIa inhibitory activity.

BACKGROUND ART

When disorders in blood vessels occur in vivo, platelets and/or coagulation cascades are activated for preventing blood leakage to form thrombi, which in turn suppress hemorrhage. Thrombin formed by the coagulation cascade activation cleaves fibrinogen to form insoluble fibrin. Fibrin is present in the form of a network in thrombi and works to strengthen the thrombi. This reaction is called coagulation. The formed fibrin is then degraded through in-vivo reaction. This reaction is fibrinolysis. Under normal conditions, coagulation and fibrinolysis are balanced, and abnormal amounts of thrombi do not accumulate in blood vessels. However, once the balance is disrupted to accelerate coagulation, it may come into a state that a thrombus is likely to be formed in blood vessels, leading to various diseases attributed to thrombosis. The thrombus formation is caused by three factors (Virchow's triad: change in the properties of vascular walls, change in blood components, and change in blood flow). Diseases attributed to the thrombus formation are one of the most general causes of death among advanced nations.

TAFI (thrombin-activatable fibrinolysis inhibitor) is a carboxypeptidase that is produced in the liver and secreted into blood. This enzyme is activated through the cleavage of N-terminal 92 amino acid residues by thrombin or thrombin/thrombomodulin complexes. TAFI is also called procarboxypeptidase U, procarboxypeptidase R, or plasma procarboxypeptidase B.

The activated TAFI is called TAFIa. TAFIa inhibits fibrinolysis by removing the C-terminal Lys or Arg residue of fibrin or fibrin degradation products (FDPs), which are main components of thrombi. Two enzymes, tPA (tissue-type plasminogen activator) and plasminogen, which induce and promote fibrinolysis, bind to the Lys residue of fibrin or FDPs via their Lys-binding sites. On the surface of the fibrin molecule, tPA subsequently activates plasminogen and converts it into plasmin to initiate fibrinolysis. Plasmin cleaves fibrin, and a Lys or Arg residue appears at the C-termini of the formed FDPs. The continuation of fibrinolysis allows plasminogen and tPA to newly bind to the Lys residues of the FDPs to further form plasmin. This efficiently promotes fibrinolysis (positive feedback mechanism of fibrinolysis). TAFIa inhibits the plasminogen activation of tPA on the fibrin molecule by removing the C-terminal Lys residues of FDPs. As a result, efficient fibrinolysis does not occur. TAFIa suppresses the positive feedback mechanism of fibrinolysis. These findings are described in detail in a review on TAFI and its inhibitors (Non Patent Literature 1).

As described above, the fine balance between coagulation and fibrinolysis is achieved in vivo. When coagulation is accelerated by diseases or the like, thrombi come to be likely to be formed, developing various diseases. Such diseases include myocardial infarction, angina pectoris, acute coronary syndrome, cerebral infarction, deep vein thrombosis, pulmonary embolism, peripheral arterial occlusion, sepsis, disseminated intravascular coagulation syndrome, and pulmonary fibrosis.

The previous treatment of thrombosis has often targeted enzymes in the coagulation cascades. These enzymes include activated coagulation factor X (Xa), thrombin, and the like. Inhibitors against these enzymes have the risk of potential adverse reaction such as hemorrhage. Heparin or low-molecular-weight heparin cannot be expected to exert drug efficacy in oral administration and requires administration in hospitals. Warfarin is orally administrable but requires periodic blood tests by reason of interaction with other drugs, etc. Aspirin is an orally administrable drug that inhibits thrombus formation by suppressing the activation of platelets, but has adverse reaction such as gastrorrhagia. A goal for further improving the current therapies is to prevent bleeding time from being prolonged while maintaining high therapeutic effect by drug administration. TAFIa inhibitors are thought to have a small risk of hemorrhage, because they do not influence the process of hemostasis involving coagulation and platelets.

In pathologies where it may arise that a thrombus is likely to be formed due to accelerated coagulation reactions, thrombi can be removed more quickly by making fibrinolysis efficient through the inhibition of TAFIa. This can be expected to exert excellent effects on the treatment/prevention of diseases attributed to thrombi. Some cases of animal experiments that showed an antithrombotic effect by inhibiting TAFIa have been reported so far.

There is a report that the intravenous administration of a TAFIa-inhibiting polypeptide consisting of 39 amino acids (potato carboxypeptidase inhibitor (PCI)) to mice showed an antithrombotic effect in iron chloride-induced thrombus models (Non Patent Literature 2).

A low-molecular-weight TAFIa inhibitor reduced the amount of thrombi by approximately 35% in intravenous administration to rabbit models of venous thrombosis (Non Patent Literature 3).

A low-molecular-weight TAFIa-inhibiting compound showed, in rat models of thromboembolism, a reduction in the amount of thrombus deposits in the kidney with the effect of increasing a fibrinolysis marker D-dimer as well as comparable antithrombotic effect at a reduced dose of tPA in combined use with tPA (Non Patent Literatures 4 and 5).

Patent Literatures 1 to 5 disclose compounds that exhibit TAFIa inhibitory activity.

CITATION LIST

Patent Literature

Patent Literature 1: Pamphlet of International Publication No. WO 2003/013526
Patent Literature 2: Pamphlet of International Publication No. WO 2005/105781
Patent Literature 3: Pamphlet of International Publication No. WO 2002/014285
Patent Literature 4: Pamphlet of International Publication No. WO 2003/061652

Patent Literature 5: Pamphlet of International Publication No. WO 2003/061653

Non Patent Literature

Non Patent Literature 1: Willemse J L, Journal of Thrombosis and Haemostasis, 2009, 7, 1962-71
Non Patent Literature 2: Wang X. et al., Journal of Thrombosis and Haemostasis, 2006, 3, 403-410
Non Patent Literature 3: Bunnage M E., et al., Journal of Medicinal Chemistry, 2007, 50, 6095-6103
Non Patent Literature 4: Muto, Y., et al., Critical Care Med., 2009, 37, 1744-1749,
Non Patent Literature 5: Suzuki, K., The Journal of Pharmacology and Experimental Therapeutics, 2004, 309, 607-615

SUMMARY OF INVENTION

Technical Problem

Currently known compounds having TAFIa inhibitory activity are less than satisfactory in terms of efficacy or safety such as the risk of hemorrhage, and there is a great demand on a TAFIa inhibitor excellent in safety and efficacy.

Solution to Problem

The present inventors have conducted various syntheses and studies with the aim of obtaining a therapeutic drug for myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis having excellent TAFIa inhibitory activity. As a result, the present inventors have completed the present invention by finding that a cyclopropanecarboxylic acid derivative having a particular structure or a pharmacologically acceptable salt thereof exhibits excellent TAFIa inhibitory activity.

The present invention provides a cyclopropanecarboxylic acid derivative or a pharmacologically acceptable salt thereof, which exhibits excellent TAFIa inhibitory activity, and a pharmaceutical drug containing the same.

Specifically, the present invention provides:

(1) a compound represented by the general formula (I) or a pharmacologically acceptable salt thereof:

[Formula 1]

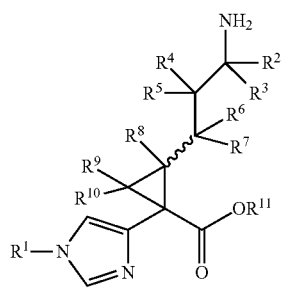

(I)

wherein $R^1$ represents a C1 to C6 alkyl group which may be substituted by one to three identical or different groups selected from substituent group A, a C2 to C6 alkenyl group which may be substituted by one to three identical or different groups selected from substituent group A, a C3 to C8 cycloalkyl group which may be substituted by one to three identical or different groups selected from substituent group A, an aryl group which may be substituted by one to three identical or different groups selected from substituent group A (provided that when the aryl group is a phenyl group having a substituent, the substituent is substituted at a meta or para position on the benzene ring), a saturated heterocyclyl group which may be substituted by one to three identical or different groups selected from substituent group A, or an unsaturated heterocyclyl group which may be substituted by one to three identical or different groups selected from substituent group A (the substituent group A consists of a hydroxy group, a halogeno group, a cyano group, a nitro group, an amino group, a carboxy group, a C1 to C3 alkyl group, a halogeno-C1 to C3 alkyl group, a C3 to C8 cycloalkyl group, a C1 to C3 alkoxy group, a halogeno-C1 to C3 alkoxy group, a C1 to C3 alkylsulfonyl group, an aryl group, a saturated heterocyclyl group, an unsaturated heterocyclyl group, and an aryloxy group); $R^2$, $R^3$, and $R^8$ each independently represent a hydrogen atom or a C1 to C3 alkyl group; $R^4$, $R^5$, $R^6$, $R^7$, $R^9$, and $R^{10}$ each independently represent a hydrogen atom, a fluoro group, or a C1 to C3 alkyl group; and $R^{11}$ represents a hydrogen atom, a methyl group, or an ethyl group;

(2) the compound according to (1) or a pharmacologically acceptable salt thereof, wherein $R^1$ is a C1 to C6 alkyl group which may be substituted by one to three identical or different groups selected from a hydroxy group, a halogeno group, an amino group, a C1 to C3 alkyl group, a phenyl group, and a phenoxy group; a C2 to C6 alkenyl group which may be substituted by one to three identical or different groups selected from a hydroxy group, a halogeno group, an amino group, a C1 to C3 alkyl group, a phenyl group, and a phenoxy group; a C3 to C8 cycloalkyl group which may be substituted by one to three identical or different groups selected from a hydroxy group, a halogeno group, an amino group, and a C1 to C3 alkyl group; a phenyl group which may be substituted by one to three identical or different groups selected from a hydroxy group, a halogeno group, a cyano group, an amino group, a C1 to C3 alkyl group, a halogeno-C1 to C3 alkyl group, a C1 to C3 alkoxy group, a C1 to C3 alkylsulfonyl group, and a phenoxy group (provided that when the phenyl group has a substituent, the substituent is substituted at a meta or para position on the benzene ring); a naphthyl group which may be substituted by one to three identical or different groups selected from a hydroxy group, a halogeno group, a cyano group, an amino group, a C1 to C3 alkyl group, a halogeno-C1 to C3 alkyl group, a C1 to C3 alkoxy group, a C1 to C3 alkylsulfonyl group, and a phenoxy group; a pyridyl group which may be substituted by one to three identical or different groups selected from a hydroxy group, a halogeno group, an amino group, a C1 to C3 alkyl group, a halogeno-C1 to C3 alkyl group, a C1 to C3 alkoxy group, a C1 to C3 alkylsulfonyl group, and a phenoxy group; a pyrimidinyl group which may be substituted by one to three identical or different groups selected from a hydroxy group, a halogeno group, an amino group, a C1 to C3 alkyl group, a halogeno-C1 to C3 alkyl group, a C1 to C3 alkoxy group, a C1 to C3 alkylsulfonyl group, and a phenoxy group; or a benzofuranyl group which may be substituted by one to three identical or different groups selected from a hydroxy group, a halogeno group, an amino group, a C1 to C3 alkyl group, a halogeno-C1 to C3 alkyl group, a C1 to C3 alkoxy group, a C1 to C3 alkylsulfonyl group, and a phenoxy group;

(3) the compound according to (1) or a pharmacologically acceptable salt thereof, wherein $R^1$ is an unsubstituted C1 to C6 alkyl group; a C2 to C6 alkenyl group which may be substituted by one phenyl group; a C3 to C8 cycloalkyl group which may be substituted by one to three identical or different C1 to C3 alkyl groups; a phenyl group which may be substituted by one to three identical or different groups selected from a halogeno group, a C1 to C3 alkyl group, a halogeno-C1 to C3 alkyl group, a C1 to C3 alkoxy group, a C1 to C3 alkylsulfonyl group, and a phenoxy group (provided that when the phenyl group has a substituent, the substituent is substituted at a meta or para position on the benzene ring); a pyridyl group which may be substituted by one group selected from a halogeno group, a C1 to C3 alkyl group, and a C1 to C3 alkoxy group; or an unsubstituted pyrimidinyl group;

(4) the compound according to (1) or a pharmacologically acceptable salt thereof, wherein $R^1$ is an unsubstituted C1 to C6 alkyl group, a C3 to C8 cycloalkyl group which may be substituted by one C1 to C3 alkyl group, an unsubstituted phenyl group, an unsubstituted pyridyl group, or an unsubstituted pyrimidinyl group;

(5) the compound according to (1) or a pharmacologically acceptable salt thereof, wherein $R^1$ is a propyl group, a 3,3-dimethylbutyl group, a 2-phenylvinyl group, a cyclohexyl group, a 4-methylcyclohexyl group, a phenyl group, a 3-fluorophenyl group, a 3-chlorophenyl group, a 3-methylphenyl group, a 4-fluorophenyl group, a 4-chlorophenyl group, a 4-methylphenyl group, a 4-ethylphenyl group, a 4-trifluoromethylphenyl group, a 4-methoxyphenyl group, a 4-phenoxyphenyl group, a 3,4-dimethylphenyl group, a 3,4-difluorophenyl group, a pyridin-2-yl group, a pyridin-3-yl group, a pyridin-4-yl group, a pyrimidin-2-yl group, or a 2-naphthyl group;

(6) the compound according to (1) or a pharmacologically acceptable salt thereof, wherein $R^4$ is a 3,3-dimethylbutyl group, a 4-methylcyclohexyl group, a phenyl group, a pyridin-2-yl group, or a pyrimidin-2-yl group;

(7) the compound according to any one of (1) to (6) or a pharmacologically acceptable salt thereof, wherein $R^2$, $R^3$, $R^7$, $R^8$, $R^9$, and $R^{10}$ are each a hydrogen atom, and $R^4$, $R^5$, and $R^6$ are each independently a hydrogen atom or a C1 to C3 alkyl group;

(8) the compound according to any one of (1) to (6) or a pharmacologically acceptable salt thereof, wherein $R^2$, $R^3$, $R^6$, $R^7$, $R^8$, $R^9$, and $R^{10}$ are each a hydrogen atom, and $R^4$ and $R^5$ are each independently a hydrogen atom or a C1 to C3 alkyl group;

(9) the compound according to any one of (1) to (6) or a pharmacologically acceptable salt thereof, wherein $R^2$, $R^3$, $R^4$, $R^5$, $R^6$, $R^7$, and $R^8$ are each a hydrogen atom, and $R^9$ and $R^{10}$ are each independently a hydrogen atom or a fluoro group;

(10) the compound according to any one of (1) to (6) or a pharmacologically acceptable salt thereof, wherein all of $R^2$, $R^3$, $R^4$, $R^5$, $R^6$, $R^7$, $R^8$, $R^9$, and $R^{10}$ are hydrogen atoms;

(11) the compound according to any one of (1) to (10) or a pharmacologically acceptable salt thereof, wherein $R^{11}$ is a hydrogen atom;

(12) the compound according to any one of (1) to (11) or a pharmacologically acceptable salt thereof, wherein the cyclopropane moiety in the general formula (I) has a (1R*, 2S*) configuration (the configuration is a configuration determined when all of $R^2$, $R^3$, $R^4$, $R^5$, $R^6$, $R^7$, $R^8$, $R^9$, and $R^{10}$ are hydrogen atoms);

(13) the compound according to any one of (1) to (11) or a pharmacologically acceptable salt thereof, wherein the cyclopropane moiety in the general formula (I) has a (1R,2S) configuration (the configuration is a configuration determined when all of $R^2$, $R^3$, $R^4$, $R^5$, $R^6$, $R^7$, $R^8$, $R^9$, and $R^{10}$ are hydrogen atoms);

(14) a compound represented by the general formula (Ia) or a pharmacologically acceptable salt thereof:

[Formula 2]

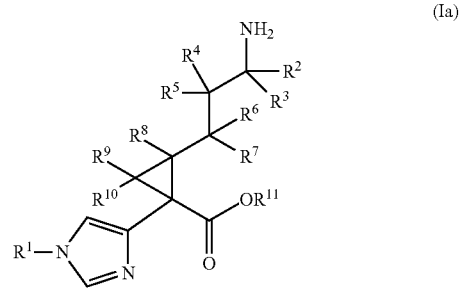

(Ia)

wherein $R^1$, $R^2$, $R^3$, $R^4$, $R^5$, $R^6$, $R^7$, $R^8$ and $R^{11}$ are as defined in (1);

(15) a compound represented by the general formula (Ic) or a pharmacologically acceptable salt thereof:

[Formula 3]

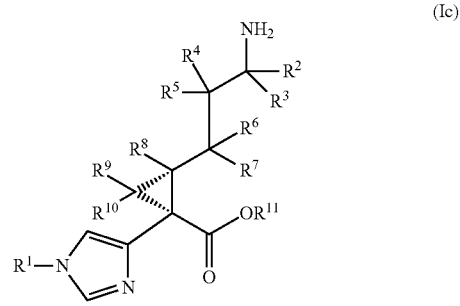

(Ic)

wherein $R^1$, $R^2$, $R^3$, $R^4$, $R^5$, $R^6$, $R^7$, $R^8$, $R^9$, $R^{10}$, and $R^{11}$ are as defined in (1);

(16) a compound represented by the general formula (I-1) or a pharmacologically acceptable salt thereof:

[Formula 4]

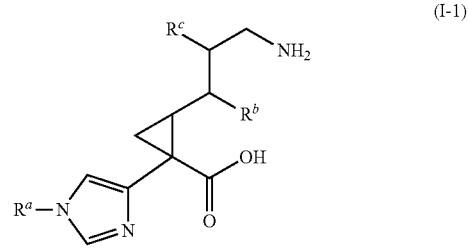

(I-1)

wherein $R^a$ represents a C3 to C6 branched alkyl group; a C3 to C6 cycloalkyl group which may be substituted by one or two identical or different C1 to C3 alkyl groups; a phenyl group which may be substituted by one or two identical or different groups selected from the group consisting of a C1 to C3 alkyl group, a C1 to C3 alkoxy group, a phenoxy group, a halogeno group, and a cyano group (the substituent is substituted at the 3- or 4-position, or both, of the phenyl group); a naphthyl group; a 5- or 6-membered heteroaryl group which may be substituted by one or two identical or different groups selected from the group consisting of a C1 to C3 alkyl group, a C1 to C3 alkoxy group, a phenoxy group, a halogeno group, and a cyano group (the heteroaryl group has one or more nitrogen atoms in the ring and may be condensed with a benzene ring); or a benzofuranyl group; and $R^b$ and $R^c$ each independently represent a hydrogen atom or a C1 to C3 alkyl group;

(17) the compound according to (16) or a pharmacologically acceptable salt thereof, wherein $R^a$ is a C4 to C6 branched alkyl group; a C5 to C6 cycloalkyl group which may be substituted by a C1 to C3 alkyl group; a phenyl group which may be substituted by one or two identical or different groups selected from the group consisting of a C1 to C3 alkyl group, a C1 to C3 alkoxy group, a phenoxy group, a halogeno group, and a cyano group (the substituent is substituted at the 3- or 4-position, or both, of the phenyl group); a naphthyl group; a pyridin-2-yl group which may be substituted by a C1 to C3 alkyl group, a C1 to C3 alkoxy group, or a halogeno group (the substituent is substituted at the 4- or 5-position of the pyridyl group); a pyrimidin-2-yl group; a thiazol-2-yl group; a quinolyl group; an isoquinolyl group; or a benzofuranyl group, and $R^b$ and $R^c$ are each independently a hydrogen atom or a C1 to C3 alkyl group;

(18) the compound according to (16) or a pharmacologically acceptable salt thereof, wherein $R^a$ is a C5 to C6 branched alkyl group; a cyclohexyl group which may be substituted by a methyl group or an ethyl group; a phenyl group which may be substituted by one or two identical or different groups selected from the group consisting of a methyl group, an ethyl group, a methoxy group, a phenoxy group, a fluoro group, a chloro group, and a cyano group (the substituent is substituted at the 3- or 4-position, or both, of the phenyl group); a 2-naphthyl group; a pyridin-2-yl group which may be substituted by a methyl group, an ethyl group, a methoxy group, a fluoro group, or a chloro group (the substituent is substituted at the 4- or 5-position of the pyridyl group); a pyrimidin-2-yl group; a quinolin-2-yl group; an isoquinolin-3-yl group; or a benzofuran-5-yl group; and $R^b$ and $R^c$ are each independently a hydrogen atom, a methyl group, or an ethyl group;

(19) the compound according to (16) or a pharmacologically acceptable salt thereof, wherein $R^a$ is a C6 branched alkyl group; a cyclohexyl group which may be substituted by a methyl group; a phenyl group which may be substituted by a methyl group, a fluoro group, a chloro group, or a cyano group (the substituent is substituted at the 4-position of the phenyl group); a 2-naphthyl group; a pyridin-2-yl group which may be substituted by a methyl group, a methoxy group, or a fluoro group (the substituent is substituted at the 4- or 5-position of the pyridyl group); a pyrimidin-2-yl group; an isoquinolin-3-yl group; or a benzofuran-5-yl group; $R^b$ is a hydrogen atom or a methyl group, and $R^c$ is a hydrogen atom, a methyl group, or an ethyl group;

(20) the compound according to (16) or a pharmacologically acceptable salt thereof, wherein $R^a$ is a 3,3-dimethylbutyl group, a cyclohexyl group, a 4-methylcyclohexyl group, a phenyl group, a 4-methylphenyl group, a 4-fluorophenyl group, a 4-chlorophenyl group, a 4-cyanophenyl group, a 2-naphthyl group, a pyridin-2-yl group, a 4-methylpyridin-2-yl group, a 5-methylpyridin-2-yl group, a 4-methoxypyridin-2-yl group, a 4-fluoropyridin-2-yl group, a pyrimidin-2-yl group, an isoquinolin-3-yl group, or a benzofuran-5-yl group, $R^b$ is a hydrogen atom or a methyl group, and $R^c$ is a hydrogen atom, a methyl group, or an ethyl group;

(21) a compound represented by the general formula (I-2) or a pharmacologically acceptable salt thereof:

[Formula 5]

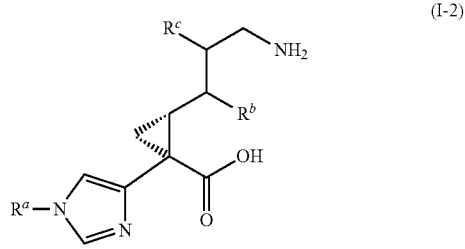

(I-2)

wherein $R^a$ represents a C3 to C6 branched alkyl group; a C3 to C6 cycloalkyl group which may be substituted by one or two identical or different C1 to C3 alkyl groups; a phenyl group which may be substituted by one or two identical or different groups selected from the group consisting of a C1 to C3 alkyl group, a C1 to C3 alkoxy group, a phenoxy group, a halogeno group, and a cyano group (the substituent is substituted at the 3- or 4-position, or both, of the phenyl group); a naphthyl group; a 5- or 6-membered heteroaryl group which may be substituted by one or two identical or different groups selected from the group consisting of a C1 to C3 alkyl group, a C1 to C3 alkoxy group, a phenoxy group, a halogeno group, and a cyano group (the heteroaryl group has one or more nitrogen atoms in the ring and may be condensed with a benzene ring); or a benzofuranyl group; and $R^b$ and $R^c$ each independently represent a hydrogen atom or a C1 to C3 alkyl group;

(22) the compound according to (21) or a pharmacologically acceptable salt thereof, wherein $R^a$ is a C4 to C6 branched alkyl group; a C5 to C6 cycloalkyl group which may be substituted by a C1 to C3 alkyl group; a phenyl group which may be substituted by one or two identical or different groups selected from the group consisting of a C1 to C3 alkyl group, a C1 to C3 alkoxy group, a phenoxy group, a halogeno group, and a cyano group (the substituent is substituted at the 3- or 4-position, or both, of the phenyl group); a naphthyl group; a pyridin-2-yl group which may be substituted by a C1 to C3 alkyl group, a C1 to C3 alkoxy group, or a halogeno group (the substituent is substituted at the 4- or 5-position of the pyridyl group); a pyrimidin-2-yl group; a thiazol-2-yl group; a quinolyl group; an isoquinolyl group; or a benzofuranyl group; and $R^b$ and $R^c$ are each independently a hydrogen atom or a C1 to C3 alkyl group;

(23) the compound according to (21) or a pharmacologically acceptable salt thereof, wherein $R^a$ is a C5 to C6 branched alkyl group; a cyclohexyl group which may be substituted by a methyl group or an ethyl group; a phenyl group which may be substituted by one or two identical or different groups selected from the group consisting of a methyl group, an ethyl group, a methoxy group, a phenoxy group, a fluoro group, a chloro group, and a cyano group (the substituent is substituted at the 3- or 4-position, or both, of the phenyl group); a 2-naphthyl group; a pyridin-2-yl group which may be substituted by a methyl group, an ethyl group, a methoxy group, a fluoro group, or a chloro group (the substituent is substituted at the 4- or 5-position of the pyridyl group); a pyrimidin-2-yl group; a quinolin-2-yl group; an isoquinolin-3-yl group; or a benzofuran-5-yl group; and $R^b$ and $R^c$ are each independently a hydrogen atom, a methyl group, or an ethyl group;

(24) the compound according to (21) or a pharmacologically acceptable salt thereof, wherein $R^a$ is a C6 branched alkyl group; a cyclohexyl group which may be substituted by a methyl group; a phenyl group which may be substituted by a methyl group, a fluoro group, a chloro group, or a cyano group (the substituent is substituted at the 4-position of the phenyl group); a 2-naphthyl group; a pyridin-2-yl group which may be substituted by a methyl group, a methoxy group, or a fluoro group (the substituent is substituted at the 4- or 5-position of the pyridyl group); a pyrimidin-2-yl group; an isoquinolin-3-yl group; or a benzofuran-5-yl group; $R^b$ is a hydrogen atom or a methyl group, and $R^c$ is a hydrogen atom, a methyl group, or an ethyl group;

(25) the compound according to (21) or a pharmacologically acceptable salt thereof, wherein $R^a$ is a 3,3-dimethylbutyl group, a cyclohexyl group, a 4-methylcyclohexyl group, a phenyl group, a 4-methylphenyl group, a 4-fluorophenyl group, a 4-chlorophenyl group, a 4-cyanophenyl group, a 2-naphthyl group, a pyridin-2-yl group, a 4-methylpyridin-2-yl group, a 5-methylpyridin-2-yl group, a 4-methoxypyridin-2-yl group, a 4-fluoropyridin-2-yl group, a pyrimidin-2-yl group, an isoquinolin-3-yl group, or a benzofuran-5-yl group, $R^b$ is a hydrogen atom or a methyl group, and $R^c$ is a hydrogen atom, a methyl group, or an ethyl group;

(26) the compound according to (1) or a pharmacologically acceptable salt thereof, wherein the compound is selected from the group consisting of 2-(3-aminopropyl)-1-[1-(3,3-dimethylbutyl)-1H-imidazol-4-yl]cyclopropanecarboxylic acid,
2-(3-aminopropyl)-1-(1-propyl-1H-imidazol-4-yl)cyclopropanecarboxylic acid,
2-(3-aminopropyl)-1-(1-cyclohexyl-1H-imidazol-4-yl)cyclopropanecarboxylic acid,
2-(3-aminopropyl)-1-[1-(trans-4-methylcyclohexyl)-1H-imidazol-4-yl]cyclopropanecarboxylic acid,
2-(3-aminopropyl)-1-(1-phenyl-1H-imidazol-4-yl)cyclopropanecarboxylic acid,
2-(3-aminopropyl)-1-[1-(4-methylphenyl)-1H-imidazol-4-yl]cyclopropanecarboxylic acid,
2-(3-aminopropyl)-1-[1-(3-methylphenyl)-1H-imidazol-4-yl]cyclopropanecarboxylic acid,
2-(3-aminopropyl)-1-[1-(3,4-dimethylphenyl)-1H-imidazol-4-yl]cyclopropanecarboxylic acid,
2-(3-aminopropyl)-1-[1-(4-ethylphenyl)-1H-imidazol-4-yl]cyclopropanecarboxylic acid,
2-(3-aminopropyl)-1-[1-(4-methoxyphenyl)-1H-imidazol-4-yl]cyclopropanecarboxylic acid,
2-(3-aminopropyl)-1-{1-[4-(trifluoromethyl)phenyl]-1H-imidazol-4-yl}cyclopropanecarboxylic acid,
2-(3-aminopropyl)-1-{1-[(E)-2-phenylvinyl]-1H-imidazol-4-yl}cyclopropanecarboxylic acid,
2-(3-aminopropyl)-1-[1-(4-fluorophenyl)-1H-imidazol-4-yl]cyclopropanecarboxylic acid,
2-(3-aminopropyl)-1-[1-(4-phenoxyphenyl)-1H-imidazol-4-yl]cyclopropanecarboxylic acid,
2-(3-aminopropyl)-1-[1-(3,4-difluorophenyl)-1H-imidazol-4-yl]cyclopropanecarboxylic acid,
2-(3-aminopropyl)-1-[1-(4-chlorophenyl)-1H-imidazol-4-yl]cyclopropanecarboxylic acid,
2-(3-aminopropyl)-1-[1-(3-chlorophenyl)-1H-imidazol-4-yl]cyclopropanecarboxylic acid,
2-(3-aminopropyl)-1-[1-(2-naphthyl)-1H-imidazol-4-yl]cyclopropanecarboxylic acid,
2-(3-aminopropyl)-1-[1-(3-fluorophenyl)-1H-imidazol-4-yl]cyclopropanecarboxylic acid,
2-(3-aminopropyl)-1-(1-pyridin-4-yl-1H-imidazol-4-yl)cyclopropanecarboxylic acid,
2-(3-aminopropyl)-1-(1-pyridin-3-yl-1H-imidazol-4-yl)cyclopropanecarboxylic acid,
2-(3-aminopropyl)-1-(1-pyridin-2-yl-1H-imidazol-4-yl)cyclopropanecarboxylic acid,
ethyl 2-(3-aminopropyl)-1-[1-(4-methylphenyl)-1H-imidazol-4-yl]cyclopropanecarboxylate,
2-(3-amino-2-methylpropyl)-1-(1-phenyl-1H-imidazol-4-yl)cyclopropanecarboxylic acid,
2-(3-amino-1-methylpropyl)-1-(1-phenyl-1H-imidazol-4-yl)cyclopropanecarboxylic acid,
2-(3-aminopropyl)-1-[1-(2-thienyl)-1H-imidazol-4-yl]cyclopropanecarboxylic acid,
2-(3-aminopropyl)-1-[1-(5-methylpyridin-2-yl)-1H-imidazol-4-yl]cyclopropanecarboxylic acid,
2-(3-aminopropyl)-1-[1-(1,3-thiazol-2-yl)-1H-imidazol-4-yl]cyclopropanecarboxylic acid,
2-(3-aminopropyl)-1-(1-pyrimidin-2-yl-1H-imidazol-4-yl)cyclopropanecarboxylic acid,
2-(3-aminopropyl)-1-[1-(4-cyanophenyl)-1H-imidazol-4-yl]cyclopropanecarboxylic acid,
2-(3-amino-2,2-dimethylpropyl)-1-(1-phenyl-1H-imidazol-4-yl)cyclopropanecarboxylic acid,
2-(3-aminopropyl)-1-[1-(5-fluoropyridin-2-yl)-1H-imidazol-4-yl]cyclopropanecarboxylic acid,
2-(3-aminopropyl)-1-(1-quinolin-2-yl-1H-imidazol-4-yl)cyclopropanecarboxylic acid,
2-[(2-aminomethyl)butyl]-1-(1-phenyl-1H-imidazol-4-yl)cyclopropanecarboxylic acid,
2-(3-aminopropyl)-1-[1-(1-benzofuran-5-yl)-1H-imidazol-4-yl]cyclopropanecarboxylic acid,
2-(3-aminopropyl)-1-[1-(5-methoxypyridin-2-yl)-1H-imidazol-4-yl]cyclopropanecarboxylic acid,
2-(3-aminopropyl)-1-[1-(1-naphthyl)-1H-imidazol-4-yl]cyclopropanecarboxylic acid,
2-(3-amino-2-methylpropyl)-1-(1-pyridin-2-yl-1H-imidazol-4-yl)cyclopropanecarboxylic acid,
2-(3-amino-2-methylpropyl)-1-[1-(5-methylpyridin-2-yl)-1H-imidazol-4-yl]cyclopropanecarboxylic acid, and
2-[2-(aminomethyl)butyl]-1-(1-pyridin-2-yl-1H-imidazol-4-yl)cyclopropanecarboxylic acid;

(27) the compound according to (1) or a pharmacologically acceptable salt thereof, wherein the compound is selected from the group consisting of 2-(3-aminopropyl)-1-(1-phenyl-1H-imidazol-4-yl)cyclopropanecarboxylic acid,
2-(3-aminopropyl)-1-[1-(3,3-dimethylbutyl)-1H-imidazol-4-yl]cyclopropanecarboxylic acid,
2-(3-aminopropyl)-1-[1-(trans-4-methylcyclohexyl)-1H-imidazol-4-yl]cyclopropanecarboxylic acid,
2-(3-aminopropyl)-1-(1-pyridin-2-yl-1H-imidazol-4-yl)cyclopropanecarboxylic acid,
2-(3-amino-2-methylpropyl)-1-(1-phenyl-1H-imidazol-4-yl)cyclopropanecarboxylic acid,
2-(3-aminopropyl)-1-[1-(5-methylpyridin-2-yl)-1H-imidazol-4-yl]cyclopropanecarboxylic acid,
2-[(2-aminomethyl)butyl]-1-(1-phenyl-1H-imidazol-4-yl)cyclopropanecarboxylic acid,
2-[(2R)-3-amino-2-methylpropyl]-1-(1-pyridin-2-yl-1H-imidazol-4-yl)cyclopropanecarboxylic acid,
2-[(2R)-3-amino-2-methylpropyl]-1-[1-(5-methylpyridin-2-yl)-1H-imidazol-4-yl]cyclopropanecarboxylic acid, and
2-[(2R)-2-(aminomethyl)butyl]-1-(1-pyridin-2-yl-1H-imidazol-4-yl)cyclopropanecarboxylic acid;

(28) the compound according to (1) or a pharmacologically acceptable salt thereof, wherein the compound is selected from the group consisting of
(1R,2S)-2-(3-aminopropyl)-1-(1-phenyl-1H-imidazol-4-yl) cyclopropanecarboxylic acid,
(1R,2S)-2-(3-aminopropyl)-1-(1-pyridin-2-yl-1H-imidazol-4-yl)cyclopropanecarboxylic acid,
(1R,2S)-2-[(2R)-3-amino-2-methylpropyl]-1-(1-pyridin-2-yl-1H-imidazol-4-yl)cyclopropanecarboxylic acid,
(1R,2S)-2-[(2R)-3-amino-2-methylpropyl]-1-[1-(5-methyl-pyridin-2-yl)-1H-imidazol-4-yl]cyclopropanecarboxylic acid, and
(1R,2S)-2-[(2R)-2-(aminomethyl)butyl]-1-(1-pyridin-2-yl-1H-imidazol-4-yl)cyclopropanecarboxylic acid;
(29) a pharmaceutical drug containing a compound according to any one of (1) to (28) or a pharmacologically acceptable salt thereof as an active ingredient;
(30) a TAFIa inhibitor containing a compound according to any one of (1) to (28) or a pharmacologically acceptable salt thereof as an active ingredient;
(31) a fibrinolysis promoter containing a compound according to any one of (1) to (28) or a pharmacologically acceptable salt thereof as an active ingredient;
(32) a preventive or therapeutic drug for a disease caused by inhibition of fibrinolysis containing a compound according to any one of (1) to (28) or a pharmacologically acceptable salt thereof as an active ingredient;
(33) a preventive or therapeutic drug for thrombosis or embolism or a sequela thereof including: acute coronary syndrome such as myocardial infarction and angina pectoris (stable angina and unstable angina); venous thromboembolism such as deep vein thrombosis and pulmonary embolism; thrombosis or embolism occurring in the cardiovascular system after surgical operation such as vessel revascularization, angioplasty, stent placement, and bypass surgery; thrombosis or embolism after artificial joint replacement operation such as knee joint replacement operation and hip joint replacement operation; inflammation-related intravascular disease such as sepsis and disseminated intravascular coagulation syndrome (DIC); peripheral vascular disorder-derived or -related disease such as peripheral arterial occlusion (PAO), arteriosclerosis, and diabetes mellitus; tumor-related disease such as solid cancer and blood cancer; or organ disorder attributed to thrombus or embolus such as pulmonary embolus, cerebral infarction, and renal infarction, containing a compound according to any one of (1) to (28) or a pharmacologically acceptable salt thereof as an active ingredient;
(34) a preventive or therapeutic drug for thrombosis or embolism including: disease caused by contact with foreign matter in the body, the foreign matter including a medical device such as a joint prosthesis used in joint replacement, a vascular catheter, a blood prosthesis, a blood stent, and a prosthetic valve; or disease caused by contact between blood and a medical device outside the body, the medical device including a pump oxygenator used in cardiac operation and a medical device used in hemodialysis, containing a compound according to any one of (1) to (28) or a pharmacologically acceptable salt thereof as an active ingredient;
(35) a preventive or therapeutic drug for a disease related to thrombosis or embolism or accompanied by fibrin deposition or fibrosis including: pulmonary disease such as pulmonary hypertension, adult respiratory distress syndrome, pulmonary fibrosis, and chronic thromboembolic pulmonary hypertension; renal disease such as glomerulonephritis (including acute glomerulonephritis, chronic glomerulonephritis, nephrotic nephritis, and rapidly progressive glomerulonephritis), renal infarction, and diabetic nephritis; hepatic disease such as hepatic fibrosis, hepatitis, and hepatic cirrhosis; eye disease associated with fibrin deposition in the eye; organ dysfunction after organ transplantation or resection; microcirculatory disorder caused by microthrombus, including thrombotic microangiopathy; or disease or symptoms associated with cancer cell migration or metastasis, containing a compound according to any one of (1) to (28) or a pharmacologically acceptable salt thereof as an active ingredient;
(36) a therapeutic drug for myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis, containing a compound according to any one of (1) to (28) or a pharmacologically acceptable salt thereof as an active ingredient;
(37) a pharmaceutical composition containing a compound according to any one of (1) to (28) or a pharmacologically acceptable salt thereof and a pharmacologically acceptable carrier;
(38) a method for treating myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis, comprising administering a pharmaceutical composition containing a compound according to any one of (1) to (28) or a pharmacologically acceptable salt thereof as an active ingredient;
(39) the compound according to any one of (1) to (28) or a pharmacologically acceptable salt thereof for use in the treatment of myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis;
(40) a pharmaceutical drug for injection containing a compound according to any one of (1) to (28) or a pharmacologically acceptable salt thereof as an active ingredient;
(41) a TAFIa inhibitor for injection containing a compound according to any one of (1) to (28) or a pharmacologically acceptable salt thereof as an active ingredient;
(42) a fibrinolysis promoter for injection containing a compound according to any one of (1) to (28) or a pharmacologically acceptable salt thereof as an active ingredient;
(43) a therapeutic drug for injection for myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis containing a compound according to any one of (1) to (28) or a pharmacologically acceptable salt thereof as an active ingredient;
(44) a therapeutic drug for injection for a thromboembolism-derived disease containing a compound according to any one of (1) to (28) or a pharmacologically acceptable salt thereof as an active ingredient;
(45) a pharmaceutical composition for injection containing a compound according to any one of (1) to (28) or a pharmacologically acceptable salt thereof and a pharmacologically acceptable carrier;
(46) a method for treating myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis, comprising administering a pharmaceutical composition for injection containing a compound according to any one of (1) to (28) or a pharmacologically acceptable salt thereof as an active ingredient; and

(47) the compound according to any one of (1) to (28) or a pharmacologically acceptable salt thereof for use in the treatment of myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis by injection.

Advantageous Effects of the Invention

A cyclopropanecarboxylic acid derivative of the present invention represented by any of the general formulae (I) and (Ia) to (If) or a pharmacologically acceptable salt thereof has excellent TAFIa inhibitory activity and exhibits good oral absorbability, plasma concentration, and retention in blood, and excellent pharmacological effect. Moreover, the compound of any of the general formulae (I) and (Ia) to (If) of the present invention or the pharmacologically acceptable salt thereof is excellent in disposition such as biodistribution and retention in blood, free from prolongation of bleeding time, and also highly safe.

Therefore, the cyclopropanecarboxylic acid derivative of the present invention represented by any of the general formulae (I) and (Ia) to (If) or the pharmacologically acceptable salt thereof is useful as a pharmaceutical drug (particularly, a preventive or therapeutic drug, preferably a therapeutic drug, for a disease caused by inhibition of fibrinolysis) and particularly useful as a preventive or therapeutic drug (preferably a therapeutic drug) for thrombosis or embolism or a sequela thereof including: acute coronary syndrome such as myocardial infarction and angina pectoris (stable angina and unstable angina); venous thromboembolism such as deep vein thrombosis and pulmonary embolism; thrombosis or embolism occurring in the cardiovascular system after a surgical operation such as vessel revascularization, angioplasty, stent placement, and bypass surgery; thrombosis or embolism after an artificial joint replacement operation such as a knee joint replacement operation and a hip joint replacement operation; inflammation-related intravascular disease such as sepsis and disseminated intravascular coagulation syndrome (DIC); peripheral vascular disorder-derived or -related disease such as peripheral arterial occlusion (PAO), arteriosclerosis, and diabetes mellitus; tumor-related disease such as solid cancer and blood cancer; and organ disorder attributed to thrombus or embolus such as pulmonary embolus, cerebral infarction, and renal infarction. Moreover, the compound of the present invention is useful as a preventive or therapeutic drug (preferably a therapeutic drug) for thrombosis or embolism including: disease caused by contact with foreign matter in the body, for example, a medical device such as a joint prosthesis used in joint replacement, a vascular catheter, a blood prosthesis, a blood stent, and a prosthetic valve; and disease caused by contact between blood and a medical device outside the body, for example, a pump oxygenator used in cardiac operations and a medical device used in hemodialysis. Furthermore, the compound of the present invention is useful as a preventive or therapeutic drug (preferably a therapeutic drug) for a disease related to thrombosis or embolism or accompanied by fibrin deposition or fibrosis, for example, a preventive or therapeutic drug (preferably a therapeutic drug) for pulmonary disease such as pulmonary hypertension, adult respiratory distress syndrome, pulmonary fibrosis, and chronic thromboembolic pulmonary hypertension; renal disease such as glomerulonephritis (acute glomerulonephritis, chronic glomerulonephritis, nephrotic nephritis, rapidly progressive glomerulonephritis, etc.), renal infarction, and diabetic nephritis; hepatic disease such as hepatic fibrosis, hepatitis, and hepatic cirrhosis; eye disease associated with fibrin deposition in the eye; organ dysfunction after organ transplantation or resection; microcirculatory disorder caused by microthrombus, including thrombotic microangiopathy; and disease or symptoms associated with cancer cell migration or metastasis.

DESCRIPTION OF EMBODIMENTS

Hereinafter, substituents in the present specification will be described.

A "halogeno group" means a fluoro, chloro, bromo, or iodo group, i.e., a fluorine, chlorine, bromine, or iodine atom.

A "C1 to C3 alkyl group" means a linear or branched saturated hydrocarbon group having 1 to 3 carbon atoms. Examples thereof include methyl, ethyl, propyl, and isopropyl groups.

A "C1 to C6 alkyl group" means a linear or branched saturated hydrocarbon group having 1 to 6 carbon atoms. Examples thereof include, in addition to the C1 to C3 alkyl groups exemplified above, n-butyl, sec-butyl, tert-butyl, isobutyl, n-pentyl, n-hexyl, 1-ethylpropyl, 2,2-dimethylpropyl, and 3,3-dimethylbutyl groups.

A "C3 to C6 branched alkyl group" means a branched saturated hydrocarbon group having 3 to 6 carbon atoms. Examples thereof include isopropyl, isobutyl, tert-butyl, and 3,3-dimethylbutyl groups. The C3 to C6 branched alkyl group is preferably a branched saturated hydrocarbon group having 4 to 6 carbon atoms (C4 to C6 branched alkyl group), more preferably a branched saturated hydrocarbon group having 5 or 6 carbon atoms (C5 to C6 branched alkyl group), even more preferably a branched saturated hydrocarbon group having 6 carbon atoms (C6 branched alkyl group), particularly preferably a 3,3-dimethylbutyl group.

A "halogeno-C1 to C3 alkyl group" means the C1 to C3 alkyl group having 1 to 3 identical or different halogeno groups described above as substituents. Examples thereof include chloromethyl, trifluoromethyl, 2-fluoroethyl, and 2-fluoro-1-methylethyl groups.

A "C1 to C3 alkoxy group" means a linear or branched alkoxy group having 1 to 3 carbon atoms. Examples thereof include methoxy, ethoxy, propoxy, and isopropoxy groups.

A "halogeno-C1 to C3 alkoxy group" means the C1 to C3 alkoxy group having 1 to 3 identical or different halogeno groups described above as substituents. Examples thereof include chloromethoxy, trifluoromethoxy, and 2-chloroethoxy groups.

A "C1 to C3 alkylsulfonyl group" means a sulfonyl group having the C1 to C3 alkyl group. Examples thereof include methylsulfonyl and ethylsulfonyl groups.

A "C2 to C6 alkenyl group" means a linear or branched alkenyl group having 2 to 6 carbon atoms. Examples thereof include vinyl, 2-propenyl, 2-butenyl, and 3-methyl-2-butenyl groups.

A "C3 to C8 cycloalkyl group" means a saturated cyclic hydrocarbon group having 3 to 8 carbon atoms. Examples thereof include cyclopropyl, cyclobutyl, cyclopentyl, cyclohexyl, cycloheptyl, and cyclooctyl groups.

An "aryl group" means an aryl group having 6 to 14 carbon atoms. Examples thereof include phenyl, naphthyl, anthryl, and phenanthryl groups.

A "phenyl group which may be substituted (the substituent is substituted at the 3- or 4-position, or both, of the phenyl group)" is an unsubstituted phenyl, 3-substituted phenyl, 4-substituted phenyl, or 3,4-disubstituted phenyl group and is preferably a phenyl or 4-substituted phenyl group.

A "saturated heterocyclyl group" means a monocyclic or bicyclic 3- to 10-membered saturated heterocyclic group containing 1 to 3 identical or different atoms selected from the group consisting of nitrogen, oxygen, and sulfur atoms. Examples thereof include aziridinyl, azetidinyl, pyrrolidinyl, and morpholinyl groups.

An "unsaturated heterocyclyl group" means the saturated heterocyclyl group partially oxidized, a partially reduced aromatic heterocyclyl group, or an aromatic heterocyclyl group. Examples thereof include pyrrolyl, furyl, thienyl, pyrazolyl, imidazolyl, oxazolyl, isothiazolyl, pyranyl, pyridyl, pyridazinyl, pyrimidinyl, pyrazinyl, benzimidazolyl, benzoxazolyl, quinolyl, pyrrolinyl, imidazolinyl, pyrazolinyl, dihydropyridyl, and tetrahydropyridyl groups.

A "5- or 6-membered heteroaryl group (the heteroaryl group has one or more nitrogen atoms in the ring and may be condensed with a benzene ring)" means an unsaturated heterocyclic group having a 5- or 6-membered ring that has one or more nitrogen atoms in the heterocyclic ring and may form a condensed heterocyclic ring with a benzene ring. Examples thereof include pyridin-2-yl, pyrimidin-2-yl, thiazol-2-yl, quinolyl, and isoquinolyl groups.

A "pyridin-2-yl group which may be substituted (the substituent is substituted at the 4- or 5-position of the pyridyl group)" is an unsubstituted pyridin-2-yl, 4-substituted pyridin-2-yl, or 5-substituted pyridin-2-yl group.

An "aryloxy group" means a group consisting of the aryl group and an oxy group. Examples thereof include phenoxy and naphthoxy groups.

Hereinafter, the compounds of the general formulae (I) and (Ia) to (If) will be described in detail.

[Formula 6]

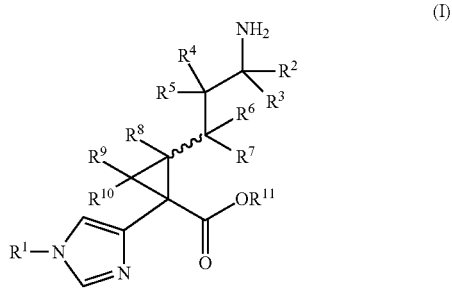

(I)

In the formula, $R^1$ represents a C1 to C6 alkyl group which may be substituted by one to three identical or different groups selected from substituent group A, a C2 to C6 alkenyl group which may be substituted by one to three identical or different groups selected from substituent group A, a C3 to C8 cycloalkyl group which may be substituted by one to three identical or different groups selected from substituent group A, an aryl group which may be substituted by one to three identical or different groups selected from substituent group A (provided that when the aryl group is a phenyl group having a substituent, the substituent is substituted at a meta or para position on the benzene ring), a saturated heterocyclyl group which may be substituted by one to three identical or different groups selected from substituent group A, or an unsaturated heterocyclyl group which may be substituted by one to three identical or different groups selected from substituent group A (the substituent group A consists of a hydroxy group, a halogeno group, a cyano group, a nitro group, an amino group, a carboxy group, a C1 to C3 alkyl group, a halogeno-C1 to C3 alkyl group, a C3 to C8 cycloalkyl group, a C1 to C3 alkoxy group, a halogeno-C1 to C3 alkoxy group, a C1 to C3 alkylsulfonyl group, an aryl group, a heterocyclyl group, and an aryloxy group).

$R^1$ is preferably a C1 to C6 alkyl group which may be substituted by one to three identical or different groups selected from a hydroxy group, a halogeno group, an amino group, a C1 to C3 alkyl group, a phenyl group, and a phenoxy group; a C2 to C6 alkenyl group which may be substituted by one to three identical or different groups selected from a hydroxy group, a halogeno group, an amino group, a C1 to C3 alkyl group, a phenyl group, and a phenoxy group; a C3 to C8 cycloalkyl group which may be substituted by one to three identical or different groups selected from a hydroxy group, a halogeno group, an amino group, and a C1 to C3 alkyl group; a phenyl group which may be substituted by one to three identical or different groups selected from a hydroxy group, a halogeno group, a cyano group, an amino group, a C1 to C3 alkyl group, a halogeno-C1 to C3 alkyl group, a C1 to C3 alkoxy group, a C1 to C3 alkylsulfonyl group, and a phenoxy group (provided that when the phenyl group has a substituent, the substituent is substituted at a meta or para position on the benzene ring); a naphthyl group which may be substituted by one to three identical or different groups selected from a hydroxy group, a halogeno group, a cyano group, an amino group, a C1 to C3 alkyl group, a halogeno-C1 to C3 alkyl group, a C1 to C3 alkoxy group, a C1 to C3 alkylsulfonyl group, and a phenoxy group; a pyridyl group which may be substituted by one to three identical or different groups selected from a hydroxy group, a halogeno group, an amino group, a C1 to C3 alkyl group, a halogeno-C1 to C3 alkyl group, a C1 to C3 alkoxy group, a C1 to C3 alkylsulfonyl group, and a phenoxy group; a pyrimidinyl group which may be substituted by one to three identical or different groups selected from a hydroxy group, a halogeno group, an amino group, a C1 to C3 alkyl group, a halogeno-C1 to C3 alkyl group, a C1 to C3 alkoxy group, a C1 to C3 alkylsulfonyl group, and a phenoxy group; or a benzofuranyl group which may be substituted by one to three identical or different groups selected from a hydroxy group, a halogeno group, an amino group, a C1 to C3 alkyl group, a halogeno-C1 to C3 alkyl group, a C1 to C3 alkoxy group, a C1 to C3 alkylsulfonyl group, and a phenoxy group.

$R^1$ is more preferably a phenyl group which may be substituted by one to three identical or different groups selected from a halogeno group, a C1 to C3 alkyl group, a halogeno-C1 to C3 alkyl group, a C1 to C3 alkoxy group, a C1 to C3 alkylsulfonyl group, and a phenoxy group (provided that when the phenyl group has a substituent, the substituent is substituted at a meta or para position on the benzene ring); an unsubstituted C1 to C6 alkyl group; a C2 to C6 alkenyl group which may be substituted by one phenyl group; a C3 to C8 cycloalkyl group which may be substituted by one to three identical or different C1 to C3 alkyl groups; a pyridyl group which may be substituted by one group selected from a halogeno group, a C1 to C3 alkyl group, and a C1 to C3 alkoxy group; or an unsubstituted pyrimidinyl group.

$R^1$ is even more preferably an unsubstituted C1 to C6 alkyl group, a C3 to C8 cycloalkyl group which may be substituted by one C1 to C3 alkyl group, an unsubstituted phenyl group, an unsubstituted pyridyl group, or an unsubstituted pyrimidinyl group.

Specific examples of $R^1$ are preferably a propyl group, a 3,3-dimethylbutyl group, a 2-phenylvinyl group, a cyclohexyl group, a 4-methylcyclohexyl group, a phenyl group, a 3-fluorophenyl group, a 3-chlorophenyl group, a 3-methylphenyl group, a 4-fluorophenyl group, a 4-chlorophenyl group, a 4-methylphenyl group, a 4-ethylphenyl group, a 4-trifluoromethylphenyl group, a 4-methoxyphenyl group, a 4-phenoxyphenyl group, a 3,4-dimethylphenyl group, a 3,4-difluorophenyl group, a pyridin-2-yl group, a pyridin-3-yl group, a pyridin-4-yl group, a pyrimidin-2-yl group, and a 2-naphthyl group, more preferably a 3,3-dimethylbutyl group, a 4-methylcyclohexyl group, a phenyl group, and a pyridin-2-yl group.

$R^2$, $R^3$, and $R^8$ each independently represent a hydrogen atom or a C1 to C3 alkyl group. $R^4$, $R^5$, $R^6$, $R^7$, $R^9$, and $R^{10}$ each independently represent a hydrogen atom, a fluoro group, or a C1 to C3 alkyl group.

Of $R^2$, $R^3$, $R^4$, $R^5$, $R^6$, $R^7$, $R^8$, $R^9$, and $R^{10}$, preferably, $R^2$, $R^3$, $R^7$, $R^8$, $R^9$, and $R^{10}$ are each a hydrogen atom, and $R^4$, $R^5$, and $R^6$ are each independently a hydrogen atom or a C1 to C3 alkyl group, or $R^2$, $R^3$, $R^6$, $R^7$, $R^8$, $R^9$, and $R^{10}$ are each a hydrogen atom, and $R^4$ and $R^5$ are each independently a hydrogen atom or a C1 to C3 alkyl group. Also preferably, $R^2$, $R^3$, $R^4$, $R^5$, $R^6$, $R^7$, and $R^8$ are each a hydrogen atom, and $R^9$ and $R^{10}$ are each independently a hydrogen atom or a fluorine atom. More preferably, all of $R^2$, $R^3$, $R^4$, $R^5$, $R^6$, $R^7$, $R^8$, $R^9$, and $R^{10}$ are hydrogen atoms.

In this context, the C1 to C3 alkyl group is preferably a methyl group.

$R^{11}$ represents a hydrogen atom, a methyl group, or an ethyl group. $R^{11}$ is preferably a hydrogen atom.

In the general formula (I), the configuration of the cyclopropane moiety is not particularly limited. The cyclopropane moiety may have any 1 to 4 of (1R,2S), (1S,2R), (1R,2R), and (1S,2S) configurations. When the cyclopropane moiety has a mixture of two or more configurations, their mixing ratio is not particularly limited. This is indicated by a wavy line in the bond in the general formula (I). The same holds true for configurations in the present specification even if no particular reference is made thereto. When some of $R^2$, $R^3$, $R^4$, $R^5$, $R^6$, $R^7$, $R^8$, $R^9$, and $R^{10}$ are a fluoro group, R and S in each configuration may be reversed and are thus complicated. Thus, in the present specification, each configuration is indicated by R and S determined when all of $R^2$, $R^3$, $R^4$, $R^5$, $R^6$, $R^7$, $R^8$, $R^9$, and $R^{10}$ are hydrogen atoms, unless otherwise specified.

The (1R*,2S*) configuration of the cyclopropane moiety in the general formula (I) means a mixture of (1R,2S) and (1S,2R) configurations of the cyclopropane moiety and is represented by the following general formula (Ia):

[Formula 7]

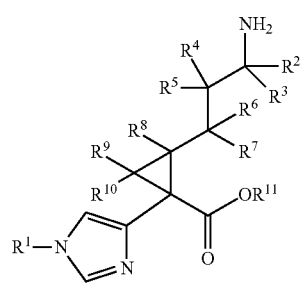

The (1R*,2R*) configuration of the cyclopropane moiety in the general formula (I) means a mixture of (1R,2R) and (1S,2S) configurations of the cyclopropane moiety and is represented by the following general formula (Ib):

[Formula 8]

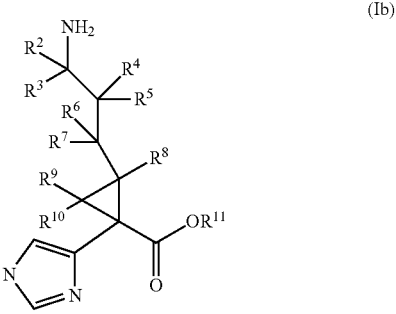

The (1R,2S) configuration of the cyclopropane moiety in the general formula (I) is represented by the following general formula (Ic):

[Formula 9]

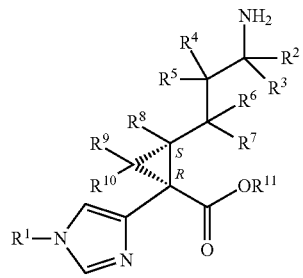

The (1S,2R) configuration of the cyclopropane moiety in the general formula (I) is represented by the following general formula (Id):

[Formula 10]

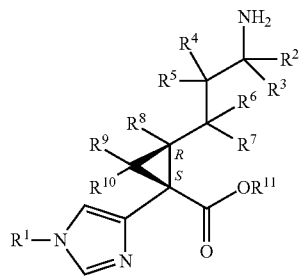

The (1R,2R) configuration of the cyclopropane moiety in the general formula (I) is represented by the following general formula (Ie):

[Formula 11]

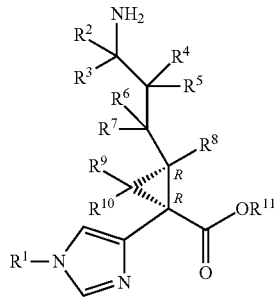

The (1S,2S) configuration of the cyclopropane moiety in the general formula (I) is represented by the following general formula (If):

[Formula 12]

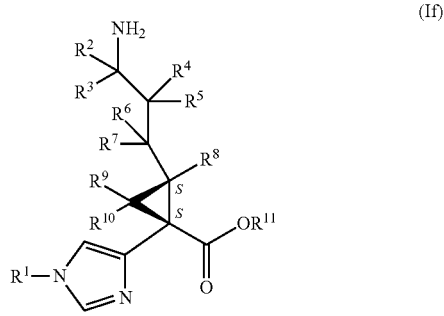

(If)

In these general formulae (Ia) to (If), $R^1$, $R^2$, $R^3$, $R^4$, $R^5$, $R^6$, $R^7$, $R^8$, $R^9$, $R^{10}$, and $R^{11}$ are as defined in the general formula (I), and their preferable examples are also the same as in the general formula (I).

Preferable specific examples of the compound represented by any the general formulae (I) and (Ia) to (If) and a pharmacologically acceptable salt thereof include the following:

2-(3-aminopropyl)-1-[1-(3,3-dimethylbutyl)-1H-imidazol-4-yl]cyclopropanecarboxylic acid,
2-(3-aminopropyl)-1-(1-propyl-1H-imidazol-4-yl)cyclopropanecarboxylic acid,
2-(3-aminopropyl)-1-(1-cyclohexyl-1H-imidazol-4-yl)cyclopropanecarboxylic acid,
2-(3-aminopropyl)-1-[1-(trans-4-methylcyclohexyl)-1H-imidazol-4-yl]cyclopropanecarboxylic acid,
2-(3-aminopropyl)-1-(1-phenyl-1H-imidazol-4-yl)cyclopropanecarboxylic acid,
2-(3-aminopropyl)-1-[1-(4-methylphenyl)-1H-imidazol-4-yl]cyclopropanecarboxylic acid,
2-(3-aminopropyl)-1-[1-(3-methylphenyl)-1H-imidazol-4-yl]cyclopropanecarboxylic acid,
2-(3-aminopropyl)-1-[1-(3,4-dimethylphenyl)-1H-imidazol-4-yl]cyclopropanecarboxylic acid,
2-(3-aminopropyl)-1-[1-(4-ethylphenyl)-1H-imidazol-4-yl]cyclopropanecarboxylic acid,
2-(3-aminopropyl)-1-[1-(4-methoxyphenyl)-1H-imidazol-4-yl]cyclopropanecarboxylic acid,
2-(3-aminopropyl)-1-{1-[4-(trifluoromethyl)phenyl]-1H-imidazol-4-yl}cyclopropanecarboxylic acid,
2-(3-aminopropyl)-1-{1-[(E)-2-phenylvinyl]-1H-imidazol-4-yl}cyclopropanecarboxylic acid,
2-(3-aminopropyl)-1-[1-(4-fluorophenyl)-1H-imidazol-4-yl]cyclopropanecarboxylic acid,
2-(3-aminopropyl)-1-[1-(4-phenoxyphenyl)-1H-imidazol-4-yl]cyclopropanecarboxylic acid,
2-(3-aminopropyl)-1-[1-(3,4-difluorophenyl)-1H-imidazol-4-yl]cyclopropanecarboxylic acid,
2-(3-aminopropyl)-1-[1-(4-chlorophenyl)-1H-imidazol-4-yl]cyclopropanecarboxylic acid,
2-(3-aminopropyl)-1-[1-(3-chlorophenyl)-1H-imidazol-4-yl]cyclopropanecarboxylic acid,
2-(3-aminopropyl)-1-[1-(2-naphthyl)-1H-imidazol-4-yl]cyclopropanecarboxylic acid,
2-(3-aminopropyl)-1-[1-(3-fluorophenyl)-1H-imidazol-4-yl]cyclopropanecarboxylic acid,
2-(3-aminopropyl)-1-(1-pyridin-4-yl-1H-imidazol-4-yl)cyclopropanecarboxylic acid,
2-(3-aminopropyl)-1-(1-pyridin-3-yl-1H-imidazol-4-yl)cyclopropanecarboxylic acid,
2-(3-aminopropyl)-1-(1-pyridin-2-yl-1H-imidazol-4-yl)cyclopropanecarboxylic acid,
ethyl 2-(3-aminopropyl)-1-[1-(4-methylphenyl)-1H-imidazol-4-yl]cyclopropanecarboxylate,
2-(3-amino-2-methylpropyl)-1-(1-phenyl-1H-imidazol-4-yl)cyclopropanecarboxylic acid,
2-(3-amino-1-methylpropyl)-1-(1-phenyl-1H-imidazol-4-yl)cyclopropanecarboxylic acid,
2-(3-aminopropyl)-1-[1-(2-thienyl)-1H-imidazol-4-yl]cyclopropanecarboxylic acid,
2-(3-aminopropyl)-1-[1-(5-methylpyridin-2-yl)-1H-imidazol-4-yl]cyclopropanecarboxylic acid,
2-(3-aminopropyl)-1-[1-(1,3-thiazol-2-yl)-1H-imidazol-4-yl]cyclopropanecarboxylic acid,
2-(3-aminopropyl)-1-(1-pyrimidin-2-yl-1H-imidazol-4-yl)cyclopropanecarboxylic acid,
2-(3-aminopropyl)-1-[1-(4-cyanophenyl)-1H-imidazol-4-yl]cyclopropanecarboxylic acid,
2-(3-amino-2,2-dimethylpropyl)-1-(1-phenyl-1H-imidazol-4-yl)cyclopropanecarboxylic acid,
2-(3-aminopropyl)-1-[1-(5-fluoropyridin-2-yl)-1H-imidazol-4-yl]cyclopropanecarboxylic acid,
2-(3-aminopropyl)-1-(1-quinolin-2-yl-1H-imidazol-4-yl)cyclopropanecarboxylic acid,
2-[(2-aminomethyl)butyl]-1-(1-phenyl-1H-imidazol-4-yl)cyclopropanecarboxylic acid,
2-(3-aminopropyl)-1-[1-(1-benzofuran-5-yl)-1H-imidazol-4-yl]cyclopropanecarboxylic acid,
2-(3-aminopropyl)-1-[1-(5-methoxypyridin-2-yl)-1H-imidazol-4-yl]cyclopropanecarboxylic acid,
2-(3-aminopropyl)-1-[1-(1-naphthyl)-1H-imidazol-4-yl]cyclopropanecarboxylic acid,
2-(3-amino-2-methylpropyl)-1-(1-pyridin-2-yl-1H-imidazol-4-yl)cyclopropanecarboxylic acid,
2-(3-amino-2-methylpropyl)-1-[1-(5-methylpyridin-2-yl)-1H-imidazol-4-yl]cyclopropanecarboxylic acid, and
2-[2-(aminomethyl)butyl]-1-(1-pyridin-2-yl-1H-imidazol-4-yl)cyclopropanecarboxylic acid.

More preferable specific examples thereof include the following:
2-(3-aminopropyl)-1-(1-phenyl-1H-imidazol-4-yl)cyclopropanecarboxylic acid,
2-(3-aminopropyl)-1-[1-(3,3-dimethylbutyl)-1H-imidazol-4-yl]cyclopropanecarboxylic acid,
2-(3-aminopropyl)-1-[1-(trans-4-methylcyclohexyl)-1H-imidazol-4-yl]cyclopropanecarboxylic acid,
2-(3-aminopropyl)-1-(1-pyridin-2-yl-1H-imidazol-4-yl)cyclopropanecarboxylic acid,
2-(3-amino-2-methylpropyl)-1-(1-phenyl-1H-imidazol-4-yl)cyclopropanecarboxylic acid,
2-(3-aminopropyl)-1-[1-(5-methylpyridin-2-yl)-1H-imidazol-4-yl]cyclopropanecarboxylic acid,
2-[(2-aminomethyl)butyl]-1-(1-phenyl-1H-imidazol-4-yl)cyclopropanecarboxylic acid,
2-[(2R)-3-amino-2-methylpropyl]-1-(1-pyridin-2-yl-1H-imidazol-4-yl)cyclopropanecarboxylic acid,
2-[(2R)-3-amino-2-methylpropyl]-1-[1-(5-methylpyridin-2-yl)-1H-imidazol-4-yl]cyclopropanecarboxylic acid, and
2-[(2R)-2-(aminomethyl)butyl]-1-(1-pyridin-2-yl-1H-imidazol-4-yl)cyclopropanecarboxylic acid.

Even more preferable specific examples thereof include the following:

(1R,2S)-2-(3-aminopropyl)-1-(1-phenyl-1H-imidazol-4-yl)cyclopropanecarboxylic acid, (1R,2S)-2-(3-aminopropyl)-1-(1-pyridin-2-yl-1H-imidazol-4-yl)cyclopropanecarboxylic acid, (1R,2S)-2-[(2R)-3-amino-2-methylpropyl]-1-(1-pyridin-2-yl-1H-imidazol-4-yl)cyclopropanecarboxylic acid, (1R,2S)-2-[(2R)-3-amino-2-methylpropyl]-1-[1-(5-methylpyridin-2-yl)-1H-imidazol-4-yl]cyclopropanecarboxylic acid, and (1R,2S)-2-[(2R)-2-(aminomethyl)butyl]-1-(1-pyridin-2-yl-1H-imidazol-4-yl)cyclopropanecarboxylic acid Hereinafter, typical production processes of the compound of the present invention will be described. However, the present invention is not limited to these processes by any means.

[Production Process 1]

The compound represented by the general formula (I) or a pharmacologically acceptable salt thereof can be produced, for example, by the following process:

[Formula 13]

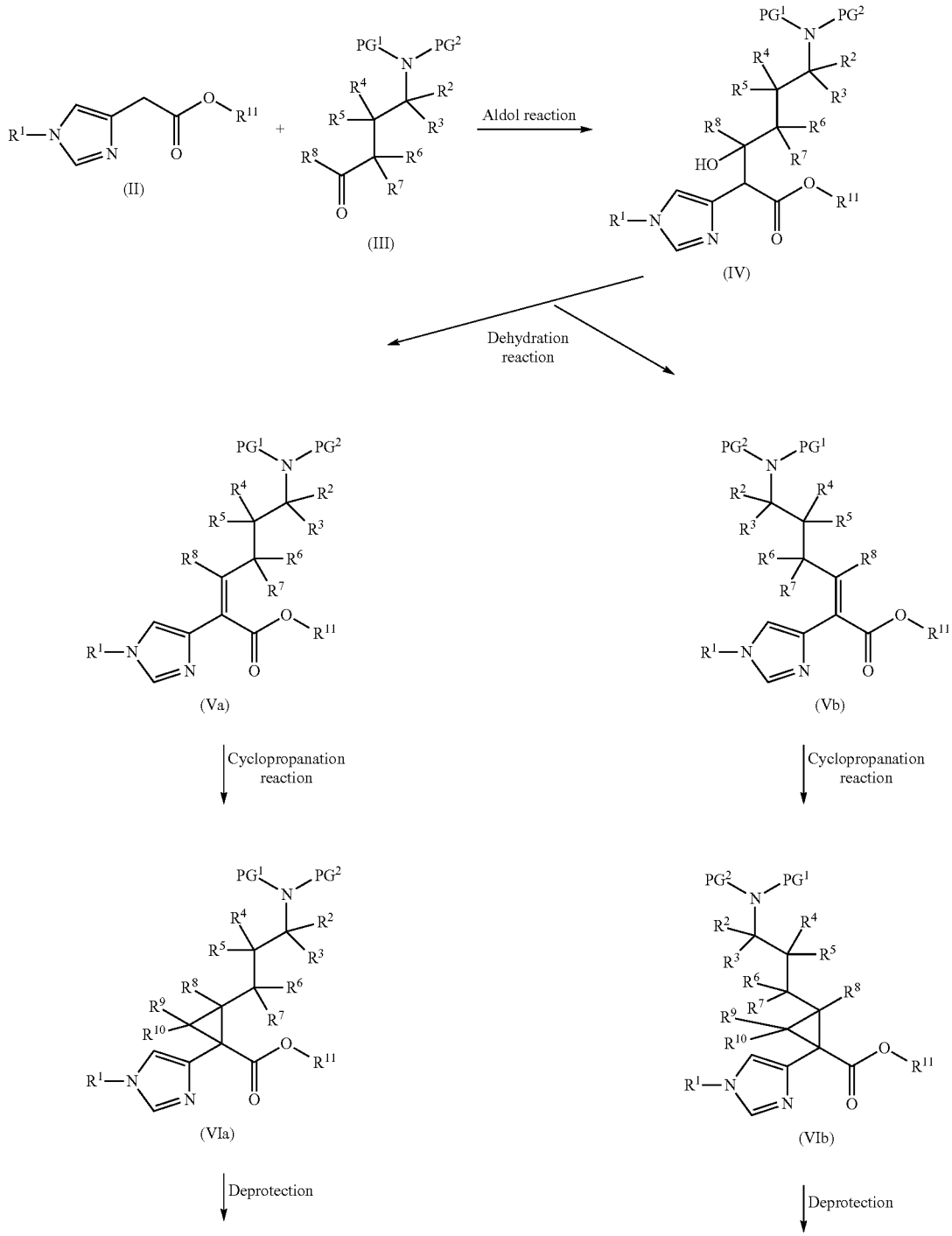

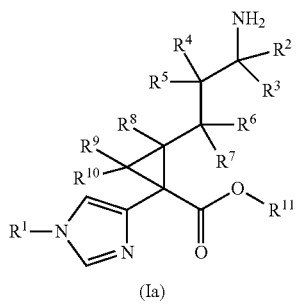

(Ia)

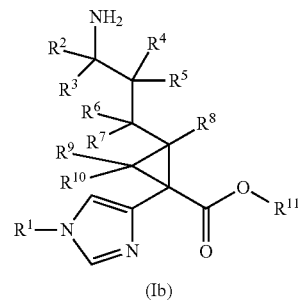

(Ib)

wherein $R^1$, $R^2$, $R^3$, $R^4$, $R^5$, $R^6$, $R^7$, $R^8$, $R^9$, $R^{10}$, and $R^{11}$ are as defined above; and $PG^1$ and $PG^2$ each independently represent a hydrogen atom or a protective group for the amino group.

Compounds (II) and (III) are subjected to an aldol reaction to produce a compound (IV). The obtained compound (IV) can be subjected to a dehydration reaction and separation/purification to produce compounds (Va) and (Vb). Subsequently, the olefin moiety of each compound can be cyclopropanated to produce compounds (VIa) and (VIb), respectively. The protective groups in the obtained compounds (VIa) and (VIb) can be removed to produce compounds (Ia) and (Ib).

The aldol reaction is, in this case, a reaction through which the compound (II) as a CH-active compound and the compound (III) containing a carbonyl group are bonded to each other in the presence of a strong base to form the compound (IV). For example, a carbonate of an alkali metal or alkaline-earth metal, an alkali metal alkoxide, or an alkali metal hydroxide or hydride (e.g., sodium carbonate, potassium carbonate, sodium ethoxide, potassium butoxide, sodium hydroxide, potassium hydroxide, sodium hydride, or potassium hydride), an organic metal base as exemplified by an alkyllithium (e.g., n-butyllithium) or a dialkylaminolithium (e.g., lithium diisopropylamide), or an organic metal base such as a bissilylamine (e.g., lithium hexamethyldisilazide) can be used as a strong base. Non-cyclic, cyclic, or aromatic hydrocarbons, alcohols, or a polar aprotic solvent, for example, tetrahydrofuran, N,N-dimethylformamide, or diethoxyethane, or a mixed solvent thereof can be used as a reaction solvent. The reaction temperature is approximately −78° C. to room temperature.

The dehydration reaction is a reaction through which a hydroxy group in the compound (IV) is treated with methanesulfonyl chloride or benzenesulfonyl chloride or the like at −78° C. to 50° C. in the presence of triethylamine in an inert solvent to convert the compound (IV) to a sulfonate, which is then further treated with a base to form a mixture of compounds (Va) and (Vb) at an arbitrary ratio or either compound (Va) or (Vb). When the mixture is formed, each of the compounds (Va) and (Vb) can be isolated using purification means such as silica gel chromatography. Examples of the inert solvent include: alkyl halide solvents such as methylene chloride, chloroform, and carbon tetrachloride; ether solvents such as tetrahydrofuran, 1,2-dimethoxyethane, and dioxane; aromatic solvents such as benzene and toluene; and amide solvents such as N,N-dimethylformamide, N,N-dimethylacetamide, and N-methylpyrrolidin-2-one. In addition to them, sulfoxide solvents such as dimethyl sulfoxide and sulfolane, ketone solvents such as acetone and methyl ethyl ketone, or acetonitrile, or the like may be used in some cases. Pyridine, 2,6-lutidine, collidine, 4-dimethylaminopyridine, triethylamine, N-methylmorpholine, diisopropylethylamine, or 1,8-diazabicyclo[5.4.0]undec-7-ene (DBU) can be used as a base. The dehydration reaction may proceed during the aldol reaction in some cases.

The cyclopropanation reaction is a reaction through which an ylide obtained from trimethylsulfoxonium iodide (or trimethylsulfoxonium bromide) is allowed to act on the electron-deficient alkene compounds (Va) and/or (Vb) to construct a cyclopropane ring (Corey-Chaykovsky reaction). The production can be achieved with reference to the following documents: 1) Corey, E. J.; Chaykovsky, M., J. Am. Chem. Soc., 1962, 84, 867, 2) Corey, E. J.; Chaykovsky, M., J. Am. Chem. Soc., 1965, 87, 1353, 3) Corey, E. J.; Chaykovsky, M., Org. Synth., 1969, 49, 78, and 4) Review: Aggarwal, V. K.; Richardson, J., Chem. Commun., 2003, 2644.

In this reaction, an appropriate amount of an organic solvent, for example dimethyl sulfoxide (DMSO) or N,N-dimethylformamide (DMF), can be used. Trimethylsulfoxonium iodide is added to a stoichiometric amount or more of sodium hydride suspended or dissolved in this solvent to form an ylide in a reactor, to which the compounds (Va) and/or (Vb) can be added to produce compounds (VIa) and/or (VIb), respectively. The reaction can be performed at a temperature of 40° C. or lower, usually at room temperature.

Any protective group usually used as a protective group for amino groups in organic compound synthesis, particularly peptide synthesis, can be used as a protective group for the amino group. Specific examples thereof can include: alkoxycarbonyl groups such as tert-butoxycarbonyl, methoxycarbonyl, and ethoxycarbonyl groups; arylmethoxycarbonyl groups such as benzyloxycarbonyl, para-methoxybenzyloxycarbonyl, and para (or ortho)-nitrobenzyloxycarbonyl groups; arylmethyl groups such as benzyl, 4-methoxybenzyl, and triphenylmethyl groups; alkanoyl groups such as formyl and acetyl groups; aroyl groups such as a benzoyl group; and arylsulfonyl groups such as 2,4-dinitrobenzenesulfonyl and ortho-nitrobenzenesulfonyl groups. These protective groups for the amino group may be selected according to, for example, the properties of the compound whose amino group is to be protected. For removal of the protective groups, reagents or conditions may be selected according to each protective group.

When $R^{11}$ is a methyl group or an ethyl group, these substituents may be understood as protective groups for the carboxy group. In this case, the deprotection reaction proceeds by acid hydrolysis or alkali hydrolysis to achieve conversion to a hydrogen atom.

Examples of references on the protection/deprotection of the amino and carboxy groups can include Greene, T. W., Wuts, P. G. M., Protective Groups in Organic Synthesis (1999), 3rd Ed., Wiley-Interscience.

[Production Process 2]

The compound (I) of the present invention can also be produced by the following process:

[Formula 14]

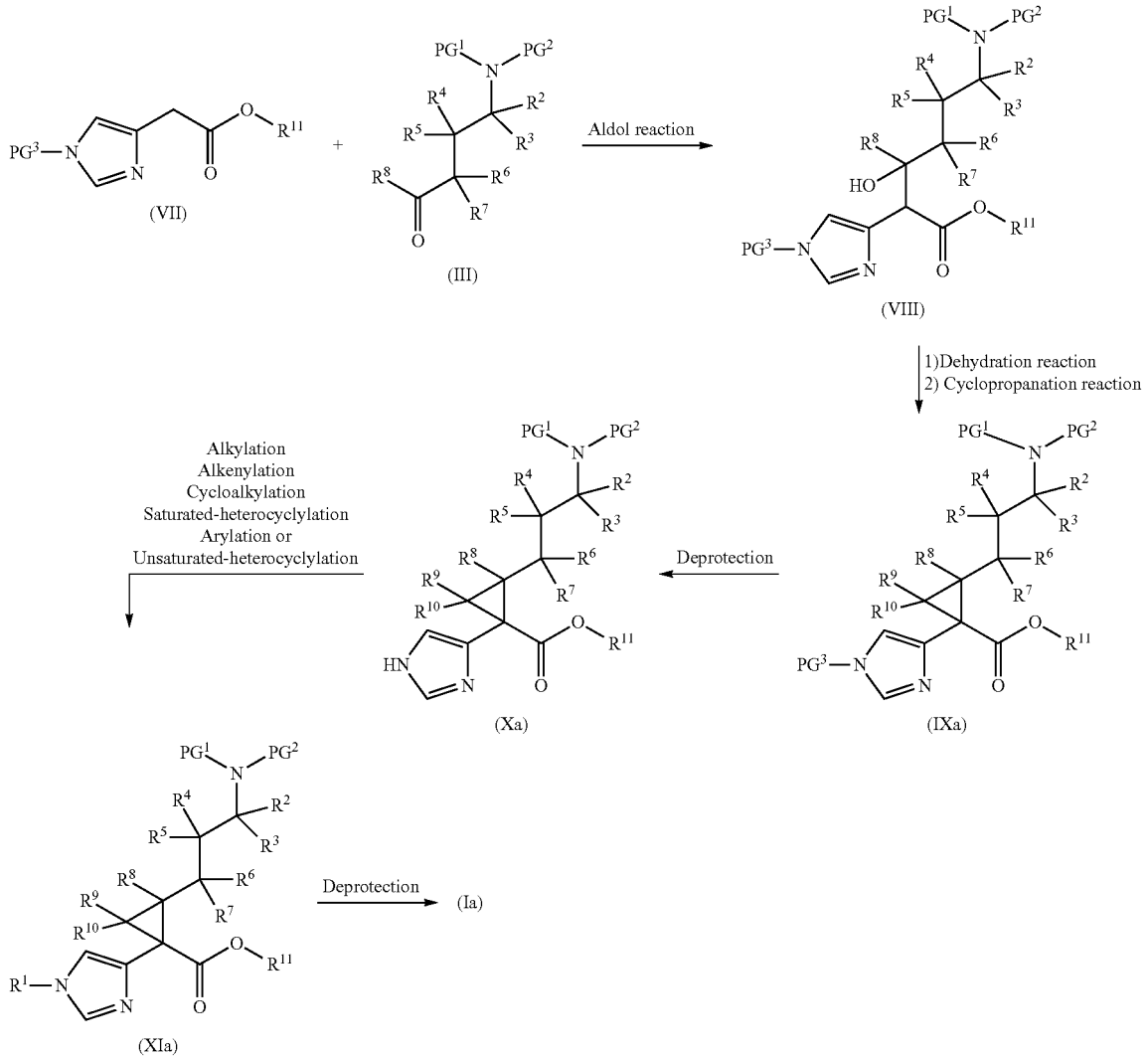

wherein $R^1$, $R^2$, $R^3$, $R^4$, $R^5$, $R^6$, $R^7$, $R^8$, $R^9$, $R^{10}$, and $R^{11}$ are as defined above; $PG^1$ and $PG^2$ each independently represent a hydrogen atom or a protective group for the amino group; and $PG^3$ represents a protective group for the nitrogen atom in imidazole.

The compound (Ia) can be produced in the same way as in Production Process 1 with a compound (VII) having a protective group introduced at the nitrogen atom of imidazole as a starting material. Specifically, compounds (VII) and (III) are subjected to an aldol reaction to produce a compound (VIII). The obtained compound (VIII) can be converted to a compound (IXa) through a dehydration reaction and cyclopropanation. Only the protective group for the nitrogen atom of imidazole in the obtained compound (IXa) is removed to convert the compound (IXa) to a compound (Xa). Then, the nitrogen atom of the imidazole moiety is alkylated, alkenylated, cycloalkylated, saturated-heterocyclylated, unsaturated-heterocyclylated, or arylated to produce a compound (XIa), and protective groups in the compound (XIa) can be removed to produce a compound (Ia).

Examples of the protective group for the nitrogen atom in imidazole include: sulfonyl groups such as benzenesulfonyl and tosyl groups; alkoxycarbonyl groups such as tert-butoxycarbonyl and benzyloxycarbonyl groups; and alkyl groups such as trityl, methoxymethyl, benzyloxymethyl, and [2-(trimethylsilyl)ethoxy]methyl groups. These protective groups for the nitrogen atom in imidazole may be selected according to, for example, the properties of the compound. For removal of the protective groups, reagents or conditions may be selected according to each protective group.

The alkylation, cycloalkylation, or saturated-heterocyclylation reaction is a reaction through which a compound having a leaving group such as $R^1$—I, $R^1$—Br, $R^1$—OSO$_2$CH$_3$, or $R^1$—OSO$_2$CF$_3$ is reacted with the compound (Xa), for example in the presence of a base to form the compound (XIa). Non-cyclic, cyclic, or aromatic hydrocarbons or a polar aprotic solvent, for example tetrahydrofuran, N,N-dimethylformamide, or diethoxyethane, or a mixed solvent thereof can be used as a reaction solvent. For example, cesium carbonate or sodium hydride can be used as a base.

The alkenylation, unsaturated-heterocyclylation, or arylation reaction is a reaction through which, for example, an unsaturated heterocyclylboronic acid or arylboronic acid compound $R^1$—$B(OH)_2$ is reacted with the compound (Xa) to form the compound (XIa). This reaction can be achieved with reference to reactions known in the art (P. Y. S. Lam et al., Tetrahedron Lett., vol. 39, p. 2941, 1998).

In another method for the unsaturated-heterocyclylation reaction, $R^1$—Br (or $R^1$—I, $R^1$—F, $R^1$—Cl, etc.) can be reacted with the compound (Xa) in the presence of copper oxide to obtain the compound (XIa). The production can be achieved with reference to, for example, WO2003/061652.

The protection/deprotection of the amino and carboxy groups can be achieved with reference to the examples described in Production Process 1.

[Production Process 3]

The compound represented by the general formula (I) or the pharmacologically acceptable salt thereof can be produced, for example, by the following process:

[Formula 15]

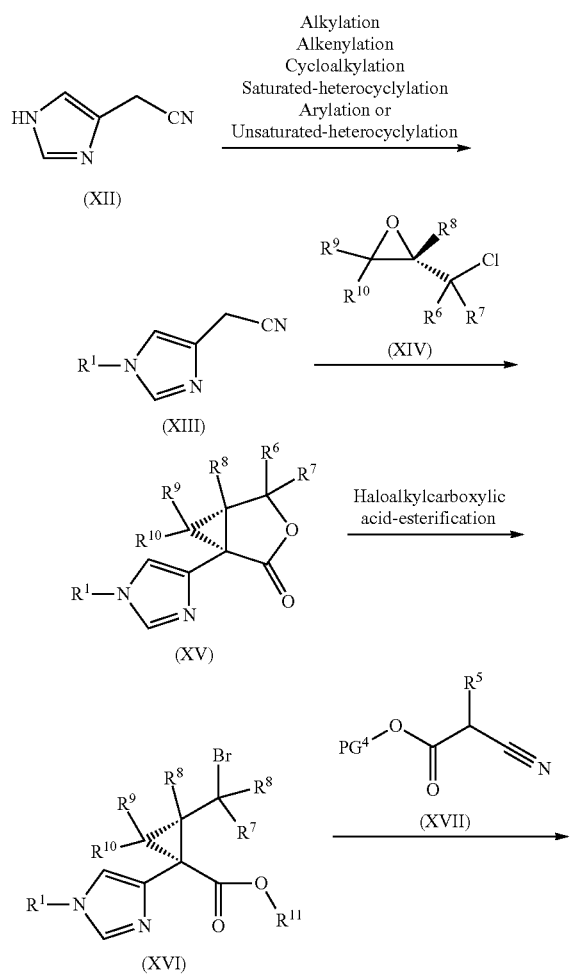

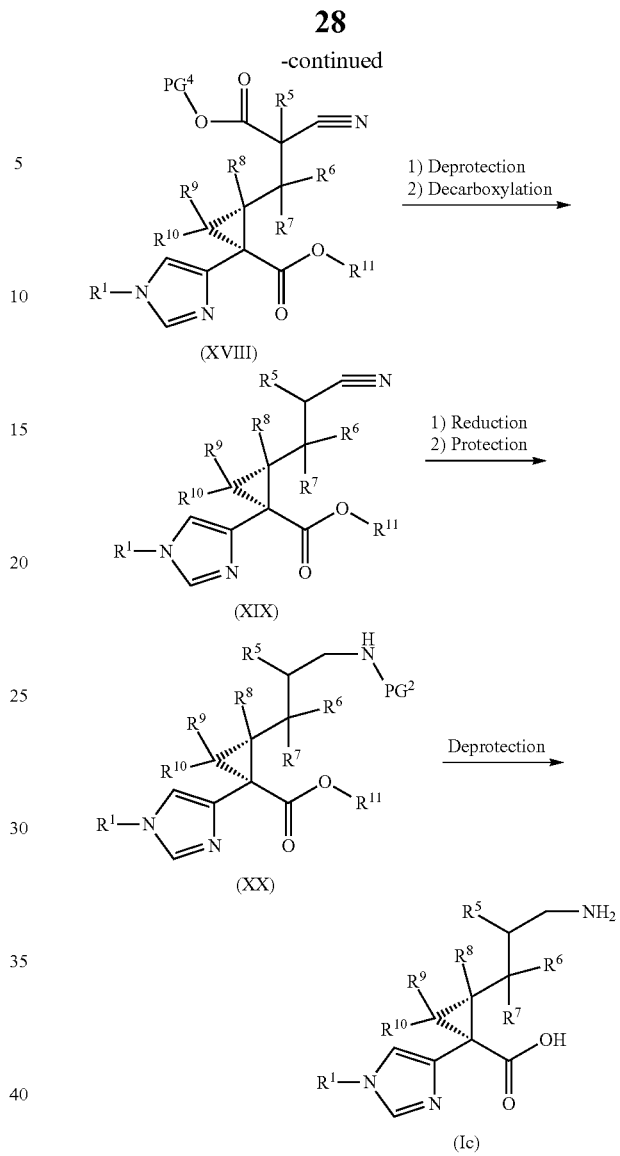

wherein $R^1$, $R^5$, $R^6$, $R^7$, $R^8$, $R^9$, $R^{10}$, and $R^{11}$ are as defined above; $PG^2$ represents a protective group for the amino group; and $PG^4$ represents a protective group for the carboxyl group.

A compound (XII) can be alkylated, alkenylated, cycloalkylated, saturated-heterocyclylated, unsaturated-heterocyclylated, or arylated to produce a compound (XIII). The obtained compound (XIII) and an optically active epichlorohydrin derivative (XIV) can be converted to a lactone compound (XV) containing a cyclopropane ring introduced therein with high enantiomeric selectivity. Subsequently, the lactone can be ring-opened through a haloalkylcarboxylic acid-esterification reaction to produce a compound (XVI). The compound (XVI) and a cyanoacetic acid derivative (XVII) can be used in an alkylation to produce a compound (XVIII). Then, a compound (XIX) can be produced by the removal of the protective group for the carboxyl group in the compound (XVIII) and a subsequent decarboxylation reaction. Further, a compound (XX) can be produced by the reduction of the cyano group in the compound (XIX) and the subsequent protection of the amino group. Finally, the protective group in the compound (XX) can be removed to produce a compound (Ic).

The alkylation, cycloalkylation, or saturated-heterocyclylation reaction is a reaction through which a compound having a leaving group such as $R^1$—I, $R^1$—Br, $R^1$—$OSO_2CH_3$, or $R^1$—$OSO_2CF_3$ is reacted with the compound (XII), for example in the presence of a base, to form the compound (XIII). Non-cyclic, cyclic, or aromatic hydrocarbons or a polar aprotic solvent, for example tetrahydrofuran, N,N-dimethylformamide, or diethoxyethane, or a mixed solvent thereof can be used as a reaction solvent. For example, cesium carbonate or sodium hydride can be used as a base.

The alkenylation, unsaturated-heterocyclylation, or arylation reaction is a reaction through which, for example, an unsaturated heterocyclylboronic acid or arylboronic acid compound $R^1$—$B(OH)_2$ is reacted with the compound (XII) to form the compound (XIII). This reaction can be achieved with reference to reactions known in the art (P. Y. S. Lam et al., Tetrahedron Lett., vol. 39, p. 2941, 1998).

In another method for the unsaturated-heterocyclylation reaction, $R^1$—Br (or $R^1$—I, $R^1$—F, $R^1$—Cl, etc.) can be reacted with the compound (XII) in the presence of copper oxide to obtain the compound (XIII). The production can be achieved with reference to, for example, WO2003/061652.

The reaction between the compound (XIII) and the optically active epichlorohydrin derivative (XIV) is a reaction through which the compound (XIII) is reacted with 2 or more equivalents of a strong base such as sodium hexamethyldisilazide, then the optically active epichlorohydrin derivative (XIV) is added thereto, and the reaction solution is stirred, subsequently reacted with a strong base such as potassium hydroxide, and further treated with a strong acid such as concentrated hydrochloric acid to form the lactone ring compound (XV) containing a cyclopropane ring introduced therein with high enantiomeric selectivity. For this reaction, the production can be achieved with reference to the following documents: 1) S. Shuto et al., J. Org. Chem., vol. 61, p. 915, 1996, 2) F. Xu et al., Organic Lett., vol. 8, p. 3885, 2006, 3) T. Vickers et al., Bioorg. Med. Chem. Lett., vol. 18, p. 3230, 2008.

The haloalkylcarboxylic acid-esterification is a reaction through which the compound (XV) is reacted with an excess amount of hydrogen bromide, thionyl bromide, or the like, for example, in the presence of an alcohol to form the compound (XVI). This reaction can be performed at room temperature.

The reaction between the compound (XVI) and the cyanoacetic acid derivative (XVII) is a reaction through which the cyanoacetic acid derivative (XVII) is treated with a base such as sodium hydride at room temperature and then reacted at around 75° C. by the addition of the compound (XVI) to form the compound (XVIII).

When $PG^4$ is, for example, a tert-butyl group, the deprotection and decarboxylation reactions of the compound (XVIII) are reactions through which lithium chloride is reacted with aqueous dimethyl sulfoxide as a solvent at around 140° C. to form the compound (XIX).

Examples of the reduction of a cyano group in the compound (XIX) and the subsequent protection of an amino group include a reaction through which a catalytic amount of nickel (II) chloride hexahydrate is reacted with an excess amount of lithium borohydride and di-tert-butyl dicarbonate at room temperature in methanol to form the compound (XX). For this reaction, the production can be achieved with reference to the document (S. Caddick et al., Tetrahedron, vol. 59, p. 5417, 2003). Alternatively, in a stepwise manner, the cyano group in the compound (XIX) is converted through a hydrogenation reaction to an amino group, which can then be protected by a method usually used.

Any protective group usually used as a protective group for amino groups in organic compound synthesis, particularly peptide synthesis, can be used as the protective group for the amino group represented by $PG^2$. Specific examples thereof can include: alkoxycarbonyl groups such as tert-butoxycarbonyl, methoxycarbonyl, and ethoxycarbonyl groups; arylmethoxycarbonyl groups such as benzyloxycarbonyl, para-methoxybenzyloxycarbonyl, and para (or ortho)-nitrobenzyloxycarbonyl groups; arylmethyl groups such as benzyl, 4-methoxybenzyl, and triphenylmethyl groups; alkanoyl groups such as formyl and acetyl groups; aroyl groups such as a benzoyl group; and arylsulfonyl groups such as 2,4-dinitrobenzenesulfonyl and ortho-nitrobenzenesulfonyl groups. These protective groups for the amino group may be selected according to, for example, the properties of the compound whose amino group is to be protected. For removal of the protective groups, reagents or conditions may be selected according to each protective group.

Examples of the protective group for the carboxy group represented by $PG^4$ include alkyl, aryl, and arylalkyl ester groups. These protective groups for the carboxy group may be selected according to, for example, the properties of the compound whose carboxy group is to be protected. For removal of the protective groups, reagents or conditions may be selected according to each protective group. When $R^{11}$ is a methyl group or an ethyl group, these substituents may be understood as protective groups for the carboxy group. In this case, the deprotection reaction proceeds by acid hydrolysis or alkali hydrolysis to achieve conversion to a hydrogen atom.

Examples of references on the protection/deprotection of the amino and carboxy groups can include Greene, T. W., Wuts, P. G. M., Protective Groups in Organic Synthesis (1999), 3rd Ed., Wiley-Interscience.

[Production Process 4]

The compound (II) can be produced by a well known method from commercially available 4-imidazoleacetic acid hydrochloride. For example, this compound can be converted to an ester through reaction in a lower alcohol in the presence of thionyl chloride. Then, this ester can be alkylated, alkenylated, cycloalkylated, saturated-heterocyclylated, unsaturated-heterocyclylated, or arylated as described in Production Process 2 to produce the compound (II).

The compound (III) can be produced by a well known method using a commercially available or known substance. The production can be achieved with reference to, for example, Tetrahedron Letters, 1996, vol. 37, p. 3379.

The compound (VII) can be produced by a well known method using a commercially available or known substance. The production can be achieved with reference to, for example, Bioorganic & Medicinal Chemistry, 1997, vol. 5, p. 1989.

When the desired compounds or intermediates in these production processes 1 to 4 are isomeric (e.g., stereoisomeric) mixtures, each isomer can be separated and purified appropriately by preparative medium-pressure chromatography, HPLC, or the like using an optically active column or the like.

When the compound of the present invention represented by any of the general formulae (I) and (Ia) to (If) or a pharmacologically acceptable salt thereof, or a production intermediate thereof has asymmetric carbon, their optical isomers are present. From these optical isomers, each isomer can be isolated and purified by a standard method such as fractional crystallization (salt resolution) using recrystallization with an appropriate solvent or column chromatography. Examples of references on a method of resolving racemic mixtures into optical isomers can include J. Jacques et al., "Enantiomers, Racemates and Resolution, John Wiley And Sons, Inc."

The cyclopropanecarboxylic acid derivative of the present invention has excellent TAFIa inhibitory activity and has good oral absorbability, excellent disposition such as retention in blood and metabolic stability, and high safety. Therefore, the cyclopropanecarboxylic acid derivative of the present invention is useful as a pharmaceutical drug and particularly useful as a therapeutic drug for myocardial infarction, angina pectoris, acute coronary syndrome, cerebral infarction, deep vein thrombosis, pulmonary embolism, peripheral arterial occlusion, sepsis, disseminated intravascular coagulation syndrome, pulmonary fibrosis, or the like. Moreover, it is useful as a therapeutic drug for a thromboembolism-derived disease. Furthermore, it is useful as a pharmaceutical drug for improving the functions of an organ after transplantation. The compound of the present invention is also useful as a therapeutic drug for coronary arterial diseases after surgery (percutaneous transluminal coronary angioplasty), transplantation or replacement of a vascular substitute (autologous or artificial blood vessel), or restenosis/reocclusion caused by stent implantation. Moreover, it is useful for the prevention of thrombus formation caused by a vascular catheter (indwelling catheter for dialysis), an extracorporeal blood circulator, and the coating of an artificial blood vessel or the filling thereof with a TAFIa inhibitor solution, and for the promotion of thrombolysis. It is also useful as a therapeutic drug for atherothrombosis or fibrosis (lung fibrosis such as chronic obstructive pulmonary disease, fibrosis after ophthalmic surgery, etc.).

The compound of the present invention represented by any of the general formulae (I) and (Ia) to (If) has a basic group such as an amino group and can therefore be made into an acid-addition salt with a pharmacologically acceptable acid. Examples of such a salt can include: hydrohalides such as hydrofluoride, hydrochloride, hydrobromide, and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as acetate, malate, fumarate, succinate, citrate, tartrate, oxalate, and maleate; and amino acid salts such as ornitate, glutamate, and aspartate. Hydrochloride and p-toluenesulfonate are preferable.

Moreover, the compound represented by any of the general formulae (I) and (Ia) to (If) has an acidic group such as a carboxy group and can therefore form a base-addition salt, in general. Examples of the pharmacologically acceptable salt can include: alkali metal salts such as sodium salts, potassium salts, and lithium salts; alkaline-earth metal salts such as calcium salts and magnesium salts; inorganic salts such as ammonium salts; organic amine salts such as dibenzylamine salts, morpholine salts, phenylglycine alkyl ester salts, ethylenediamine salts, N-methylglucamine salts, diethylamine salts, triethylamine salts, cyclohexylamine salts, dicyclohexylamine salts, N,N'-dibenzylethylenediamine salts, diethanolamine salts, N-benzyl-N-(2-phenylethoxyl)amine salts, piperazine salts, tetramethylammonium salts, and tris(hydroxymethyl)aminomethane salts; and amino acid salts such as arginine salts.

The compound of the present invention represented by any of the general formulae (I) and (Ia) to (If) or the pharmacologically acceptable salt thereof may be present in a free or solvate form. These solvates are also encompassed in the scope of the present invention. The solvate is not particularly limited as long as it is pharmacologically acceptable. Specifically, hydrates, ethanolates, or the like are preferable. Moreover, the compound of the present invention represented by any of the general formulae (I) and (Ia) to (If) contains a nitrogen atom. This nitrogen atom may be in an N-oxide form. These solvate or N-oxide forms are also encompassed in the scope of the present invention.

The compound of the present invention represented by any of the general formulae (I) and (Ia) to (If) or the pharmacologically acceptable salt thereof, and the production intermediate of the compound of the present invention can include various isomers such as geometric isomers (e.g., cis and trans forms) and optical isomers (R and S forms), depending on the combinations of substituents. The compound of the present invention encompasses all of these isomers, stereoisomers, and even mixtures of these isomers and stereoisomers in any ratio, unless otherwise specified.

Moreover, the compound of the present invention or the pharmacologically acceptable salt thereof can also contain non-natural ratios of atomic isotopes of one or more of the atoms constituting such a compound. Examples of the atomic isotopes include deuterium ($^2$H), tritium ($^3$H), carbon-13 ($^{13}$C), carbon-14 ($^{14}$C) nitrogen-15 ($^{15}$N), chlorine-37 ($^{37}$Cl), and iodine-125 ($^{125}$I). Moreover, the compound may be labeled radioactively with a radioisotope, for example, tritium ($^3$H), iodine-125 ($^{125}$I), or carbon-14 ($^{14}$C). The radioactively labeled compound is useful as a therapeutic or preventive agent, a research reagent, for example, an assay reagent, and a diagnostic agent, for example, an in-vivo diagnostic imaging agent. All the isotopic variants of the compound of the present invention are encompassed in the scope of the present invention, regardless of being radioactive or not.

Furthermore, the present invention also encompasses a "pharmaceutically acceptable prodrug compound" that is converted through reaction with an enzyme, gastric acid, or the like under physiological conditions in vivo to any of the compounds (I) and (Ia) to (If) serving as an active ingredient of a pharmaceutical composition of the present invention, i.e., a compound that is converted to any of the compounds (I) and (Ia) to (If) through enzymatic oxidation, reduction, hydrolysis, or the like, or a compound that is converted to any of the compounds (I) and (Ia) to (If) through hydrolysis or the like caused by gastric acid or the like.

A pharmaceutical composition containing the compound of the present invention represented by any of the general formulae (I) and (Ia) to (If) or the pharmacologically acceptable salt thereof can be prepared according to various formulation methods usually used by selecting an appropriate preparation according to an administration method.

The pharmaceutical composition comprising the compound of the present invention represented by any of the general formulae (I) and (Ia) to (If) or the pharmacologically acceptable salt thereof as a principal ingredient, when administered to a mammal (particularly, a human), can be administered systemically or locally through an oral or parenteral route.

Examples of oral forms of pharmaceutical drugs include tablets, pills, powders, granules, capsules, solutions, suspensions, emulsions, syrups, and elixirs. These forms of pharmaceutical drugs are usually prepared as a pharmaceutical composition containing the compound of the present invention represented by any of the general formulae (I) and (Ia) to (If) or the pharmacologically acceptable salt thereof as a principal ingredient mixed with pharmaceutically acceptable additives such as diluents, excipients, or carriers. The preparation of the pharmaceutical composition can be performed according to a conventional method using pharmaceutically acceptable diluents, excipients, or carriers, or other additives appropriately selected according to need from arbitrary appropriate pharmaceutically acceptable binders, disintegrants, lubricants, swelling agents, swelling aids, coating agents, plasticizers, stabilizers, antiseptics, antioxidants, coloring agents, solubilizing agents, suspending agents, emulsifying agents, sweeteners, preservatives, buffers, humectants, and so on.

Examples of parenteral forms of pharmaceutical drugs include injections, ointments, gels, creams, poultice, patches, aerosols, inhalants, sprays, eye drops, nasal drops, and suppositories. These forms of pharmaceutical drugs are usually prepared as a pharmaceutical composition containing the compound of the present invention represented by any of the general formulae (I) and (Ia) to (If) or the pharmacologically acceptable salt thereof as a principal ingredient mixed with pharmaceutically acceptable additives such as diluents, excipients, or carriers. The preparation of the pharmaceutical composition can be performed according to a conventional method using pharmaceutically acceptable diluents, excipients, or carriers, or other additives appropriately selected according to need from arbitrary appropriate pharmaceutically acceptable stabilizers, antiseptics, solubilizing agents, humectants, preservatives, antioxidants, flavors, gelling agents, neutralizing agents, buffers, tonicity agents, surfactants, coloring agents, buffering agents, thickeners, wetting agents, fillers, absorption promoters, suspending agents, binders, and so on.

Examples of references on the pharmaceutically acceptable excipients can include "Handbook of Pharmaceutical Excipients, 2nd Edition, (1994), Edited by A. Wade and P. J. Weller".

Moreover, examples of references on the pharmaceutically acceptable carriers or diluents can include "Remington's Pharmaceutical Sciences, Mack Publishing Co. (A. R. Gennaro edit. 1985)".

The compound of the present invention represented by any of the general formulae (I) and (Ia) to (If) or the pharmacologically acceptable salt thereof can be used in combination with an additional drug. The drugs that can be used in combination therewith include anticoagulants (warfarin, heparin, low-molecular-weight heparin, antithrombin drugs, anti-Xa drugs, etc.), antiplatelet drugs (aspirin, ticlopidine, clopidogrel, prasugrel, phosphodiesterase inhibitors, etc.), enzymes related to fibrinolysis (tPA, genetically modified tPA, plasminogen activators such as urokinase, streptokinase, plasmin, etc.), anticancer drugs, anti-inflammatory drugs, antifibrotic drugs, hypotensive drugs, anti-pulmonary hypertension drugs, and immunosuppressive drugs.

The dose of the compound of the present invention represented by any of the general formulae (I) and (Ia) to (If) or the pharmacologically acceptable salt thereof differs depending on symptoms, age, body weight, the kind or dose of the drug to be administered in combination therewith, etc. When the compound of the present invention represented by any of the general formulae (I) and (Ia) to (If) or the pharmacologically acceptable salt thereof is used as a pharmaceutical drug for the human body, its dose ranges from 0.01 mg to 5000 mg, preferably 0.1 mg to 1000 mg, more preferably 1 mg to 200 mg, in a single dose per adult in terms of the amount of any of the compounds (I) and (Ia) to (If) and ranges from 0.001 mg/kg to 100 mg/kg, preferably 0.005 mg/kg to 20 mg/kg, more preferably 0.01 mg/kg to 5 mg/kg of any of the compounds (I) and I(a) to I(f) in terms of the body weight. This daily dose is administered systemically or locally through an oral or parenteral route once every few days or at one or several dosages per day or continuously administered to veins for a duration ranging from 1 hour to 24 hours per day. Moreover, the daily dose may exceed the amount above, if necessary.

EXAMPLES

Hereinafter, the present invention will be described specifically with reference to Reference Examples, Examples, Test Examples and Preparation Examples. However, the present invention is not limited to these methods by any means.

The symbols "$^1$H-NMR", "MS", "HRMS" and "LRMS" in the Examples mean a "nuclear magnetic resonance spectrum", a "mass spectrometry spectrum", "high-resolution mass spectrometry spectrum", and a "low-resolution mass spectrometry spectrum", respectively. The ratio of eluting solvents described in chromatographic separation/purification represents a volume ratio, unless otherwise specified. The terms inside the parentheses of "$^1$H-NMR" represent assay solvents, all of which used TMS (tetramethylsilane) as an internal standard. Multiplicity in $^1$H-NMR means s=singlet, d=doublet, t=triplet, q=quartet, m=multiplet, and br=broad.

Moreover, in the present specification, the following abbreviations were used:
CDCl$_3$: deuterated chloroform;
CD$_3$OD: deuterated methanol;
Me: methyl group;
Et: ethyl group;
tBu: tert-butyl group;
Boc: tert-butoxycarbonyl group;
Tr: trityl group;
TBDMS: tert-butyl(dimethyl)silyl group;
TBDPS: tert-butyl(diphenyl)silyl group.

Reference Example 1

Ethyl [1-(3,3-dimethylbutyl)-1H-imidazol-4-yl]acetate

[Formula 16]

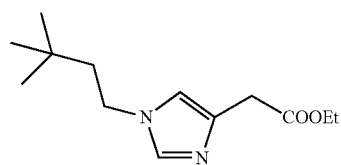

[Step 1] Ethyl 1H-imidazol-4-ylacetate

1H-Imidazol-4-ylacetic acid hydrochloride (5.00 g) was dissolved in ethanol (100 mL). To the solution, thionyl chloride (2.46 mL) was added at room temperature, and the mixture was then heated to reflux for 3.5 hours. The reaction solvent was distilled off under reduced pressure. To the residue, a saturated aqueous solution of sodium bicarbonate was then added, and organic matter was extracted five times with methylene chloride. The organic layer was dried over anhydrous sodium sulfate and filtered, and the solvent was distilled off under reduced pressure to obtain a crude product of ethyl 1H-imidazol-4-ylacetate (4.10 g).

$^1$H-NMR (CDCl$_3$) δ: 1.28 (3H, t, J=7.04 Hz), 3.69 (2H, s), 4.19 (2H, q, J=7.04 Hz), 6.98 (1H, s), 7.60 (1H, s).

[Step 2] Ethyl [1-(3,3-dimethylbutyl)-1H-imidazol-4-yl]acetate

Ethyl 1H-imidazol-4-ylacetate (3.74 g) obtained in Step 1 was dissolved in N,N-dimethylformamide (30 mL). To this solution, sodium hydride (63%, 1.02 g) and 1-iodo-3,3-dimethylbutane (5.66 g) were added under ice cooling. The mixture was stirred overnight at room temperature and then separated into aqueous and organic layers by the addition of ethyl acetate and a saturated aqueous solution of ammonium chloride. The obtained aqueous solution was washed with saturated sodium chloride solution and then dried over anhydrous magnesium sulfate. The solvent was concentrated under reduced pressure, and the obtained residue was purified by silica gel chromatography (eluting solvent: methylene chloride/methanol=95/5) to obtain the title compound (2.32 g).

$^1$H-NMR (CDCl$_3$) δ: 0.97 (9H,s), 1.27 (3H, t, J=7.0 Hz), 1.68-1.74 (2H, m), 3.63 (2H, brs), 3.85-3.92 (2H, m), 4.18 (2H, q, J=7.0 Hz), 6.89 (1H, s), 7.40 (1H, s).

Reference Example 2

Ethyl 6-[bis(tert-butoxycarbonyl)amino]-2-[1-(3,3-dimethylbutyl)-1H-imidazol-4-yl]-3-hydroxyhexanoate

[Formula 17]

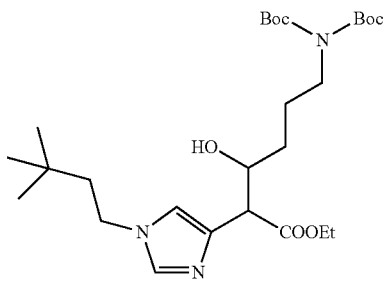

The compound (443 mg) obtained in Reference Example 1 was dissolved in tetrahydrofuran (10 mL). This solution was cooled to −78° C. Lithium hexamethyldisilazide (LHMDS, 1 N tetrahydrofuran solution, 2.05 mL) was added thereto, and the mixture was stirred for 30 minutes. To this solution, a solution containing di-tert-butyl(4-oxobutyl)imidodicarbonate (Tetrahedron Letters, 1996, vol. 37, p. 3379) (534 mg) in tetrahydrofuran (10 mL) was added, and the mixture was stirred at −78° C. for 45 minutes. This reaction solution was quenched by the addition of a saturated aqueous solution of ammonium chloride and separated into aqueous and organic layers by the addition of water and diisopropyl ether. The obtained organic layer was washed with saturated sodium chloride solution and dried over anhydrous magnesium sulfate. The obtained residue was purified by silica gel chromatography (eluting solvent: methylene chloride/methanol=95/5) to obtain the title compound (763 mg).

$^1$H-NMR (CDCl$_3$) δ: 0.93 (9H, s), 1.19-1.26 (3H, m), 1.31-1.41 (1H, m), 1.45 (18H, s), 1.54-1.81 (5H, m), 3.51 (2H, q, J=7.3 Hz), 3.58-3.73 (1H, m), 3.82-3.90 (2H, m), 4.04-4.35 (3H, m), 6.80-6.93 (1H, m), 7.33-7.41 (1H, m).

MS (ESI) m/z 526 (M+H)$^+$.

Reference Example 3

Ethyl (2Z)-6-[bis(tert-butoxycarbonyl)amino]-2-[1-(3,3-dimethylbutyl)-1H-imidazol-4-yl]hex-2-enoate and ethyl (2E)-6-[bis(tert-butoxycarbonyl)amino]-2-[1-(3,3-dimethylbutyl)-1H-imidazol-4-yl]hex-2-enoate

[Formula 18]

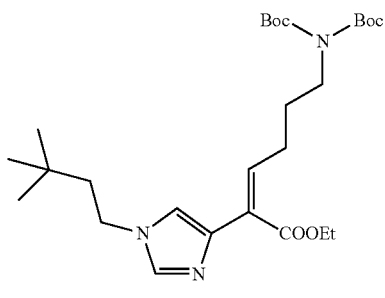

less polar compound

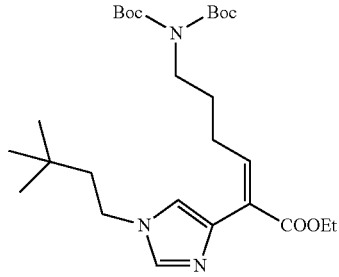

more polar compound

The compound (763 mg) obtained in Reference Example 2 was dissolved in methylene chloride (50 mL). To this solution, triethylamine (0.404 mL), methanesulfonyl chloride (0.168 mL), and 1,8-diazabicyclo[5.4.0]undec-7-ene (0.434 mL) were added at 0° C. The mixture was stirred at room temperature for 5 days and then separated into aqueous and organic layers by the addition of water, a 10% aqueous citric acid solution, and ethyl acetate. The obtained organic layer was washed with saturated sodium chloride solution, a saturated aqueous solution of sodium bicarbonate, and saturated sodium chloride solution in this order and dried over anhydrous magnesium sulfate. The obtained residue was purified by silica gel chromatography (eluting solvent: methylene chloride/ethyl acetate=4/1) to respectively obtain the Z form (237 mg, less polar compound) and the E form (228 mg, more polar compound).

Z form: $^1$H-NMR (CDCl$_3$) δ: 1.00 (9H, s), 1.40 (3H, t, J=7.1 Hz), 1.52 (18H, s), 1.70-1.76 (2H, m), 1.78-1.85 (2H, m), 2.50 (2H, q, J=7.8 Hz), 3.65 (2H, t, J=7.3 Hz), 3.88-3.94 (2H, m), 4.35 (2H, q, J=7.1 Hz), 6.89 (1H, t, J=7.8 Hz), 7.10 (1H, s), 7.40 (1H, s).

E form: $^1$H-NMR (CDCl$_3$) δ: 1.01 (9H, s), 1.34 (3H, t, J=7.1 Hz), 1.52 (18H, s), 1.73-1.83 (4H, m), 2.68 (2H, q, J=7.3 Hz), 3.58-3.64 (2H, m), 3.93-3.98 (2H, m), 4.26 (2H, q, J=7.1 Hz), 6.92 (1H, t, J=7.3 Hz), 7.21 (1H, d, J=1.5 Hz), 7.46 (1H, d, J=1.5 Hz).

Reference Example 4

Ethyl (1R*,2S*)-2-{3-[bis(tert-butoxycarbonyl)amino]propyl-1-[1-(3,3-dimethylbutyl)-1H-imidazol-4-yl]cyclopropanecarboxylate

[Formula 19]

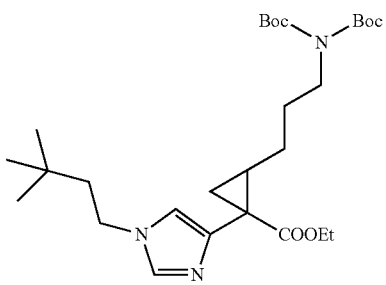

Sodium hydride (63% oil, 48.0 mg) was dissolved in dimethyl sulfoxide (4 mL). To this solution, trimethylsulfoxonium iodide (286 mg) was added at room temperature. The mixture was stirred at room temperature for 1 hour. Then, a solution containing ethyl (2Z)-6-[bis(tert-butoxycarbonyl)amino]-2-[1-(3,3-dimethylbutyl)-1H-imidazol-4-yl]hex-2-enoate (213 mg) obtained in Reference Example 3 in dimethyl sulfoxide (3 mL) was added thereto, and the mixture was stirred at room temperature for 40 minutes. To this solution, saturated sodium chloride solution and water were added, followed by extraction several times with methylene chloride. The obtained organic layers were combined, washed with saturated sodium chloride solution, and dried over anhydrous magnesium sulfate. The obtained residue was purified by silica gel chromatography (eluting solvent: ethyl acetate/methylene chloride=1/1) to obtain the title compound (65.2 mg).

$^1$H-NMR (CDCl$_3$) δ: 0.97 (9H, s), 1.27 (3H, t, J=7.0 Hz), 1.49 (18H, s), 1.51-1.84 (9H, m), 3.57 (2H, t, J=7.2 Hz), 3.84-3.88 (2H, m), 4.19 (2H, q, J=7.0 Hz), 7.06 (1H, d, J=1.2 Hz), 7.29 (1H, d, J=1.2 Hz).

MS (ESI) m/z 522 (M+H)$^+$.

Reference Example 5

Ethyl (1R*,2R*)-2-{3-[bis(tert-butoxycarbonyl)amino]propyl-1-[1-(3,3-dimethylbutyl)-1H-imidazol-4-yl]cyclopropanecarboxylate

[Formula 20]

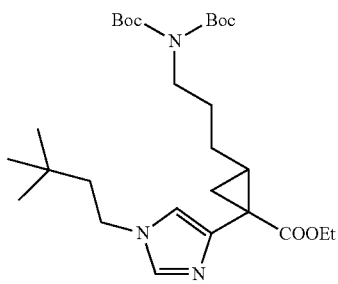

The title compound (104 mg) was obtained from ethyl (2E)-6-[bis(tert-butoxycarbonyl)amino]-2-[1-(3,3-dimethylbutyl)-1H-imidazol-4-yl]hex-2-enoate (220 mg) obtained in Reference Example 3 in the same way as in Reference Example 4.

$^1$H-NMR (CDCl$_3$) δ: 0.81-0.94 (1H, m), 0.97 (9H, s), 1.20 (3H, t, J=7.0 Hz), 1.24-1.38 (1H, m), 1.42 (1H, dd, J=7.0, 3.9 Hz), 1.48 (18H, s), 1.58-1.83 (6H, m), 3.40-3.54 (2H, m), 3.86-3.94 (2H, m), 4.04-4.16 (2H, m), 6.95 (1H, d, J=1.2 Hz), 7.35 (1H, d, J=1.2 Hz).

MS (ESI) m/z 522 (M+H)$^+$.

Reference Example 6

Methyl (2Z)-6-[bis(tert-butoxycarbonyl)amino]-2-(1-trityl-1H-imidazol-4-yl)hex-2-enoate

[Formula 21]

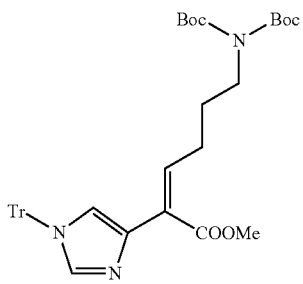

The title compound (5.36 g) was obtained from methyl (1-trityl-1H-imidazol-4-yl)acetate (Bioorganic & Medicinal Chemistry, 1997, vol. 5, p. 1989) (8.18 g) in the same way as in Reference Examples 2 and 3.

$^1$H-NMR (CDCl$_3$) δ: 1.49 (18H, s), 1.72-1.83 (2H, m), 2.46 (2H, dt, J=7.8, 7.8 Hz), 3.55-3.65 (2H, m), 3.73 (3H, s), 6.89 (1H, t, J=7.8 Hz), 7.00 (1H, d, J=1.2 Hz), 7.13-7.18 (6H, m), 7.31-7.36 (10H, m).

MS (ESI) m/z 652 (M+H)$^+$, 674 (M+Na)$^+$.

Reference Example 7

Methyl (1R*,2S*)-2-{3-[bis(tert-butoxycarbonyl)amino]propyl}-1-(1-trityl-1H-imidazol-4-yl)cyclopropanecarboxylate

[Formula 22]

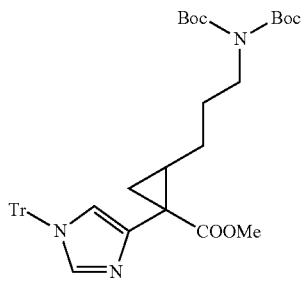

The title compound (3.24 g) was obtained using the compound (5.36 g) obtained in Reference Example 6 in the same way as in Reference Example 4.

¹H-NMR (CDCl₃) δ: 1.48 (18H, s), 1.50-1.78 (7H, m), 3.56 (2H, t, J=7.2 Hz), 3.64 (3H, s), 6.89 (1H, s), 7.11-7.17 (6H, m), 7.31-7.37 (10H, m).
MS (ESI) m/z 666 (M+H)⁺, 688 (M+Na)⁺.

Reference Example 8

Methyl (1R*,2S*)-2-{3-[bis(tert-butoxycarbonyl)amino]propyl}-1-(1H-imidazol-4-yl)cyclopropanecarboxylate

[Formula 23]

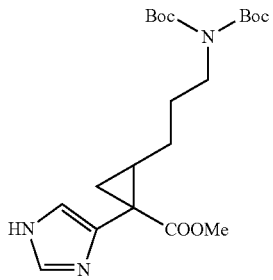

10% palladium-carbon catalyst (hydrated, 1 g) was added to a solution of the compound (3.24 g) obtained in Reference Example 7 in methanol (50 mL), and the mixture was stirred overnight at room temperature under a hydrogen atmosphere. The catalyst was filtered off, and the filtrate was concentrated under reduced pressure. The residue was purified by silica gel chromatography (eluting solvent: methylene chloride/methanol=95/5) to obtain the title compound (2.06 g).
¹H-NMR (CDCl₃) δ: 1.52 (18H, s), 1.53-1.77 (7H, m), 3.55-3.65 (2H, m), 3.67 (3H, s), 6.89 (1H, s), 7.54 (1H, s).
MS (ESI) m/z 424 (M+H)⁺.

Reference Example 9

Ethyl [1-(trans-4-methylcyclohexyl)-1H-imidazol-4-yl]acetate

[Formula 24]

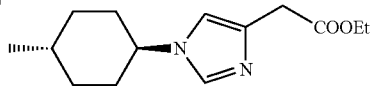

Methanesulfonyl chloride (19.3 mL) was slowly added dropwise to a solution of cis-4-methylcyclohexanol (14.2 g) and triethylamine (34.5 mL) in methylene chloride (250 mL) with stirring at 0° C. The mixture was heated to room temperature, stirred for 3 hours, and then separated into aqueous and organic layers by the addition of water, followed by extraction with methylene chloride. The organic layer was washed with saturated sodium bicarbonate and saturated sodium chloride solution and then dried over anhydrous sodium sulfate. After filtration and concentration under reduced pressure, the obtained crude product of cis-4-methylcyclohexyl methanesulfonate (approximately 24 g) was used without further purification in the next reaction. Cesium carbonate (60.1 g) and cis-4-methylcyclohexyl methanesulfonate (approximately 24 g) were added to a solution of ethyl 1H-imidazol-4-ylacetate (9.48 g) in N,N-dimethylformamide (120 mL). The mixture was stirred at 110° C. for 9 hours and then separated into aqueous and organic layers by the addition of water, followed by extraction with ethyl acetate. The organic layer was washed with saturated sodium chloride solution and then dried over anhydrous sodium sulfate. After filtration and concentration under reduced pressure, the obtained crude product was purified by silica gel column chromatography to obtain the title compound (1.77 g).
¹H-NMR (CDCl₃) δ: 0.88 (3H, d, J=6.4 Hz), 1.06-1.14 (2H, m), 1.27 (3H, t, J=7.3 Hz), 1.43-1.50 (1H, m), 1.61-1.70 (2H, m), 1.83-1.87 (2H, m), 2.07-2.12 (2H, m), 3.62 (2H, s), 3.82 (1H, tt, J=3.9, 12.2 Hz), 4.17 (2H, q, J=7.3 Hz), 6.92 (1H, s), 7.44 (1H, s).

Reference Example 10

Ethyl (2Z)-6-[bis(tert-butoxycarbonyl)amino]-2-[1-(trans-4-methylcyclohexyl)-1H-imidazol-4-yl]hex-2-enoate

[Formula 25]

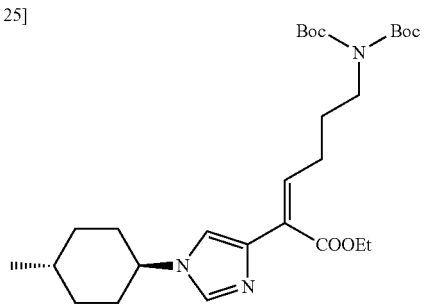

The title compound (685 mg) was obtained from the compound (1.77 g) obtained in Reference Example 9 in the same way as in Reference Examples 2 and 3.
¹H-NMR (CDCl₃) δ: 0.94 (3H, t, J=6.3 Hz), 1.05-1.15 (2H, m), 1.37 (3H, t, J=7.0 Hz), 1.49 (18H, s), 1.49-1.53 (1H, m), 1.62-1.87 (6H, m), 2.06-2.12 (2H, m), 2.46 (2H, dt, J=7.8, 7.8 Hz), 3.60-3.64 (2H, m), 3.82 (1H, tt, J=3.9, 12.1 Hz), 4.32 (2H, q, J=7.0 Hz), 6.85 (1H, t, J=7.8 Hz), 7.11-7.12 (1H, m), 7.43-7.44 (1H, m).

Reference Example 11

Ethyl (1R*,2S*)-2-{3-[bis(tert-butoxycarbonyl)amino]propyl}-1-[1-(trans-4-methylcyclohexyl)-1H-imidazol-4-yl]cyclopropanecarboxylate

[Formula 26]

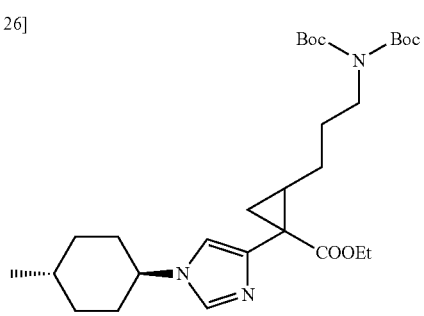

The title compound (299 mg) was obtained from the compound (685 mg) obtained in Reference Example 10 in the same way as in Reference Example 4.
¹H-NMR (CDCl₃) δ: 0.94 (3H, d, J=6.7 Hz), 1.04-1.15 (2H, m), 1.28 (3H, t, J=7.4 Hz), 1.48 (18H, s), 1.48-1.52 (1H, m), 1.55-1.75 (9H, m), 1.82-1.87 (2H, m), 2.06-2.12

(2H, m), 3.57 (2H, t, J=7.4 Hz), 3.80 (1H, tt, J=3.9, 12.1 Hz), 4.19 (2H, q, J=7.0 Hz), 7.11-7.12 (1H, m), 7.34-7.35 (1H, m).

Reference Example 12

Ethyl (1-trityl-1H-imidazol-4-yl)acetate

[Formula 27]

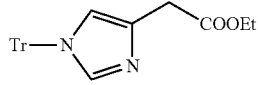

A mixture of 1H-imidazol-4-ylacetonitrile (10 g) and 30% hydrochloric acid in ethanol (50 mL) was stirred for 4 hours under heating to reflux. After standing to cool to room temperature, the solvent was then distilled off under reduced pressure. The obtained residue was suspended in methylene chloride (100 mL). To the suspension, triethylamine (64 mL) was added under ice cooling, and trityl chloride (39 g) was then added in four portions. The mixture was stirred for 10 minutes under ice cooling and then stirred overnight at room temperature. To the reaction solution, a saturated aqueous solution of sodium bicarbonate was added to separate a methylene chloride layer. Methylene chloride was further added to the aqueous layer, and this extraction procedure was performed three times. The combined organic layer was dried by the addition of anhydrous magnesium sulfate, and the solvent was then distilled off under reduced pressure. The obtained residue was purified by silica gel column chromatography (eluting solvent: hexane→hexane/ethyl acetate=60/40) to obtain the title compound (24.8 g).

$^1$H-NMR (CDCl$_3$) δ: 1.23 (3H, t, J=7.0 Hz), 3.61 (2H, s), 4.15 (2H, q, J=7.0 Hz), 6.77-6.78 (1H, m), 7.13-7.17 (6H, m), 7.31-7.35 (9H, m), 7.37-7.38 (1H, m).

Reference Example 13

Ethyl 6-[bis(tert-butoxycarbonyl)amino]-3-hydroxy-2-(1-trityl-1H-imidazol-4-yl)hexanoate

[Formula 28]

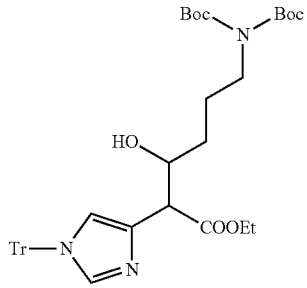

The compound (22.4 g) obtained in Reference Example 12 was dissolved in anhydrous tetrahydrofuran (200 mL), and the solution was cooled to −78° C. under a nitrogen atmosphere. To this reaction solution, lithium hexamethyldisilazide (1.0 M tetrahydrofuran solution, 62.2 mL) was added dropwise over 20 minutes, and the mixture was stirred at the same temperature for 1 hour. A solution of di-tert-butyl(4-oxobutyl)imidodicarbonate (21.1 g) in anhydrous tetrahydrofuran (100 mL) was added dropwise thereto over 30 minutes, and the mixture was stirred at the same temperature for 1.5 hours. A saturated aqueous solution of ammonium chloride was added thereto, followed by extraction three times with ethyl acetate. The combined organic layer was dried by the addition of anhydrous magnesium sulfate, and the solvent was then distilled off under reduced pressure. The obtained residue was purified by silica gel column chromatography (NH silica, eluting solvent: hexane-→hexane/ethyl acetate=50/50) to obtain the title compound (37.8 g).

$^1$H-NMR (CDCl$_3$) δ: 1.17-1.22 (3H, m), 1.48 (18H, s), 1.57-1.85 (4H, m), 3.51-3.58 (2H, m), 3.62 (0.5H, d, J=5.9 Hz), 3.72 (0.5H, d, J=5.9 Hz), 4.13-4.18 (2H, m), 4.20-4.26 (0.5H, m), 4.44-4.48 (0.5H, m), 6.73 (0.5H, s), 6.80 (0.5H, s), 7.10-7.15 (6H, m), 7.32-7.35 (9H, m), 7.37 (0.5H, s), 7.40 (0.5H, s).

MS (ESI) m/z 706 (M+Na)$^+$, 684 (M+H)$^+$.

Reference Example 14

Ethyl (2Z)-6-[bis(tert-butoxycarbonyl)amino]-2-(1-trityl-1H-imidazol-4-yl)hex-2-enoate

[Formula 29]

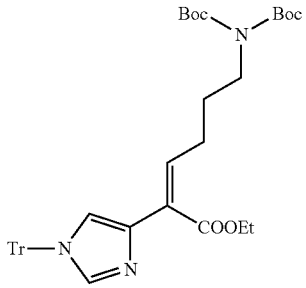

The compound (32.0 g) obtained in Reference Example 13 was dissolved in methylene chloride (400 mL). To the solution, triethylamine (32.4 mL, 234 mmol) and methanesulfonyl chloride (12.7 mL) were added under ice cooling, and the mixture was stirred for 10 minutes and then stirred at room temperature for 2.3 hours. Triethylamine (3.6 mL) and methanesulfonyl chloride (9.7 mL) were further added thereto, and the mixture was stirred overnight at room temperature. A saturated aqueous solution of ammonium chloride was added thereto to separate an organic layer. The organic layer was further washed with a saturated aqueous solution of ammonium chloride and saturated sodium chloride solution and dried by the addition of anhydrous magnesium sulfate, and the solvent was then distilled off under reduced pressure. The obtained residue was purified by silica gel column chromatography (eluting solvent: methylene chloride→methylene chloride/ethyl acetate=85/15) to obtain the title compound (11.2 g). An isomer of the title compound, ethyl (2E)-6-[bis(tert-butoxycarbonyl)amino]-2-(1-trityl-1H-imidazol-4-yl)hex-2-enoate (11.7 g), was further obtained from another fraction.

$^1$H-NMR (CDCl$_3$) δ: 1.18 (3H, t, J=7.0 Hz), 1.49 (18H, s), 1.74-1.83 (2H, m), 2.45-2.52 (2H, m), 3.62 (2H, t, J=7.4 Hz), 4.18 (2H, q, J=7.0 Hz), 6.89 (1H, t, J=7.4 Hz), 6.98 (1H, s), 7.13-7.18 (6H, m), 7.31-7.37 (10H, m).

MS (ESI) m/z 688 (M+Na)$^+$, 666 (M+H)$^+$.

Reference Example 15

Ethyl (1R*,2S*)-2-{3-[bis(tert-butoxycarbonyl)amino]propyl}-1-(1-trityl-1H-imidazol-4-yl)cyclopropanecarboxylate

[Formula 30]

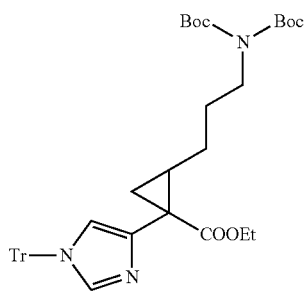

Trimethylsulfoxonium iodide (11.7 g) was added in several portions under water cooling to sodium hydride (63%, 1.91 g) dissolved in dimethyl sulfoxide (50 mL). The mixture was stirred at room temperature for 1 hour. Then, a solution of the compound (11.1 g) obtained in Reference Example 14 in dimethyl sulfoxide (150 mL) was added dropwise thereto, and the mixture was stirred at room temperature for 2 hours. Ice water was added thereto, followed by extraction with ethyl acetate. The organic layer was washed with saturated sodium chloride solution and dried by the addition of anhydrous magnesium sulfate, and the solvent was then distilled off under reduced pressure. The obtained residue was purified by silica gel column chromatography (eluting solvent: methylene chloride→methylene chloride/ethyl acetate=80/20) to obtain the title compound (7.5 g).

$^1$H-NMR (CDCl$_3$) δ: 1.14 (3H, t, J=7.0 Hz), 1.41-1.81 (25H, m), 3.56 (2H, t, J=7.4 Hz), 4.01-4.17 (2H, m), 6.92 (1H, s), 7.12-7.17 (6H, m), 7.31-7.35 (10H, m).
MS (ESI) m/z 702 (M+Na)$^+$, 680 (M+H)$^+$.

Reference Example 16

Ethyl (1R*,2S*)-2-{3-[bis(tert-butoxycarbonyl)amino]propyl}-1-(1H-imidazol-4-yl)cyclopropanecarboxylate

[Formula 31]

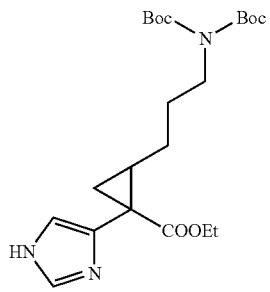

The compound (7.4 g) obtained in Reference Example 15 was dissolved in ethanol (80 mL). To the reaction solution, 10% palladium-carbon catalyst (hydrated, 4.0 g) was added, and the mixture was stirred overnight at room temperature under a hydrogen atmosphere (1 atmospheric pressure). 10% palladium-carbon catalyst (hydrated, 3.0 g) was further added thereto, and the mixture was stirred for 7 hours under a hydrogen atmosphere (1 atmospheric pressure). The reaction solution was filtered through celite, and the solvent was distilled off under reduced pressure. The obtained residue was purified by silica gel column chromatography (eluting solvent: methylene chloride→methylene chloride/methanol=97/3) to obtain the title compound (2.4 g).

$^1$H-NMR (CDCl$_3$) δ: 1.22 (3H, t, J=7.0 Hz), 1.46-1.73 (25H, m), 3.54-3.67 (2H, m), 4.09-4.20 (2H, m), 6.89 (1H, s), 7.56 (1H, s).
MS (ESI) m/z 460 (M+Na)$^+$, 438 (M+H)$^+$.

Reference Example 17

Methyl 1H-imidazol-4-ylacetate

[Formula 32]

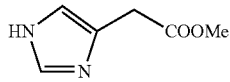

1H-Imidazol-4-ylacetic acid hydrochloride (20.0 g) was suspended in methanol (200 mL). To this suspension, thionyl chloride (8.87 mL) was added at room temperature, and the mixture was heated to reflux for 3 hours. After cooling to room temperature, the solvent was distilled off under reduced pressure. To this reaction solution, a saturated aqueous solution of sodium bicarbonate was added, and the solvent was distilled off under reduced pressure. To the obtained residue, tetrahydrofuran and anhydrous magnesium sulfate were added, and insoluble matter was filtered off. The solvent in the filtrate was distilled off under reduced pressure to obtain the title compound (14.3 g).

$^1$H-NMR (CDCl$_3$) δ: 3.66-3.73 (5H, m), 6.94-6.98 (1H, m), 7.57-7.60 (1H, m).
MS (ESI) m/z 141 (M+H)$^+$.

Reference Example 18

Methyl 1-(3,3-dimethylbutyl)-1H-imidazol-4-yl]acetate

[Formula 33]

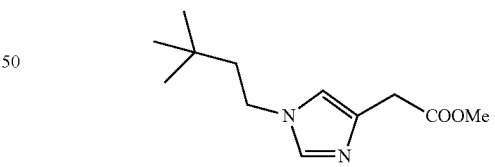

The compound (10.0 g) obtained in Reference Example 17 was dissolved in a mixed solvent of N,N-dimethylformamide (50 mL) and tetrahydrofuran (50 mL). To this solution, sodium hydride (63%, 2.99 g) and 1-iodo-3,3-dimethylbutane (16.7 g) were added under ice cooling. The mixture was stirred overnight at room temperature and then separated into aqueous and organic layers by the addition of ethyl acetate and a saturated aqueous solution of ammonium chloride. The obtained aqueous solution was washed with saturated sodium chloride solution and then dried over anhydrous magnesium sulfate. The solvent was concentrated under reduced pressure, and the obtained residue was purified by silica gel chromatography (eluting solvent: methylene chloride/methanol=97/3) to obtain the title compound (8.13 g).

$^1$H-NMR (CDCl$_3$) δ: 0.97 (9H, s), 1.68-1.74 (2H, m), 3.64 (2H, s), 3.72 (3H, s), 3.85-3.92 (2H, m), 6.88 (1H, s), 7.40 (1H, s).

Reference Example 19

Methyl (2Z)-6-[bis(tert-butoxycarbonyl)amino]-2-[1-(3,3-dimethylbutyl)-1H-imidazol-4-yl]hex-2-enoate

[Formula 34]

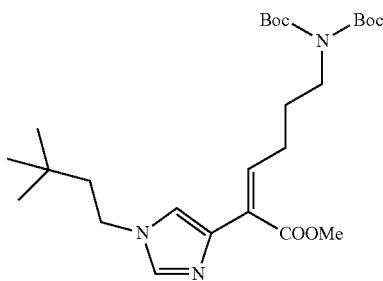

The title compound (5.0 g) was obtained from the compound (14.3 g) obtained in Reference Example 18 in the same way as in Reference Examples 2 and 3.

$^1$H-NMR (CDCl$_3$) δ: 0.97 (9H, s), 1.50 (18H, s), 1.67-1.74 (2H, m), 1.74-1.83 (2H, m), 2.47 (2H, q, J=7.8 Hz), 3.63 (2H, t, J=7.4 Hz), 3.84 (3H, s), 3.86-3.92 (2H, m), 6.88 (1H, t, J=7.8 Hz), 7.08 (1H, d, J=1.2 Hz), 7.38 (1H, d, J=1.2 Hz).

Reference Example 20

Methyl (1R*,2S*)-2-{3-[bis(tert-butoxycarbonyl)amino]propyl-1-[1-(3,3-dimethylbutyl)-1H-imidazol-4-yl]cyclopropanecarboxylate

[Formula 35]

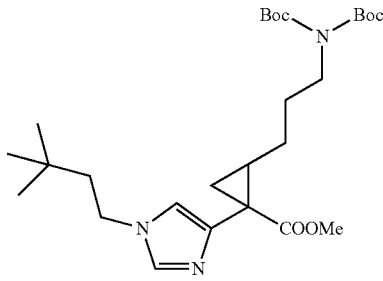

The title compound (2.67 g) was obtained from the compound (4.74 g) obtained in Reference Example 19 in the same way as in Reference Example 4.

$^1$H-NMR (CDCl$_3$) δ: 0.97 (9H, s), 1.49 (18H, s), 1.51-1.76 (9H, m), 3.57 (2H, t, J=7.4 Hz), 3.71 (3H, s), 3.83-3.90 (2H, m), 7.02 (1H, d, J=1.6 Hz), 7.30 (1H, d, J=1.6 Hz).

Reference Example 21

(1-Phenyl-1H-imidazol-4-yl) acetonitrile

[Formula 36]

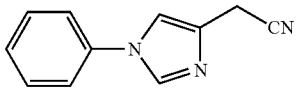

Molecular sieve 4A (4.88 g), copper (II) sulfate (7.71 g), phenylboronic acid (6.76 g), and pyridine (4.49 mL) were added to a solution of 4-cyanomethylimidazole (3.00 g) in methylene chloride (120 mL), and the mixture was stirred overnight at room temperature under an air atmosphere at normal pressure. The reaction solution was filtered through celite and washed with methylene chloride. Then, a saturated aqueous solution of sodium bicarbonate (200 mL) and disodium dihydrogen ethylenediaminetetraacetate dihydrate (15.5 g) were added to the filtrate, and the mixture was stirred at room temperature for 20 minutes. After separation into aqueous and organic layers, the organic layer was washed with saturated sodium chloride solution and dried over anhydrous sodium sulfate. After filtration and concentration under reduced pressure, the obtained crude product was purified by silica gel column chromatography to obtain the title compound (2.34 g).

$^1$H-NMR (CDCl$_3$) δ: 3.78 (2H, d, J=1.2 Hz), 7.32-7.33 (1H, m), 7.37-7.42 (3H, m), 7.48-7.53 (2H, m), 7.80 (1H, d, J=1.6 Hz).

Reference Example 22

(1R,5S)-1-(1-Phenyl-1H-imidazol-4-yl)-3-oxabicyclo[3.1.0]hexan-2-one

[Formula 37]

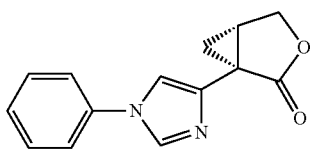

Sodium hexamethyldisilazane (NaHMDS, 1.9 M tetrahydrofuran solution, 35.89 mL) was added dropwise at 0° C. over 25 minutes to a solution of the compound (5.00 g) obtained in Reference Example 21 in toluene (250 mL). The mixture was stirred at 0° C. for 25 minutes, and (S)-epichlorohydrin (3.25 g) was then added dropwise thereto over 5 minutes. The mixture was reacted at 0° C. for 3.5 hours and subsequently at room temperature for 13 hours. The reaction mixture was treated with ethyl alcohol (24 mL) and a 1 N aqueous potassium hydroxide solution (24 mL), and volatile matter was distilled off under reduced pressure. To the obtained oil, ethyl alcohol (240 mL) and a 1 N aqueous potassium hydroxide solution (120 mL) were added, and the mixture was stirred at 80° C. for 7.5 hours. After standing to cool to room temperature, the reaction solution was further cooled to 0° C., and concentrated hydrochloric acid (60 mL) was added dropwise thereto over 30 minutes. The mixture was neutralized with a saturated aqueous solution of sodium bicarbonate, followed by extraction with ethyl acetate. The organic layer was dried over anhydrous magnesium sulfate. The solvent was distilled off under reduced pressure, and the residue was purified by silica gel column chromatography to obtain the title compound (2.06 g). Its optical purity was determined using a chiral column CHIRALPAK IC (4.6×250 mm, eluting solvent: 50% ethanol/hexane, 0.7 mL/min, 40° C.). (1R,5S)-form: 81% ee, retention time: 14.3 minutes ((1S,5R)-form: retention time: 12.1 minutes).

$^1$H-NMR (CDCl$_3$) δ: 1.36 (1H, t, J=4.7 Hz), 1.95 (1H, dd, J=4.7, 7.8 Hz), 2.77 (1H, dt, J=7.8, 4.7 Hz), 4.27 (1H, d, J=9.4 Hz), 4.42 (1H, dd, J=4.7, 9.4 Hz), 7.32-7.39 (3H, m), 7.42-7.48 (2H, m), 7.65-7.67 (1H, m), 7.70-7.72 (1H, m).

Reference Example 23

Methyl (1R,2S)-2-(bromomethyl)-1-(1-phenyl-1H-imidazol-4-yl)cyclopropanecarboxylate

[Formula 38]

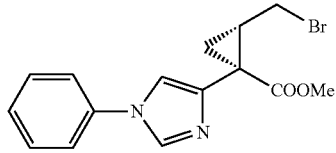

Thionyl bromide (4.28 g) was added dropwise over 5 minutes to a solution of the compound (0.60 g) obtained in Reference Example 22 in methanol (20 mL). The mixture was stirred at 0° C. for 10 minutes and then stirred at room temperature for 3 hours. Thionyl bromide (1.34 g) was added dropwise thereto over 5 minutes, and the mixture was subsequently reacted at room temperature for 22 hours. The mixture was neutralized with a saturated aqueous solution of sodium bicarbonate, followed by extraction with ethyl acetate. The organic layer was dried over anhydrous magnesium sulfate. The solvent was distilled off under reduced pressure, and the residue was purified by silica gel column chromatography to obtain the title compound (0.56 g).

$^1$H-NMR (CDCl$_3$) δ: 1.92 (1H, dd, J=4.4, 7.3 Hz), 1.94 (1H, dd, J=4.4, 8.8 Hz), 2.40 (1H, dddd, J=6.8, 7.3, 8.8, 9.8 Hz), 3.71 (1H, dd, J=9.8, 10.3 Hz), 3.83 (3H, s), 3.86 (1H, dd, J=6.8, 10.3 Hz), 7.38-7.45 (3H, m), 7.48-7.53 (3H, m), 7.78 (1H, s).

MS (ESI) m/z 335, 337 (M+H)$^+$.

Reference Example 24

Methyl (1R,2S)-2-(3-tert-butoxy-2-cyano-3-oxopropyl)-1-(1-phenyl-1H-imidazol-4-yl)cyclopropanecarboxylate

[Formula 39]

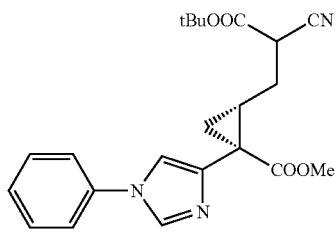

tert-Butyl cyanoacetate (1.61 g) was added dropwise at room temperature over 10 minutes to a solution of sodium hydride (63%, 0.30 g) in tetrahydrofuran (20 mL). The mixture was stirred at room temperature for 15 minutes. Then, a solution of the compound (0.50 g) obtained in Reference Example 23 in tetrahydrofuran (10 mL) was added dropwise thereto over 1 minute, and the mixture was heated to 75° C. and stirred for 3.5 hours. The reaction mixture was cooled to 0° C. and treated with a saturated aqueous solution of ammonium chloride, followed by extraction with ethyl acetate. The organic layer was dried over anhydrous magnesium sulfate. The solvent was distilled off under reduced pressure, and the residue was purified by silica gel column chromatography to obtain the title compound (0.44 g).

$^1$H-NMR (CDCl$_3$) δ: 1.52 (9H, s), 1.53 (9H, s), 1.72-1.85 (2H, m), 1.93-2.03 (1H, m), 2.29-2.46 (2H, m), 3.80 (3H, s), 3.82 (3H, s), 7.37-7.54 (6H), 7.76-7.80 (1H, m).

MS (ESI) m/z 396 (M+H)$^+$.

Reference Example 25

Methyl (1R,2S)-2-(2-cyanoethyl)-1-(1-phenyl-1H-imidazol-4-yl)cyclopropanecarboxylate

[Formula 40]

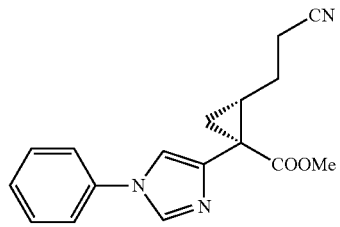

A solution of the compound (0.44 g) obtained in Reference Example 24, lithium chloride (0.09 g), and water (0.08 g) in dimethyl sulfoxide (10 mL) was heated to 140° C. and stirred for 3.3 hours. After standing to cool to room temperature, the reaction mixture was treated with an excess amount of water, followed by extraction with ethyl acetate. The organic layer was dried over anhydrous magnesium sulfate. The solvent was distilled off under reduced pressure, and the residue was purified by silica gel column chromatography to obtain the title compound (0.12 g). Its optical purity was determined using a chiral column CHIRALPAK IC (4.6×250 mm, eluting solvent: 50% ethanol/hexane, 0.7 mL/min, 40° C.). (1R,2S)-form: 81% ee, retention time: 9.1 minutes ((1S,2R)-form: retention time: 11.1 minutes).

$^1$H-NMR (CDCl$_3$) δ: 1.74 (1H, dd, J=4.4, 7.3 Hz), 1.77 (1H, dd, J=4.4, 8.8 Hz), 1.97 (1H, dt, J=8.8, 7.3 Hz), 2.07 (1H, quint, J=7.3 Hz), 2.11 (1H, quint, J=7.3 Hz), 2.49 (2H, t, J=7.3 Hz), 3.81 (3H, s), 7.39-7.57 (6H, m), 7.79 (1H, s).

MS (ESI) m/z 296 (M+H)$^+$.

Reference Example 26

Methyl (1R,2S)-2-{3-[(tert-butoxycarbonyl)amino]propyl}-1-(1-phenyl-1H-imidazol-4-yl)cyclopropanecarboxylate

[Formula 41]

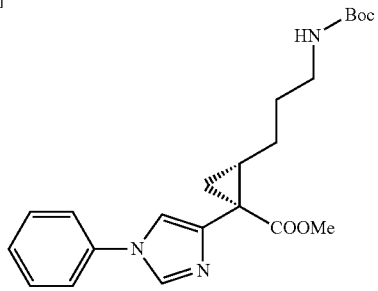

A solution of the compound (0.12 g) obtained in Reference Example 25, di-tert-butyl dicarbonate (0.18 g), and nickel (II) chloride hexahydrate (0.01 g) in methanol (6 mL) was cooled to 0° C., and lithium borohydride (0.07 g) was added portionwise thereto over 15 minutes. The mixture was stirred at room temperature for 2 hours, and lithium borohydride (0.03 g) was then again added portionwise thereto over 5 minutes. The mixture was stirred at room temperature for 14 hours and treated with an excess amount of water, followed by extraction with ethyl acetate. The organic layer was dried over anhydrous magnesium sulfate. The solvent was distilled off under reduced pressure, and the residue was purified by silica gel column chromatography to obtain the title compound (0.10 g). Its optical purity was determined using a chiral column CHIRALPAK IC (4.6×250 mm, eluting solvent: 50% ethanol/hexane, 0.7 mL/min, 40° C.). (1R,2S)-form: 81% ee, retention time: 7.1 minutes ((1S,2R)-form: retention time: 8.6 minutes).

$^1$H-NMR (CDCl$_3$) δ: 1.44-1.72 (15H, m), 1.82-1.88 (1H, m), 3.15-3.24 (2H, m), 3.78 (3H, s), 4.65 (1H, br), 7.36-7.46 (4H, m), 7.48-7.54 (2H, m), 7.79 (1H, s).

MS (ESI) m/z 400 (M+H)$^+$.

Reference Example 27

Methyl 4-(1,3-dioxo-1,3-dihydro-2H-isoindol-2-yl)-3-methylbut-2-enoate

[Formula 42]

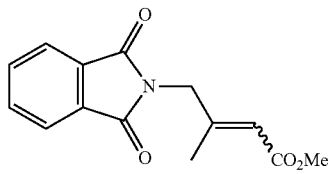

A solution of methyl dimethylphosphonoacetate (21.5 g) in N,N-dimethylformamide (50 mL) was added dropwise to a suspension of sodium hydride (63%, 4.50 g) in N,N-dimethylformamide (100 mL) with stirring at 0° C. The mixture was stirred at 0° C. for 30 minutes. Then, a solution of phthalimidoacetone (20.0 g) in N,N-dimethylformamide (50 mL) was added dropwise thereto, and the mixture was heated to room temperature and stirred overnight. To the reaction solution, water was added, followed by extraction with ethyl acetate. The organic layer was washed with a saturated aqueous solution of ammonium chloride and saturated sodium chloride solution and dried over anhydrous sodium sulfate. After filtration and concentration under reduced pressure, the obtained crude product was purified by silica gel column chromatography to obtain the title compound (20.6 g).

$^1$H-NMR (CDCl$_3$) δ: 1.78-1.79 (0.9H, m), 2.21-2.22 (2.1H, m), 3.67 (2.1H, s), 3.75 (0.9H, s), 4.31-4.32 (1.4H, m), 5.03-5.03 (0.6H, m), 5.66-5.67 (0.7H, m), 5.86-5.88 (0.3H, m), 7.72-7.78 (2H, m), 7.85-7.91 (2H, m).

Reference Example 28

Methyl 4-(1,3-dioxo-1,3-dihydro-2H-isoindol-2-yl)-3-methylbutyrate

[Formula 43]

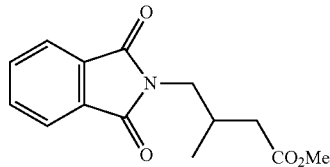

10% palladium-carbon (hydrated, 10.0 g) was added to a solution of the compound (20.6 g) obtained in Reference Example 27 in methanol (300 mL), and the mixture was stirred overnight at room temperature under a hydrogen atmosphere. Since the starting materials remained, the reaction mixture was filtered through celite and then concentrated under reduced pressure. The obtained residue was dissolved again in methanol (300 mL). To the solution, 20% palladium hydroxide-carbon (7.00 g) was added, and the mixture was stirred overnight at room temperature under a hydrogen atmosphere. After filtration through celite and concentration under reduced pressure, the obtained crude product was purified by silica gel column chromatography to obtain the title compound (16.0 g).

$^1$H-NMR (CDCl$_3$) δ: 1.02 (3H, d, J=6.6 Hz), 2.21 (1H, dd, J=15.2, 8.2 Hz), 2.41 (1H, dd, J=15.6, 5.9 Hz), 2.48-2.56 (1H, m), 3.61 (3H, s), 3.63 (2H, d, J=7.0 Hz), 7.70-7.75 (2H, m), 7.83-7.88 (2H, m).

Reference Example 29

2-(4-Hydroxy-2-methylbutyl)-1H-isoindole-1,3(2H)-dione

[Formula 44]

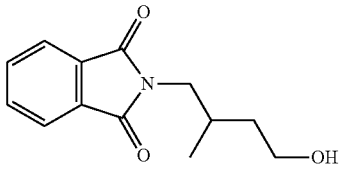

A solution of diisobutylaluminum hydride in hexane (1.02 M, 118 mL) was slowly added dropwise to a solution of the compound (15.0 g) obtained in Reference Example 28 in tetrahydrofuran (300 mL) with stirring at −78° C., and the mixture was then heated to room temperature and stirred for 2 hours. The reaction solution was cooled to 0° C., and 1 M hydrochloric acid was added thereto, followed by extraction with methylene chloride. Then, the organic layer was washed with saturated sodium chloride solution and dried over anhydrous sodium sulfate. After filtration and concentration under reduced pressure, the obtained crude product was purified by silica gel column chromatography to obtain the title compound (5.14 g).

$^1$H-NMR (CDCl$_3$) δ: 0.97 (3H, d, J=6.6 Hz), 1.42-1.51 (1H, m), 1.62-1.70 (1H, m), 2.11-2.19 (1H, m), 3.57 (1H, dd, J=13.4, 7.4 Hz), 3.65 (1H, dd, J=13.4, 6.8 Hz), 3.67-3.74 (1H, m), 3.77-3.83 (1H, m), 7.70-7.74 (2H, m), 7.83-7.87 (2H, m).

Reference Example 30

2-(4,4-Dimethoxy-2-methylbutyl)-1H-isoindole-1,3(2H)-dione

[Formula 45]

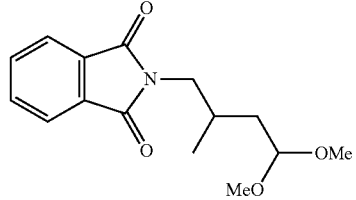

Dimethyl sulfoxide (4.70 mL) was added to a solution of oxalyl chloride (2.83 mL) in methylene chloride (60 mL) with stirring at −78° C. The mixture was stirred at the same temperature for 5 minutes, and a solution of the compound (5.14 g) obtained in Reference Example 29 in methylene chloride (20 mL) was then added to this reaction solution. The mixture was further stirred for 15 minutes. Then, triethylamine (12.2 mL) was added thereto, and the mixture was heated to room temperature and stirred. The reaction solution was separated into aqueous and organic layers by the addition of 0.1 M hydrochloric acid. The organic layer was washed with 0.1 M hydrochloric acid, water, and saturated sodium chloride solution and then dried over anhydrous sodium sulfate. After filtration and concentration under reduced pressure, the obtained crude product was dissolved in methanol (60 mL). To the solution, trimethyl orthoformate (13.9 mL) and p-toluenesulfonic acid monohydrate (0.40 g) were added with stirring at room temperature, and the mixture was stirred overnight. The reaction solution was concentrated under reduced pressure, and a saturated aqueous solution of sodium bicarbonate was then added thereto, followed by extraction with diethyl ether. The organic layer was washed with saturated sodium chloride solution and dried over anhydrous sodium sulfate. The obtained crude product was purified by silica gel column chromatography to obtain the title compound (4.95 g).

$^1$H-NMR (CDCl$_3$) δ: 0.97 (3H, d, J=6.6 Hz), 1.46 (1H, ddd, J=14.1, 8.6, 4.9 Hz), 1.71 (1H, ddd, J=14.1, 6.8, 5.1 Hz), 2.09-2.21 (1H, m), 3.29 (3H, s), 3.32 (3H, s), 3.53 (1H, dd, J=13.6, 7.6 Hz), 3.62 (1H, dd, J=13.6, 6.6 Hz), 4.50 (1H, dd, J=6.8, 4.9 Hz), 7.69-7.74 (2H, m), 7.82-7.87 (2H, m).

Reference Example 31

4,4-Dimethoxy-2-methylbutane-1-amine

[Formula 46]

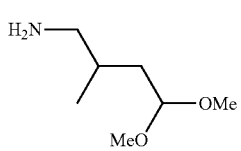

Hydrazine monohydrate (8.66 mL) was added to a solution of the compound (4.95 g) obtained in Reference Example 30 in ethanol (100 mL), and the mixture was stirred overnight at room temperature. The mixture was further heated to 80° C. and stirred for 3 hours. Then, insoluble matter was filtered off, and the filtrate was concentrated under reduced pressure. To the residue, ethyl acetate was added. Insoluble matter was filtered off again, and the filtrate was concentrated under reduced pressure to obtain the title compound (2.32 g).

$^1$H-NMR (CDCl$_3$) δ: 0.95 (3H, d, J=6.7 Hz), 1.36-1.43 (1H, m), 1.56-1.73 (2H, m), 2.53 (1H, dd, J=12.8, 6.7 Hz), 2.63 (1H, dd, J=12.8, 5.7 Hz), 3.32 (6H, s), 4.48 (1H, dd, J=6.5, 4.9 Hz).

Reference Example 32 tert-Butyl (4,4-dimethoxy-2-methylbutyl)carbamate

[Formula 47]

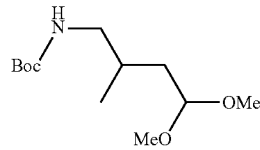

The compound (2.32 g) obtained in Reference Example 31 was dissolved in a mixed solvent of acetone (80 mL) and water (20 mL). To the solution, sodium bicarbonate (7.94 g) and di-tert-butyl dicarbonate (5.16 g) were added with stirring at room temperature. The mixture was stirred overnight at room temperature. Then, the reaction solution was concentrated under reduced pressure, and water was added to the residue, followed by extraction with diethyl ether. The organic layer was washed with saturated sodium chloride solution and dried over anhydrous sodium sulfate. After filtration and concentration under reduced pressure, the obtained crude product was purified by silica gel column chromatography to obtain the title compound (3.19 g).

$^1$H-NMR (CDCl$_3$) δ: 0.94 (3H, d, J=7.0 Hz), 1.39-1.44 (1H, m), 1.44 (9H, s), 1.63-1.69 (1H, m), 1.72-1.81 (1H, m), 3.01-3.04 (2H, m), 3.32 (3H, s), 3.32 (3H, s), 4.46 (1H, dd, J=6.5, 4.9 Hz), 4.68 (1H, br s).

Reference Example 33 di-tert-Butyl (2-methyl-4-oxobutyl)imidodicarbonate

[Formula 48]

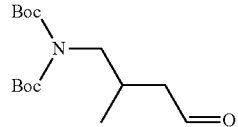

A solution of n-butyllithium in hexane (8.63 mL) was added dropwise to a solution of the compound (3.19 g) obtained in Reference Example 32 in tetrahydrofuran (50 mL) with stirring at 0° C. The mixture was stirred for 30 minutes. Then, a solution of di-tert-butyl dicarbonate (2.96 g) in tetrahydrofuran (20 mL) was added dropwise thereto, and the mixture was heated to room temperature and stirred for 1 hour. The reaction solution was separated into aqueous and organic layers by the addition of an aqueous ammonium chloride solution, followed by extraction with ethyl acetate. The organic layer was washed with a saturated aqueous solution of sodium bicarbonate and saturated sodium chloride solution and dried over anhydrous sodium sulfate. After filtration and concentration under reduced pressure, the obtained residue was dissolved in a mixed solvent of acetic acid (32 mL) and water (11 mL), and the solution was stirred at room temperature for 5 hours. To the reaction solution, saturated sodium chloride solution was added, followed by extraction with hexane. Then, the organic layer was washed with a saturated aqueous solution of sodium bicarbonate and saturated sodium chloride solution and dried over anhydrous sodium sulfate. After filtration and concentration under reduced pressure, the obtained crude product was purified by silica gel column chromatography to obtain the title compound (2.89 g).

$^1$H-NMR (CDCl$_3$) δ: 0.96 (3H, d, J=6.6 Hz), 1.51 (18H, s), 2.21-2.29 (1H, m), 2.42-2.51 (2H, m), 3.53 (2H, d, J=7.0 Hz), 9.74-9.75 (1H, m).

Reference Example 34

Methyl (2Z)-6-[bis(tert-butoxycarbonyl)amino]-5-methyl-2-(1-trityl-1H-imidazol-4-yl)hex-2-enoate

[Formula 49]

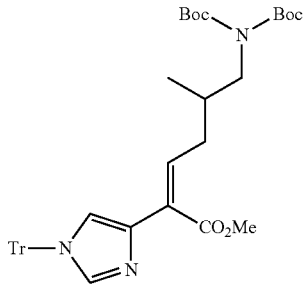

The title compound (1.80 g) was obtained from methyl (1-trityl-1H-imidazol-4-yl)acetate (2.04 g) and the compound (2.40 g) obtained in Reference Example 33 in the same way as in Reference Examples 2 and 3.

$^1$H-NMR (CDCl$_3$) δ: 0.94 (3H, d, J=6.6 Hz), 1.49 (18H, s), 1.95-2.10 (1H, m), 2.23-2.34 (1H, m), 2.44-2.56 (1H, m), 3.45-3.58 (2H, m), 3.73 (3H, s), 6.87-6.91 (1H, m), 6.98-7.01 (1H, m), 7.13-7.16 (6H, m), 7.32-7.35 (10H, m).

Reference Example 35

Methyl (1R*,2S*)-2-{3-[bis(tert-butoxycarbonyl)amino]-2-methylpropyl}-1-(1-trityl-1H-imidazol-4-yl)cyclopropanecarboxylate

[Formula 50]

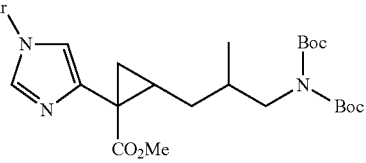

The title compound (1.49 g, diastereomeric mixture) was obtained from the compound (1.80 g) obtained in Reference Example 34 in the same way as in Reference Example 4.

$^1$H-NMR (CDCl$_3$) δ: 0.89 (1.2H, d, J=6.7 Hz), 0.94 (1.8H, d, J=7.0 Hz), 1.47 (18H, s), 1.52-1.74 (4H, m), 1.86-2.01 (2H, m), 3.38-3.56 (2H, m), 3.63 (3H, s), 6.92-6.92 (1H, m), 7.11-7.16 (6H, m), 7.30-7.34 (10H, m).

Reference Example 36

Methyl (1R*,2S*)-2-{3-[bis(tert-butoxycarbonyl)amino]-2-methylpropyl}-1-(1H-imidazol-4-yl)cyclopropanecarboxylate

[Formula 51]

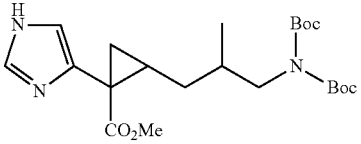

The title compound (797 mg, diastereomeric mixture) was obtained from the compound (1.49 g) obtained in Reference Example 35 in the same way as in Reference Example 8.

$^1$H-NMR (CDCl$_3$) δ: 0.89 (1H, d, J=6.8 Hz), 0.95 (2H, d, J=6.8 Hz), 1.50 (12H, s), 1.53 (6H, s), 1.53-1.66 (4H, m), 1.69-1.93 (2H, m), 3.38 (0.7H, dd, J=13.9, 8.5 Hz), 3.44 (0.3H, dd, J=13.7, 9.8 Hz), 3.56 (0.7H, dd, J=13.9, 5.6 Hz), 3.64 (1.0H, s), 3.70 (2H, s), 3.70-3.72 (0.3H, m), 6.87 (0.3H, br s), 6.94 (0.7H, br s), 7.54 (0.7H, br s), 7.55 (0.3H, br s).

Reference Example 37

4-Iodo-1-phenyl-1H-imidazole

[Formula 52]

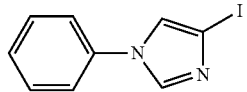

The title compound (663 mg) was obtained from 4-iodo-1H-imidazole (1.00 g) and phenylboronic acid (1.26 g) in the same way as in Reference Example 21.

$^1$H-NMR (CDCl$_3$) δ: 7.34-7.37 (3H, m), 7.38-7.42 (1H, m), 7.47-7.52 (2H, m), 7.73 (1H, d, J=1.6 Hz).

Reference Example 38

1-Phenyl-4-(tributylstannyl)-1H-imidazole

[Formula 53]

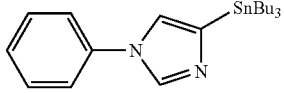

A solution of ethyl magnesium bromide in diethyl ether (3 M, 0.440 mL) was added to a solution of the compound (300 mg) obtained in Reference Example 37 in tetrahydrofuran (6 mL) with stirring at room temperature. The mixture was stirred at room temperature for 30 minutes. Then, tributyltin chloride (0.384 mL) was added thereto, and the mixture was stirred overnight. To the reaction solution, an aqueous ammonium chloride solution was added, followed by extraction with ethyl acetate. Then, the organic layer was dried over anhydrous sodium sulfate. After filtration and concentration under reduced pressure, the obtained crude product was purified by silica gel column chromatography to obtain the title compound (231 mg).

$^1$H-NMR (CDCl$_3$) δ: 0.90 (9H, t, J=7.4 Hz), 1.08-1.12 (6H, m), 1.31-1.40 (6H, m), 1.55-1.63 (6H, m), 7.24-7.26 (1H, m), 7.32-7.36 (1H, m), 7.39-7.41 (2H, m), 7.45-7.49 (2H, m), 8.05-8.06 (1H, m).

Reference Example 39 tert-Butyl (4-{[tert-butyl(dimethyl)silyl]oxy}-3-methylbutyl)carbamate

[Formula 54]

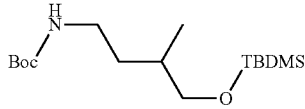

A solution of di-tert-butyl dicarbonate (11.1 g) in methylene chloride (30 mL) was added to a solution of 4-amino-2-methylbutan-1-ol (5.00 g) in methylene chloride (50 mL) with stirring at room temperature. After stirring overnight at room temperature, the reaction solution was washed with a saturated aqueous solution of ammonium chloride, a saturated aqueous solution of sodium bicarbonate, and saturated sodium chloride solution in this order. The organic layer was dried over anhydrous sodium sulfate, then filtered, and concentrated under reduced pressure. The obtained residue was dissolved in methylene chloride (150 mL). To the solution, tert-butyldimethylchlorosilane (8.77 g) and imidazole (8.25 g) were added with stirring at 0° C. The mixture was heated to room temperature and stirred overnight, and the reaction solution was then washed with water, a 1 M aqueous citric acid solution, and saturated sodium chloride solution in this order. The organic layer was dried over anhydrous sodium sulfate, then filtered, and concentrated under reduced pressure to obtain the title compound (16.2 g).

$^1$H-NMR (CDCl$_3$) δ: 0.04 (6H, s), 0.89 (3H, d, J=6.6 Hz), 0.89 (9H, s), 1.27-1.38 (1H, m), 1.44 (9H, s), 1.53-1.70 (2H, m), 3.07-3.15 (1H, m), 3.17-3.25 (1H, m), 3.39-3.47 (2H, m), 4.70 (1H, br s).

Reference Example 40 di-tert-Butyl (3-methyl-4-oxobutyl)imidodicarbonate

[Formula 55]

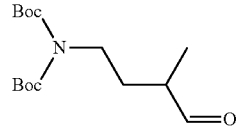

A solution of n-butyllithium in hexane (1.57 M, 32.4 mL) was added dropwise to a solution of the compound (15.4 g) obtained in Reference Example 39 in tetrahydrofuran (150 mL) with stirring at 0° C. The mixture was stirred for 30 minutes. Then, a solution of di-tert-butyl dicarbonate (11.1 g) in tetrahydrofuran (50 mL) was added dropwise thereto, and the mixture was heated to room temperature and stirred for 1 hour. The reaction solution was separated into aqueous and organic layers by the addition of an aqueous ammonium chloride solution, followed by extraction with ethyl acetate. The organic layer was washed with a saturated aqueous solution of sodium bicarbonate, water, and saturated sodium chloride solution and dried over anhydrous sodium sulfate. After filtration and concentration under reduced pressure, the obtained residue was dissolved in tetrahydrofuran (100 mL). To the solution, a solution of tetrabutylammonium fluoride in tetrahydrofuran (1 M, 72.7 mL) was added with stirring at room temperature. The mixture was stirred overnight at room temperature, and water was then added to the reaction solution, followed by extraction with ethyl acetate. The organic layer was washed with water and saturated sodium chloride solution and dried over anhydrous sodium sulfate. Filtration and concentration under reduced pressure were performed to obtain a crude product of di-tert-butyl (4-hydroxy-3-methylbutyl)imidodicarbonate (19.8 g).

Dimethyl sulfoxide (5.17 mL) was added to a solution of oxalyl chloride (3.12 mL) in methylene chloride (70 mL) with stirring at −78° C., and the mixture was stirred at the same temperature for 5 minutes. Then, a solution of the crude product of di-tert-butyl (4-hydroxy-3-methylbutyl) imidodicarbonate (19.8 g) in methylene chloride (50 mL) was added thereto. The mixture was stirred at the same temperature for 15 minutes. Then, triethylamine (13.4 mL) was added thereto, and the mixture was heated to room temperature and stirred. The reaction solution was separated into aqueous and organic layers by the addition of water. The organic layer was washed with water and saturated sodium chloride solution and then dried over anhydrous sodium sulfate. After filtration and concentration under reduced pressure, the obtained crude product was purified by silica gel column chromatography to obtain the title compound (6.75 g).

$^1$H-NMR (CDCl$_3$) δ: 1.14 (3H, d, J=7.0 Hz), 1.51 (18H, s), 1.55-1.67 (1H, m), 1.99-2.08 (1H, m), 2.34-2.43 (1H, m), 3.63 (2H, t, J=7.6 Hz), 9.65 (1H, d, J=1.6 Hz).

Reference Example 41

Methyl (2E)-6-[bis(tert-butoxycarbonyl)amino]-2-bromo-4-methylhex-2-enoate

[Formula 56]

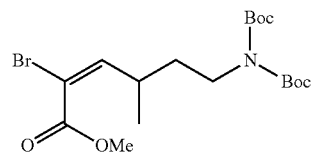

A solution of methyl [bis(2,2,2-trifluoroethoxy)phosphoryl]acetate (95%, 8.33 g) in tetrahydrofuran (20 mL) was slowly added to a suspension of sodium hydride (63%, 950 mg) in tetrahydrofuran (30 mL) with stirring at −30° C. The mixture was stirred at the same temperature for 30 minutes, and bromine (1.29 mL) was then slowly added thereto. After completion of addition, the reaction solution was temporarily heated to −10° C. The reaction solution was cooled to −78° C., and sodium hydride (63%, 950 mg) was then added thereto at once. The mixture was stirred at the same temperature for 30 minutes, and the compound (20 mL) obtained in Reference Example 40 was then added thereto. The mixture was stirred at −78° C. for 1 hour and then gradually heated to 10° C. over 1 hour with care to prevent foaming. The mixture was further stirred at the same temperature for 1 hour, and an aqueous ammonium chloride solution was then added to the reaction solution, followed by extraction with ethyl acetate. The organic layer was washed with water and saturated sodium chloride solution and dried over anhydrous sodium sulfate. After filtration and concentration under reduced pressure, the obtained crude product was purified by silica gel column chromatography to obtain the title compound (4.23 g).

¹H-NMR (CDCl₃) δ: 1.07 (3H, d, J=7.0 Hz), 1.51 (18H, s), 1.57-1.70 (2H, m), 3.11-3.22 (1H, m), 3.50 (1H, ddd, J=13.7, 9.8, 5.9 Hz), 3.56 (1H, ddd, J=13.7, 10.2, 5.9 Hz), 3.82 (3H, s), 6.46 (1H, d, J=10.2 Hz).

Reference Example 42

Methyl (2Z)-6-[bis(tert-butoxycarbonyl)amino]-4-methyl-2-(1-phenyl-1H-imidazol-4-yl)hex-2-enoate

[Formula 57]

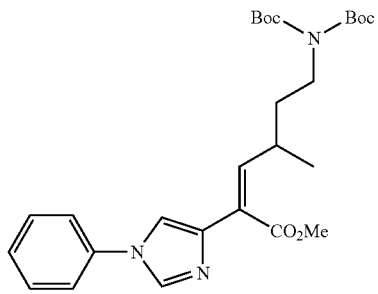

The compound (231 mg) obtained in Reference Example 38, the compound (267 mg) obtained in Reference Example 41, tetrakis(triphenylphosphine)palladium (0) (30.8 mg), and copper (I) iodide (10.4 mg) were heated to reflux for 3 hours in 1,4-dioxane (6 mL). The reaction solution was concentrated, and methylene chloride was added to the residue. After filtration through celite and concentration under reduced pressure, the obtained crude product was purified by silica gel column chromatography to obtain the title compound (230 mg).

¹H-NMR (CDCl₃) δ: 1.15 (3H, d, J=6.6 Hz), 1.49 (18H, s), 1.65-1.77 (2H, m), 2.92-3.03 (1H, m), 3.57-3.61 (2H, m), 3.87 (3H, s), 6.77 (1H, d, J=10.6 Hz), 7.34-7.40 (3H, m), 7.44-7.50 (3H, m), 7.78 (1H, d, J=1.6 Hz).

Reference Example 43

Methyl (1R*,2R*)-2-{3-[bis(tert-butoxycarbonyl)amino]-1-methylpropyl}-1-(1-phenyl-1H-imidazol-4-yl)cyclopropanecarboxylate

[Formula 58]

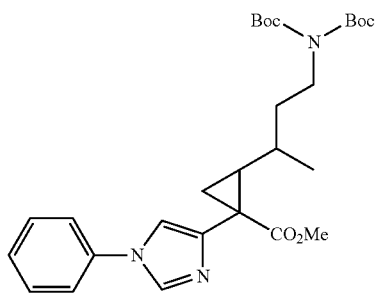

The title compound (177 mg, diastereomeric mixture) was obtained from the compound (230 mg) obtained in Reference Example 42 in the same way as in Reference Example 4.

¹H-NMR (CDCl₃) δ: 1.01 (1.2H, d, J=6.3 Hz), 1.11 (1.8H, d, J=5.5 Hz), 1.47 (10.8H, s), 1.52 (7.2H, s), 1.56-1.71 (5H, m), 1.75-1.84 (1H, m), 3.44-3.70 (2H, m), 3.74 (1.2H, s), 3.75 (1.8H, s), 7.32-7.49 (5H, m), 7.59-7.60 (1H, m), 7.71 (0.4H, d, J=1.6 Hz), 7.72 (0.6H, d, J=1.2 Hz).

Reference Example 44

(1-Trityl-1H-imidazol-4-yl)acetic acid

[Formula 59]

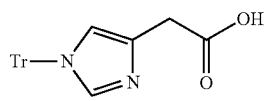

A 5 N aqueous sodium hydroxide solution (200 mL) was added to a solution of (1-trityl-1H-imidazol-4-yl)acetonitrile (33 g) in methanol (100 mL), and the mixture was heated to reflux for 4 hours. To this reaction solution, water and methylene chloride were added, and the mixture was neutralized with a 1 N aqueous hydrochloric acid solution. Methanol was added thereto until insoluble matter was dissolved, and the organic layer was then separated. The aqueous layer was further subjected to extraction three times with a methylene chloride:methanol (9:1) mixed solvent, and the extracts were combined with the foregoing separated organic layer and dried over anhydrous magnesium sulfate. The solvent was distilled off under reduced pressure, and the obtained white solid was washed with a hexane-diisopropyl ether mixed solvent. The solid was dried under reduced pressure to obtain the title compound (34 g).

¹H-NMR (CDCl₃) δ: 3.63 (2H, s), 6.67 (1H, s), 7.10-7.13 (6H, m), 7.34-7.37 (9H, m), 7.46-7.48 (1H, m).

Reference Example 45 tert-Butyl (1-trityl-1H-imidazol-4-yl)acetate

[Formula 60]

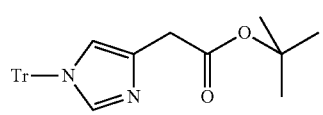

Borane trifluoride-diethyl ether (0.7 mL) was added dropwise to a solution of the compound (10 g) obtained in Reference Example 44 and tert-butyl 2,2,2-trichloroacetimidate (14.8 g) in methylene chloride (300 mL), and the mixture was stirred at room temperature for 19 hours. Since the starting materials still remained, tert-butyl 2,2,2-trichloroacetimidate (14.8 g) and borane trifluoride-diethyl ether (0.7 mL) were further added thereto, and the mixture was further stirred for 23 hours. Anhydrous sodium bicarbonate was added thereto, and insoluble matter was filtered off through celite. The solvent in the filtrate was distilled off under reduced pressure. The obtained residue was purified by silica gel column chromatography (eluting solvent: hexane→hexane/ethyl acetate=60/40). The solvent was distilled off under reduced pressure, and a hexane-methylene chloride mixed solvent was added to the obtained residue. Insoluble matter was filtered off, and the filtrate was then distilled off under reduced pressure. The residue was dried to obtain the title compound (6.6 g).

$^1$H-NMR (CDCl$_3$) δ: 1.41 (9H, s), 3.53 (2H, s), 6.75 (1H, s), 7.12-7.17 (6H, m), 7.31-7.35 (9H, m), 7.39 (1H, s).

Reference Example 46 tert-Butyl (2Z)-6-[bis(tert-butoxycarbonyl)amino]-2-(1-trityl-1H-imidazol-4-yl)hex-2-enoate

[Formula 61]

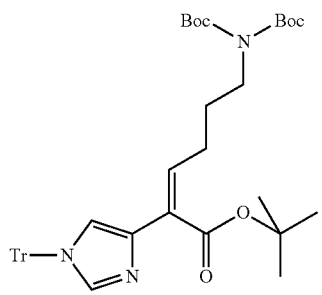

A solution of the compound (6.5 g) obtained in Reference Example 45 in anhydrous tetrahydrofuran (60 mL) was cooled to −78° C. under a nitrogen atmosphere. To this solution, lithium bis(trimethylsilyl)amide (1.0 M tetrahydrofuran solution, 18.0 mL) was added dropwise over 10 minutes, and the mixture was stirred at the same temperature for 80 minutes. Then, di-tert-butyl(4-oxobutyl)imidodicarbonate (6.1 g) dissolved in anhydrous tetrahydrofuran (40 mL) was added dropwise thereto over 20 minutes, and the mixture was stirred at the same temperature for 1.8 hours. A saturated aqueous solution of ammonium chloride was added thereto, followed by extraction twice with ethyl acetate. The combined organic layer was dried by the addition of anhydrous magnesium sulfate, and the solvent was distilled off under reduced pressure. Triethylamine (13.6 mL) and methanesulfonyl chloride (5.1 mL) were added to a solution of the obtained residue in methylene chloride (60 mL) under ice cooling, and the mixture was stirred for 10 minutes under ice cooling and then stirred at room temperature for 14 hours. 1,8-diazabicyclo[5.4.0]undec-7-ene (2.5 mL) was added thereto at room temperature, and the mixture was stirred for 4 days. A saturated aqueous solution of ammonium chloride was added thereto to separate an organic layer. The organic layer was further washed with a saturated aqueous solution of sodium bicarbonate and saturated sodium chloride solution and dried by the addition of anhydrous magnesium sulfate, and the solvent was then distilled off under reduced pressure. The obtained residue was purified by silica gel column chromatography (eluting solvent: methylene chloride→methylene chloride/ethyl acetate=85/15) to respectively obtain the title compound (Z-form, less polar compound, 1.7 g) and its isomer (E-form, more polar compound, 2.7 g).

Z-form: $^1$H-NMR (CDCl$_3$) δ: 1.37 (9H, s), 1.49 (18H, s), 1.74-1.82 (2H, m), 2.41-2.47 (2H, m), 3.60-3.64 (2H, m), 6.76 (1H, t, J=7.0 Hz), 6.89 (1H, s), 7.12-7.18 (6H, m), 7.31-7.37 (10H, m).
MS (ESI) m/z 694 (M+H)$^+$.

E-form: $^1$H-NMR (CDCl$_3$) δ: 1.38 (9H, s), 1.48 (18H, s), 1.70-1.78 (2H, m), 2.55-2.61 (2H, m), 3.53-3.57 (2H, m), 6.81 (1H, t, J=7.4 Hz), 6.97 (1H, d, J=1.6 Hz), 7.15-7.18 (6H, m), 7.32-7.35 (9H, m), 7.41 (1H, s).
MS (ESI) m/z 694 (M+H)$^+$.

Reference Example 47 tert-Butyl (1R*,2S*)-2-{3-[bis(tert-butoxycarbonyl)amino]propyl}-1-(1-trityl-1H-imidazol-4-yl)cyclopropanecarboxylate

[Formula 62]

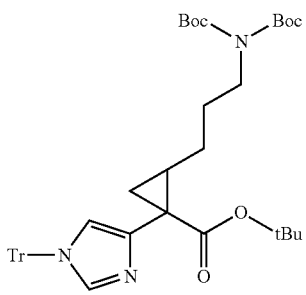

The title compound (1.08 g) was obtained from the compound (1.66 g) obtained in Reference Example 46 in the same way as in Reference Example 4.

$^1$H-NMR (CDCl$_3$) δ: 1.32 (9H, s), 1.38-1.51 (3H, m), 1.48 (18H, s), 1.59-1.75 (4H, m), 3.57 (2H, t, J=7.4 Hz), 6.86 (1H, d, J=1.6 Hz), 7.12-7.16 (6H, m), 7.24 (1H, d, J=1.6 Hz), 7.31-7.34 (9H, m).

Reference Example 48 tert-Butyl (1R*,2S*)-2-{3-[bis(tert-butoxycarbonyl)amino]propyl}-1-(1H-imidazol-4-yl)cyclopropanecarboxylate

[Formula 63]

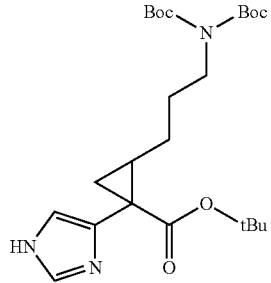

The title compound (689 mg) was obtained from the compound (1.08 g) obtained in Reference Example 47 in the same way as in Reference Example 8.

$^1$H-NMR (CDCl$_3$) δ: 1.42 (9H, s), 1.45-1.59 (3H, m), 1.52 (18H, s), 1.61-1.74 (4H, m), 3.55-3.69 (2H, m), 6.83 (1H, br s), 7.52 (1H, br s).

Reference Example 49 di-tert-Butyl [(4Z)-5-cyano-5-(1-trityl-1H-imidazol-4-yl)pent-4-en-1-yl]imidodicarbonate

[Formula 64]

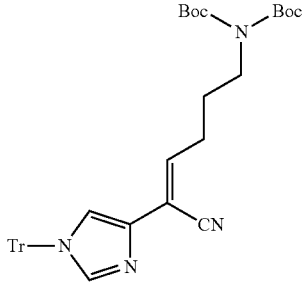

The title compound (24.1 g) was obtained from (1-trityl-1H-imidazol-4-yl)acetonitrile (48.3 g) in the same way as in Reference Examples 2 and 3.

$^1$H-NMR (CDCl$_3$) δ: 1.50 (18H, s), 1.77-1.84 (2H, m), 2.47-2.53 (2H, m), 3.62-3.66 (2H, m), 6.98 (1H, d, J=1.2 Hz), 7.11-7.15 (7H, m), 7.33-7.37 (9H, m), 7.40 (1H, d, J=1.2 Hz).

Reference Example 50 tert-Butyl {3-[(1R*,2S*)-2-cyano-2-(1-trityl-1H-imidazol-4-yl)cyclopropyl]propyl}carbamate

[Formula 65]

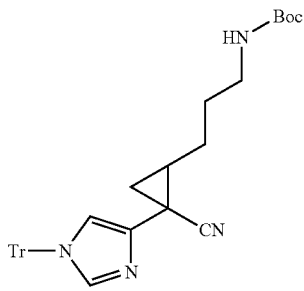

The title compound (16.9 g) was obtained in the same way as in Reference Example 4 using the compound (24.1 g) obtained in Reference Example 49.

$^1$H-NMR (CDCl$_3$) δ: 1.28-1.30 (1H, m), 1.44 (9H, s), 1.69-1.83 (6H, m), 3.16-3.20 (2H, m), 4.62 (1H, brs), 6.91 (1H, d, J=1.6 Hz), 7.10-7.14 (6H, m), 7.28 (1H, d, J=1.6 Hz), 7.32-7.36 (9H, m).

Reference Example 51 tert-Butyl {3-[(1R*,2S*)-2-cyano-2-(1H-imidazol-4-yl)cyclopropyl]propyl}carbamate

[Formula 66]

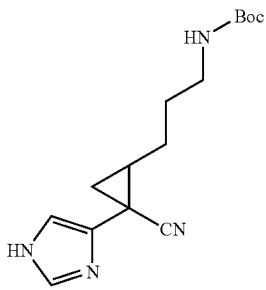

The compound (16.9 g) obtained in Reference Example 50 was dissolved in a 90% aqueous acetic acid solution (200 mL), and the solution was stirred at 50° C. for 3 hours. The reaction solution was concentrated under reduced pressure and separated into aqueous and organic layers by the addition of a saturated aqueous solution of sodium bicarbonate and methylene chloride. The obtained organic layer was dried over anhydrous magnesium sulfate. The obtained residue was purified by silica gel chromatography (eluting solvent: methylene chloride→methylene chloride/methanol=90/10) to obtain the title compound (9.0 g).

$^1$H-NMR (CDCl$_3$) δ: 1.32-1.34 (1H, m), 1.44 (9H, s), 1.72-1.76 (6H, m), 3.17-3.22 (2H, m), 4.62 (1H, brs), 7.10 (1H, s), 7.52 (1H, s).

Reference Example 52

[1-(1-Naphthyl)-1H-imidazol-4-yl]acetonitrile

[Formula 67]

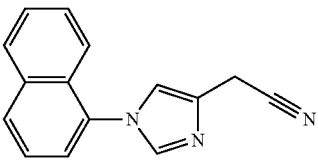

The title compound (0.3 g) was obtained in the same way as in Step 1 of Example 6 using 1H-imidazol-4-ylacetonitrile (1.3 g) and naphthaleneboronic acid (2.3 g).

$^1$H-NMR (CDCl$_3$) δ: 3.86 (2H, s), 7.29-7.34 (1H, m), 7.46 (1H, dd, J=7.4, 1.2 Hz), 7.53-7.62 (4H, m), 7.74 (1H, brs), 7.95-7.99 (2H, m).

Reference Example 53 di-tert-Butyl {(4Z)-5-cyano-5-[1-(1-naphthyl)-1H-imidazol-4-yl]pent-4-en-1-yl}imidodicarbonate

[Formula 68]

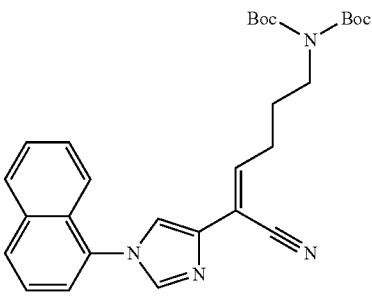

The title compound (237 mg) was obtained from the compound (314 mg) obtained in Reference Example 52 in the same way as in Reference Examples 2 and 3.

$^1$H-NMR (CDCl$_3$) δ: 1.53 (18H, s), 1.84-1.91 (2H, m), 2.57-2.63 (2H, m), 3.70 (2H, t, J=7.4 Hz), 7.22-7.25 (1H, m), 7.41 (1H, d, J=0.8 Hz), 7.47 (1H, dd, J=7.0, 0.8 Hz), 7.52-7.63 (4H, m), 7.71 (1H, d, J=1.2 Hz), 7.96-8.00 (2H, m).

Reference Example 54 di-tert-Butyl (3-{(1R*,2S*)-2-cyano-2-[1-(1-naphthyl)-1H-imidazol-4-yl]cyclopropyl}propyl)imidodicarbonate

[Formula 69]

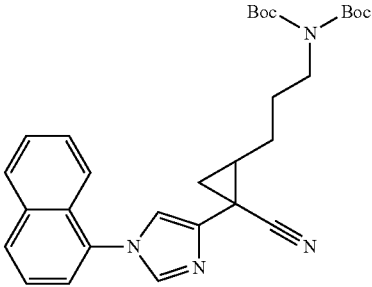

The title compound (210 mg) was obtained from the compound (237 mg) obtained in Reference Example 53 in the same way as in Reference Example 4.

$^1$H-NMR (CDCl$_3$) δ: 1.41 (1H, dd, J=7.0, 4.7 Hz), 1.51 (18H, s), 1.62-1.68 (1H, m), 1.79-1.97 (5H, m), 3.69 (2H, t, J=7.0 Hz), 7.37 (1H, d, J=1.6 Hz), 7.44 (1H, dd, J=7.0, 1.2 Hz), 7.52-7.60 (3H, m), 7.61 (1H, d, J=1.6 Hz), 7.63-7.65 (1H, m), 7.95-7.98 (1H, m).

Reference Example 55

(1-Pyridin-2-yl-1H-imidazol-4-yl) acetonitrile

[Formula 70]

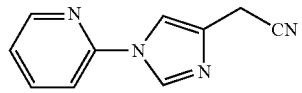

Sodium hydride (63% mineral oil dispersion, 4.71 g) was added over 15 minutes to a solution of 1H-imidazol-4-ylacetonitrile (13.25 g) in N,N-dimethylformamide (46 mL) cooled to 0° C. Then, a solution of 2-fluoropyridine (12.61 g) in N,N-dimethylformamide (23 mL) was added thereto at room temperature, and the mixture was stirred at 100° C. for 5 hours. To the reaction solution, ice water was added, and methylene chloride was added. The formed solid was removed by suction filtration, and the organic layer was then separated and dried over anhydrous magnesium sulfate. Volatile matter was distilled off under reduced pressure, and the residue was purified by silica gel column chromatography to obtain the title compound (18.5 g, mixture with N,N-dimethylformamide).

$^1$H-NMR (CDCl$_3$) δ: 0.81 (2H, s), 7.31 (1H, dd, J=4.9, 7.3 Hz), 7.39 (1H, d, J=8.3 Hz), 7.72 (1H, s), 7.89 (1H, dd, J=7.3, 8.3 Hz), 8.35 (1H, s), 8.52 (1H, d, J=4.9 Hz).

Reference Example 56

(1R,5S)-1-(1-Pyridin-2-yl-1H-imidazol-4-yl)-3-oxabicyclo[3.1.0]hexan-2-one

[Formula 71]

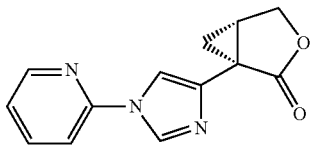

A 1.9 N solution of N,N,N',N'-sodium hexamethyldisilazane in tetrahydrofuran (242.87 mL) was added dropwise at 0° C. over 30 minutes to a solution of the compound (37.80 g) obtained in Reference Example 55 in toluene (1250 mL). The mixture was stirred at room temperature for 30 minutes, and (S)-epichlorohydrin (22.02 g) was then added dropwise thereto over 5 minutes. After reaction at room temperature for 17.5 hours, ethyl alcohol (700 mL) and a 1 N aqueous potassium hydroxide solution (700 mL) were added to the reaction solution, and volatile matter was distilled off under reduced pressure. To the obtained oil, ethyl alcohol (240 mL) and a 1 N aqueous potassium hydroxide solution (120 mL) were added, and the mixture was stirred at 80° C. for 7.5 hours. After standing to cool to room temperature, the reaction mixture was further cooled to 0° C., and concentrated hydrochloric acid (135 mL) was added dropwise thereto over 30 minutes. The mixture was neutralized with a saturated aqueous solution of sodium bicarbonate, followed by extraction with ethyl acetate. The organic layer was dried over anhydrous magnesium sulfate. The solvent was distilled off under reduced pressure, and the residue was purified by silica gel column chromatography to obtain the title compound (13.00 g, 76% ee).

$^1$H-NMR (CDCl$_3$) δ: 1.41 (1H, dd, J=4.3, 4.7 Hz), 2.01 (1H, dd, J=4.3, 7.8 Hz), 2.81 (1H, ddt, J=0.8, 7.8, 4.7 Hz), 4.32 (1H, d, J=9.0 Hz), 4.47 (1H, dd, J=4.7, 9.0 Hz), 7.26 (1H, ddd, J=0.8, 4.7, 7.4 Hz), 7.38 (1H, d, J=8.2 Hz), 7.85 (1H, ddd, J=2.0, 7.4, 8.2 Hz), 7.96 (1H, d, J=1.2 Hz), 8.33 (1H, d, J=1.2 Hz), 8.49 (1H, ddd, J=0.8, 2.0, 4.7 Hz).

LC: Daicel Chiralpak (registered trademark) IC, 4.6 mm×250 mm (5 μm), eluting solvent: hexane/ethanol=1/1, 0.7 mL/min: 15.5 minutes (enantiomer), 18.1 minutes (title compound).

Reference Example 57

Methyl (1R,2S)-2-(bromomethyl)-1-(1-pyridin-2-yl-1H-imidazol-4-yl)cyclopropanecarboxylate

[Formula 72]

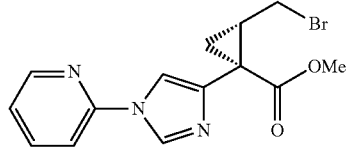

Thionyl bromide (95.93 g) was added dropwise at 10° C. over 10 minutes to a solution of the compound (13.50 g) obtained in Reference Example 56 in methanol (272 mL), and the mixture was then stirred at room temperature for 14 hours. The mixture was neutralized with a saturated aqueous solution of sodium bicarbonate, followed by extraction with ethyl acetate. The organic layer was dried over anhydrous magnesium sulfate. The solvent was distilled off under reduced pressure, and the residue was purified by silica gel column chromatography to obtain a crude product of the title compound (15.00 g). The obtained crude product was immediately used in the next reaction.

Reference Example 58

Methyl (1R,2S)-2-(3-tert-butoxy-2-cyano-3-oxopropyl)-1-(1-pyridin-2-yl-1H-imidazol-4-yl)cyclopropanecarboxylate

[Formula 73]

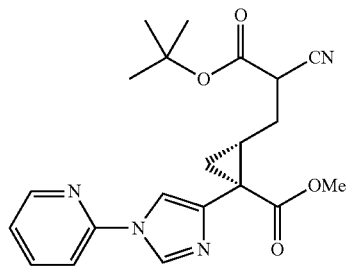

tert-Butyl cyanoacetate (37.66 g) was added dropwise at room temperature over 10 minutes to a solution of sodium hydride (63% mineral oil dispersion, 7.03 g) in tetrahydrofuran (500 mL). The mixture was stirred at room temperature for 15 minutes. Then, a solution of the compound (12.40 g) obtained in Reference Example 57 in tetrahydrofuran (53 mL) was added dropwise thereto over 1 minute, and the mixture was heated to 75° C. and stirred for 2.5 hours. The reaction mixture was cooled to 0° C. and treated with a saturated aqueous solution of ammonium chloride, followed by extraction with ethyl acetate. The organic layer was dried over anhydrous magnesium sulfate. The solvent was distilled off under reduced pressure, and the residue was purified by silica gel column chromatography to obtain the title compound (12.00 g).

Reference Example 59

Methyl (1R,2S)-2-(2-cyanoethyl)-1-(1-pyridin-2-yl-1H-imidazol-4-yl)cyclopropanecarboxylate

[Formula 74]

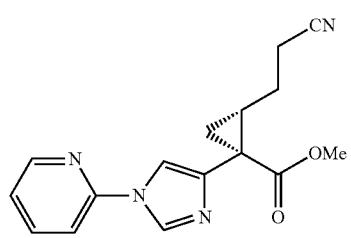

A solution of the compound (12.00 g) obtained in Reference Example 58, lithium chloride (3.85 g), and water (8.18 g) in dimethyl sulfoxide (150 mL) was heated to 135° C. and stirred for 4.3 hours. After standing to cool to room temperature, an excess amount of a saturated aqueous solution of sodium bicarbonate was added to the reaction solution, followed by extraction with ethyl acetate. The organic layer was dried over anhydrous magnesium sulfate. The solvent was distilled off under reduced pressure, and the residue was purified by silica gel column chromatography to obtain the title compound (4.90 g).

$^1$H-NMR (CDCl$_3$) δ: 1.68-1.74 (2H, m), 1.89-2.12 (3H, m), 2.41-2.49 (2H, m), 3.78 (3H, s), 7.21-7.28 (1H, m), 7.32-7.39 (1H, m), 7.74 (1H, s), 7.80-7.86 (1H, m), 8.23 (1H, s), 8.45-8.52 (1H, m).

Reference Example 60

Methyl (1R,2S)-2-{3-[(tert-butoxycarbonyl)amino]propyl}-1-(1-pyridin-2-yl-1H-imidazol-4-yl)cyclopropanecarboxylate

[Formula 75]

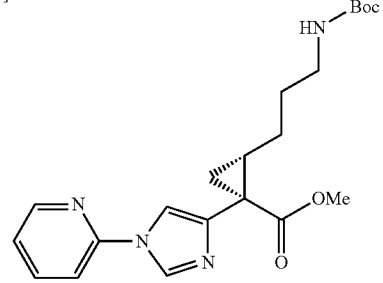

A solution of the compound (4.90 g) obtained in Reference Example 59, di-tert-butyl dicarbonate (7.22 g), and nickel (II) chloride hexahydrate (0.39 g) in methanol (200 mL) was cooled to 0° C., and lithium borohydride (2.65 g) was added portionwise thereto over 45 minutes. The mixture was stirred at room temperature for 23 hours. Then, diethylenetriamine (0.4 mL) was added thereto, and the mixture was stirred for 1 hour. An excess amount of water was added thereto, and volatile matter was distilled off under reduced pressure. Extraction was performed with ethyl acetate from the obtained mixture, and the organic layer was dried over anhydrous magnesium sulfate. The solvent was distilled off under reduced pressure, and the residue was purified by silica gel column chromatography to obtain 3.8 g of a mixture containing the desired compound. This mixture was fractionated and purified using Daicel Chiralpak IC column (2 cm×25 cm, eluting solvent: hexane/ethanol=1/2, 7 mL/min) to collect fractions at 13.7-16.5 minutes. Volatile matter was distilled off under reduced pressure to obtain the title compound (2.80 g).

$^1$H-NMR (CDCl$_3$) δ: 1.44 (9H, s), 1.52-1.70 (6H, m), 1.78-2.06 (1H, m), 3.15 (2H, br), 3.85 (3H, s), 4.62 (1H, br), 7.20-7.25 (1H, m), 7.35-7.39 (1H, m), 7.72 (1H, s), 7.79-7.84 (1H, m), 8.23 (1H, s), 8.44-8.50 (1H, m).

Reference Example 61

[1-(5-Methylpyridin-2-yl)-1H-imidazol-4-yl]acetonitrile

[Formula 76]

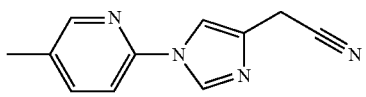

The title compound (1.6 g) was obtained from 1H-imidazol-4-ylacetonitrile (2.0 g) and 6-fluoro-3-picoline (2.1 mL) in the same way as in Reference Example 55.

$^1$H-NMR (CDCl$_3$) δ: 2.39 (3H, s), 3.78 (2H, s), 7.25 (1H, d, J=8.2 Hz), 7.64-7.66 (2H, m), 8.26 (1H, d, J=1.6 Hz), 8.29-8.31 (1H, m).

Reference Example 62 di-tert-Butyl {(4Z)-5-cyano-5-[1-(5-methylpyridin-2-yl)-1H-imidazol-4-yl]pent-4-en-1-yl}imidodicarbonate

[Formula 77]

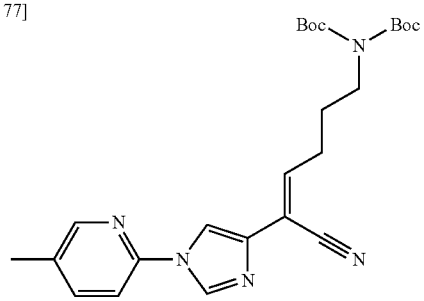

The title compound (1.2 g) was obtained from the compound (1.6 g) obtained in Reference Example 61 in the same way as in Reference Examples 2 and 3.

$^1$H-NMR (CDCl$_3$) δ: 1.52 (18H, s), 1.80-1.88 (2H, m), 2.53-2.59 (2H, m), 3.67 (2H, t, J=7.4 Hz), 7.19 (1H, t, J=7.8 Hz), 7.26 (1H, d, J=8.2 Hz), 7.65 (1H, dd, J=8.2, 2.4 Hz), 7.72 (1H, d, J=1.2 Hz), 8.29-8.32 (2H, m).

Reference Example 63 di-tert-Butyl (3-{(1R*,2S*)-2-cyano-2-[1-(5-methyl-pyridin-2-yl)-1H-imidazol-4-yl]cyclopropyl}propyl)imidodicarbonate

[Formula 78]

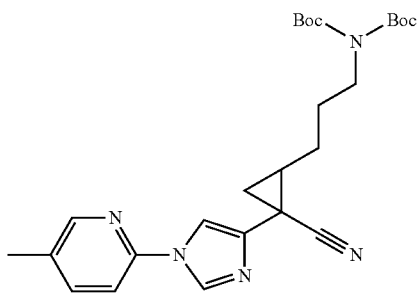

The title compound (1.1 g) was obtained from the compound (1.2 g) obtained in Reference Example 62 in the same way as in Reference Example 4.

$^1$H-NMR (CDCl$_3$) δ: 1.35 (1H, dd, J=6.7, 4.3 Hz), 1.50 (18H, s), 1.63-1.89 (6H, m), 2.38 (3H, s), 3.66 (2H, t, J=7.2 Hz), 7.24 (1H, d, J=8.2 Hz), 7.64 (1H, dd, J=8.2, 2.2 Hz), 7.68 (1H, d, J=1.6 Hz), 8.18 (1H, d, J=1.6 Hz), 8.28-8.30 (1H, m).

Reference Example 64

(1R,5S)-1-(1-Phenyl-1H-imidazol-4-yl)-3-oxabicyclo[3.1.0]hexan-2-one

[Formula 79]

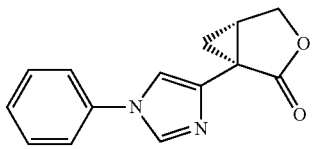

A solution of sodium bis(trimethylsilyl)amide in tetrahydrofuran (1.9 M, 432 mL, 820 mmol) was slowly added to a solution of (1-phenyl-1H-imidazol-4-yl)acetonitrile (60.1 g, 328 mmol) obtained in Reference Example 21 in toluene (1500 mL) with stirring at 0° C. The mixture was stirred at 0° C. for 45 minutes. Then, a solution of (S)-epichlorohydrin (40.7 g, 427 mmol) in tetrahydrofuran (100 mL) was added dropwise thereto over 30 minutes, and the mixture was stirred at 0° C. for 1.5 hours. The reaction mixture was heated to room temperature and stirred overnight, and a 2 M aqueous potassium hydroxide solution (100 mL) and ethanol (100 mL) were then added to the reaction solution. A similar process was carried out using (1-phenyl-1H-imidazol-4-yl)acetonitrile (60.0 g, 327 mmol). These two reaction solutions were combined and concentrated. Then, ethanol (600 mL), water (600 mL), and potassium hydroxide (125 g, 1.89 mol) were added to the residue, and the mixture was heated to reflux for 3 hours. The reaction solution was concentrated. Then, water was added to the residue, and the aqueous layer was washed with toluene. To the aqueous layer, concentrated hydrochloric acid (400 mL) was added with stirring at 0° C., and the mixture was stirred for 1 hour after heating to room temperature and then stirred for 3 hours after heating to 50° C. The reaction solution was neutralized by the addition of an aqueous sodium bicarbonate solution, followed by extraction with ethyl acetate. The organic layer was dried over anhydrous magnesium sulfate. After filtration and concentration under reduced pressure, the obtained crude product was purified by silica gel column chromatography to obtain the desired compound. The compound was further recrystallized from hexane and ethyl acetate to obtain the desired compound as a yellow solid (46.5 g, 29%, >98% ee). Its optical purity was confirmed by analytical HPLC (Daicel CHIRALPAK IC 4.6×250 mm, eluting solvent: hexane/ethanol=50/50, 1.0 mL/min, 254 nm, $t_R$=7.6 minutes ((1S, 5R)-isomer), $t_R$=8.8 minutes ((1R,5S)-isomer)).

Reference Example 65

Methyl (1R,2S)-2-(bromomethyl)-1-(1-phenyl-1H-imidazol-4-yl)cyclopropanecarboxylate

[Formula 80]

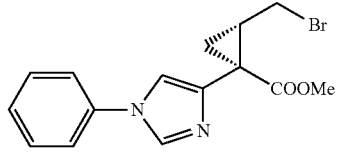

The title compound (62.2 g) was obtained from the compound (46.4 g) obtained in Reference Example 64 in the same way as in Reference Example 23.

Reference Example 66

Methyl (1R,2R)-2-(3-tert-butoxy-2-cyano-2-methyl-3-oxopropyl)-1-(1-phenyl-1H-imidazol-4-yl)cyclopropanecarboxylate

[Formula 81]

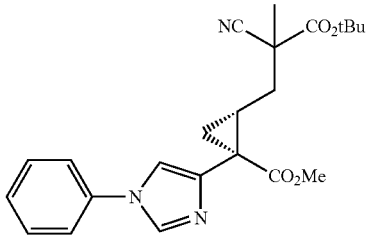

The title compound (899 mg) was obtained from the compound (840 mg) obtained in Reference Example 65 and tert-butyl 2-cyanopropionate (Tetrahedron, 1994, vol. 50, p. 4439) (730 mg) in the same way as in Reference Example 24.

$^1$H-NMR (CDCl$_3$) δ: 1.49 (4.95H, s), 1.50 (4.05H, s), 1.59 (1.65H, s), 1.61 (1.35H, s), 1.69 (0.55H, dd, J=7.4, 4.3 Hz), 1.75-1.83 (1.45H, m), 1.86-1.94 (1H, m), 2.07 (0.45H, dd, J=14.1, 7.8 Hz), 2.27 (1.1H, d, J=7.0 Hz), 2.43 (0.45H, dd, J=14.1, 5.9 Hz), 3.76 (1.65H, s), 3.77 (1.35H, s), 7.34-7.42 (3H, m), 7.45-7.50 (3H, m), 7.71 (0.45H, d, J=1.6 Hz), 7.72 (0.55H, d, J=1.2 Hz).

Reference Example 67

Methyl (1R,2S)-2-(2-cyanopropyl)-1-(1-phenyl-1H-imidazol-4-yl)cyclopropanecarboxylate

[Formula 82]

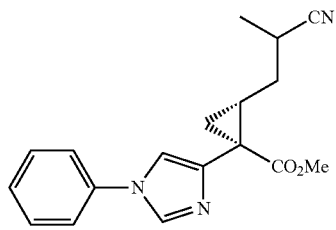

The compound (827 mg) obtained in Reference Example 66 and p-toluenesulfonic acid monohydrate (768 mg) were stirred overnight at 155° C. in xylene (15 mL). After standing to cool, an aqueous sodium bicarbonate solution was added to the reaction solution, followed by extraction with ethyl acetate. The organic layer was dried over anhydrous sodium sulfate. After filtration and concentration under reduced pressure, the obtained crude product was purified by silica gel column chromatography to obtain the title compound (126 mg).

$^1$H-NMR (CDCl$_3$) δ: 1.36 (1.5H, d, J=7.0 Hz), 1.39 (1.5H, d, J=7.4 Hz), 1.64-1.68 (1H, m), 1.73-1.80 (1H, m), 1.86-2.01 (2H, m), 2.08-2.38 (1H, m), 2.65-2.79 (1H, m), 3.76 (1.5H, s), 3.77 (1.5H, s), 7.34-7.43 (4H, m), 7.46-7.50 (2H, m), 7.72-7.73 (1H, m).

Reference Example 68

Methyl (1R,2S)-2-{3-[(tert-butoxycarbonyl)amino]-2-methylpropyl}-1-(1-phenyl-1H-imidazol-4-yl)cyclopropanecarboxylate

[Formula 83]

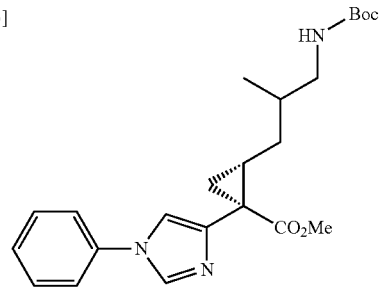

The title compound (124 mg) was obtained from the compound (126 mg) obtained in Reference Example 67 in the same way as in Reference Example 26.

$^1$H-NMR (CDCl$_3$) δ: 0.95 (1.5H, d, J=6.6 Hz), 0.99 (1.5H, d, J=6.6 Hz), 1.44 (9H, s), 1.52-1.97 (6H, m), 2.93-3.19 (2H, m), 3.74 (1.5H, s), 3.76 (1.5H, s), 4.68 (1H, br s), 7.33-7.49 (6H, m), 7.72-7.73 (1H, m).

Reference Example 69

2-(4-{[tert-Butyl(diphenyl)silyl]oxy}-2,2-dimethylbutyl)-1H-isoindole-1,3(2H)-dione

[Formula 84]

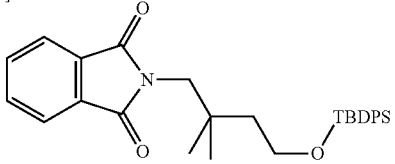

A solution of diethyl azodicarboxylate in toluene (2.2 M, 14.0 mL) was added to a solution of 4-{[tert-butyl(diphenyl)silyl]oxy}-2,2-dimethylbutan-1-ol (J. Am. Chem. Soc., 2007, vol. 129, p. 4456) (9.15 g), triphenylphosphine (7.40 g), and phthalimide (4.15 g) in tetrahydrofuran (150 mL) with stirring at room temperature. The mixture was stirred overnight at room temperature, and sodium chloride solution was then added thereto, followed by extraction with ethyl acetate. The organic layer was dried over anhydrous magnesium sulfate, filtered, and concentrated under reduced pressure, and diethyl ether was then added to the residue. Insoluble matter was filtered off through celite, and the filtrate was concentrated under reduced pressure. Then, the obtained crude product was purified by silica gel column chromatography to obtain the title compound (11.8 g).

$^1$H-NMR (CDCl$_3$) δ: 0.92 (6H, s), 1.04 (9H, s), 1.62 (2H, t, J=6.8 Hz), 3.53 (2H, s), 3.80 (2H, t, J=6.8 Hz), 7.35-7.45 (6H, m), 7.67-7.69 (4H, m), 7.71-7.73 (2H, m), 7.83-7.86 (2H, m).

Reference Example 70

2-(4-Hydroxy-2,2-dimethylbutyl)-1H-isoindole-1,3 (2H)-dione

[Formula 85]

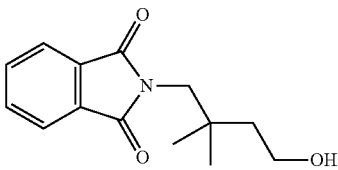

A solution of tetrabutylammonium fluoride in tetrahydrofuran (1 M, 36.5 mL) was added to a solution of the compound (11.8 g) obtained in Reference Example 69 in tetrahydrofuran (50 mL) with stirring at room temperature. The mixture was stirred overnight at room temperature, and water was then added to the reaction solution, followed by extraction with ethyl acetate. The organic layer was washed with saturated sodium chloride solution and dried over anhydrous sodium sulfate. After filtration and concentration under reduced pressure, the obtained crude product was purified by silica gel column chromatography to obtain the title compound (3.48 g).

$^1$H-NMR (CDCl$_3$) δ: 1.00 (6H, s), 1.55 (2H, t, J=7.0 Hz), 2.01 (1H, br s), 3.63 (2H, s), 3.83 (2H, t, J=7.0 Hz), 7.72-7.75 (2H, m), 7.84-7.87 (2H, m).

Reference Example 71

Methyl (2E)-2-bromo-6-(1,3-dioxo-1,3-dihydro-2H-isoindol-2-yl)-5,5-dimethylhex-2-enoate

[Formula 86]

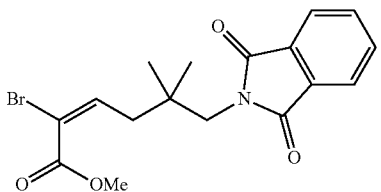

[Step 1] 4-(1,3-Dioxo-1,3-dihydro-2H-isoindol-2-yl)-3,3-dimethylbutanal

Dimethyl sulfoxide (3.00 mL) was added to a solution of oxalyl chloride (1.81 mL) in methylene chloride (40 mL) with stirring at −78° C., and the mixture was stirred at the same temperature for 5 minutes. Then, a solution of 2-(4-hydroxy-2,2-dimethylbutyl)-1H-isoindole-1,3(2H)-dione (3.48 g) obtained in Reference Example 70 in methylene chloride (30 mL) was added thereto. The mixture was stirred at the same temperature for 15 minutes. Then, triethylamine (7.80 mL) was added thereto, and the mixture was heated to room temperature and stirred. The reaction solution was separated into aqueous and organic layers by the addition of 0.1 M hydrochloric acid. The organic layer was washed with 0.1 M hydrochloric acid, water, and saturated sodium chloride solution and then dried over anhydrous magnesium sulfate. Filtration and concentration under reduced pressure were performed to obtain a crude product of 4-(1,3-dioxo-1,3-dihydro-2H-isoindol-2-yl)-3,3-dimethylbutanal (3.59 g).

[Step 2] Methyl (2E)-2-bromo-6-(1,3-dioxo-1,3-dihydro-2H-isoindol-2-yl)-5,5-dimethylhex-2-enoate A solution of methyl [bis(2,2,2-trifluoroethoxy)phosphoryl]acetate (95%, 9.42 g) in tetrahydrofuran (20 mL) was slowly added to a suspension of sodium hydride (63%, 1.07 g) in tetrahydrofuran (40 mL) with stirring at −30° C. The mixture was stirred at the same temperature for 30 minutes, and bromine (1.46 mL) was then slowly added thereto. After completion of addition, the reaction solution was temporarily heated to −10° C. The reaction solution was cooled to −78° C., and sodium hydride (63%, 1.07 g) was then added thereto at once. The mixture was stirred at the same temperature for 30 minutes, and a solution of the crude product of 4-(1,3-dioxo-1,3-dihydro-2H-isoindol-2-yl)-3,3-dimethylbutanal (3.59 g) obtained in Step 1 in tetrahydrofuran (20 mL) was then added thereto. The mixture was stirred at −78° C. for 1 hour and then gradually heated to 10° C. over 1 hour with care to prevent foaming. The reaction mixture was further stirred at the same temperature for 1 hour, and an aqueous ammonium chloride solution was then added to the reaction solution, followed by extraction with ethyl acetate. The organic layer was washed with water and saturated sodium chloride solution and dried over anhydrous sodium sulfate. After filtration and concentration under reduced pressure, the obtained crude product was purified by silica gel column chromatography to obtain the title compound (4.53 g).

$^1$H-NMR (CDCl$_3$) δ: 1.01 (6H, s), 2.53 (2H, d, J=7.8 Hz), 3.56 (2H, s), 3.81 (3H, s), 6.87 (1H, dd, J=8.0, 7.8 Hz), 7.71-7.75 (2H, m), 7.84-7.88 (2H, m).

Reference Example 72

Methyl (2Z)-6-(1,3-dioxo-1,3-dihydro-2H-isoindol-2-yl)-5,5-dimethyl-2-(1-trityl-1H-imidazol-4-yl)hex-2-enoate

[Formula 87]

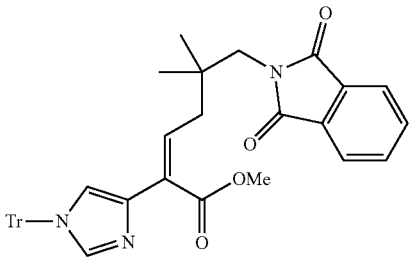

The title compound (1.54 g) was obtained from 4-(tributylstannyl)-1-trityl-1H-imidazole (Synthesis, 1998, p. 829) (3.15 g) and the compound (2.00 g) obtained in Reference Example 71 in the same way as in Reference Example 42.

$^1$H-NMR (CDCl$_3$) δ: 1.03 (6H, s), 2.50 (2H, d, J=8.2 Hz), 3.61 (2H, s), 3.71 (3H, s), 6.97 (1H, d, J=1.6 Hz), 7.05 (1H, t, J=8.2 Hz), 7.13-7.17 (6H, m), 7.31-7.35 (9H, m), 7.35-7.36 (1H, m), 7.69-7.73 (2H, m), 7.82-7.86 (2H, m).

Reference Example 73

Methyl (1R*,2S*)-2-[3-(1,3-dioxo-1,3-dihydro-2H-isoindol-2-yl)-2,2-dimethylpropyl]-1-(1-trityl-1H-imidazol-4-yl)cyclopropanecarboxylate

[Formula 88]

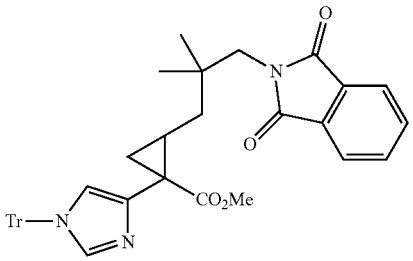

The title compound (370 mg) was obtained from the compound (598 mg) obtained in Reference Example 72 in the same way as in Reference Example 4.

$^1$H-NMR (CDCl$_3$) δ: 0.96 (3H, s), 1.00 (3H, s), 1.44-1.50 (1H, m), 1.56-1.59 (1H, m), 1.63-1.72 (2H, m), 1.80-1.88 (1H, m), 3.55 (2H, s), 3.63 (3H, d, J=5.5 Hz), 6.96 (1H, d, J=1.6 Hz), 7.12-7.17 (6H, m), 7.27 (1H, d, J=1.6 Hz), 7.30-7.34 (9H, m), 7.68-7.72 (2H, m), 7.80-7.84 (2H, m).

Reference Example 74

Methyl (1R*,2S*)-2-[3-(1,3-dioxo-1,3-dihydro-2H-isoindol-2-yl)-2,2-dimethylpropyl]-1-(1H-imidazol-4-yl)cyclopropanecarboxylate

[Formula 89]

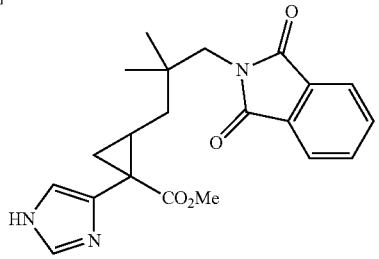

10% palladium-carbon (hydrated, 400 mg) was added to a solution of the compound (370 mg) obtained in Reference Example 73 in methanol (6 mL), and the mixture was stirred overnight at room temperature under a hydrogen atmosphere. Since the starting materials remained, the reaction mixture was filtered through celite and concentrated under reduced pressure, and the obtained residue was then dissolved in methanol (10 mL). To the solution, 20% palladium hydroxide-carbon (300 mg) was added, and the mixture was stirred overnight at room temperature under a hydrogen atmosphere. Since the starting materials remained, the reaction mixture was filtered through celite and concentrated under reduced pressure, and the obtained residue was then stirred at 60° C. for 5 hours in 90% acetic acid (8 mL). The reaction solution was added to a saturated aqueous solution of sodium bicarbonate, followed by extraction with methylene chloride. The organic layer was dried over anhydrous sodium sulfate. After filtration and concentration under reduced pressure, the obtained crude product was purified by silica gel column chromatography to obtain the title compound (110 mg).

$^1$H-NMR (CDCl$_3$) δ: 1.00 (6H, s), 1.44-1.73 (5H, m), 3.57 (2H, s), 3.67 (3H, d, J=2.0 Hz), 7.00 (1H, br s), 7.59 (1H, br s), 7.73-7.75 (2H, m), 7.86-7.88 (2H, m).

Reference Example 75

Methyl (1R*,2S*)-2-[3-(1,3-dioxo-1,3-dihydro-2H-isoindol-2-yl)-2,2-dimethylpropyl]-1-(1-phenyl-1H-imidazol-4-yl)cyclopropanecarboxylate

[Formula 90]

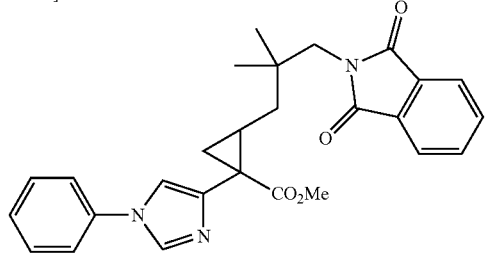

The title compound (97.7 mg) was obtained from the compound (100 mg) obtained in Reference Example 74 and phenylboronic acid (64.2 mg) in the same way as in Step 1 of Example 6.

$^1$H-NMR (CDCl$_3$) δ: 1.01 (3H, s), 1.04 (3H, s), 1.52-1.57 (1H, m), 1.67 (1H, dd, J=7.8, 4.3 Hz), 1.71-1.77 (2H, m), 1.91-1.97 (1H, m), 3.59 (2H, s), 3.73 (3H, s), 7.33-7.37 (1H, m), 7.39-7.40 (1H, m), 7.41-7.42 (1H, m), 7.45-7.46 (1H, m), 7.46-7.48 (1H, m), 7.49-7.50 (1H, m), 7.70-7.73 (2H, m), 7.73-7.74 (1H, m), 7.83-7.86 (2H, m).

Reference Example 76

Methyl (1R*,2S*)-2-{3-[(tert-butoxycarbonyl)amino]-2,2-dimethylpropyl}-1-(1-phenyl-1H-imidazol-4-yl)cyclopropanecarboxylate

[Formula 91]

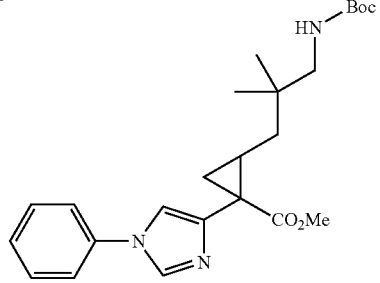

Hydrazine monohydrate (1.55 mL) was added to a solution of the compound (97.7 mg) obtained in Reference Example 75 in ethanol (6 mL) with stirring at room temperature, and the mixture was stirred overnight. The reaction solution was concentrated under reduced pressure. Then, ethyl acetate was added thereto, and insoluble matter was filtered off through celite. The filtrate was concentrated under reduced pressure, and the obtained residue was then dissolved in a mixed solvent of acetone (8 mL) and water (2 mL). To the solution, di-tert-butyl dicarbonate (69.9 mg) and sodium bicarbonate (108 mg) were added with stirring at room temperature, and the mixture was stirred overnight. The reaction solution was concentrated under reduced pressure. Then, ethyl acetate was added to the residue, and the organic layer was washed with water and saturated sodium chloride solution and dried over anhydrous sodium sulfate. After filtration and concentration under reduced pressure, the obtained crude product was purified by silica gel column chromatography to obtain the title compound (77.6 mg).

$^1$H-NMR (CDCl$_3$) δ: 0.93 (3H, s), 0.95 (3H, s), 1.44 (9H, s), 1.56-1.69 (4H, m), 1.78-1.85 (1H, m), 3.02 (2H, d, J=6.3 Hz), 3.75 (3H, s), 4.69 (1H, br s), 7.33-7.49 (6H, m), 7.72 (1H, br s).

Reference Example 77

Methyl (1R,2R)-2-[2-(tert-butoxycarbonyl)-2-cyanobutyl]-1-(1-phenyl-1H-imidazol-4-yl)cyclopropanecarboxylate

[Formula 92]

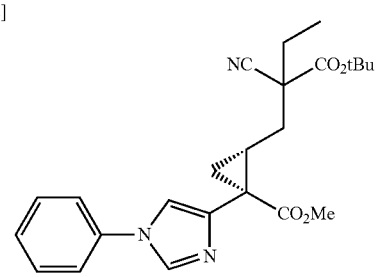

The title compound (1.60 g) was obtained from the compound (2.00 g) obtained in Reference Example 65 and tert-butyl 2-cyanobutyrate (J. Am. Chem. Soc., 2007, vol. 129, p. 1038) (2.42 g) in the same way as in Reference Example 24.

$^1$H-NMR (CDCl$_3$) δ: 1.08 (1.8H, t, J=7.4 Hz), 1.09 (1.2H, t, J=7.4 Hz), 1.49 (5.4H, s), 1.50 (3.6H, s), 1.64-2.09 (5.4H, m), 2.21 (0.6H, dd, J=14.2, 7.2 Hz), 2.32 (0.6H, dd, J=14.2, 6.7 Hz), 2.39 (0.4H, dd, J=14.1, 5.5 Hz), 3.76 (1.8H, s), 3.77 (1.2H, s), 7.35-7.41 (3H, m), 7.45-7.49 (3H, m), 7.70-7.72 (1H, m).

Reference Example 78

Methyl (1R,2S)-2-(2-cyanobutyl)-1-(1-phenyl-1H-imidazol-4-yl)cyclopropanecarboxylate

[Formula 93]

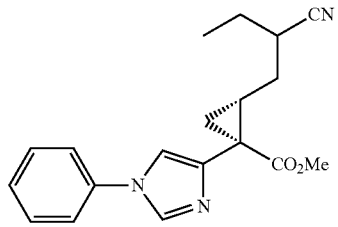

The compound (1.60 g) obtained in Reference Example 77 and p-toluenesulfonic acid monohydrate (1.44 g) were stirred overnight at 140° C. in xylene (25 mL). After standing to cool, an aqueous sodium bicarbonate solution was added to the reaction solution, followed by extraction with ethyl acetate. The organic layer was dried over anhydrous sodium sulfate. After filtration and concentration under reduced pressure, the obtained crude product was purified by silica gel column chromatography to obtain the title compound (223 mg).

$^1$H-NMR (CDCl$_3$) δ: 1.09 (1.5H, t, J=7.4 Hz), 1.11 (1.5H, t, J=7.4 Hz), 1.64-1.77 (4H, m), 1.85-2.00 (2.5H, m), 2.08-2.16 (0.5H, m), 2.50-2.65 (1H, m), 3.76 (1.5H, s), 3.77 (1.5H, s), 7.35-7.42 (4H, m), 7.46-7.50 (2H, m), 7.72-7.73 (1H, m).

Reference Example 79

Methyl (1R,2S)-2-(2-{[(tert-butoxycarbonyl)amino]methyl}butyl)-1-(1-phenyl-1H-imidazol-4-yl)cyclopropanecarboxylate

[Formula 94]

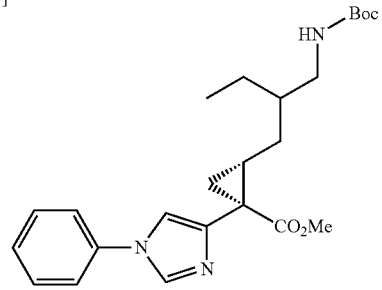

The title compound (159 mg) was obtained from the compound (223 mg) obtained in Reference Example 78 in the same way as in Reference Example 26.

$^1$H-NMR (CDCl$_3$) δ: 0.90 (1.5H, t, J=7.2 Hz), 0.92 (1.5H, t, J=7.3 Hz), 1.33-1.86 (8H, m), 1.43 (9H, s), 3.08-3.13 (1H, m), 3.14-3.21 (1H, m), 3.74 (1.5H, s), 3.76 (1.5H, s), 4.70 (0.5H, br s), 4.76 (0.5H, br s), 7.31-7.49 (6H, m), 7.71-7.72 (1H, m).

Reference Example 80

(1-Pyridin-2-yl-1H-imidazol-4-yl)acetic acid

[Formula 95]

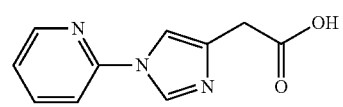

The compound (3.00 g) obtained in Reference Example 55 was stirred at 100° C. for 6 hours in a mixed solvent of ethanol (20 mL) and a 5 M aqueous sodium hydroxide solution (10 mL). The reaction solution was concentrated. To the obtained residue, water was added, and the mixture was then neutralized with 5 N hydrochloric acid. The precipitated solid was collected by filtration and washed with methylene chloride to obtain the title compound (2.33 g).

$^1$H-NMR (DMSO-d$_6$) δ: 3.53 (2H, s), 7.35-7.38 (1H, m), 7.78-7.81 (2H, m), 7.97-8.02 (1H, m), 8.46 (1H, d, J=1.6 Hz), 8.48-8.50 (1H, m).

Reference Example 81

Methyl (1-pyridin-2-yl-1H-imidazol-4-yl)acetate

[Formula 96]

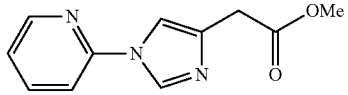

Thionyl chloride (0.90 mL) was slowly added to a solution of the compound (2.40 g) obtained in Reference Example 80 in methanol (25 mL) with stirring at room temperature, and the mixture was then heated to reflux for 3 hours. The reaction solution was concentrated, and a saturated aqueous solution of sodium bicarbonate was then added to the residue, followed by extraction with methylene chloride. The organic layer was dried over anhydrous sodium sulfate. After filtration and concentration under reduced pressure, the obtained crude product was purified by silica gel column chromatography to obtain the title compound (2.46 g).

$^1$H-NMR (CDCl$_3$) δ: 3.73 (2H, s), 3.75 (3H, s), 7.22-7.25 (1H, m), 7.32-7.35 (1H, m), 7.61 (1H, d, J=1.6 Hz), 7.80-7.84 (1H, m), 8.31 (1H, d, J=1.6 Hz), 8.47-8.48 (1H, m).

Reference Example 82 di-tert-Butyl [(2R)-4-{[tert-butyl(diphenyl)silyl]oxy}-2-methylbutyl]imidodicarbonate

[Formula 97]

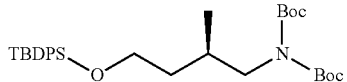

1,1'-(Azodicarbonyl)dipiperidine (6.33 g) was added to a solution of (2R)-4-{[tert-butyl(diphenyl)silyl]oxy}-2-methylbutan-1-ol (Synthesis, 2002, p. 1993) (4.30 g), di-tert-butyl iminodicarboxylate (5.45 g), and tributylphosphine (4.65 mL) in toluene (130 mL) with stirring at 0° C. The mixture was heated to room temperature and stirred overnight. Then, the reaction solution was diluted with hexane, and insoluble matter was filtered off through celite. The filtrate was concentrated under reduced pressure, and the obtained crude product was then purified by silica gel column chromatography to obtain the title compound (3.86 g).

$^1$H-NMR (CDCl$_3$) δ: 0.83 (3H, d, J=6.7 Hz), 1.03 (9H, s), 1.25-1.35 (1H, m), 1.48 (18H, s), 1.64-1.73 (1H, m), 1.96-2.03 (1H, m), 3.42 (1H, dd, J=13.7, 7.8 Hz), 3.47 (1H, dd, J=13.7, 6.7 Hz), 3.63-3.74 (2H, m), 7.35-7.44 (6H, m), 7.64-7.67 (4H, m).

Reference Example 83 di-tert-Butyl [(2R)-4-hydroxy-2-methylbutyl]imidodicarbonate

[Formula 98]

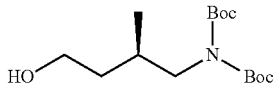

A solution of tetrabutylammonium fluoride in tetrahydrofuran (1 M, 10.7 mL) was added to a solution of the compound (3.86 g) obtained in Reference Example 82 in tetrahydrofuran (50 mL) with stirring at room temperature. The mixture was stirred overnight at room temperature, and water was then added to the reaction solution, followed by extraction with ethyl acetate. The organic layer was washed with saturated sodium chloride solution and dried over anhydrous sodium sulfate. After filtration and concentration under reduced pressure, the obtained crude product was purified by silica gel column chromatography to obtain the title compound (2.02 g).

$^1$H-NMR (CDCl$_3$) δ: 0.92 (3H, d, J=6.7 Hz), 1.38-1.48 (1H, m), 1.50 (18H, s), 1.54-1.62 (1H, m), 1.91-2.02 (1H, m), 3.45 (1H, dd, J=13.9, 8.0 Hz), 3.55 (1H, dd, J=13.9, 6.3 Hz), 3.62-3.78 (2H, m).

Reference Example 84 di-tert-Butyl [(2R)-2-methyl-4-oxobutyl]imidodicarbonate

[Formula 99]

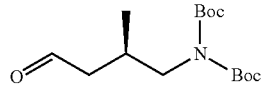

Dimethyl sulfoxide (1.42 mL) was added to a solution of oxalyl chloride (0.86 mL) in methylene chloride (30 mL) with stirring at −78° C., and the mixture was stirred at the same temperature for 5 minutes. Then, a solution of the compound (2.02 g) obtained in Reference Example 83 in methylene chloride (20 mL) was added thereto. The mixture was stirred at the same temperature for 15 minutes. Then, triethylamine (3.69 mL) was added thereto, and the mixture was heated to room temperature and stirred. The reaction solution was separated into aqueous and organic layers by the addition of water. The organic layer was washed with water and saturated sodium chloride solution and then dried over anhydrous sodium sulfate. Filtration and concentration under reduced pressure were performed to obtain the title compound (1.99 g).

$^1$H-NMR (CDCl$_3$) δ: 0.96 (3H, d, J=6.7 Hz), 1.51 (18H, s), 2.21-2.28 (1H, m), 2.42-2.51 (2H, m), 3.52-3.54 (2H, m), 9.74 (1H, t, J=2.0 Hz).

Reference Example 85

Methyl (2Z,5R)-6-[bis(tert-butoxycarbonyl)amino]-5-methyl-2-(1-pyridin-2-yl-1H-imidazol-4-yl)hex-2-enoate

[Formula 100]

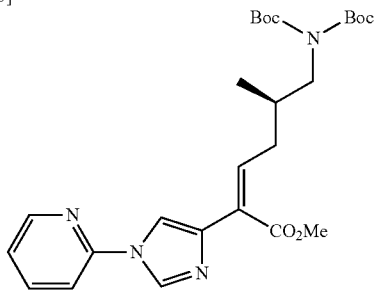

The title compound (1.24 g) was obtained from the compound (1.10 g) obtained in Reference Example 81 and the compound (1.98 g) obtained in Reference Example 84 in the same way as in Reference Examples 2 and 3.

$^1$H-NMR (CDCl$_3$) δ: 0.96 (3H, d, J=7.0 Hz), 1.51 (18H, s), 2.05-2.14 (1H, m), 2.37 (1H, ddd, J=15.1, 8.6, 8.6 Hz), 2.57 (1H, ddd, J=15.1, 7.2, 5.1 Hz), 3.52 (1H, dd, J=13.7, 7.6 Hz), 3.59 (1H, dd, J=13.7, 7.0 Hz), 3.88 (3H, s), 7.03 (1H, t, J=7.8 Hz), 7.21-7.25 (1H, m), 7.35 (1H, d, J=8.2 Hz), 7.76 (1H, d, J=1.2 Hz), 7.79-7.84 (1H, m), 8.33 (1H, d, J=1.2 Hz), 8.47-8.48 (1H, m).

Reference Example 86

Methyl (1R,2S)-2-{(2R)-3-[bis(tert-butoxycarbonyl)amino]-2-methylpropyl}-1-(1-pyridin-2-yl-1H-imidazol-4-yl)cyclopropanecarboxylate and methyl (1S,2R)-2-{(2R)-3-[bis(tert-butoxycarbonyl)amino]-2-methylpropyl}-1-(1-pyridin-2-yl-1H-imidazol-4-yl)cyclopropanecarboxylate

[Formula 101]

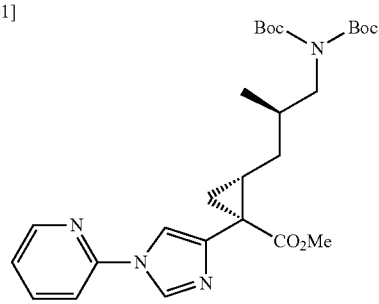

79
-continued

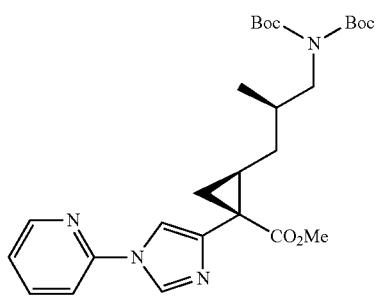

A diastereomeric mixture of the desired compounds (887 mg) was obtained from the compound (1.24 g) obtained in Reference Example 85 in the same way as in Reference Example 4. This mixture was diastereomerically resolved in several portions by preparative HPLC (Daicel CHIRALPAK IC, 20×250 mm, eluting solvent: hexane/ethanol=70/30, 13 mL/min, 210 nm) to respectively obtain methyl (1R,2S)-2-{(2R)-3-[bis(tert-butoxycarbonyl)amino]-2-methylpropyl}-1-(1-pyridin-2-yl-1H-imidazol-4-yl)cyclopropanecarboxylate (236 mg) as the first peak and methyl (1S,2R)-2-{(2R)-3-[bis(tert-butoxycarbonyl)amino]-2-methylpropyl}-1-(1-pyridin-2-yl-1H-imidazol-4-yl)cyclopropanecarboxylate (491 mg) as the second peak. Their purities were confirmed by analytical HPLC (Daicel CHIRALPAK IC, 4.6×150 mm, eluting solvent: hexane/ethanol=70/30, 1.0 mL/min, 210 nm, $t_R$=4.9 minutes (first peak), $t_R$=5.6 minutes (second peak)).

(1R,2S)-isomer: $^1$H-NMR (CDCl$_3$) δ: 0.93 (3H, d, J=6.7 Hz), 1.50 (18H, s), 1.50-1.65 (4H, m), 1.78-1.85 (1H, m), 1.94-2.04 (1H, m), 3.47 (1H, dd, J=13.7, 8.2 Hz), 3.58 (1H, dd, J=13.7, 6.3 Hz), 3.74 (3H, s), 7.20-7.23 (1H, m), 7.37 (1H, d, J=8.2 Hz), 7.77 (1H, d, J=1.6 Hz), 7.78-7.83 (1H, m), 8.24 (1H, d, J=1.6 Hz), 8.45-8.47 (1H, m).

(1S,2R)-isomer: $^1$H-NMR (CDCl$_3$) δ: 0.97 (3H, d, J=6.7 Hz), 1.39-1.48 (1H, m), 1.49 (18H, s), 1.64-1.74 (3H, m), 1.78-1.86 (1H, m), 1.91-2.00 (1H, m), 3.42 (1H, dd, J=14.0, 8.0 Hz), 3.56 (1H, dd, J=14.0, 6.7 Hz), 3.75 (3H, s), 7.20-7.23 (1H, m), 7.34-7.37 (1H, m), 7.77 (1H, d, J=1.6 Hz), 7.78-7.83 (1H, m), 8.24 (1H, d, J=1.6 Hz), 8.45-8.47 (1H, m).

Reference Example 87 di-tert-Butyl [(2S)-2-methyl-4-oxobutyl]imidodicarbonate

[Formula 102]

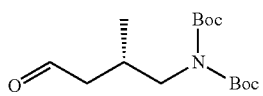

The title compound (2.79 g) was obtained from (2S)-4-{[tert-butyl(diphenyl)silyl]oxy}-2-methylbutan-1-ol (Org. Lett., 2010, vol. 12, p. 340) (6.66 g) in the same way as in Reference Examples 82, 83 and 84.

Reference Example 88

Methyl (2Z,5S)-6-[bis(tert-butoxycarbonyl)amino]-5-methyl-2-(1-pyridin-2-yl-1H-imidazol-4-yl)hex-2-enoate

[Formula 103]

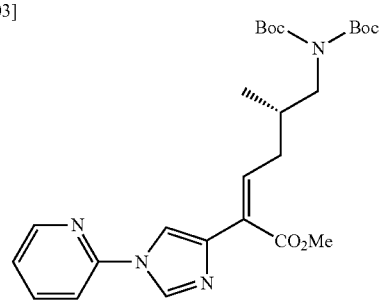

The title compound (1.33 g) was obtained from the compound (1.37 g) obtained in Reference Example 81 and the compound (2.66 g) obtained in Reference Example 87 in the same way as in Reference Examples 2 and 3.

Reference Example 89

Methyl (1R,2S)-2-{(2S)-3-[bis(tert-butoxycarbonyl)amino]-2-methylpropyl}-1-(1-pyridin-2-yl-1H-imidazol-4-yl)cyclopropanecarboxylate and methyl (1S,2R)-2-{(2S)-3-[bis(tert-butoxycarbonyl)amino]-2-methylpropyl}-1-(1-pyridin-2-yl-1H-imidazol-4-yl)cyclopropanecarboxylate

[Formula 104]

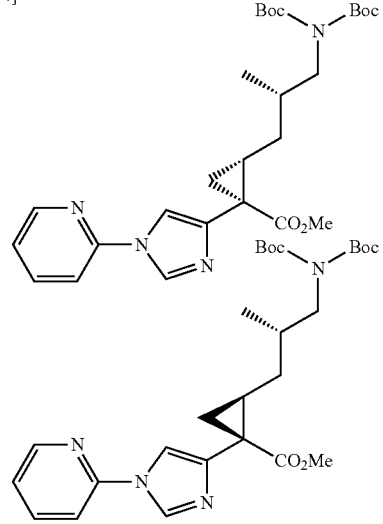

A diastereomeric mixture of the desired compounds was obtained (880 mg) from the compound (1.33 g) obtained in Reference Example 88 in the same way as in Reference Example 4. This mixture was diastereomerically resolved in several portions by preparative HPLC (Daicel CHIRALPAK IC, 20×250 mm, eluting solvent: hexane/ethanol=65/35, 10 mL/min, 210 nm) to respectively obtain methyl (1R,2S)-2-{(2S)-3-[bis(tert-butoxycarbonyl)amino]-2-methylpropyl}-1-(1-pyridin-2-yl-1H-imidazol-4-yl)cyclopropanecarboxylate (532 mg) as the first peak and methyl (1S,2R)-2-{(2S)-3-[bis(tert-butoxycarbonyl)amino]-2-methylpropyl}-1-(1- pyridin-2-yl-1H-imidazol-4-yl)cyclopropanecarboxylate (221 mg) as the second peak. Their purities were confirmed by analytical HPLC (Daicel CHIRALPAK IC 4.6×150 mm, eluting solvent: hexane/ethanol=60/40, 1.0 mL/min, 210 nm, $t_R$=3.8 min (first peak), $t_R$=4.8 min (second peak)).

(1R,2S)-isomer: $^1$H-NMR (CDCl$_3$) δ: 0.97 (3H, d, J=7.0 Hz), 1.39-1.49 (1H, m), 1.49 (18H, s), 1.64-1.74 (3H, m), 1.78-1.85 (1H, m), 1.91-2.00 (1H, m), 3.42 (1H, dd, J=13.9, 8.0 Hz), 3.56 (1H, dd, J=13.9, 6.7 Hz), 3.75 (3H, s), 7.20-7.24 (1H, m), 7.34-7.37 (1H, m), 7.77 (1H, d, J=1.6 Hz), 7.78-7.83 (1H, m), 8.24 (1H, d, J=1.6 Hz), 8.46-8.47 (1H, m).

(1S,2R)-isomer: $^1$H-NMR (CDCl$_3$) δ: 0.93 (3H, d, J=7.0 Hz), 1.50 (18H, s), 1.51-1.65 (4H, m), 1.78-1.85 (1H, m), 1.94-2.03 (1H, m), 3.47 (1H, dd, J=13.9, 8.2 Hz), 3.58 (1H, dd, J=13.9, 6.5 Hz), 3.74 (3H, s), 7.20-7.24 (1H, m), 7.36-7.38 (1H, m), 7.77 (1H, d, J=1.6 Hz), 7.79-7.83 (1H, m), 8.25 (1H, d, J=1.6 Hz), 8.46-8.47 (1H, m).

Reference Example 90

Methyl [1-(5-methylpyridin-2-yl)-1H-imidazol-4-yl]acetate

[Formula 105]

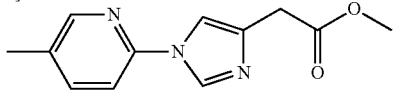

The compound (4.6 g) obtained in Reference Example 61 was dissolved in ethanol (40 mL) and a 5 N aqueous sodium hydroxide solution (20 mL), and the solution was heated to reflux for 2 hours. The reaction solution was concentrated under reduced pressure. The obtained residue was dissolved in methanol (60 mL). To the solution, thionyl chloride (5.1 mL) was added dropwise, and the mixture was heated to reflux for 3 hours. The reaction solution was concentrated, and the residue was neutralized with a saturated aqueous solution of sodium bicarbonate, followed by extraction with methylene chloride. The organic layer was washed with saturated sodium chloride solution and dried over anhydrous sodium sulfate. The obtained residue was purified by silica gel column chromatography (eluting solvent: methylene chloride/ethyl acetate=80/20→50/50) to obtain the title compound (1.9 g).

$^1$H-NMR (CDCl$_3$) δ: 2.38 (3H, s), 3.75 (5H, s), 7.24-7.27 (1H, m), 7.59 (1H, s), 7.62-7.64 (1H, m), 8.29-8.31 (2H, m).

Reference Example 91

Methyl (2Z,5R)-6-[bis(tert-butoxycarbonyl)amino]-5-methyl-2-[1-(5-methylpyridin-2-yl)-1H-imidazol-4-yl]hex-2-enoate

[Formula 106]

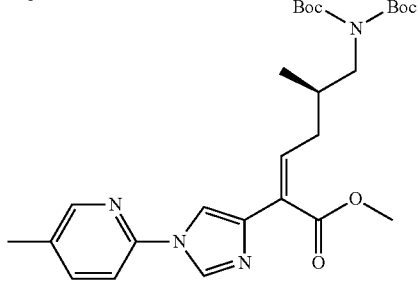

The title compound (0.4 g) was obtained from the compound (1.9 g) obtained in Reference Example 90 and the compound (3.2 g) obtained in Reference Example 84 in the same way as in Reference Examples 2 and 3.

$^1$H-NMR (CDCl$_3$) δ: 0.96 (3H, d, J=6.7 Hz), 1.51. (18H, s), 2.06-2.14 (1H, m), 2.32-2.40 (1H, m), 2.38 (3H, s), 2.53-2.60 (1H, m), 3.49-3.61 (2H, m), 3.88 (3H, s), 7.01 (1H, t, J=7.8 Hz), 7.25 (1H, d, J=8.2 Hz), 7.62 (1H, dd, J=8.2, 2.4 Hz), 7.72 (1H, s), 8.28-8.29 (1H, m).

Reference Example 92

Methyl (1R,2S)-2-{(2R)-3-[bis(tert-butoxycarbonyl)amino]-2-methylpropyl}-1-[1-(5-methylpyridin-2-yl)-1H-imidazol-4-yl]cyclopropanecarboxylate and methyl (1S,2R)-2-{(2R)-3-[bis(tert-butoxycarbonyl)amino]-2-methylpropyl}-1-[1-(5-methylpyridin-2-yl)-1H-imidazol-4-yl]cyclopropanecarboxylate

[Formula 107]

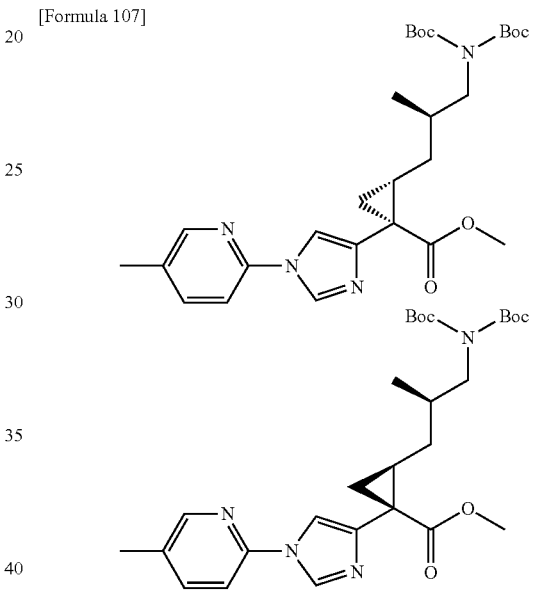

A diastereomeric mixture (537 mg) was obtained from the compound (608 mg) obtained in Reference Example 91 in the same way as in Reference Example 4 and then purified in several portions by HPLC (Chiral Pak IC, 2.0×25 cm, eluting solvent: hexane/isopropanol=60/40, 10 mL/min) to obtain methyl (1R,2S)-2-{(2R)-3-[bis(tert-butoxycarbonyl)amino]-2-methylpropyl}-1-[1-(5-methylpyridin-2-yl)-1H-imidazol-4-yl]cyclopropanecarboxylate (145 mg) and methyl (1S,2R)-2-{(2R)-3-[bis(tert-butoxycarbonyl)amino]-2-methylpropyl}-1-[1-(5-methylpyridin-2-yl)-1H-imidazol-4-yl]cyclopropanecarboxylate (316 mg). The compounds were analyzed using Chiral Pak IC (4.6×150 mm, eluting solvent: hexane/isopropanol=70/30, 1.0 mL/min). Retention time: (1R,2S) form: 5.9 minutes, (1S,2R) form: 6.6 minutes.

(1R,2S)-form: $^1$H-NMR (CDCl$_3$) δ: 0.93 (1H, d, J=6.7 Hz), 1.55-1.65 (4H, m), 1.77-1.83 (1H, m), 1.94-2.02 (1H, m), 2.37 (3H, s), 3.43-3.60 (2H, m), 3.73 (3H, s), 7.25-7.27 (1H, m), 7.60 (1H, dd, J=8.2, 2.0 Hz), 7.73 (1H, d, J=1.2 Hz), 8.19 (1H, d, J=1.2 Hz), 8.25-8.28 (1H, m).

(1S,2R)-form: $^1$H-NMR (CDCl$_3$) δ: 0.97 (3H, d, J=6.7 Hz), 1.65-1.74 (4H, m), 1.77-1.85 (1H, m), 1.91-2.00 (1H, m), 2.37 (3H, s), 3.42 (1H, dd, J=13.8, 6.7 Hz), 3.56 (1H, dd, J=13.7, 6.7 Hz), 3.75 (3H, s), 7.24-7.27 (1H, m), 7.60 (1H, dd, J=7.8, 2.4 Hz), 7.73 (1H, d, J=1.6 Hz), 8.19 (1H, d, J=1.6 Hz), 8.27-8.28 (1H, m).

Reference Example 93

(3R)-1,1-Dimethoxy-3-(nitromethyl)pentane

[Formula 108]

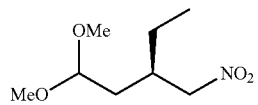

Nitromethane (4.33 mL) was added to a solution of trans-2-pentenal (2.27 g) and (2S)-2-{diphenyl[(trimethylsilyl)oxy]methyl}pyrrolidine (Org. Lett., 2007, vol. 9, p. 5307) (920 mg) in methanol (54 mL) with stirring at room temperature. The mixture was stirred at room temperature for 4 days. Then, trimethyl orthoformate (17.7 mL) and p-toluenesulfonic acid monohydrate (1.03 g) were added to the reaction solution, and the mixture was further stirred overnight. The reaction solution was concentrated, and a saturated aqueous solution of sodium bicarbonate was added to the residue, followed by extraction with ethyl acetate. The organic layer was washed with saturated sodium chloride solution and then dried over anhydrous sodium sulfate. Filtration and concentration under reduced pressure were performed to obtain the title compound (4.81 g).

$^1$H-NMR (CDCl$_3$) δ: 0.96 (3H, t, J=7.4 Hz), 1.45 (2H, dq, J=7.0, 7.4 Hz), 1.64 (1H, ddd, J=14.5, 7.4, 5.9 Hz), 1.72 (1H, ddd, J=14.5, 5.5, 5.5 Hz), 2.26-2.36 (1H, m), 3.32 (3H, s), 3.33 (3H, s), 4.33 (1H, dd, J=12.5, 7.0 Hz), 4.44-4.49 (2H, m).

Reference Example 94

(2R)-2-Ethyl-4,4-dimethoxybutan-1-amine

[Formula 109]

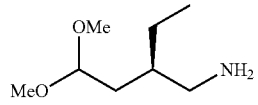

A solution of the compound (2.81 g) obtained in Reference Example 93 in tetrahydrofuran (30 mL) was slowly added to a suspension of lithium aluminum hydride (1.67 g) in tetrahydrofuran (30 mL) with stirring at 0° C. The mixture was heated to room temperature and stirred for 3 hours. Then, water (1.7 mL), a 15% aqueous sodium hydroxide solution (1.7 mL), and water (5.1 mL) were added in this order to the reaction solution under ice cooling, and the mixture was heated to room temperature and stirred overnight. The reaction mixture was filtered through celite and concentrated under reduced pressure to obtain the title compound (2.21 g).

$^1$H-NMR (CDCl$_3$) δ: 0.90 (3H, t, J=7.4 Hz), 1.33-1.47 (3H, m), 1.56-1.60 (2H, m), 2.65 (2H, d, J=5.5 Hz), 3.32 (3H, s), 3.33 (3H, s), 4.47 (1H, t, J=5.7 Hz).

Reference Example 95 tert-Butyl [(2R)-2-ethyl-4,4-dimethoxybutyl]carbamate

[Formula 110]

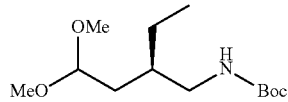

The compound (2.21 g) obtained in Reference Example 94 was dissolved in a mixed solvent of acetone (60 mL) and water (15 mL). To the solution, sodium bicarbonate (6.91 g) and di-tert-butyl dicarbonate (4.49 g) were added with stirring at room temperature. The mixture was stirred overnight at room temperature, and the reaction solution was then concentrated. To the residue, water was added, followed by extraction with ethyl acetate. The organic layer was washed with saturated sodium chloride solution and dried over anhydrous sodium sulfate. After filtration and concentration under reduced pressure, the obtained crude product was purified by silica gel column chromatography to obtain the title compound (1.85 g).

$^1$H-NMR (CDCl$_3$) δ: 0.91 (3H, t, J=7.4 Hz), 1.30-1.37 (2H, m), 1.44 (9H, s), 1.53-1.59 (3H, m), 3.01-3.08 (1H, m), 3.13-3.19 (1H, m), 3.33 (3H, s), 3.33 (3H, s), 4.46 (1H, t, J=5.5 Hz), 4.73 (1H, br s).

Reference Example 96 di-tert-Butyl [(2R)-2-ethyl-4-oxobutyl]imidodicarbonate

[Formula 111]

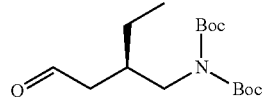

A solution of n-butyllithium in hexane (1.65 M, 6.18 mL) was added dropwise to a solution of the compound (2.54 g) obtained in Reference Example 95 in tetrahydrofuran (40 mL) with stirring at 0° C. The mixture was stirred for 30 minutes. Then, a solution of di-tert-butyl dicarbonate (2.23 g) in tetrahydrofuran (20 mL) was added dropwise thereto, and the mixture was heated to room temperature and stirred for 1 hour. The reaction solution was separated into aqueous and organic layers by the addition of an aqueous ammonium chloride solution, followed by extraction with ethyl acetate. The organic layer was washed with a saturated aqueous solution of sodium bicarbonate and saturated sodium chloride solution and dried over anhydrous sodium sulfate. After filtration and concentration under reduced pressure, the obtained residue was dissolved in a mixed solvent of acetic acid (20 mL) and water (10 mL). The solution was stirred overnight at room temperature, and saturated sodium chloride solution was then added to the reaction solution, followed by extraction with hexane. The organic layer was washed with a saturated aqueous solution of sodium bicarbonate and saturated sodium chloride solution and dried over anhydrous sodium sulfate. After filtration and concentration under reduced pressure, the obtained crude product was purified by silica gel column chromatography to obtain the title compound (1.94 g).

$^1$H-NMR (CDCl$_3$) δ: 0.92 (3H, t, J=7.6 Hz), 1.30-1.49 (2H, m), 1.51 (18H, s), 2.27-2.46 (3H, m), 3.53 (1H, dd, J=14.1, 8.2 Hz), 3.63 (1H, dd, J=14.1, 5.9 Hz), 9.75 (1H, t, J=2.0 Hz).

Reference Example 97

Methyl (2Z,5R)-5-{[bis(tert-butoxycarbonyl)amino]methyl}-2-(1-pyridin-2-yl-1H-imidazol-4-yl)hept-2-enoate

[Formula 112]

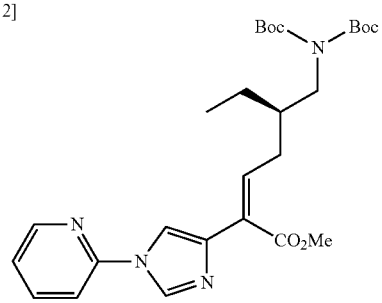

The title compound (1.06 g) was obtained from the compound (1.33 g, 6.12 mmol) obtained in Reference Example 81 and the compound (1.93 g) obtained in Reference Example 96 in the same way as in Reference Examples 2 and 3.

$^1$H-NMR (CDCl$_3$) δ: 0.93 (3H, t, J=7.4 Hz), 1.34-1.50 (2H, m), 1.50 (18H, s), 1.90-1.97 (1H, m), 2.47-2.59 (2H, m), 3.58 (1H, dd, J=14.1, 7.8 Hz), 3.64 (1H, dd, J=14.1, 6.6 Hz), 3.88 (3H, s), 7.06 (1H, t, J=7.6 Hz), 7.24-7.26 (1H, m), 7.37 (1H, d, J=8.2 Hz), 7.79 (1H, br s), 7.81-7.86 (1H, m), 8.40 (1H, br s), 8.48-8.49 (1H, m).

Reference Example 98

Methyl (1R,2S)-2-[(2R)-2-{[bis(tert-butoxycarbonyl)amino]methyl}butyl]-1-(1-pyridin-2-yl-1H-imidazol-4-yl)cyclopropanecarboxylate and methyl (1S,2R)-2-[(2R)-2-{[bis(tert-butoxycarbonyl)amino]methyl}butyl]-1-(1-pyridin-2-yl-1H-imidazol-4-yl)cyclopropanecarboxylate

[Formula 113]

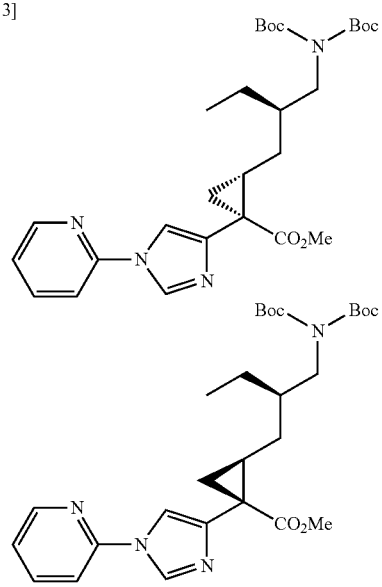

A diastereomeric mixture of the desired compounds was obtained (871 mg) from the compound (960 mg) obtained in Reference Example 97 in the same way as in Reference Example 4. This mixture was diastereomerically resolved in several portions by preparative HPLC (Daicel CHIRALPAK IC, 20×250 mm, eluting solvent: hexane/ethanol=75/25, 10 mL/min, 210 nm) to respectively obtain methyl (1R,2S)-2-[(2R)-2-{[bis(tert-butoxycarbonyl)amino]methyl}butyl]-1-(1-pyridin-2-yl-1H-imidazol-4-yl)cyclopropanecarboxylate (249 mg) as the first peak and methyl (1S,2R)-2-[(2R)-2-{[bis(tert-butoxycarbonyl)amino]methyl}butyl]-1-(1-pyridin-2-yl-1H-imidazol-4-yl)cyclopropanecarboxylate (387 mg) as the second peak. Their purities were confirmed by analytical HPLC (Daicel CHIRALPAK IC, 4.6×150 mm, eluting solvent: hexane/ethanol=80/20, 1.0 mL/min, 210 nm, $t_R$=6.6 minutes (first peak), $t_R$=7.9 minutes (second peak)).

(1R,2S)-form: $^1$H-NMR (CDCl$_3$) δ: 0.89 (3H, t, J=7.4 Hz), 1.33-1.40 (2H, m), 1.46-1.71 (4H, m), 1.49 (18H, s), 1.75-1.88 (2H, m), 3.59 (1H, dd, J=13.9, 7.6 Hz), 3.65 (1H, dd, J=13.9, 6.8 Hz), 3.73 (3H, s), 7.21-7.24 (1H, m), 7.41 (1H, d, J=8.2 Hz), 7.79-7.83 (2H, m), 8.31 (1H, br s), 8.46-8.48 (1H, m).

(1S,2R)-form: $^1$H-NMR (CDCl$_3$) δ: 0.91 (3H, t, J=7.4 Hz), 1.39-1.45 (2H, m), 1.49 (18H, s), 1.53-1.70 (4H, m), 1.76-1.82 (2H, m), 3.53 (1H, dd, J=13.7, 7.0 Hz), 3.58 (1H, dd, J=13.7, 7.4 Hz), 3.75 (3H, s), 7.22-7.25 (1H, m), 7.38 (1H, d, J=8.2 Hz), 7.80-7.84 (2H, m), 8.31 (1H, br s), 8.46-8.48 (1H, m).

Reference Example 99

[1-(4-Methylpyridin-2-yl)-1H-imidazol-4-yl]acetonitrile

[Formula 114]

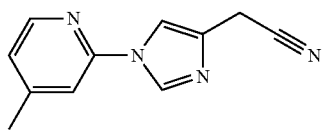

The title compound (630 mg) was obtained from 1H-imidazol-4-ylacetonitrile (800 mg) and 2-fluoro-4-picoline (0.85 mL) in the same way as in Reference Example 55.

$^1$H-NMR (CDCl$_3$) δ: 2.46 (3H, s), 3.78 (2H, s), 7.09 (1H, d, J=5.1 Hz), 7.17 (1H, s), 7.67 (1H, d, J=1.2 Hz), 8.30 (1H, d, J=1.2 Hz), 8.33 (1H, d, J=5.1 Hz).

Reference Example 100

Methyl [1-(4-methylpyridin-2-yl)-1H-imidazol-4-yl]acetate

[Formula 115]

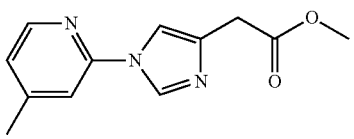

The title compound (441 mg) was obtained from the compound (630 mg) obtained in Reference Example 99 in the same way as in Reference Example 90.

$^1$H-NMR (CDCl$_3$) δ: 2.44 (3H, s), 3.73 (2H, s), 3.75 (3H, s), 7.05 (1H, d, J=5.1 Hz), 7.16 (1H, s), 7.59 (1H, s), 8.29 (1H, s), 8.32 (1H, d, J=5.1 Hz).

Reference Example 101

Methyl (2Z)-6-[bis(tert-butoxycarbonyl)amino]-2-[1-(4-methylpyridin-2-yl)-1H-imidazol-4-yl]hex-2-enoate

[Formula 116]

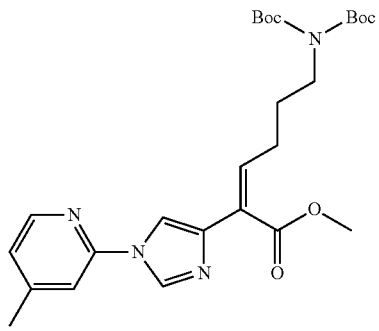

The title compound (124 mg) was obtained from the compound (441 mg) obtained in Reference Example 100 and di-tert-butyl(4-oxobutyl)imidodicarbonate (337 mg) in the same way as in Reference Examples 2 and 3.

$^1$H-NMR (CDCl$_3$) δ: 1.51 (18H, s), 1.78-1.85 (2H, m), 2.44 (3H, s), 2.50-2.60 (2H, m), 3.65 (2H, t, J=7.2 Hz), 3.88 (3H, s), 7.02-7.06 (2H, m), 7.16 (1H, d, J=0.8 Hz), 7.76 (1H, d, J=1.2 Hz), 8.31 (1H, d, J=1.2 Hz), 8.33 (1H, s).

Reference Example 102

Methyl (1R*,2S*)-2-{3-[bis(tert-butoxycarbonyl)amino]propyl}-1-[1-(4-methylpyridin-2-yl)-1H-imidazol-4-yl]cyclopropanecarboxyliate

[Formula 117]

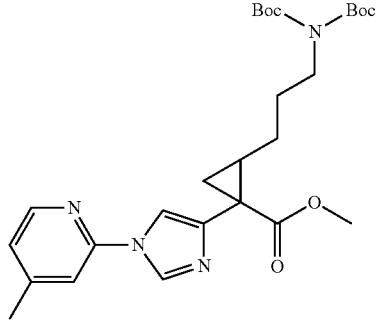

The title compound (97.5 mg) was obtained from the compound (124 mg) obtained in Reference Example 101 in the same way as in Reference Example 4.

$^1$H-NMR (CDCl$_3$) δ: 1.50 (18H, s), 1.60-1.75 (6H, m), 1.78-1.86 (1H, m), 2.43 (3H, s), 3.60 (2H, t, J=7.4 Hz), 3.75 (3H, s), 7.04 (1H, d, J=5.1 Hz), 7.16 (1H, s), 7.72 (1H, d, J=1.2 Hz), 8.20-8.22 (1H, m), 8.30 (1H, d, J=5.1 Hz).

Reference Example 103

[1-(6-Methylpyridin-2-yl)-1H-imidazol-4-yl]acetonitrile

[Formula 118]

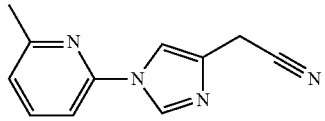

The title compound (960 mg) was obtained from 1H-imidazol-4-ylacetonitrile (800 mg) and 6-fluoro-2-picoline (0.86 mL) in the same way as in Reference Example 55.

$^1$H-NMR (CDCl$_3$) δ: 2.58 (3H, s), 3.78 (2H, s), 7.11-7.16 (2H, m), 7.69-7.74 (2H, m), 8.29 (1H, d, J=1.2 Hz).

Reference Example 104

Methyl [1-(6-methylpyridin-2-yl)-1H-imidazol-4-yl]acetate

[Formula 119]

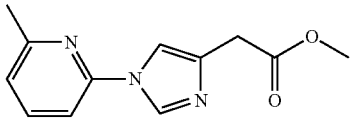

The title compound (448.3 mg) was obtained from the compound (960 mg) obtained in Reference Example 103 in the same way as in Reference Example 90.

$^1$H-NMR (CDCl$_3$) δ: 2.56 (3H, s), 3.73 (2H, s), 3.75 (3H, s), 7.08 (1H, d, J=7.6 Hz), 7.13 (1H, d, J=7.6 Hz), 7.61 (1H, s), 7.69 (1H, t, J=7.6 Hz), 8.29 (1H, s).

Reference Example 105

Methyl (2Z)-6-[bis(tert-butoxycarbonyl)amino]-2-[1-(6-methylpyridin-2-yl)-1H-imidazol-4-yl]hex-2-enoate

[Formula 120]

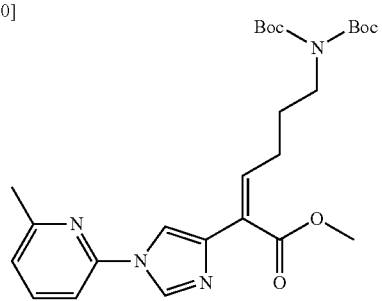

The title compound (200 mg) was obtained from the compound (448.3 mg) obtained in Reference Example 104 and di-tert-butyl(4-oxobutyl)imidodicarbonate (420 mg) in the same way as in Reference Examples 2 and 3.

$^1$H-NMR (CDCl$_3$) δ: 1.51 (18H, s), 1.78-1.85 (2H, m), 2.49-2.57 (2H, m), 2.57 (3H, s) 3.65 (2H, t, J=7.4 Hz), 3.88 (3H, s), 7.02 (1H, t, J=7.8 Hz), 7.08 (1H, d, J=7.4 Hz), 7.14 (1H, d, J=8.2 Hz), 7.68 (1H, t, J=7.8 Hz), 7.77 (1H, d, J=1.2 Hz), 8.31 (1H, d, J=1.2 Hz).

Reference Example 106

Methyl (1R*,2S*)-2-{3-[bis(tert-butoxycarbonyl)amino]propyl}-1-[1-(6-methylpyridin-2-yl)-1H-imidazol-4-yl]cyclopropanecarboxylate

[Formula 121]

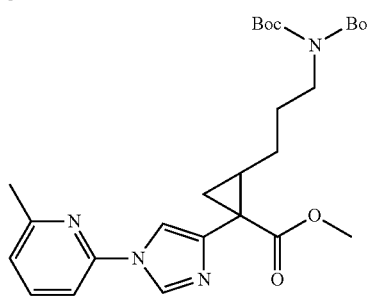

The title compound (123 mg) was obtained from the compound (200 mg) obtained in Reference Example 105 in the same way as in Reference Example 4.

¹H-NMR (CDCl₃) δ: 1.50 (18H, s), 1.60-1.74 (6H, m), 1.80-1.83 (1H, m), 2.56 (3H, s), 3.60 (2H, t, J=7.6 Hz), 3.74 (3H, s), 7.06 (1H, dd, J=7.4, 0.8 Hz), 7.15 (1H, d, J=8.2 Hz), 7.68 (1H, dt, J=7.8, 0.8 Hz), 7.72-7.74 (1H, m), 8.21-8.22 (1H, m).

Reference Example 107

(3R)-1,1-Dimethoxy-3-(nitromethyl)hexane

[Formula 122]

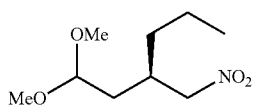

The title compound (5.27 g) was obtained from trans-2-hexenal (3.00 g) in the same way as in Reference Example 93.

¹H-NMR (CDCl₃) δ: 0.93 (3H, t, J=7.2 Hz), 1.33-1.76 (6H, m), 2.31-2.41 (1H, m), 3.33 (6H, s), 4.32 (1H, dd, J=12.3, 6.8 Hz), 4.46 (1H, dd, J=12.3, 6.5 Hz), 4.54 (1H, dd, J=6.7, 4.7 Hz).

Reference Example 108 tert-Butyl [(2R)-2-(2,2-dimethoxyethyl)pentyl]carbamate

[Formula 123]

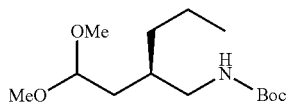

The title compound (1.59 g) was obtained from the compound (5.27 g) obtained in Reference Example 107 in the same way as in Reference Examples 94 and 95.

¹H-NMR (CDCl₃) δ: 0.90 (3H, t, J=7.0 Hz), 1.22-1.37 (4H, m), 1.44 (9H, s), 1.55-1.58 (2H, m), 1.61-1.66 (1H, m), 2.99-3.06 (1H, m), 3.13-3.19 (1H, m), 3.33 (3H, s), 3.33 (3H, s), 4.46 (1H, t, J=5.7 Hz), 4.73 (1H, br s).

Reference Example 109 di-tert-Butyl [(2R)-2-(2-oxoethyl)pentyl]imidodicarbonate

[Formula 124]

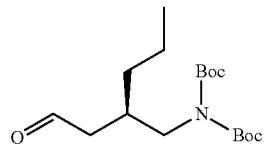

The title compound (1.11 g) was obtained from the compound (1.59 g) obtained in Reference Example 108 in the same way as in Reference Example 96.

¹H-NMR (CDCl₃) δ: 0.90 (3H, t, J=6.8 Hz), 1.22-1.38 (4H, m), 1.51 (18H, s), 2.30-2.45 (3H, m), 3.53 (1H, dd, J=14.1, 7.8 Hz), 3.62 (1H, dd, J=14.1, 5.5 Hz), 9.74 (1H, t, J=1.8 Hz).

Reference Example 110

(1R)-1-Phenylethyl (1-pyridin-2-yl-1H-imidazol-4-yl)acetate

[Formula 125]

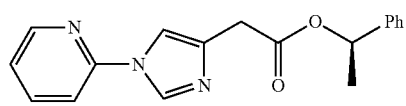

The compound (63.4 g) obtained in Reference Example 80 was suspended in methylene chloride (1000 mL). To the suspension, (R)-(+)-phenylethyl alcohol (37.7 mL), 1-ethyl-3-(3-dimethylaminopropyl)carbodiimide hydrochloride (72 g), and N,N-dimethylaminopyridine (45.7 g) were added, and the mixture was stirred at room temperature for 21 hours. To the reaction solution, water was added, followed by extraction with methylene chloride. The organic layer was washed with a saturated aqueous solution of sodium bicarbonate, a saturated aqueous solution of ammonium chloride, and saturated sodium chloride solution and dried over anhydrous sodium sulfate. The obtained residue was purified by silica gel column chromatography (eluting solvent: methylene chloride→methylene chloride/methanol=90/10) to obtain the title compound (94.9 g).

¹H-NMR (CDCl₃) δ: 1.58 (3H, d, J=7.8 Hz), 3.75 (2H, d, J=4.3 Hz), 5.96 (1H, q, J=6.7 Hz), 7.21-7.24 (1H, m), 7.27-7.39 (7H, m), 7.56 (1H, s), 7.80 (1H, tt, J=7.8, 1.6 Hz), 8.32 (1H, s), 8.46 (1H, d, J=5.1 Hz).

Reference Example 111

(1R)-1-Phenylethyl (2Z,5R)-5-{[bis(tert-butoxycarbonyl)amino]methyl}-2-(1-pyridin-2-yl-1H-imidazol-4-yl)oct-2-enoate

[Formula 126]

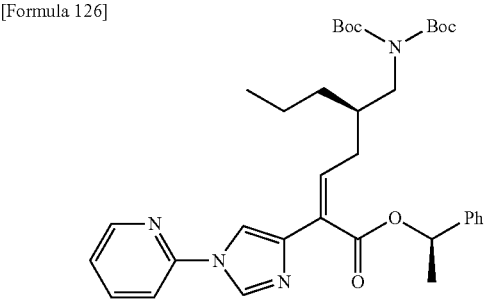

The title compound (559 mg) was obtained from the compound (860 mg) obtained in Reference Example 110 and the compound (1.11 g) obtained in Reference Example 109 in the same way as in Reference Examples 2 and 3.

$^1$H-NMR (CDCl$_3$) δ: 0.86 (3H, t, J=6.8 Hz), 1.27-1.46 (4H, m), 1.49 (18H, s), 1.69 (3H, d, J=6.7 Hz), 1.96-2.03 (1H, m), 2.46-2.63 (2H, m), 3.55 (1H, dd, J=14.1, 7.0 Hz), 3.61 (1H, dd, J=14.1, 7.2 Hz), 6.12 (1H, q, J=6.7 Hz), 7.02 (1H, t, J=7.8 Hz), 7.16-7.19 (1H, m), 7.21-7.24 (1H, m), 7.30-7.39 (3H, m), 7.44-7.46 (2H, m), 7.59 (1H, br s), 7.76-7.81 (1H, m), 8.38 (1H, br s), 8.45-8.46 (1H, m).

Reference Example 112

(1R)-1-Phenylethyl (1R,2S)-2-[(2R)-2-{[bis(tert-butoxycarbonyl)amino]methyl}pentyl]-1-(1-pyridin-2-yl-1H-imidazol-4-yl)cyclopropanecarboxylate and (1R)-1-phenylethyl (1S,2R)-2-[(2R)-2-{[bis(tert-butoxycarbonyl)amino]methyl}pentyl]-1-(1-pyridin-2-yl-1H-imidazol-4-yl)cyclopropanecarboxylate

[Formula 127]

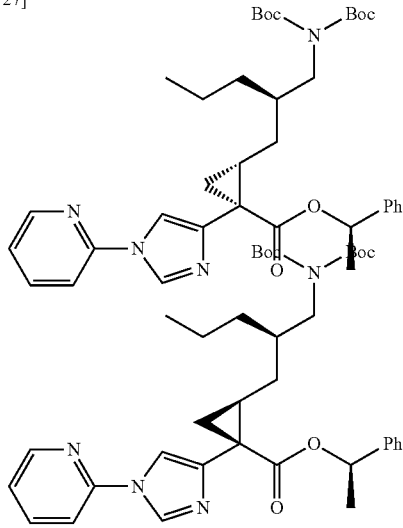

A mixture of the title compounds was obtained from the compound (559 mg) obtained in Reference Example 112 in the same way as in Reference Example 4. This mixture was purified by silica gel column chromatography (hexane/ethyl acetate) to obtain (1R)-1-phenylethyl (1R,2S)-2-{[bis(tert-butoxycarbonyl)amino]methyl}pentyl]-1-(1-pyridin-2-yl-1H-imidazol-4-yl)cyclopropanecarboxylate (189 mg, Rf=0.25, hexane/ethyl acetate=1/1) and (1R)-1-phenylethyl (1S,2R)-2-[(2R)-2-{[bis(tert-butoxycarbonyl)amino]methyl}pentyl]-1-(1-pyridin-2-yl-1H-imidazol-4-yl)cyclopropanecarboxylate (227 mg, Rf=0.35, hexane/ethyl acetate=1/1).

(1R,2S)-form: $^1$H-NMR (CDCl$_3$) δ: 0.81 (3H, t, J=7.0 Hz), 1.03-1.13 (1H, m), 1.15-1.31 (3H, m), 1.42-1.84 (6H, m), 1.47 (18H, s), 1.57 (3H, d, J=6.5 Hz), 3.53 (1H, dd, J=13.8, 8.0 Hz), 3.60 (1H, dd, J=13.8, 6.6 Hz), 5.95 (1H, q, J=6.5 Hz), 7.22-7.39 (7H, m), 7.79-7.83 (1H, m), 7.89 (1H, br s), 8.34 (1H, br s), 8.46-8.48 (1H, m).

(1S,2R)-form: $^1$H-NMR (CDCl$_3$) δ: 0.85 (3H, t, J=6.1 Hz), 1.19-1.32 (4H, m), 1.43-1.87 (6H, m), 1.48 (18H, s), 1.60 (3H, d, J=6.5 Hz), 3.51 (1H, dd, J=13.9, 8.4 Hz), 3.57 (1H, dd, J=13.9, 6.5 Hz), 5.99 (1H, q, J=6.5 Hz), 7.16-7.23 (2H, m), 7.28-7.42 (5H, m), 7.67 (1H, br s), 7.76-7.80 (1H, m), 8.29 (1H, br s), 8.44-8.46 (1H, m).

Reference Example 113

Methyl (3R)-4-{[tert-butyl(diphenyl)silyl]oxy}-3-methylbutyrate

[Formula 128]

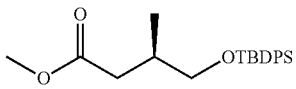

tert-Butyl(chloro)diphenylsilane (26.5 g) was added dropwise to a solution of methyl (R)-4-hydroxy-3-methyl-butyrate (11.0 g) and imidazole (8.5 g) in methylene chloride (200 mL) under ice cooling, and the mixture was then stirred at room temperature for 24 hours. Water was added thereto to separate an organic layer. The organic layer was washed with saturated sodium chloride solution and dried over anhydrous magnesium sulfate. The solvent was distilled off under reduced pressure, and the obtained residue was purified by silica gel column chromatography (eluting solvent: hexane→hexane/ethyl acetate=97/3) to obtain the title compound (29.8 g).

$^1$H-NMR (CDCl3) δ: 0.95 (3H, d, J=6.7 Hz), 1.05 (9H, s), 2.15 (1H, dd, J=14.9, 8.2 Hz), 2.18-2.27 (1H, m), 2.59 (1H, dd, J=14.5, 5.1 Hz), 3.45 (1H, dd, J=9.8, 6.3 Hz), 3.55 (1H, dd, J=9.8, 5.5 Hz), 3.65 (3H, s), 7.36-7.44 (6H, m), 7.64-7.66 (4H, m).

LRMS (ESI) m/z 371 (M+H)$^+$.

Reference Example 114

(3R)-4-{[tert-Butyl(diphenyl)silyl]oxy}-3-methylbutan-1-ol

[Formula 129]

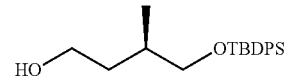

The compound (1.0 g) obtained in Reference Example 113 dissolved in anhydrous tetrahydrofuran (5.0 mL) was cooled to −78° C. under a nitrogen atmosphere, and diisobutyl aluminum hydride (1.0 M tetrahydrofuran solution, 8.1 mL) was added dropwise thereto over 5 minutes. The mixture was stirred at the same temperature for approximately 2 hours. Then, a saturated aqueous solution of ammonium chloride was added thereto, and the mixture was stirred for 10 minutes. The cooling bath was removed, and the reaction mixture was further stirred for 30 minutes. Insoluble matter was filtered off through celite, and the filtrate was subjected to extraction with ethyl acetate. The organic layer was dried over anhydrous magnesium sulfate. The solvent was distilled off under reduced pressure, and the obtained residue was purified by silica gel column chromatography (eluting solvent: hexane→hexane/ethyl acetate=90/10) to obtain the title compound (0.72 g).

$^1$H-NMR (CDCl3) δ: 0.90 (3H, d, J=6.7 Hz), 1.06 (9H, s), 1.48-1.57 (1H, m), 1.64-1.73 (1H, m), 1.77-1.88 (1H, m), 2.05 (1H, t, J=5.5 Hz), 3.48-3.55 (2H, m), 3.63-3.76 (2H, m), 7.37-7.46 (6H, m), 7.65-7.69 (4H, m).

LRMS (ESI) m/z 343 (M+H)$^+$, 365 (M+Na)$^+$.

Reference Example 115 di-tert-Butyl [(3R)-4-{[tert-butyl(diphenyl)silyl] oxy}-3-methylbutyl]imidodicarbonate

[Formula 130]

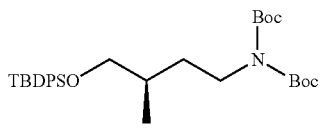

Tributylphosphine (2.4 g) was added at room temperature to 1,1'-(azodicarbonyl)dipiperidine (3.0 g) dissolved in an anhydrous toluene solution (10 mL). The mixture was stirred for 20 minutes, and a solution of the compound (2.0 g) obtained in Reference Example 114 and di-tert-butyl iminodicarboxylate (2.5 g) in toluene (20 mL) was then added dropwise thereto at room temperature over 10 minutes. The mixture was stirred for 15 hours. Then, insoluble matter was filtered off through celite, and this celite was further washed with hexane. The solvent in the obtained filtrate was distilled off under reduced pressure, and the residue was purified by silica gel column chromatography (eluting solvent: hexane→hexane/ethyl acetate=95/5) to obtain the title compound (2.8 g).

$^1$H-NMR (CDCl3) δ: 0.95 (3.0H, d, J=6.7 Hz), 1.05 (9.0H, s), 1.32-1.38 (1.0H, m), 1.48 (18.0H, s), 1.64-1.80 (2.0H, m), 3.45 (1.0H, dd, J=9.8, 5.9 Hz), 3.49 (1.0H, dd, J=9.8, 5.9 Hz), 3.53-3.64 (2.0H, m), 7.35-7.44 (6.0H, m), 7.64-7.67 (4.0H, m).

LRMS (ESI) m/z 564 (M+Na)$^+$.

Reference Example 116 di-tert-Butyl [(3R)-4-hydroxy-3-methylbutyl]imidodicarbonate

[Formula 131]

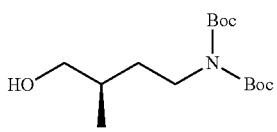

Tetrabutylammonium fluoride (1.0 M tetrahydrofuran solution, 7.7 mL) was added at room temperature to the compound (2.8 g) obtained in Reference Example 115 dissolved in anhydrous tetrahydrofuran (30 mL), and the mixture was stirred for 4 hours. A saturated aqueous solution of ammonium chloride was added thereto, followed by extraction with ethyl acetate. The organic layer was dried over anhydrous magnesium sulfate. The solvent was distilled off under reduced pressure, and the obtained residue was purified by silica gel column chromatography (eluting solvent: hexane→ethyl acetate) to obtain the title compound (1.3 g).

$^1$H-NMR (CDCl3) δ: 0.96 (3H, d, J=6.6 Hz), 1.43-1.72 (21H, m), 3.50 (2H, t, J=5.7 Hz), 3.55-3.68 (2H, m).

LRMS (ESI) m/z 326 (M+Na)$^+$.

Reference Example 117 di-tert-Butyl [(3R)-3-methyl-4-oxobutyl]imidodicarbonate

[Formula 132]

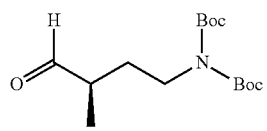

Oxalyl chloride (0.45 mL) dissolved in anhydrous methylene chloride (10 mL) was cooled to −78° C. under a nitrogen atmosphere, and dimethyl sulfoxide (0.74 mL) was added dropwise thereto over 5 minutes. The mixture was stirred at the same temperature for 40 minutes, and the compound (1.1 g) obtained in Reference Example 116 dissolved in anhydrous methylene chloride (10 mL) was then added dropwise thereto over 10 minutes. The mixture was stirred at the same temperature for 1 hour. Then, triethylamine (1.9 mL) was added dropwise thereto over 5 minutes, and the mixture was stirred at the same temperature for 2 hours. Water was added thereto to separate an organic layer. The aqueous layer was further subjected to extraction with methylene chloride. The combined organic layer was dried over anhydrous magnesium sulfate. The solvent was distilled off under reduced pressure, and the obtained residue was purified by silica gel column chromatography (eluting solvent: hexane→hexane/ethyl acetate=95/5) to obtain the title compound (0.8 g).

$^1$H-NMR (CDCl3) δ: 1.15 (3H, d, J=7.0 Hz), 1.51 (18H, s), 1.55-1.67 (1H, m), 1.94-2.06 (1H, m), 2.34-2.43 (1H, m), 3.63 (2H, t, J=7.4 Hz), 9.65 (1H, d, J=1.6 Hz).

LRMS (ESI) m/z 324 (M+Na)$^+$.

Reference Example 118

(1R)-1-Phenylethyl (2Z,4R)-6-[bis(tert-butoxycarbonyl)amino]-4-methyl-2-[1-(pyridin-2-yl)-1H-imidazol-4-yl]hex-2-enoate

[Formula 133]

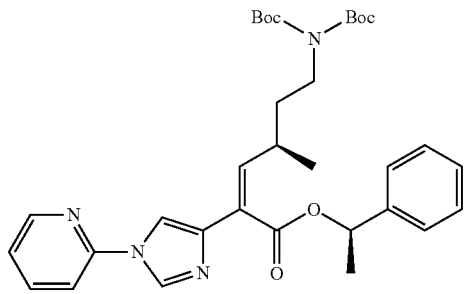

The compound (700 mg) obtained in Reference Example 110 dissolved in anhydrous tetrahydrofuran (10 mL) was cooled to −78° C. under a nitrogen atmosphere. To this solution, lithium bis(trimethylsilyl)amide (1.0 M tetrahydrofuran solution, 2.3 mL) was added dropwise over 10 minutes, and the mixture was stirred at the same temperature for 1 hour. The compound (755 mg) obtained in Reference Example 117 dissolved in anhydrous tetrahydrofuran (10 mL) was added dropwise thereto over 10 minutes, and the mixture was stirred at the same temperature for 5 hours. The mixture was further stirred for 2 hours while the temperature was allowed to spontaneously rise to around −20° C. Then, a saturated aqueous solution of ammonium chloride was added thereto, followed by extraction with ethyl acetate. The organic layer was dried over anhydrous magnesium sulfate. The solvent was distilled off under reduced pressure, and the residue was dried. The obtained residue was dissolved in methylene chloride (20 mL). To the solution, triethylamine (1.89 mL) and methanesulfonyl chloride (0.53 mL) were added under ice cooling, and the mixture was stirred at the same temperature for 10 minutes and further stirred at room temperature for 30 hours. To the reaction solution, 1,8-diazabicyclo[5.4.0]undec-7-ene (0.34 mL) was added at room temperature, and the mixture was stirred for approximately 6 days. A saturated aqueous solution of ammonium chloride was added thereto to separate an organic layer. The aqueous layer was further subjected to extraction with methylene chloride. The combined organic layer was dried over anhydrous magnesium sulfate. The solvent was distilled off under reduced pressure, and the obtained residue was purified by silica gel column chromatography (eluting solvent: methylene chloride→methylene chloride/ethyl acetate=80/20) to respectively obtain crude products of an isomer of the title compound (less polar) and the title compound (more polar). They were further purified by preparative thin-layer chromatography (eluting solvent: hexane/ethyl acetate=2/1) to respectively obtain the isomer of the title compound (132 mg) and the title compound (58 mg).

Title compound ((Z)-form): $^1$H-NMR (CDCl$_3$) δ: 1.14 (3H, d, J=6.7 Hz), 1.47 (18H, s), 1.66-1.72 (5H, m), 2.92-2.99 (1H, m), 3.51-3.55 (2H, m), 6.13 (1H, q, J=6.7 Hz), 6.77 (1H, d, J=10.6 Hz), 7.15-7.47 (7H, m), 7.55 (1H, d, J=1.6 Hz), 7.76-7.80 (1H, m), 8.33 (1H, d, J=1.2 Hz), 8.44-8.46 (1H, m).
LRMS (ESI) m/z 591 (M+H)$^+$.

Isomer of title compound ((E)-form): $^1$H-NMR (CDCl$_3$) δ: 1.14 (3H, d, J=6.7 Hz), 1.48 (18H, s), 1.60 (3H, d, J=6.7 Hz), 1.66-1.72 (2H, m), 3.32-3.39 (1H, m), 3.49-3.61 (2H, m), 6.00 (1H, q, J=6.5 Hz), 6.86 (1H, d, J=10.2 Hz), 7.21-7.40 (7H, m), 7.79-7.83 (2H, m), 8.38 (1H, d, J=1.2 Hz), 8.46-8.48 (1H, m).
LRMS (ESI) m/z 591 (M+H)$^+$.

Reference Example 119

(1R)-1-Phenylethyl 2-{(2R)-4-[bis(tert-butoxycarbonyl)amino]butan-2-yl}-1-[1-(pyridin-2-yl)-1H-imidazol-4-yl]cyclopropanecarboxylate

[Formula 134]

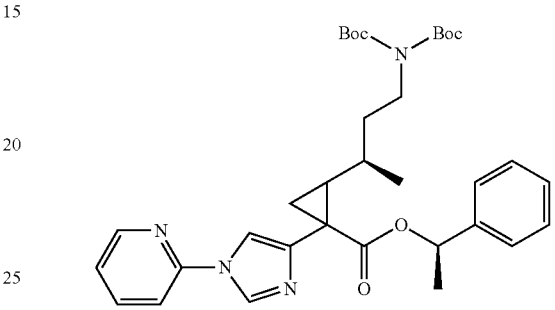

Sodium hydride (63% oil, 15.0 mg) suspended in dimethyl sulfoxide (3.0 mL) was cooled in a water bath. Trimethylsulfoxonium iodide (92.2 mg) was added thereto in several portions. The mixture was stirred at room temperature for 1 hour, and the compound (55.0 mg) obtained in Reference Example 118 dissolved in dimethyl sulfoxide (5.0 mL) was then added dropwise thereto. The mixture was stirred at room temperature for several hours, and ice water was then added thereto, followed by extraction several times with ethyl acetate. The combined organic layer was washed with saturated sodium chloride solution and dried over anhydrous magnesium sulfate. The solvent was distilled off under reduced pressure, and the obtained residue was purified by preparative thin-layer chromatography (eluting solvent: methylene chloride/ethyl acetate=2/1) to obtain the title compound (38 mg).

$^1$H-NMR (CDCl3) δ: 0.89 (1.5H, d, J=5.9 Hz), 1.07 (1.5H, d, J=6.3 Hz), 1.46 (9.0H, s), 1.50 (9.0H, s), 1.53-1.79 (9.0H, m), 3.43-3.69 (2.0H, m), 5.97-6.03 (1.0H, m), 7.19-7.41 (7.0H, m), 7.74-7.83 (2.0H, m), 8.23 (0.5H, d, J=1.2 Hz), 8.27 (0.5H, d, J=1.2 Hz), 8.44-8.48 (1.0H, m).
LRMS (ESI) m/z 591 (M+H)$^+$.

Example 1

(1R*,2S*)-2-(3-Aminopropyl)-1-[1-(3,3-dimethylbutyl)-1H-imidazol-4-yl]cyclopropanecarboxylic acid

[Formula 135]

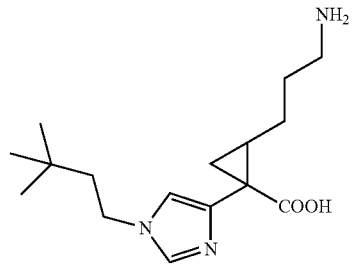

5 N hydrochloric acid (5 mL) was added to the compound (65.2 mg) obtained in Reference Example 4, and the mixture was heated to reflux for 3 hours. The solvent was distilled off under reduced pressure, and the residue was then purified using an ion-exchange resin (DOWEX (registered trademark) 50WX8-200 mesh, 2 g, eluting solvent: water→water/28% ammonia water=97/3) to obtain the title compound (33.4 mg).

$^1$H-NMR (CD$_3$OD) δ: 0.98 (9H, s), 1.17 (1H, dd, J=8.6, 3.9 Hz), 1.29 (1H, dd, J=6.6, 3.9 Hz), 1.37-1.46 (1H, m), 1.56-1.74 (4H, m), 1.75-1.85 (2H, m), 2.85-3.03 (2H, m), 3.92-4.00 (2H, m), 7.09 (1H, s), 7.47 (1H, s).

MS (ESI) m/z 294 (M+H)$^+$.

HRMS (ESI) m/z 294.21763 (M+H)$^+$. (Calcd C$_{16}$H$_{28}$N$_3$O$_2$: 294.21815).

Example 2

(1R*,2R*)-2-(3-Aminopropyl)-1-[1-(3,3-dimethylbutyl)-1H-imidazol-4-yl]cyclopropanecarboxylic acid

[Formula 136]

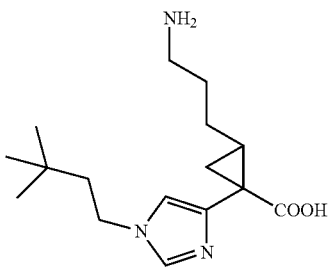

The title compound (25.1 mg) was obtained from the compound (104 mg) obtained in Reference Example 5 in the same way as in Example 1.

$^1$H-NMR (CD$_3$OD) δ: 0.95-1.02 (10H, m), 1.12-1.27 (2H, m), 1.44 (1H, dd, J=9.0, 3.5 Hz), 1.59-1.78 (5H, m), 2.77-2.97 (2H, m), 3.95-4.03 (2H, m), 7.01 (1H, s), 7.53 (1H, s).

MS (ESI) m/z 294 (M+H)$^+$.

HRMS (ESI) m/z 294.21772 (M+H)$^+$. (Calcd C$_{16}$H$_{28}$N$_3$O$_2$: 294.21815).

Example 3

(1R*,2S*)-2-(3-Aminopropyl)-1-(1-propyl-1H-imidazol-4-yl)cyclopropanecarboxylic acid

[Step 1] Methyl (1R*,2S*)-2-{3-[bis(tert-butoxycarbonyl)amino]propyl}-1-(1-propyl-1H-imidazol-4-yl)cyclopropanecarboxylate

[Formula 137]

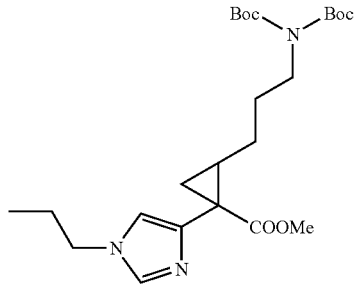

Sodium hydride (63%, 38.8 mg) was added to a solution of the compound (392 mg) obtained in Reference Example 8 in N,N-dimethylformamide (6 mL) with stirring at 0° C. The mixture was stirred at the same temperature for 20 minutes. Then, a solution of 1-iodopropane (173 mg) in N,N-dimethylformamide (2 mL) was added thereto, and the mixture was heated to room temperature and stirred overnight. The reaction solution was separated into aqueous and organic layers by the addition of water, followed by extraction with ethyl acetate. The organic layer was washed with saturated sodium chloride solution and then dried over anhydrous sodium sulfate. After filtration and concentration under reduced pressure, the obtained crude product was purified by silica gel column chromatography to obtain the title compound (247 mg).

$^1$H-NMR (CDCl$_3$) δ: 0.93 (3H, t, J=7.4 Hz), 1.49 (18H, s), 1.52-1.74 (7H, m), 1.80 (2H, tq, J=7.4, 7.4 Hz), 3.58 (2H, dd, J=7.4, 7.4 Hz), 3.72 (3H, s), 3.82 (2H, dd, J=7.0, 7.0 Hz), 7.01-7.02 (1H, m), 7.29-7.30 (1H, m).

[Step 2] (1R*,2S*)-2-(3-Aminopropyl)-1-(1-propyl-1H-imidazol-4-yl)cyclopropanecarboxylic acid

[Formula 138]

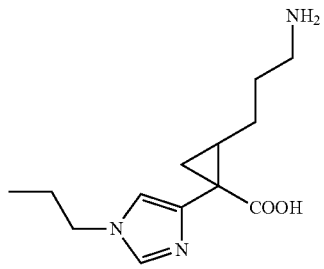

The title compound (108 mg) was obtained from the compound (247 mg) obtained in Step 1 of this Example in the same way as in Example 1.

$^1$H-NMR (CD$_3$OD) δ: 0.91 (3H, t, J=7.4 Hz), 1.18 (1H, dd, J=8.8, 4.2 Hz), 1.29 (1H, dd, J=6.7, 4.2 Hz), 1.38-1.46 (1H, m), 1.57-1.72 (2H, m), 1.74-1.84 (4H, m), 2.89-3.01 (2H, m), 3.89 (2H, t, J=7.0 Hz), 7.09 (1H, d, J=1.2 Hz), 7.44 (1H, d, J=1.2 Hz).

MS (ESI) m/z 252 (M+H)$^+$, 274 (M+Na)$^+$.

HRMS (ESI) m/z 252.1707 (M+H)$^+$. (Calcd C$_{13}$H$_{22}$N$_3$O$_2$: 252.1712).

Example 4

(1R*,2S*)-2-(3-Aminopropyl)-1-(1-cyclohexyl-1H-imidazol-4-yl)cyclopropanecarboxylic acid

[Step 1] Methyl (1R*,2S*)-2-{3-[bis(tert-butoxycarbonyl)amino]propyl}-1-(1-cyclohexyl-1H-imidazol-4-yl)cyclopropanecarboxylate

[Formula 139]

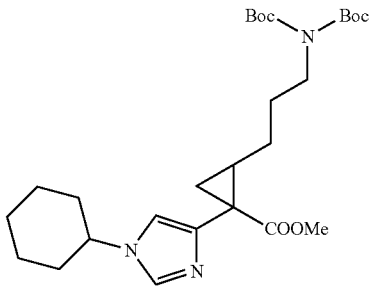

Method A)

Cyclohexanol (0.279 mL) was dissolved in toluene (10 mL), and the compound (747 mg) obtained in Reference Example 8 was added to the solution. To this reaction solution, cyanomethylenetributylphosphorane (639 mg) was added, and the mixture was stirred overnight at 100° C. Cyclohexanol (0.279 mL) and cyanomethylenetributylphosphorane (639 mg) were further added thereto, and the mixture was stirred overnight at 100° C. and then left to room temperature. The obtained reaction solution was purified by silica gel chromatography (eluting solvent: ethyl acetate/methylene chloride=1/1) to obtain a crude product of the title compound (450 mg). The crude product was further purified repetitively and purified by silica gel chromatography (eluting solvent: methylene chloride/methanol=98/2) to obtain the title compound (280 mg).

Method B)

Methyl (1R*,2S*)-2-{3-[bis(tert-butoxycarbonyl)amino]propyl}-1-(1-cyclohex-2-en-1-yl-1H-imidazol-4-yl)cyclopropanecarboxylate (564 mg) was obtained according to Step 1 of Example 3 using the compound (670 mg) obtained in Reference Example 8 and 3-bromocyclohexene (424 mg). This compound was dissolved in methanol (10 mL). To this solution, 10% palladium-carbon catalyst (hydrated, 150 mg) was added, and the mixture was stirred at room temperature for 3 hours under a hydrogen atmosphere. The reaction solution was filtered through celite, and the solvent in the filtrate was distilled off under reduced pressure. The residue was purified by preparative thin-layer chromatography (200×200×1 mm, eluting solvent: methylene chloride/methanol=95/5) to obtain the title compound (256 mg).

$^1$H-NMR (CDCl$_3$) δ: 1.19-1.29 (2H, m), 1.32-1.45 (2H, m), 1.49 (18H, s), 1.50-1.78 (9H, m), 1.84-1.93 (2H, m), 2.05-2.15 (2H, m), 3.57 (2H, t, J=7.4 Hz), 3.71 (3H, s), 4.33 (1H, tt, J=11.9, 3.8 Hz), 7.07 (1H, d, J=1.2 Hz), 7.38 (1H, d, J=1.2 Hz).

MS (ESI) m/z 506 (M+H)$^+$, 528 (M+Na)$^+$.

[Step 2] (1R*,2S*)-2-(3-Aminopropyl)-1-(1-cyclohexyl-1H-imidazol-4-yl)cyclopropanecarboxylic acid

[Formula 140]

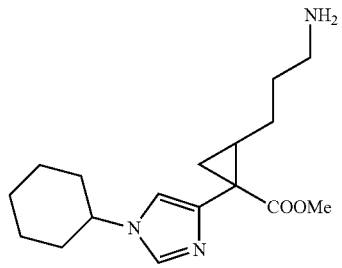

The title compound (106 mg) was obtained from the compound (254 mg) obtained in Step 1 in the same way as in Example 1.

$^1$H-NMR (CD$_3$OD) δ: 1.17 (1H, dd, J=9.0, 3.9 Hz), 1.21-1.34 (2H, m), 1.37-1.52 (3H, m), 1.55-1.92 (9H, m), 2.00-2.10 (2H, m), 2.85-3.02 (2H, m), 3.95 (1H, tt, J=12.1, 3.5 Hz), 7.15 (1H, d, J=1.2 Hz), 7.50 (1H, d, J=1.2 Hz).

MS (ESI) m/z 292 (M+H)$^+$, 314 (M+Na)$^+$.

HRMS (ESI) m/z 292.20210 (M+H)$^+$. (Calcd C$_{16}$H$_{26}$N$_3$O$_2$: 292.20250).

Example 5

(1R*,2S*)-2-(3-Aminopropyl)-1-[1-(trans-4-methylcyclohexyl)-1H-imidazol-4-yl]cyclopropanecarboxylic acid

[Formula 141]

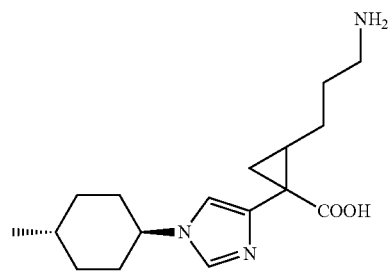

The title compound (138 mg) was obtained from the compound (299 mg) obtained in Reference Example 11 in the same way as in Example 1.

$^1$H-NMR (CD$_3$OD) δ: 0.95 (3H, d, J=6.7 Hz), 1.10-1.20 (3H, m), 1.28 (1H, dd, J=3.9, 6.7 Hz), 1.38-1.52 (2H, m), 1.58-1.86 (8H, m), 2.02-2.07 (2H, m), 2.88-3.01 (2H, m), 3.94 (1H, tt, J=3.9, 12.1 Hz), 7.14-7.15 (1H, m), 7.50-7.51 (1H, m).

MS (ESI) m/z 306 (M+H)$^+$, 328 (M+Na)$^+$.

HRMS (ESI) m/z 306.2180 (M+H)$^+$. (Calcd C$_{17}$H$_{28}$N$_3$O$_2$: 306.2182).

Example 6

(1R*,2S*)-2-(3-Aminopropyl)-1-(1-phenyl-1H-imidazol-4-yl)cyclopropanecarboxylic acid

[Step 1] Methyl (1R*,2S*)-2-{3-[bis(tert-butoxycarbonyl)amino]propyl}-1-(1-phenyl-1H-imidazol-4-yl)cyclopropanecarboxylate

[Formula 142]

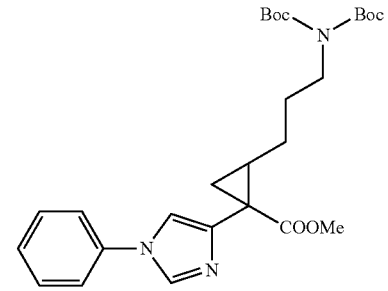

Molecular sieve 4A (140 mg), copper (II) sulfate (222 mg), phenylboronic acid (194 mg), and pyridine (129 μL) were added to a solution of the compound (337 mg) obtained in Reference Example 8 in methylene chloride (10 mL), and the mixture was stirred overnight at room temperature under an air atmosphere at normal pressure. To the reaction solution, a saturated aqueous solution of sodium bicarbonate (10 mL) and disodium dihydrogen ethylenediaminetetraacetate dihydrate (445 mg) were added, and the mixture was stirred at room temperature for 20 minutes. Then, insoluble matter was filtered off and washed with methylene chloride and a saturated aqueous solution of sodium bicarbonate. The filtrate was separated into aqueous and organic layers, followed by extraction with methylene chloride. Then, the organic layer was dried over anhydrous sodium sulfate. After filtration and concentration under reduced pressure, the obtained crude product was purified by silica gel column chromatography to obtain the title compound (271 mg).

$^1$H-NMR (CDCl$_3$) δ: 1.49 (18H, s), 1.57-1.74 (6H, m), 1.78-1.86 (1H, m), 3.60 (2H, t, J=7.4 Hz), 3.75 (3H, s), 7.32-7.36 (1H, m), 7.38-7.41 (2H, m), 7.44-7.48 (3H, m), 7.71 (1H, d, J=1.2 Hz).

[Step 2] (1R*,2S*)-2-(3-Aminopropyl)-1-(1-phenyl-1H-imidazol-4-yl)cyclopropanecarboxylic acid

[Formula 143]

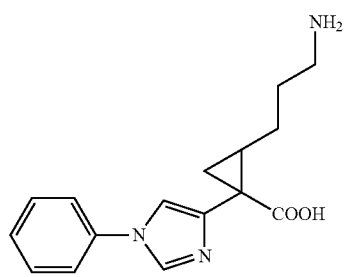

The compound (271 mg) obtained in Step 1 of this Example was heated to reflux for 2 hours in 5 N hydrochloric acid (10 mL). The reaction solution was concentrated, and the residue was then charged to Dowex 50WX8 (1.5 g) adjusted in advance with dilute hydrochloric acid and deionized water. The resin was washed with deionized water, followed by elution with 5% ammonia water. The eluate was concentrated to obtain the title compound (134 mg).

$^1$H-NMR (CD$_3$OD) δ: 1.27 (1H, dd, J=8.8, 4.0 Hz), 1.38 (1H, dd, J=6.6, 4.0 Hz), 1.47-1.55 (1H, m), 1.62-1.86 (4H, m), 2.91-3.03 (2H, m), 7.34-7.38 (1H, m), 7.47-7.54 (5H, m), 7.93 (1H, d, J=1.2 Hz).

MS (ESI) m/z 286 (M+H)$^+$, 308 (M+Na)$^+$.

HRMS (ESI) m/z 286.1551 (M+H)$^+$. (Calcd C$_{16}$H$_{20}$N$_3$O$_2$: 286.1556).

Example 7

(1R*,2S*)-2-(3-Aminopropyl)-1-[1-(4-methylphenyl)-1H-imidazol-4-yl]cyclopropanecarboxylic acid

[Step 1] Methyl (1R*,2S*)-2-{3-[bis(tert-butoxycarbonyl)amino]propyl}-1-[1-(4-methylphenyl)-1H-imidazol-4-yl]cyclopropanecarboxylate

[Formula 144]

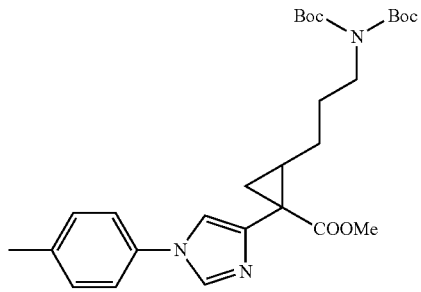

The title compound (477 mg) was obtained from the compound (671 mg) obtained in Reference Example 8 and 4-methylphenylboronic acid in the same way as in Step 1 of Example 6.

$^1$H-NMR (CDCl$_3$) δ: 1.49 (18H, s), 1.54-1.85 (7H, m), 2.39 (3H, s), 3.60 (2H, t, J=7.8 Hz), 3.74 (3H, s), 7.22-7.31 (4H, m), 7.40 (1H, s), 7.66 (1H, s).

MS (ESI) m/z 514 (M+H)$^+$, 536 (M+Na)$^+$.

[Step 2] (1R*,2S*)-2-(3-Aminopropyl)-1-[1-(4-methylphenyl)-1H-imidazol-4-yl]cyclopropanecarboxylate

[Formula 145]

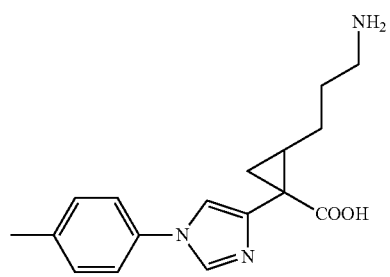

The title compound (79 mg) was obtained from the compound (238 mg) obtained in Step 1 of this Example in the same way as in Step 2 of Example 6.

$^1$H-NMR (CD$_3$OD) δ: 1.26 (1H, dd, J=8.8, 4.1 Hz), 1.37 (1H, dd, J=6.8, 4.1 Hz), 1.45-1.55 (1H, m), 1.61-1.87 (4H, m), 2.38 (3H, s), 2.88-3.03 (2H, m), 7.30 (2H, d, J=8.6 Hz), 7.39 (2H, d, J=8.6 Hz), 7.49 (1H, d, J=1.6 Hz), 7.87 (1H, d, J=1.6 Hz).

MS (ESI) m/z 300 (M+H)$^+$, 322 (M+Na)$^+$.

HRMS (ESI) m/z 300.17197 (M+H)$^+$. (Calcd C$_{17}$H$_{22}$N$_3$O$_2$: 300.17120).

Example 8

(1R*,2S*)-2-(3-Aminopropyl)-1-[1-(3-methylphenyl)-1H-imidazol-4-yl]cyclopropanecarboxylic acid

[Step 1] Methyl (1R*,2S*)-2-{3-[bis(tert-butoxycarbonyl)amino]propyl}-1-[1-(3-methylphenyl)-1H-imidazol-4-yl]cyclopropanecarboxylate

[Formula 146]

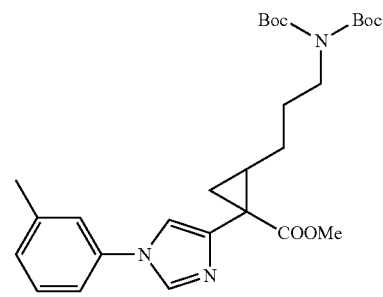

The title compound (285 mg) was obtained from the compound (314 mg) obtained in Reference Example 8 and 3-methylphenylboronic acid (201 mg) in the same way as in Step 1 of Example 6.

¹H-NMR (CDCl₃) δ: 1.49 (18H, s), 1.53-1.73 (6H, m), 1.76-1.85 (1H, m), 2.42 (3H, s), 3.59-3.61 (2H, m), 3.74 (3H, s), 7.15-7.21 (3H, m), 7.31-7.35 (1H, m), 7.41-7.43 (1H, m), 7.68-7.69 (1H, m).

[Step 2] (1R*,2S*)-2-(3-Aminopropyl)-1-[1-(3-methylphenyl)-1H-imidazol-4-yl]cyclopropanecarboxylate

[Formula 147]

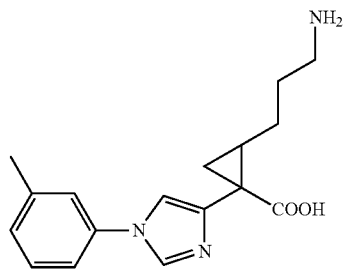

The title compound (142 mg) was obtained from the compound (285 mg) obtained in Step 1 of this Example in the same way as in Step 2 of Example 6.

¹H-NMR (CD₃OD) δ: 1.27 (1H, dd, J=8.8, 4.1 Hz), 1.38 (1H, dd, J=6.8, 4.1 Hz), 1.47-1.54 (1H, m), 1.62-1.86 (4H, m), 2.41 (3H, s), 2.91-3.03 (2H, m), 7.18-7.20 (1H, m), 7.29-7.31 (1H, m), 7.35-7.39 (2H, m), 7.52 (1H, d, J=1.6 Hz), 7.91 (1H, d, J=1.6 Hz).

MS (ESI) m/z 300 (M+H)⁺, 322 (M+Na)⁺.

HRMS (ESI) m/z 300.1713 (M+H)⁺. (Calcd C₁₇H₂₂N₃O₂: 300.1712).

Example 9

(1R*,2S*)-2-(3-Aminopropyl)-1-[1-(2-methylphenyl)-1H-imidazol-4-yl]cyclopropanecarboxylic acid

[Step 1] Methyl (1R*,2S*)-2-{3-[bis(tert-butoxycarbonyl)amino]propyl}-1-[1-(2-methylphenyl)-1H-imidazol-4-yl]cyclopropanecarboxylate

[Formula 148]

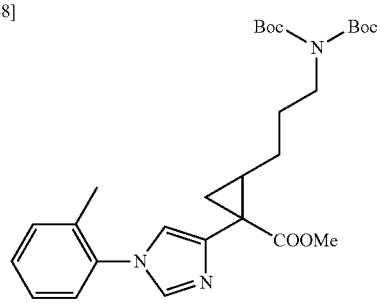

The title compound (287 mg) was obtained from the compound (334 mg) obtained in Reference Example 8 and 2-methylphenylboronic acid (95%, 226 mg) in the same way as in Step 1 of Example 6.

¹H-NMR (CDCl₃) δ: 1.49 (18H, s), 1.58-1.74 (6H, m), 1.80-1.88 (1H, m), 2.21 (3H, s), 3.60 (2H, t, J=7.2 Hz), 3.73 (3H, s), 7.18 (1H, d, J=1.2 Hz), 7.22-7.25 (1H, m), 7.27-7.31 (1H, m), 7.32-7.36 (2H, m), 7.42 (1H, d, J=1.2 Hz).

[Step 2] (1R*,2S*)-2-(3-Aminopropyl)-1-[1-(2-methylphenyl)-1H-imidazol-4-yl]cyclopropanecarboxylic acid

[Formula 149]

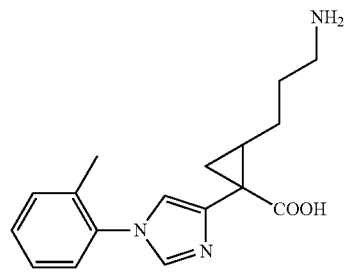

The title compound (142 mg) was obtained from the compound (287 mg) obtained in Step 1 of this Example in the same way as in Step 2 of Example 6.

¹H-NMR (CD₃OD) δ: 1.28 (1H, dd, J=8.8, 4.0 Hz), 1.37 (1H, dd, J=6.6, 4.0 Hz), 1.48-1.55 (1H, m), 1.62-1.76 (2H, m), 1.77-1.86 (2H, m), 2.21 (3H, s), 2.91-3.04 (2H, m), 7.24 (1H, d, J=1.2 Hz), 7.25-7.27 (1H, m), 7.29-7.34 (1H, m), 7.35-7.39 (2H, m), 7.57 (1H, d, J=1.2 Hz).

MS (ESI) m/z 300 (M+H)⁺, 322 (M+Na)⁺.

HRMS (ESI) m/z 300.1711 (M+H)⁺. (Calcd C₁₇H₂₂N₃O₂: 300.1712).

Example 10

(1R*,2S*)-2-(3-Aminopropyl)-1-[1-(3,4-dimethylphenyl)-1H-imidazol-4-yl]cyclopropanecarboxylic acid

[Step 1] Methyl (1R*,2S*)-2-{3-[bis(tert-butoxycarbonyl)amino]propyl}-1-[1-(3,4-dimethylphenyl)-1H-imidazol-4-yl]cyclopropanecarboxylate

[Formula 150]

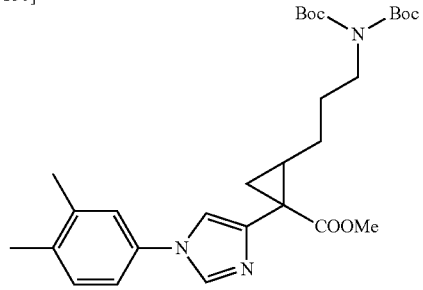

The title compound (197 mg) was obtained from the compound (218 mg) obtained in Reference Example 8 and 3,4-dimethylphenylboronic acid (154 mg) in the same way as in Step 1 of Example 6.

¹H-NMR (CDCl₃) δ: 1.49 (18H, s), 1.53-1.73 (6H, m), 1.78-1.85 (1H, m), 2.30 (3H, s), 2.32 (3H, s), 3.60 (2H, t, J=7.2 Hz), 3.75 (3H, s), 7.10-7.25 (3H, m), 7.41-7.44 (1H, m), 7.72-7.76 (1H, m).

[Step 2] (1R*,2S*)-2-(3-Aminopropyl)-1-[1-(3,4-dimethylphenyl)-1H-imidazol-4-yl]cyclopropanecarboxylic acid

[Formula 151]

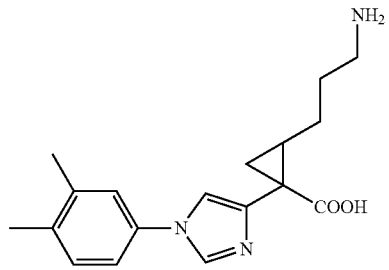

The title compound (88.7 mg) was obtained from the compound (197 mg) obtained in Step 1 of this Example in the same way as in Step 2 of Example 6.

$^1$H-NMR (CD$_3$OD) δ: 1.26 (1H, dd, J=9.0, 4.1 Hz), 1.37 (1H, dd, J=6.7, 4.1 Hz), 1.46-1.53 (1H, m), 1.61-1.86 (4H, m), 2.29 (3H, s), 2.33 (3H, s), 2.91-3.03 (2H, m), 7.19-7.25 (2H, m), 7.29-7.30 (1H, m), 7.48 (1H, d, J=1.6 Hz), 7.85 (1H, d, J=1.6 Hz).

MS (ESI) m/z 314 (M+H)$^+$, 336 (M+Na)$^+$.

HRMS (ESI) m/z 314.1862 (M+H)$^+$. (Calcd C$_{18}$H$_{24}$N$_3$O$_2$: 314.1869).

Example 11

(1R*,2S*)-2-(3-Aminopropyl)-1-[1-(4-ethylphenyl)-1H-imidazol-4-yl]cyclopropanecarboxylic acid

[Step 1] Methyl (1R*,2S*)-2-{3-[bis(tert-butoxycarbonyl)amino]propyl}-1-[1-(4-ethylphenyl)-1H-imidazol-4-yl]cyclopropanecarboxylate

[Formula 152]

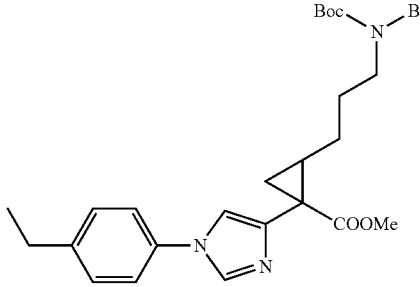

The title compound (353 mg) was obtained from the compound (378 mg) obtained in Reference Example 8 and 4-ethylphenylboronic acid (268 mg) in the same way as in Step 1 of Example 6.

$^1$H-NMR (CDCl$_3$) δ: 1.26 (3H, t, J=7.4 Hz), 1.49 (18H, s), 1.58-1.65 (4H, m), 1.66-1.74 (2H, m), 178-1.86 (1H, m), 2.69 (2H, q, J=7.4 Hz), 3.60 (2H, t, J=7.4 Hz), 3.74 (3H, s), 7.26-7.31 (4H, m), 7.40-7.41 (1H, m), 7.66-7.68 (1H, m).

[Step 2] (1R*,2S*)-2-(3-Aminopropyl)-1-[1-(4-ethylphenyl)-1H-imidazol-4-yl]cyclopropanecarboxylic acid

[Formula 153]

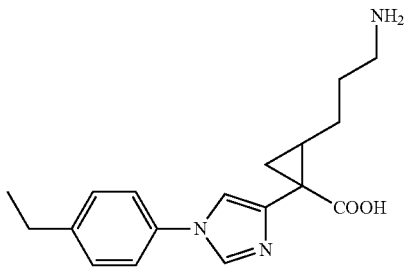

The title compound (112 mg) was obtained from the compound (353 mg) obtained in Step 1 of this Example in the same way as in Step 2 of Example 6.

$^1$H-NMR (CD$_3$OD) δ: 1.25 (3H, t, J=7.4 Hz), 1.26-1.29 (1H, m), 1.37 (1H, dd, J=3.9, 6.7 Hz), 1.47-1.54 (1H, m), 1.62-1.85 (4H, m), 2.69 (2H, q, J=7.4 Hz), 2.91-3.04 (2H, m), 7.32-7.34 (2H, m), 7.41-7.43 (2H, m), 7.50 (1H, d, J=1.6 Hz), 7.87 (1H, d, J=1.6 Hz).

MS (ESI) m/z 314 (M+H)$^+$, 336 (M+Na)$^+$.

HRMS (ESI) m/z 314.1872 (M+H)$^+$. (Calcd C$_{18}$H$_{24}$N$_3$O$_2$: 314.1869).

Example 12

(1R*,2S*)-2-(3-Aminopropyl)-1-[1-(4-methoxyphenyl)-1H-imidazol-4-yl]cyclopropanecarboxylic acid

[Step 1] Methyl (1R*,2S*)-2-{3-[bis(tert-butoxycarbonyl)amino]propyl}-1-[1-(4-methoxyphenyl)-1H-imidazol-4-yl]cyclopropanecarboxylate

[Formula 154]

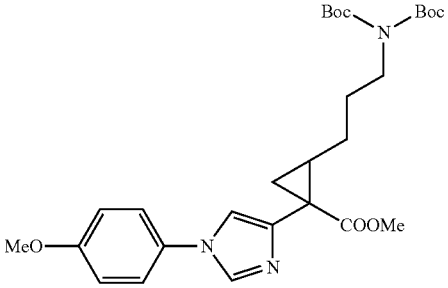

The title compound (399 mg) was obtained from the compound (418 mg) obtained in Reference Example 8 and 4-methoxyphenylboronic acid (300 mg) in the same way as in Step 1 of Example 6.

$^1$H-NMR (CDCl$_3$) δ: 1.49 (18H, s), 1.59-1.66 (4H, m), 1.66-1.76 (2H, m), 1.76-1.85 (1H, m), 3.59 (2H, t, J=7.2 Hz), 3.74 (3H, s), 3.85 (3H, s), 6.95-6.98 (2H, m), 7.28-7.32 (2H, m), 7.35 (1H, d, J=1.6 Hz), 7.61 (1H, d, J=1.6 Hz).

[Step 2] (1R*,2S*)-2-(3-Aminopropyl)-1-[1-(4-methoxyphenyl)-1H-imidazol-4-yl]cyclopropanecarboxylic acid

[Formula 155]

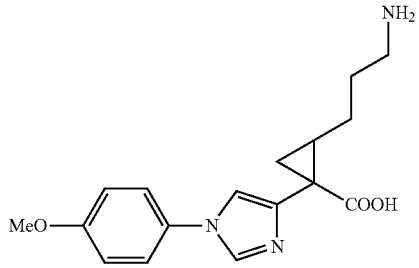

The title compound (151 mg) was obtained from the compound (399 mg) obtained in Step 1 of this Example in the same way as in Step 2 of Example 6.

$^1$H-NMR (CD$_3$OD) δ: 1.26 (1H, dd, J=9.0, 3.9 Hz), 1.37 (1H, dd, J=6.7, 3.9 Hz), 1.46-1.53 (1H, m), 1.61-1.68 (1H, m), 1.70-1.76 (1H, m), 1.76-1.85 (2H, m), 2.90-3.03 (2H, m), 3.83 (3H, s), 7.01-7.05 (2H, m), 7.40-7.41 (1H, m), 7.42-7.44 (2H, m), 7.79-7.80 (1H, m).

MS (ESI) m/z 316 (M+H)$^{30}$, 338 (M+Na)$^+$.

HRMS (ESI) m/z 316.1658 (M+H)$^{30}$. (Calcd C$_{17}$H$_{22}$N$_3$O$_3$: 316.1661).

Example 13

(1R*,2S*)-2-(3-Aminopropyl)-1-{1-[4-(trifluoromethyl)phenyl]-1H-imidazol-4-yl}cyclopropanecarboxylic acid

[Step 1] Methyl (1R*,2S*)-2-{3-[bis(tert-butoxycarbonyl)amino]propyl}-1-{1-[4-(trifluoromethyl)phenyl]-1H-imidazol-4-yl}cyclopropanecarboxylate

[Formula 156]

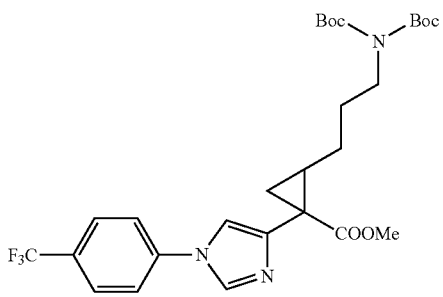

The title compound (126 mg) was obtained from the compound (227 mg) obtained in Reference Example 8 and 4-(trifluoromethyl) phenylboronic acid (208 mg) in the same way as in Step 1 of Example 6.

$^1$H-NMR (CDCl$_3$) δ: 1.50 (18H, s), 1.58-1.74 (6H, m), 1.79-1.87 (1H, m), 3.60 (2H, t, J=7.2 Hz), 3.75 (3H, s), 7.52-7.57 (3H, m), 7.73-7.75 (2H, m), 7.82 (1H, br s).

[Step 2] (1R*,2S*)-2-(3-Aminopropyl)-1-{1-[4-(trifluoromethyl)phenyl]-1H-imidazol-4-yl}cyclopropanecarboxylic acid

[Formula 157]

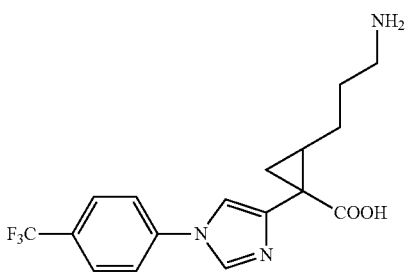

The title compound (38.0 mg) was obtained from the compound (126 mg) obtained in Step 1 of this Example in the same way as in Step 2 of Example 6.

$^1$H-NMR (CD$_3$OD) δ: 1.27-1.30 (1H, m), 1.40 (1H, dd, J=6.7, 3.9 Hz), 1.48-1.55 (1H, m), 1.64-1.75 (2H, m), 1.77-1.86 (2H, m), 2.91-3.03 (2H, m), 7.64 (1H, d, J=1.6 Hz), 7.76 (2H, d, J=8.6 Hz), 7.81 (2H, d, J=8.6 Hz), 8.08-8.11 (1H, br m).

MS (ESI) m/z 354 (M+H)$^+$, 376 (M+Na)$^+$.

HRMS (ESI) m/z 354.1426 (M+H)$^+$. (Calcd C$_{17}$H$_{19}$F$_3$N$_3$O$_2$: 354.1429).

Example 14

(1R*,2S*)-2-(3-Aminopropyl)-1-{1-[(E)-2-phenylvinyl]-1H-imidazol-4-yl}cyclopropanecarboxylic acid

[Step 1] Methyl (1R*,2S*)-2-{3-[bis(tert-butoxycarbonyl)amino]propyl}-1-{1-[(E)-2-phenylvinyl]-1H-imidazol-4-yl}cyclopropanecarboxylate

[Formula 158]

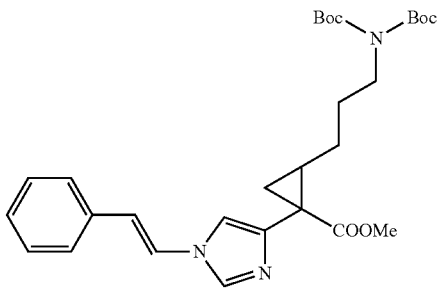

The title compound (128 mg) was obtained from the compound (162 mg) obtained in Reference Example 8 and trans-2-phenylboronic acid (117 mg) in the same way as in Step 1 of Example 6.

$^1$H-NMR (CDCl$_3$) δ: 1.50 (18H, s), 1.50-1.83 (7H, m), 3.59 (2H, t, J=7.4 Hz), 3.75 (3H, s), 6.74 (1H, d, J=14.5 Hz), 7.27-7.31 (2H, m), 7.34-7.41 (4H, m), 7.47 (1H, br s), 7.63 (1H, br s).

[Step 2] (1R*,2S*)-2-(3-Aminopropyl)-1-{1-[(E)-2-phenylvinyl]-1H-imidazol-4-yl}cyclopropanecarboxylic acid

[Formula 159]

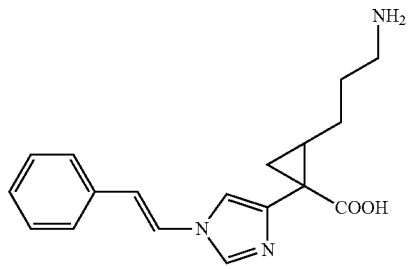

The title compound (48.6 mg) was obtained from the compound (128 mg) obtained in Step 1 of this Example in the same way as in Step 2 of Example 6.

$^1$H-NMR (CD$_3$OD) δ: 1.25 (1H, dd, J=9.0, 4.2 Hz), 1.37 (1H, dd, J=6.6, 4.2 Hz), 1.45-1.51 (1H, m), 1.62-1.69 (1H, m), 1.71-1.85 (3H, m), 2.94-2.99 (2H, m), 6.88 (1H, d, J=14.6 Hz), 7.25 (1H, dd, J=7.6, 7.6 Hz), 7.34 (2H, dd, J=7.6, 7.6 Hz), 7.48 (2H, d, J=7.6 Hz), 7.57 (1H, s), 7.60 (1H, d, J=14.6 Hz), 7.79 (1H, s).

MS (ESI) m/z 312 (M+H)$^+$, 334 (M+Na)$^+$.

HRMS (ESI) m/z 312.1706 (M+H)$^+$. (Calcd C$_{18}$H$_{22}$N$_3$O$_2$: 312.1712).

Example 15

(1R*,2S*)-2-(3-Aminopropyl)-1-[1-(4-fluorophenyl)-1H-imidazol-4-yl]cyclopropanecarboxylic acid

[Step 1] Methyl (1R*,2S*)-2-{3-[bis(tert-butoxycarbonyl)amino]propyl}-1-[1-(4-fluorophenyl)-1H-imidazol-4-yl]cyclopropanecarboxylate

[Formula 160]

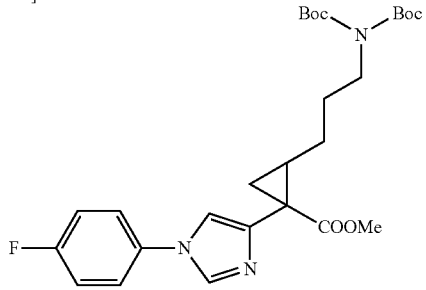

The title compound (161 mg) was obtained from the compound (225 mg) obtained in Reference Example 8 and 4-fluorophenylboronic acid (149 mg) in the same way as in Step 1 of Example 6.

$^1$H-NMR (CDCl$_3$) δ: 1.49 (18H, s), 1.53-1.85 (7H, m), 3.60 (2H, t, J=7.2 Hz), 3.74 (3H, s), 7.13-7.18 (2H, m), 7.35-7.39 (2H, m), 7.41-7.42 (1H, m), 7.67 (1H, br s).

[Step 2] (1R*,2S*)-2-(3-Aminopropyl)-1-[1-(4-fluorophenyl)-1H-imidazol-4-yl]cyclopropanecarboxylic acid

[Formula 161]

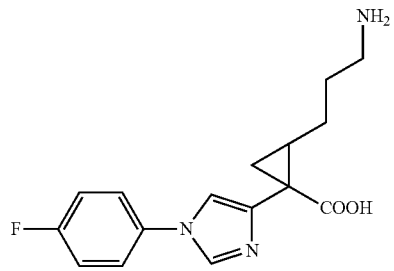

The title compound (77.2 mg) was obtained from the compound (161 mg) obtained in Step 1 of this Example in the same way as in Step 2 of Example 6.

$^1$H-NMR (CD$_3$OD) δ: 1.26 (1H, dd, J=8.8, 4.0 Hz), 1.38 (1H, dd, J=6.6, 4.0 Hz), 1.47-1.53 (1H, m), 1.63-1.71 (1H, m), 1.71-1.77 (1H, m), 1.78-1.86 (2H, m), 2.91-3.02 (2H, m), 7.22-7.26 (2H, m), 7.49 (1H, d, J=1.5 Hz), 7.53-7.56 (2H, m), 7.88 (1H, br s).

MS (ESI) m/z 304 (M+H)$^+$, 326 (M+Na)$^+$.

HRMS (ESI) m/z 304.1461 (M+H)$^+$. (Calcd C$_{16}$H$_{19}$F$_1$N$_3$O$_2$: 304.1461).

Example 16

(1R*,2S*)-2-(3-Aminopropyl)-1-[1-(4-phenoxyphenyl)-1H-imidazol-4-yl]cyclopropanecarboxylic acid

[Step 1] Methyl (1R*,2S*)-2-{3-[bis(tert-butoxycarbonyl)amino]propyl}-1-[1-(4-phenoxyphenyl)-1H-imidazol-4-yl]cyclopropanecarboxylate

[Formula 162]

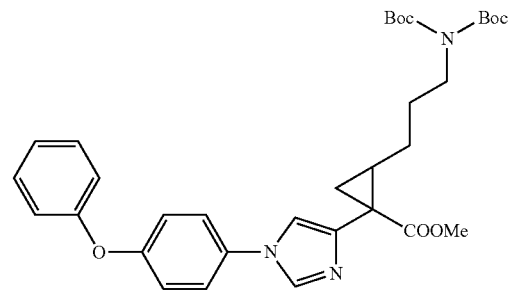

The title compound (222 mg) was obtained from the compound (222 mg) obtained in Reference Example 8 and 4-phenoxyphenyl boronic acid (224 mg) in the same way as in Step 1 of Example 6.

$^1$H-NMR (CDCl$_3$) δ: 1.49 (18H, s), 1.54-1.75 (6H, m), 1.77-1.86 (1H, m), 3.60 (2H, t, J=7.2 Hz), 3.74 (3H, s), 7.02-7.06 (2H, m), 7.07-7.10 (2H, m), 7.13-7.18 (1H, m), 7.32-7.40 (5H, m), 7.66 (1H, d, J=1.6 Hz).

111

[Step 2] (1R*,2S*)-2-(3-Aminopropyl)-1-[1-(4-phenoxyphenyl)-1H-imidazol-4-yl]cyclopropanecarboxylic acid

[Formula 163]

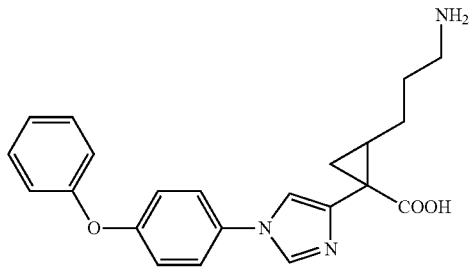

The title compound (46.3 mg) was obtained from the compound (222 mg) obtained in Step 1 of this Example in the same way as in Step 2 of Example 6.

$^1$H-NMR (CD$_3$OD) δ: 1.27 (1H, dd, J=8.8, 4.0 Hz), 1.38 (1H, dd, J=6.7, 4.0 Hz), 1.47-1.54 (1H, m), 1.62-1.86 (4H, m), 2.91-3.03 (2H, m), 7.02-7.05 (2H, m), 7.07-7.11 (2H, m), 7.13-7.17 (1H, m), 7.36-7.41 (2H, m), 7.49-7.52 (3H, m), 7.87 (1H, br s).

MS (ESI) m/z 378 (M+H)$^+$, 400 (M+Na)$^+$.

HRMS (ESI) m/z 378.1811 (M+H)$^+$. (Calcd C$_{22}$H$_{24}$N$_3$O$_3$: 378.1818).

Example 17

(1R*,2S*)-2-(3-Aminopropyl)-1-[1-(3,4-difluorophenyl)-1H-imidazol-4-yl]cyclopropanecarboxylic acid

[Step 1] Methyl (1R*,2S*)-2-{3-[bis(tert-butoxycarbonyl)amino]propyl}-1-[1-(3,4-difluorophenyl)-1H-imidazol-4-yl]cyclopropanecarboxylate

[Formula 164]

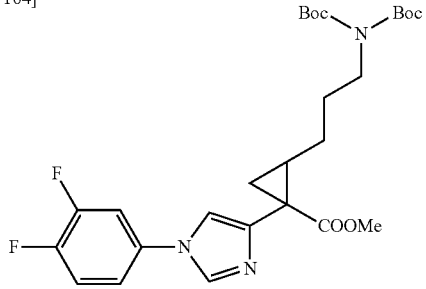

The title compound (169 mg) was obtained from the compound (220 mg) obtained in Reference Example 8 and 3,4-difluorophenyl boronic acid (164 mg) in the same way as in Step 1 of Example 6.

$^1$H-NMR (CDCl$_3$) δ: 1.49 (18H, s), 1.54-1.74 (6H, m), 1.76-1.85 (1H, m), 3.60 (2H, t, J=7.2 Hz), 3.74 (3H, s), 7.13-7.17 (1H, m), 7.24-7.30 (2H, m), 7.44 (1H, d, J=1.2 Hz), 7.67 (1H, br s).

112

[Step 2] (1R*,2S*)-2-(3-Aminopropyl)-1-[1-(3,4-difluorophenyl)-1H-imidazol-4-yl]cyclopropanecarboxylic acid

[Formula 165]

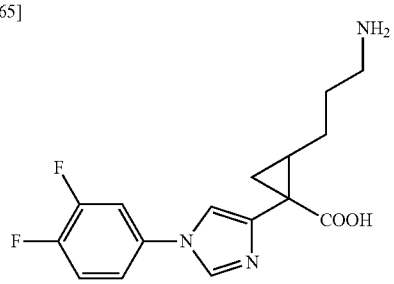

The title compound (62.6 mg) was obtained from the compound (169 mg) obtained in Step 1 of this Example in the same way as in Step 2 of Example 6.

$^1$H-NMR (CD$_3$OD) δ: 1.26 (1H, dd, J=8.8, 4.1 Hz), 1.38 (1H, dd, J=6.8, 4.1 Hz), 1.46-1.54 (1H, m), 1.63-1.85 (4H, m), 2.90-3.03 (2H, m), 7.36-7.45 (2H, m), 7.52 (1H, d, J=1.6 Hz), 7.57-7.62 (1H, m), 7.94 (1H, br s).

MS (ESI) m/z 322 (M+H)$^+$, 344 (M+Na)$^+$.

HRMS (ESI) m/z 322.1368 (M+H)$^+$. (Calcd C$_{16}$H$_{18}$F$_2$N$_3$O$_2$: 322.1367).

Example 18

(1R*,2S*)-2-(3-Aminopropyl)-1-[1-(4-chlorophenyl)-1H-imidazol-4-yl]cyclopropanecarboxylic acid

[Step 1] Ethyl (1R*,2S*)-2-{3-[bis(tert-butoxycarbonyl)amino]propyl}-1-[1-(4-chlorophenyl)-1H-imidazol-4-yl]cyclopropanecarboxylate

[Formula 166]

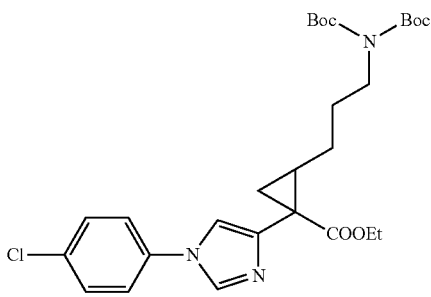

The compound (180 mg) obtained in Reference Example 16 was dissolved in methylene chloride (5 mL). To the solution, copper (II) acetate (76 mg), pyridine (67 μL), molecular sieve 4A (36 mg), and 4-chlorophenylboronic acid (129 mg) were added, and the mixture was stirred overnight at room temperature under an oxygen atmosphere. The progress of the reaction was checked by TLC. Then, a saturated aqueous solution of sodium bicarbonate (10 mL)

and disodium ethylenediaminetetraacetate dihydrate (184 mg, 0.49 mmol) were added thereto, and the mixture was stirred for a while. The reaction solution was filtered using a syringe with a filter (Biotage, ISOLUTE Phase Separator) containing an appropriate amount of celite. The filtrate was further washed with methylene chloride. The collected organic layers were combined, and the solvent was distilled off under reduced pressure. The obtained residue was purified by silica gel column chromatography (eluting solvent: methylene chloride→methylene chloride/ethyl acetate=80/20) to obtain the title compound (190 mg).

$^1$H-NMR (CDCl$_3$) δ: 1.29 (3H, t, J=7.0 Hz), 1.49 (18H, s), 1.58-1.74 (6H, m), 1.77-1.86 (1H, m), 3.60 (2H, t, J=7.4 Hz), 4.22 (2H, q, J=7.0 Hz), 7.32-7.36 (2H, m), 7.42-7.46 (2H, m), 7.48 (1H, d, J=1.6 Hz), 7.68-7.70 (1H, m).

MS (ESI) m/z 548 (M+H)$^+$.

[Step 2] (1R*,2S*)-2-(3-Aminopropyl)-1-[1-(4-chlorophenyl)-1H-imidazol-4-yl]cyclopropanecarboxylic acid

[Formula 167]

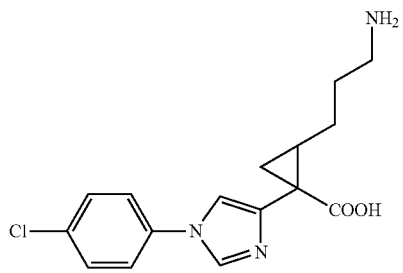

A mixture of the compound (184 mg) obtained in Step 1 of this Example and a 5 N aqueous hydrochloric acid solution (Nacalai Tesque, Inc., 8 mL) was heated to reflux for 4 days. The solvent was distilled off under reduced pressure, and the obtained residue was dissolved in deionized water. To the solution, an ion-exchange resin (Waters Corp., PoraPak Rxn CX, bulk, 1.5 g) was added, and the mixture was stirred for a while. The reaction mixture was transferred to a syringe with a filter (Shoko Scientific Co., Ltd.) to remove water. The resin was further washed with deionized water until the washings became neutral to a pH test paper. A solution of 28% ammonia water diluted 10-fold with methanol was added to the resin, and the eluate was concentrated under reduced pressure. The obtained residue was dissolved by the addition of deionized water, and the solution was concentrated under reduced pressure. This procedure was repeated several times, and the residue was then dried under reduced pressure to obtain the title compound (48 mg).

$^1$H-NMR (CD$_3$OD) δ: 1.21-1.30 (1H, m), 1.33-1.42 (1H, m), 1.44-1.55 (1H, m), 1.61-1.88 (4H, m), 2.87-3.02 (2H, m), 7.46-7.57 (5H, m), 7.91-7.98 (1H, m).

MS (ESI) m/z 320 [(M+H)$^+$, $^{35}$Cl].

HRMS (ESI) m/z 320.11658 (M+H)$^+$. (Calcd C$_{16}$H$_{19}$ClN$_3$O$_2$: 320.11591).

Example 19

(1R*,2S*)-2-(3-Aminopropyl)-1-[1-(3-chlorophenyl)-1H-imidazol-4-yl]cyclopropanecarboxylic acid

[Step 1] Ethyl (1R*,2S*)-2-{3-[bis(tert-butoxycarbonyl)amino]propyl}-1-[1-(3-chlorophenyl)-1H-imidazol-4-yl]cyclopropanecarboxylate

[Formula 168]

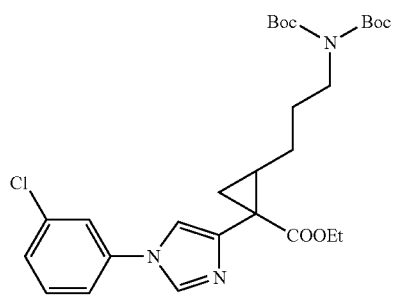

The title compound (107 mg) was obtained from the compound (200 mg) obtained in Reference Example 16 and 3-chlorophenyl boronic acid (143 mg) in the same way as in Step 1 of Example 18.

$^1$H-NMR (CDCl$_3$) δ: 1.30 (3H, t, J=7.0 Hz), 1.49 (18H, s), 1.57-1.86 (7H, m), 3.60 (2H, t, J=7.2 Hz), 4.20-4.26 (2H, m), 7.28-7.34 (2H, m), 7.38-7.42 (2H, m), 7.50 (1H, d, J=1.6 Hz), 7.71 (1H, d, J=1.2 Hz).

MS (ESI) m/z 570 (M+Na)$^+$, 548 (M+H)$^+$.

[Step 2] (1R*,2S*)-2-(3-Aminopropyl)-1-[1-(3-chlorophenyl)-1H-imidazol-4-yl]cyclopropanecarboxylic acid

[Formula 169]

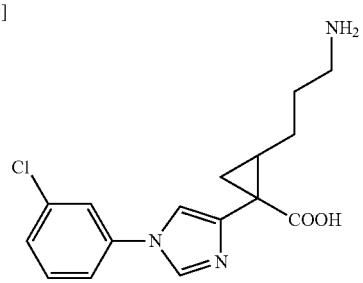

The title compound (26 mg) was obtained from the compound (105 mg) obtained in Step 1 of this Example in the same way as in Step 2 of Example 18.

$^1$H-NMR (CD$_3$OD) δ: 1.27 (1H, dd, J=8.6, 3.9 Hz), 1.39 (1H, dd, J=6.6, 4.3 Hz), 1.47-1.55 (1H, m), 1.63-1.86 (4H, m), 2.90-3.03 (2H, m), 7.36-7.39 (1H, m), 7.48-7.52 (2H, m), 7.63-7.65 (1H, m), 7.99-8.01 (1H, m), 7.99-8.01 (1H, m).

MS (ESI) m/z 320 (M+H)$^+$.

HRMS (ESI) m/z 320.11644 (M+H)$^+$. (Calcd C$_{16}$H$_{19}$ClN$_3$O$_2$: 320.11658).

Example 20

(1R*,2S*)-2-(3-Aminopropyl)-1-[1-(2-chlorophenyl)-1H-imidazol-4-yl]cyclopropanecarboxylic acid hydrochloride

[Step 1] Ethyl (1R*,2S*)-2-{3-[bis(tert-butoxycarbonyl)amino]propyl}-1-[1-(2-chlorophenyl)-1H-imidazol-4-yl]cyclopropanecarboxylate

[Formula 170]

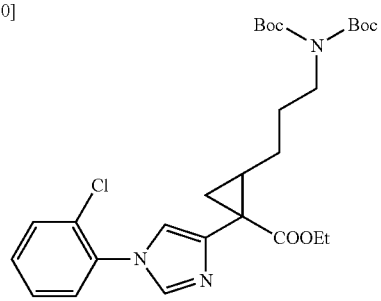

The title compound (5.5 mg) was obtained from the compound (200 mg) obtained in Reference Example 16 and 2-chlorophenylboronic acid (143 mg) in the same way as in Step 1 of Example 18. This reaction was performed at room temperature to 40° C.

$^1$H-NMR (CDCl$_3$) δ: 1.29 (3H, t, J=7.0 Hz), 1.49 (18H, s), 1.57-1.90 (7H, m), 3.60 (2H, t, J=7.2 Hz), 4.22 (2H, q, J=7.0 Hz), 7.33 (1H, d, J=1.2 Hz), 7.34-7.38 (3H, m), 7.52-7.58 (2H, m).

MS (ESI) m/z 548 (M+H)$^+$, 570 (M+Na)$^+$.

[Step 2] (1R*,2S*)-2-(3-Aminopropyl)-1-[1-(2-chlorophenyl)-1H-imidazol-4-yl]cyclopropanecarboxylic acid hydrochloride

[Formula 171]

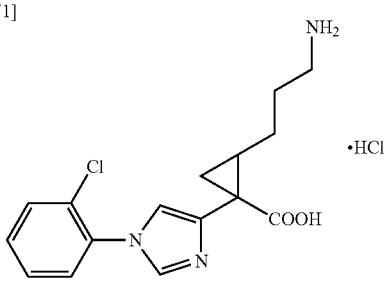

A mixture of the compound (5.5 mg) obtained in Step 1 of this Example and a 5 N aqueous hydrochloric acid solution (8 mL) was heated to reflux for 1 hour. The solvent was distilled off under reduced pressure. To the obtained residue, a small amount of acetone was added, and a solid was deposited by scrubbing with a spatula. Acetone was distilled off under reduced pressure, and the residue was then dried by the spraying of nitrogen gas and further dried under reduced pressure to obtain the title compound (3.4 mg).

$^1$H-NMR (CD$_3$OD) δ: 1.63-1.69 (1H, m), 1.70-1.75 (1H, m), 1.78-1.94 (5H, m), 2.96-3.03 (2H, m), 7.57-7.63 (1H, m), 7.64-7.69 (1H, m), 7.70-7.74 (1H, m), 7.75 (1H, dd, J=7.8, 1.6 Hz), 7.84 (1H, s), 9.31 (1H, s).

MS (ESI) m/z 320 (M+H)$^+$.

HRMS (ESI) m/z 320.11628 (M+H)$^+$. (Calcd C$_{16}$H$_{19}$ClN$_3$O$_2$: 320.11658).

Example 21

(1R*,2S*)-2-(3-Aminopropyl)-1-[1-(2-naphthyl)-1H-imidazol-4-yl]cyclopropanecarboxylic acid

[Step 1] Ethyl (1R*,2S*)-2-{3-[bis(tert-butoxycarbonyl)amino]propyl}-1-[1-(2-naphthyl)-1H-imidazol-4-yl]cyclopropanecarboxylate

[Formula 172]

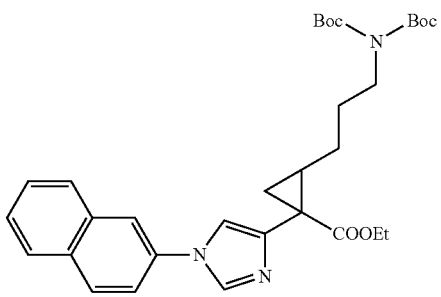

The title compound (103 mg) was obtained from the compound (150 mg) obtained in Reference Example 16 and 2-naphthyl boronic acid (118 mg) in the same way as in Step 1 of Example 18.

$^1$H-NMR (CDCl$_3$) δ: 1.31 (3H, t, J=7.0 Hz), 1.49 (18H, s), 1.63-1.82 (6H, m), 1.84-1.92 (1H, m), 3.61 (2H, t, J=7.2 Hz), 4.25 (2H, q, J=7.0 Hz), 7.53-7.61 (3H, m), 7.70 (1H, s), 7.85-7.87 (1H, m), 7.87-7.92 (2H, m), 7.98 (1H, d, J=8.6 Hz), 8.01-8.09 (1H, m).

MS (ESI) m/z 564 (M+H)$^+$, 586 (M+Na)$^+$.

[Step 2] (1R*,2S*)-2-(3-Aminopropyl)-1-[1-(2-naphthyl)-1H-imidazol-4-yl]cyclopropanecarboxylic acid

[Formula 173]

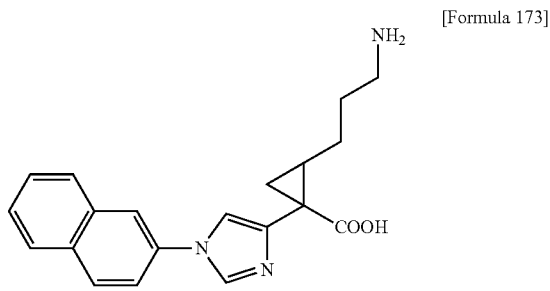 [SMILES: NCCCC1CC1(C(=O)O)c1cn(-c2ccc3ccccc3c2)cn1]

The title compound (55.4 mg) was obtained from the compound (100 mg) obtained in Step 1 of this Example in the same way as in Step 2 of Example 18.

$^1$H-NMR (CD$_3$OD) δ: 1.30 (1H, dd, J=8.8, 4.1 Hz), 1.41 (1H, dd, J=6.6, 4.0 Hz), 1.49-1.58 (1H, m), 1.64-1.87 (4H, m), 2.92-3.05 (2H, m), 7.50-7.59 (2H, m), 7.67-7.71 (2H, m), 7.90-7.96 (2H, m), 7.99-8.04 (2H, m), 8.09 (1H, s).

MS (ESI) m/z 336 [(M+H)$^+$].

HRMS (ESI) m/z 336.17050 (M+H)$^+$. (Calcd C$_{20}$H$_{22}$N$_3$O$_2$: 336.17120).

Example 22

(1R*,2S*)-2-(3-Aminopropyl)-1-[1-(3-fluorophenyl)-1H-imidazol-4-yl]cyclopropanecarboxylic acid

[Step 1] Ethyl (1R*,2S*)-2-{3-[bis(tert-butoxycarbonyl)amino]propyl}-1-[1-(3-fluorophenyl)-1H-imidazol-4-yl]cyclopropanecarboxylate

[Formula 174]

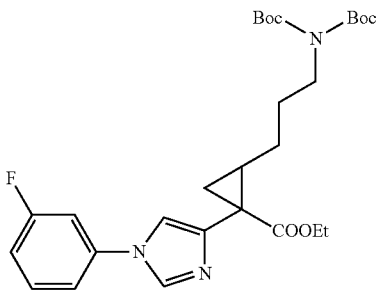

The title compound (87.7 mg) was obtained from the compound (105 mg) obtained in Reference Example 16 and 3-fluorophenyl boronic acid (69.4 mg) in the same way as in Step 1 of Example 18.

¹H-NMR (CDCl₃) δ: 1.30 (3H, t, J=7.0 Hz), 1.49 (18H, s), 1.55-1.86 (7H, m), 3.60 (2H, t, J=7.2 Hz), 4.23 (2H, q, J=7.0 Hz), 7.02-7.07 (1H, m), 7.11-7.15 (1H, m), 7.18-7.21 (1H, m), 7.40-7.46 (1H, m), 7.51 (1H, d, J=1.6 Hz), 7.71 (1H, d, J=1.6 Hz).

[Step 2] (1R*,2S*)-2-(3-Aminopropyl)-1-[1-(3-fluorophenyl)-1H-imidazol-4-yl]cyclopropanecarboxylic acid

[Formula 175]

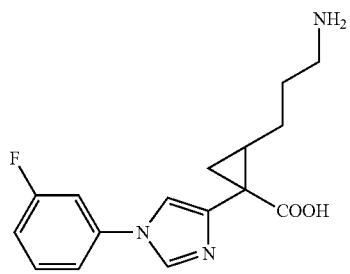

The title compound (39.3 mg) was obtained from the compound (87.7 mg) obtained in Step 1 of this Example in the same way as in Step 2 of Example 18.

¹H-NMR (CD₃OD) δ: 1.27 (1H, dd, J=9.0, 3.9 Hz), 1.39 (1H, dd, J=6.6, 3.9 Hz), 1.47-1.55 (1H, m), 1.63-1.85 (4H, m), 2.91-3.03 (2H, m), 7.08-7.14 (1H, m), 7.37-7.41 (2H, m), 7.48-7.54 (1H, m), 7.57 (1H, d, J=1.6 Hz), 8.00 (1H, d, J=1.6 Hz).

MS (ESI) m/z 304 (M+H)⁺, 326 (M+Na)⁺.

HRMS (ESI) m/z 304.1467 (M+H)⁺. (Calcd C₁₆H₁₉FN₃O₂: 304.1461).

Example 23

(1R*,2S*)-2-(3-Aminopropyl)-1-(1-pyridin-4-yl-1H-imidazol-4-yl)cyclopropanecarboxylic acid hydrochloride

[Step 1] Ethyl (1R*,2S*)-2-{3-[bis(tert-butoxycarbonyl)amino]propyl}-1-(1-pyridin-4-yl-1H-imidazol-4-yl)cyclopropanecarboxylate

[Formula 176]

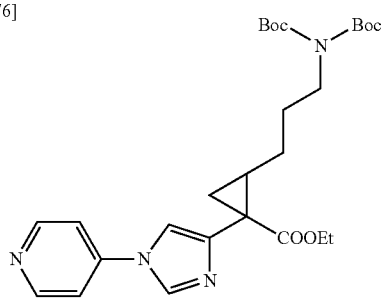

The title compound (6.0 mg) was obtained from the compound (100 mg) obtained in Reference Example 16 and pyridin-4-yl boronic acid (56 mg) in the same way as in Step 1 of Example 18.

¹H-NMR (CDCl₃) δ: 1.30 (3H, t, J=7.0 Hz), 1.49 (18H, s), 1.60-1.74 (6H, m), 1.76-1.86 (1H, m), 3.60 (2H, t, J=7.2 Hz), 4.23 (2H, q, J=7.0 Hz), 7.35 (2H, d, J=6.3 Hz), 7.66 (1H, d, J=1.6 Hz), 7.87 (1H, d, J=1.2 Hz), 8.68 (2H, d, J=5.5 Hz).

MS (ESI) m/z 515 (M+H)⁺, 537 (M+Na)⁺.

[Step 2] (1R*,2S*)-2-(3-Aminopropyl)-1-(1-pyridin-4-yl-1H-imidazol-4-yl)cyclopropanecarboxylic acid hydrochloride

[Formula 177]

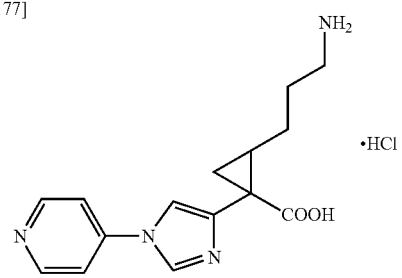

A mixture of the compound (6.0 mg) obtained in Step 1 of this Example and a 5 N aqueous hydrochloric acid solution (3 mL) was heated to reflux for 2 hours. The solvent was distilled off under reduced pressure. To the obtained residue, a small amount of acetone was added, and a solid was deposited by scrubbing with a spatula. Acetone was distilled off under reduced pressure, and the residue was then dried by the spraying of nitrogen gas and further dried under reduced pressure to obtain the title compound (3.6 mg).

¹H-NMR (CD₃OD) δ: 1.69 (1H, dd, J=9.0, 4.7 Hz), 1.73 (1H, dd, J=7.4, 4.7 Hz), 1.80-2.00 (5H, m), 2.98-3.04 (2H, m), 8.42-8.47 (3H, m), 9.09 (2H, s), 9.77 (1H, s).

MS (ESI) m/z 287 (M+H)⁺.

HRMS (ESI) m/z 287.15080 (M+H)⁺. (Calcd C₁₅H₁₉N₄O₂: 287.15042).

Example 24

(1R*,2S*)-2-(3-Aminopropyl)-1-(1-pyridin-3-yl-1H-imidazol-4-yl)cyclopropanecarboxylic acid

[Step 1] Ethyl (1R*,2S*)-2-{3-[bis(tert-butoxycarbonyl)amino]propyl}-1-(1-pyridin-3-yl-1H-imidazol-4-yl)cyclopropanecarboxylate

[Formula 178]

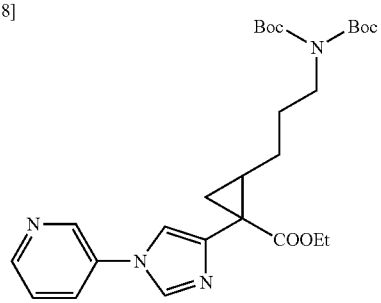

The title compound (83 mg) was obtained from the compound (250 mg) obtained in Reference Example 16 and pyridin-3-ylboronic acid (140 mg) in the same way as in Step 1 of Example 18. This reaction was performed at room temperature to 40° C.

$^1$H-NMR (CDCl$_3$) δ: 1.30 (3H, t, J=7.0 Hz), 1.49 (18H, s), 1.60-1.74 (6H, m), 1.80-1.88 (1H, m), 3.60 (2H, t, J=7.2 Hz), 4.23 (2H, q, J=7.0 Hz), 7.45 (1H, dd, J=8.2, 4.7 Hz), 7.58-7.59 (1H, m), 7.74-7.79 (1H, m), 7.87 (1H, s), 8.63-8.65 (1H, m), 8.77 (1H, d, J=2.7 Hz).

MS (ESI) m/z 515 (M+H)$^+$, 537 (M+Na)$^+$.

[Step 2] (1R*,2S*)-2-(3-Aminopropyl)-1-(1-pyridin-3-yl-1H-imidazol-4-yl)cyclopropanecarboxylic acid

[Formula 179]

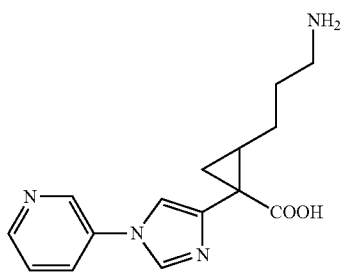

The title compound (37.5 mg) was obtained from the compound (80 mg) obtained in Step 1 of this Example in the same way as in Step 2 of Example 18.

$^1$H-NMR (CD$_3$OD) δ: 1.28 (1H, dd, J=8.8, 4.1 Hz), 1.41 (1H, dd, J=6.6, 4.3 Hz), 1.48-1.57 (1H, m), 1.65-1.86 (4H, m), 2.91-3.04 (2H, m), 7.58 (1H, dd, J=8.4, 4.9 Hz), 7.61-7.64 (1H, m), 8.03-8.09 (2H, m), 8.54-8.57 (1H, m), 8.83-8.85 (1H, m).

MS (ESI) m/z 287 (M+H)$^+$.

HRMS (ESI) m/z 287.15136 (M+H)$^+$. (Calcd C$_{15}$H$_{19}$N$_4$O$_2$: 287.15080).

Example 25

(1R*,2S*)-2-(3-Aminopropyl)-1-(1-pyridin-2-yl-1H-imidazol-4-yl)cyclopropanecarboxylic acid

[Step 1] Ethyl (1R*,2S*)-2-{3-[bis(tert-butoxycarbonyl)amino]propyl}-1-(1-pyridin-2-yl-1H-imidazol-4-yl)cyclopropanecarboxylate

[Formula 180]

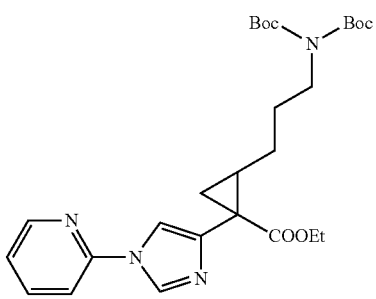

A mixture of the compound (200 mg) obtained in Reference Example 16, copper (II) oxide (4.0 mg), potassium carbonate (95 mg), and 2-bromopyridine (1.0 mL) was stirred at 100 to 110° C. for 44 hours. The cooled reaction solution was purified by silica gel column chromatography (eluting solvent: methylene chloride→methylene chloride/ethyl acetate=50/50) to obtain the title compound (114 mg).

$^1$H-NMR (CDCl$_3$) δ: 1.30 (3H, t, J=7.0 Hz), 1.49 (18H, s), 1.59-1.87 (7H, m), 3.60 (2H, t, J=7.4 Hz), 4.23 (2H, q, J=7.0 Hz), 7.24 (1H, dd, J=7.4, 4.7 Hz), 7.38 (1H, d, J=8.2 Hz), 7.79-7.85 (2H, m), 8.32 (1H, s), 8.46-8.49 (1H, m).

MS (ESI) m/z 515 (M+H)$^+$, 537 (M+Na)$^+$.

[Step 2] (1R*,2S*)-2-(3-Aminopropyl)-1-(1-pyridin-2-yl-1H-imidazol-4-yl)cyclopropanecarboxylic acid

[Formula 181]

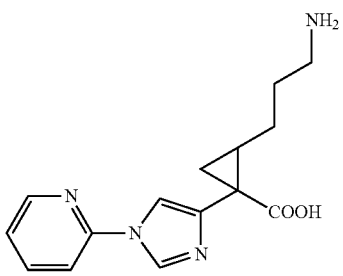

A mixture of the compound (113 mg) obtained in Step 1 of this Example and a 5 N aqueous hydrochloric acid solution (8 mL) was heated to reflux for 7 hours. The solvent was distilled off under reduced pressure, and the obtained residue was dissolved in deionized water. To the solution, an ion-exchange resin (Waters Corp., PoraPak Rxn CX, bulk, 1.5 g) was added, and the mixture was stirred for a while. The reaction mixture was transferred to a syringe with a filter (Shoko Scientific Co., Ltd.) to remove water. The resin was further washed with deionized water until the washings became neutral to a pH test paper. A solution of 28% ammonia water diluted 10-fold with methanol was added to the resin, and the eluate was concentrated under reduced pressure. The obtained residue was dissolved by the addition of deionized water, and the solution was concentrated under reduced pressure. This procedure was repeated several times, and the residue was then dried under reduced pressure to obtain the title compound (48 mg).

$^1$H-NMR (CD$_3$OD) δ: 1.26-1.31 (1H, m), 1.37-1.42 (1H, m), 1.47-1.56 (1H, m), 1.62-1.90 (4H, m), 2.89-3.04 (2H, m), 7.29-7.35 (1H, m), 7.59-7.65 (1H, m), 7.83-7.87 (1H, m), 7.90-7.98 (1H, m), 8.33-8.38 (1H, m), 8.43-8.48 (1H, m).

MS (ESI) m/z 287 (M+H)$^+$, 309 (M+Na)$^+$.

HRMS (ESI) m/z 287.15002 (M+H)$^+$. (Calcd C$_{15}$H$_{19}$N$_4$O$_2$: 287.15080).

Example 26

Ethyl (1R*,2S*)-2-(3-aminopropyl)-1-[1-(4-methylphenyl)-1H-imidazol-4-yl]cyclopropanecarboxylate hydrochloride

[Formula 182]

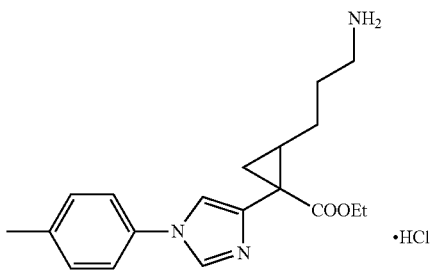

The compound (238 mg) obtained in Step 1 of Example 7 was treated in the same way as in Step 2 of Example 6 to obtain a free form of the title compound except that the heating to reflux was performed using 1 N hydrochloric acid/ethanol instead of hydrochloric acid. To the obtained free form, 1 N hydrochloric acid/ethanol and ethyl acetate were added, and the mixture was concentrated to obtain the title compound (82 mg).

$^1$H-NMR (CD$_3$OD) δ: 1.26 (3H, t, J=7.2 Hz), 1.68 (1H, dd, J=9.2, 4.9 Hz), 1.74 (1H, dd, J=7.6, 4.9 Hz), 1.78-1.99 (5H, m), 2.44 (3H, s), 3.00 (2H, t, J=6.8 Hz), 4.24 (2H, q, J=7.2 Hz), 7.45 (2H, d, J=8.6 Hz), 7.60 (2H, d, J=8.6 Hz), 8.03 (1H, d, J=1.8 Hz), 9.39 (1H, d, J=1.8 Hz).

MS (ESI) m/z 328 (M+H)$^+$, 350 (M+Na)$^+$.

HRMS (ESI) m/z 328.20154 (M+H)$^+$. (Calcd C$_{19}$H$_{26}$N$_3$O$_2$: 328.20250).

Example 27

(1S,2R)-2-(3-Aminopropyl)-1-[1-(3,3-dimethylbutyl)-1H-imidazol-4-yl]cyclopropanecarboxylic acid

[Step 1] Methyl (1S,2R)-2-{3-[bis(tert-butoxycarbonyl)amino]propyl-1-[1-(3,3-dimethylbutyl)-1H-imidazol-4-yl]cyclopropanecarboxylate and methyl (1R,2S)-2-{3-[bis(tert-butoxycarbonyl)amino]propyl-1-[1-(3,3-dimethylbutyl)-1H-imidazol-4-yl]cyclopropanecarboxylate

[Formula 183]

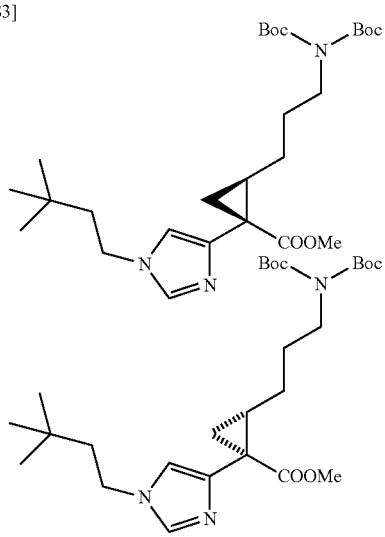

The compound (400 mg) obtained in Reference Example 20 was dissolved in 7.5% ethanol/hexane (10 mL), and this solution was purified in 4 portions by HPLC. The column used was CHIRALPAK AD-H (Daicel Corp., diameter: 2.0×25 cm). Elution was performed with 7.5% ethanol/hexane to respectively obtain methyl (1S,2R)-2-{3-[bis(tert-butoxycarbonyl)amino]propyl-1-[1-(3,3-dimethylbutyl)-1H-imidazol-4-yl]cyclopropanecarboxylate (123 mg) and methyl (1R,2S)-2-{3-[bis(tert-butoxycarbonyl)amino]propyl-1-[1-(3,3-dimethylbutyl)-1H-imidazol-4-yl]cyclopropanecarboxylate (140 mg). Their optical purities were determined using a chiral column CHIRALPAK AD-H (4.6×250 mm, eluting solvent: 7.5% ethanol/hexane, 1.0 mL/min, 40° C.). (1S,2R)-form: 96% ee (retention time: 4.5 minutes). (1R,2S)-form: 99% ee (retention time: 7.9 minutes).

[Step 2] (1S,2R)-2-(3-Aminopropyl)-1-[1-(3,3-dimethylbutyl)-1H-imidazol-4-yl]cyclopropanecarboxylic acid

[Formula 184]

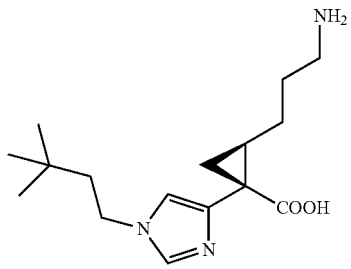

The title compound (56 mg) was obtained from methyl (1S,2R)-2-{3-[bis(tert-butoxycarbonyl)amino]propyl-1-[1-(3,3-dimethylbutyl)-1H-imidazol-4-yl]cyclopropanecarboxylate (123 mg) obtained in Step 1 of this Example in the same way as in Step 2 of Example 6. [α]$_D$−35° (c=1.0, methanol).

Example 28

(1R,2S)-2-(3-Aminopropyl)-1-[1-(3,3-dimethylbutyl)-1H-imidazol-4-yl]cyclopropanecarboxylic acid

[Formula 185]

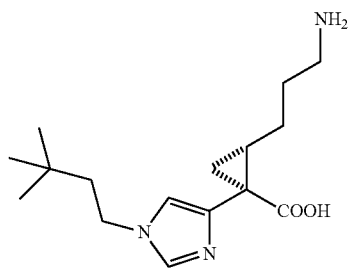

The title compound (53 mg) was obtained from methyl (1R,2S)-2-{3-[bis(tert-butoxycarbonyl)amino]propyl-1-[1-(3,3-dimethylbutyl)-1H-imidazol-4-yl]cyclopropanecarboxylate (140 mg) obtained in Step 1 of Example 27 in the same way as in Step 2 of Example 6. [α]$_D$+38° (c=1.0, methanol).

Example 29

(1S,2R)-2-(3-Aminopropyl)-1-(1-phenyl-1H-imidazol-4-yl)cyclopropanecarboxylic acid

[Step 1] Methyl (1S,2R)-2-{3-[bis(tert-butoxycarbonyl)amino]propyl}-1-(1-phenyl-1H-imidazol-4-yl)cyclopropanecarboxylate and methyl (1R,2S)-2-{3-[bis(tert-butoxycarbonyl)amino]propyl}-1-(1-phenyl-1H-imidazol-4-yl)cyclopropanecarboxylate

[Formula 183]

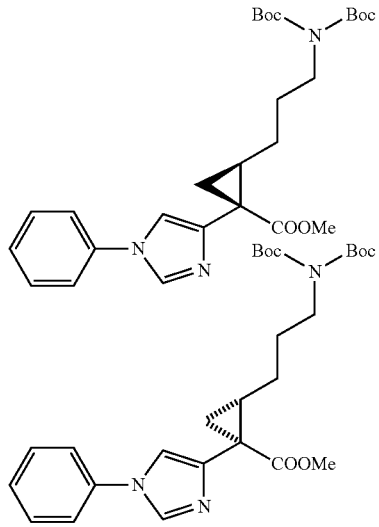

Methyl (1S,2R)-2-{3-[bis(tert-butoxycarbonyl)amino]propyl}-1-(1-phenyl-1H-imidazol-4-yl)cyclopropanecarboxylate (269 mg) and methyl (1R,2S)-2-{3-[bis(tert-butoxycarbonyl)amino]propyl}-1-(1-phenyl-1H-imidazol-4-yl)cyclopropanecarboxylate (278 mg) were respectively obtained from the compound (564 mg) obtained in Step 1 of Example 6 in the same way as in Step 1 of Example 27. Their optical purities were determined using a chiral column CHIRALPAK AD-H (4.6×250 mm, eluting solvent: 7% ethanol/hexane, 1.0 mL/min, 40° C.). (1S,2R)-form: >99% ee (retention time: 6.0 minutes). (1R,2S)-form: 99% ee (retention time: 8.7 minutes).

[Step 2] (1S,2R)-2-(3-Aminopropyl)-1-(1-phenyl-1H-imidazol-4-yl)cyclopropanecarboxylic acid

[Formula 187]

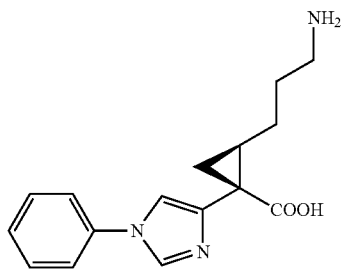

The title compound (74.0 mg) was obtained from methyl (1S,2R)-2-{3-[bis(tert-butoxycarbonyl)amino]propyl}-1-(1-phenyl-1H-imidazol-4-yl)cyclopropanecarboxylate (269 mg) obtained in Step 1 of this Example in the same way as in Step 2 of Example 6.

Example 30

(1R,2S)-2-(3-Aminopropyl)-1-(1-phenyl-1H-imidazol-4-yl)cyclopropanecarboxylic acid

[Formula 188]

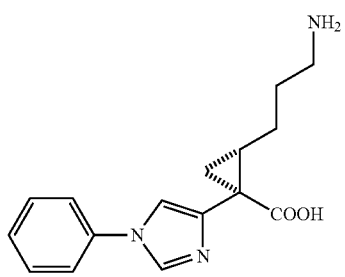

The title compound (75.8 mg) was obtained from methyl (1R,2S)-2-{3-[bis(tert-butoxycarbonyl)amino]propyl}-1-(1-phenyl-1H-imidazol-4-yl)cyclopropanecarboxylate (278 mg) obtained in Step 1 of Example 29 in the same way as in Step 2 of Example 6.

Example 31

(1R,2S)-2-(3-Aminopropyl)-1-(1-phenyl-1H-imidazol-4-yl)cyclopropanecarboxylic acid di-p-toluenesulfonate

[Formula 189]

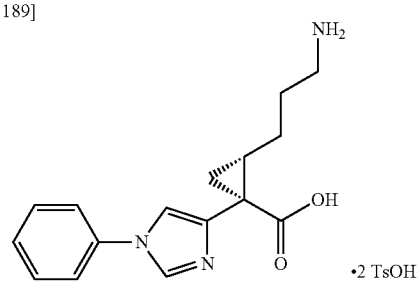

The compound (0.10 g) obtained in Reference Example 26 was dissolved in 5 N hydrochloric acid (5 mL), and the solution was heated to reflux at 105° C. for 3.5 hours. After standing to cool to room temperature, the reaction mixture was purified using an ion-exchange resin GL-Science Inertsep SCX, and the obtained solid was dissolved in an ethyl acetate-methanol mixed solution. To this solution, a solution of p-toluenesulfonic acid hydrate (0.1 g) in ethyl acetate (2 mL) was added, and the mixture was left standing overnight. Volatile matter was distilled off under reduced pressure, and a solid was deposited by the addition of ethyl acetate and ethanol, subsequently suction-filtered, and dried under reduced pressure to obtain the title compound (0.05 g).

$^1$H-NMR (CD$_3$OD) δ: 1.64-1.68 (1H, m), 1.71-1.75 (1H, m), 1.80-1.94 (5H, m), 2.37 (6H, s), 2.98-3.03 (2H, m), 7.24 (4H, d, J=7.8 Hz), 7.58-7.72 (5H, m), 7.71 (4H, d, J=7.8 Hz), 8.00 (1H, d, J=1.6 Hz), 9.36 (1H, d, J=1.6 Hz).

MS (ESI) m/z 286 (M+H)$^+$, 268 [M–H$_2$O+H]$^+$.
HRMS (ESI) m/z 286.15512 (M+H)$^+$. (Calcd C$_{16}$H$_{20}$N$_3$O$_2$: 286.1556).

Example 32

(1R*,2S*)-2-(3-Amino-2-methylpropyl)-1-(1-phenyl-1H-imidazol-4-yl)cyclopropanecarboxylic acid

[Step 1] Methyl (1R*,2S*)-2-{3-[bis(tert-butoxycarbonyl)amino]-2-methylpropyl}-1-(1-phenyl-1H-imidazol-4-yl)cyclopropanecarboxylate

[Formula 190]

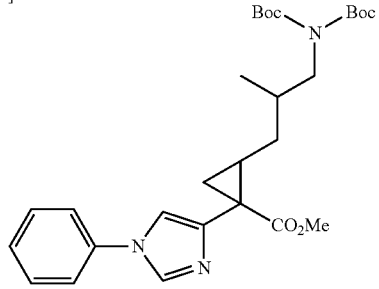

The title compound (213 mg, diastereomeric mixture) was obtained from the compound (242 mg) obtained in Reference Example 36 and phenylboronic acid (135 mg) in the same way as in Step 1 of Example 6.

$^1$H-NMR (CDCl$_3$) δ: 0.93 (1H, d, J=6.7 Hz), 0.97 (2H, d, J=7.0 Hz), 1.38-1.75 (4H, m), 1.49 (12H, s), 1.50 (6H, s), 1.77-1.85 (1H, m), 1.91-2.03 (1H, m), 3.42 (0.67H, dd, J=13.7, 7.8 Hz), 3.47 (0.33H, dd, J=13.6, 8.2 Hz), 3.56 (0.67H, dd, J=13.7, 7.0 Hz), 3.58 (0.33H, dd, J=13.6, 6.8 Hz), 3.73 (1H, s), 3.75 (2H, s), 7.32-7.37 (1H, m), 7.38-7.41 (2H, m), 7.44-7.49 (3H, m), 7.72 (0.67H, d, J=1.6 Hz), 7.73 (0.33H, d, J=1.6 Hz).

[Step 2] (1R*,2S*)-2-(3-Amino-2-methylpropyl)-1-(1-phenyl-1H-imidazol-4-yl)cyclopropanecarboxylic acid

[Formula 191]

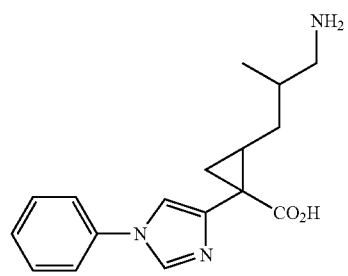

The title compound (109 mg, diastereomeric ratio=2:1) was obtained from the compound (213 mg) obtained in Step 1 of this Example in the same way as in Step 2 of Example 6.

$^1$H-NMR (CD$_3$OD) δ: 1.07 (2H, d, J=7.0 Hz), 1.08 (1H, d, J=7.0 Hz), 1.28-1.39 (2H, m), 1.51-1.78 (3H, m), 1.94-2.03 (1H, m), 2.78 (0.33H, dd, J=12.8, 6.3 Hz), 2.83 (0.67H, dd, J=12.5, 6.7 Hz), 2.86 (0.67H, dd, J=12.5, 6.3 Hz), 2.97 (0.33H, dd, J=12.8, 7.6 Hz), 7.34-7.39 (1H, m), 7.48-7.55 (5H, m), 7.93-7.94 (1H, m).

MS (ESI) m/z 300 (M+H)$^+$, 322 (M+Na)$^+$.
HRMS (ESI) m/z 322.1522 (M+Na)$^+$. (Calcd C$_{17}$H$_{21}$N$_3$NaO$_2$: 322.1532).

Example 33

(1R*,2S*)-2-(3-Amino-2-methylpropyl)-1-[1-(4-methylphenyl)-1H-imidazol-4-yl]cyclopropanecarboxylic acid

[Step 1] Methyl (1R*,2S*)-2-{3-[bis(tert-butoxycarbonyl)amino]-2-methylpropyl}-1-[1-(4-methylphenyl)-1H-imidazol-4-yl]cyclopropanecarboxylate

[Formula 192]

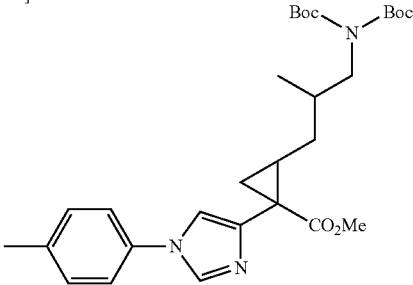

The title compound (246 mg, diastereomeric mixture) was obtained from the compound (251 mg) obtained in Reference Example 36 and 4-methylphenyl boronic acid (156 mg) in the same way as in Step 1 of Example 6.

¹H-NMR (CDCl₃) δ: 0.93 (1H, d, J=7.0 Hz), 0.97 (2H, d, J=6.6 Hz), 1.37-1.74 (4H, m), 1.48 (12H, s), 1.49 (6H, s), 1.76-1.84 (1H, m), 1.91-2.01 (1H, m), 2.39 (3H, s), 3.42 (0.67H, dd, J=13.7, 7.8 Hz), 3.47 (0.33H, dd, J=13.7, 8.2 Hz), 3.53-3.60 (1H, m), 3.73 (1H, s), 3.74 (2H, s), 7.24-7.29 (4H, m), 7.43-7.44 (1H, m), 7.68-7.69 (1H, m).

[Step 2] (1R*,2S*)-2-(3-Amino-2-methylpropyl)-1-[1-(4-methylphenyl)-1H-imidazol-4-yl]cyclopropanecarboxylic acid

[Formula 193]

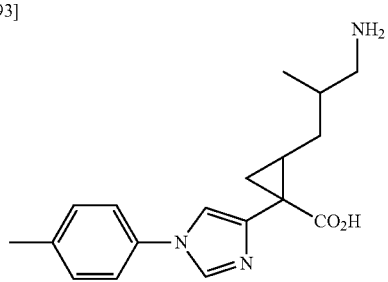

The title compound (107 mg, diastereomeric ratio=2:1) was obtained from the compound (246 mg) obtained in Step 1 of this Example in the same way as in Step 2 of Example 6.

¹H-NMR (CD₃OD) δ: 1.07 (2H, d, J=6.7 Hz), 1.08 (1H, d, J=7.0 Hz), 1.28-1.38 (2H, m), 1.50-1.78 (3H, m), 1.93-2.02 (1H, m), 2.38 (3H, s), 2.78 (0.33H, dd, J=12.7, 6.3 Hz), 2.82 (0.67H, dd, J=12.5, 6.7 Hz), 2.86 (0.67H, dd, J=12.5, 5.9 Hz), 2.97 (0.33H, dd, J=12.7, 7.8 Hz), 7.30 (2H, d, J=8.2 Hz), 7.39 (2H, d, J=8.2 Hz), 7.49 (0.67H, d, J=1.2 Hz), 7.50 (0.33H, d, J=1.6 Hz), 7.87-7.88 (1H, m).

MS (ESI) m/z 314 (M+H)⁺, 336 (M+Na)⁺.

HRMS (ESI) m/z 314.1863 (M+H)⁺. (Calcd C₁₈H₂₄N₃O₂: 314.1869).

Example 34

(1R*,2S*)-2-(3-Amino-2-methylpropyl)-1-{1-[4-(methylsulfonyl)phenyl]-1H-imidazol-4-yl}cyclopropanecarboxylic acid

[Step 1] Methyl (1R*,2S*)-2-{3-[bis(tert-butoxycarbonyl)amino]-2-methylpropyl}-1-{1-[4-(methylsulfonyl)phenyl]-1H-imidazol-4-yl}cyclopropanecarboxylate

[Formula 194]

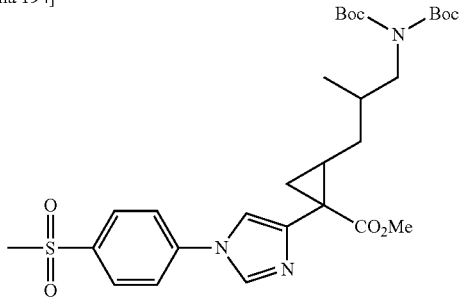

The title compound (141 mg, diastereomeric mixture) was obtained from the compound (253 mg) obtained in Reference Example 36 and (4-methanesulfonyl)phenylboronic acid (231 mg) in the same way as in Step 1 of Example 6.

¹H-NMR (CDCl₃) δ: 0.92 (1H, d, J=6.6 Hz), 0.97 (2H, d, J=6.6 Hz), 1.43-1.74 (4H, m), 1.49 (12H, s), 1.50 (6H, s), 1.79-1.87 (1H, m), 1.90-2.00 (1H, m), 3.10 (3H, s), 3.42 (0.67H, dd, J=14.1, 7.8 Hz), 3.47 (0.33H, dd, J=13.7, 8.2 Hz), 3.56 (0.67H, dd, J=14.1, 6.6 Hz), 3.59 (0.33H, dd, J=13.7, 6.6 Hz), 3.74 (1H, s), 3.76 (2H, s), 7.60-7.64 (3H, m), 7.85 (0.67H, br s), 7.87 (0.33H, br s), 8.04-8.08 (2.00H, m).

[Step 2] (1R*,2S*)-2-(3-Amino-2-methylpropyl)-1-{1-[4-(methylsulfonyl)phenyl]-1H-imidazol-4-yl}cyclopropanecarboxylic acid

[Formula 195]

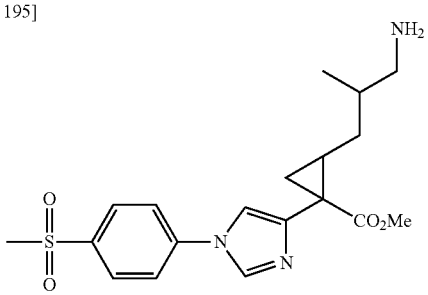

The title compound (72.8 mg, diastereomeric ratio=2:1) was obtained from the compound (141 mg) obtained in Step 1 of this Example in the same way as in Step 2 of Example 6.

¹H-NMR (CD₃OD) δ: 1.07 (2H, d, J=6.6 Hz), 1.08 (1H, d, J=7.0 Hz), 1.28-1.35 (1H, m), 1.37-1.42 (1H, m), 1.53-1.61 (1H, m), 1.61-1.67 (2H, m), 1.93-2.03 (1H, m), 2.79 (0.33H, dd, J=12.8, 6.5 Hz), 2.84 (1.34H, d, J=6.6 Hz), 2.97 (0.33H, dd, J=12.8, 7.4 Hz), 3.16 (3H, s), 7.69 (0.67H, d, J=1.2 Hz), 7.69 (0.33H, d, J=1.6 Hz), 7.84 (2H, d, J=8.6 Hz), 8.08 (2H, d, J=8.6 Hz), 8.16 (1H, br s).

MS (ESI) m/z 378 (M+H)⁺, 400 (M+Na)⁺.

HRMS (ESI) m/z 378.1485 (M+H)⁺. (Calcd C₁₈H₂₄N₃O₄S: 378.1488).

Example 35

(1R*,2S*)-2-(3-Aminopropyl)-1-[1-(6-hydroxypyridin-3-yl)-1H-imidazol-4-yl]cyclopropanecarboxylic acid

[Step 1] Ethyl (1R*,2S*)-1-[1-(5-bromopyridin-2-yl)-1H-imidazol-4-yl)-2-{3-[(tert-butoxycarbonyl)amino]propyl}cyclopropanecarboxylate

[Formula 196]

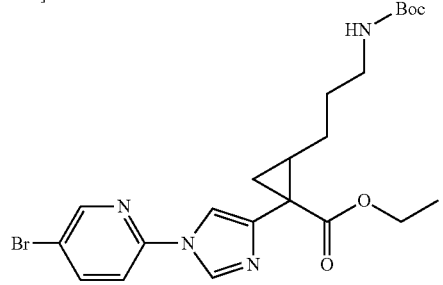

A mixture of the compound (210 mg) obtained in Reference Example 16, copper (II) oxide (4 mg), potassium carbonate (100 mg), and 2-bromo-5-fluoropyridine (253 mg)

was stirred at 120° C. for 27 hours. To the cooled reaction solution, a saturated aqueous solution of sodium bicarbonate was added, followed by extraction with ethyl acetate. The organic layer was washed with saturated sodium chloride solution and dried over anhydrous magnesium sulfate, and the solvent was then distilled off under reduced pressure. The obtained residue was purified by preparative thin-layer chromatography (200×200×1 mm, developing solvent: methylene chloride/ethyl acetate=1/9) to obtain the title compound (67 mg).

$^1$H-NMR (CDCl$_3$) δ: 1.30 (3H, t, J=7.0 Hz), 1.43 (9H, s), 1.56-1.70 (6H, m), 1.78-1.86 (1H, m), 3.11-3.19 (2H, m), 4.24 (2H, q, J=7.0 Hz), 4.57 (1H, br s), 7.49 (1H, s), 7.60-7.61 (2H, m), 7.69 (1H, d, J=1.2 Hz), 8.50-8.51 (1H, m).

MS (ESI) m/z 494 (M+H)$^+$.

[Step 2] (1R*,2S*)-2-(3-Aminopropyl)-1-[1-(6-hydroxypyridin-3-yl)-1H-imidazol-4-yl]cyclopropanecarboxylic acid

[Formula 197]

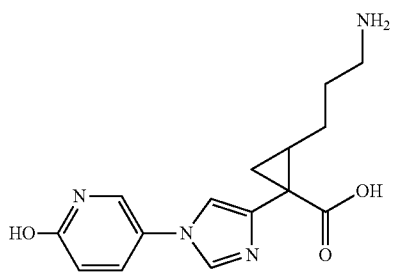

A mixture of the compound (63 mg) obtained in Step 1 of this Example and a 5 N aqueous hydrochloric acid solution (4 mL) was heated to reflux for 17 hours, and the solvent was distilled off under reduced pressure. The obtained residue was dissolved in deionized water (4 mL), and the solution was heated to reflux for 6 hours. The solvent was distilled off under reduced pressure, and the obtained residue was dissolved in deionized water. To the solution, an ion-exchange resin (Waters Corp., PoraPak Rxn CX, bulk, 1.5 g) was added, and the mixture was stirred. The reaction mixture was transferred to a syringe with a filter (Shoko Scientific Co., Ltd.) to remove water. The resin was further washed with deionized water until the washings became neutral to a pH test paper. A solution of 28% ammonia water diluted 10-fold with methanol was added to the resin, and the eluate was concentrated under reduced pressure. The obtained residue was dissolved by the addition of deionized water, and the solution was concentrated under reduced pressure. This procedure was repeated several times, and the residue was then dried under reduced pressure to obtain the title compound (36 mg) as a white solid.

$^1$H-NMR (CD$_3$OD) δ: 1.23 (1H, dd, J=8.8, 4.1 Hz), 1.37 (1H, dd, J=6.8, 4.1 Hz), 1.44-1.53 (1H, m), 1.64-1.85 (4H, m), 2.90-3.00 (2H, m), 6.63 (1H, d, J=9.4 Hz), 7.34-7.36 (1H, m), 7.72-7.82 (3H, m).

MS (ESI) m/z 303 (M+H)$^+$.

HRMS (ESI) m/z 303.14670 (M+H)$^+$. (Calcd C$_{15}$H$_{19}$N$_4$O$_3$: 303.14571).

Example 36

(1R*,2R*)-2-(3-Amino-1-methylpropyl)-1-(1-phenyl-1H-imidazol-4-yl)cyclopropanecarboxylic acid

[Formula 198]

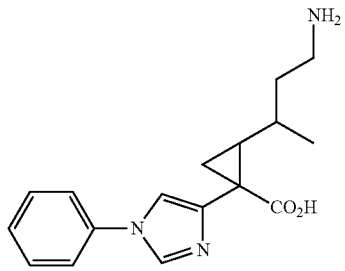

The title compound (90.0 mg, diastereomeric ratio=3:2) was obtained from the compound (177 mg) obtained in Reference Example 43 in the same way as in Step 2 of Example 18.

$^1$H-NMR (CD$_3$OD) δ: 1.09 (1.2H, d, J=6.3 Hz), 1.11 (1.8H, d, J=6.3 Hz), 1.24-1.32 (2H, m), 1.36-1.53 (1H, m), 1.66-1.82 (3H, m), 2.94-3.08 (2H, m), 7.34-7.39 (1H, m), 7.47-7.59 (5H, m), 7.91 (0.4H, br s), 7.94 (0.6H, br s).

MS (ESI) m/z 300 (M+H)$^+$, 322 (M+Na)$^+$.

HRMS (ESI) m/z 300.17074 (M+H)$^+$. (Calcd for C$_{17}$H$_{22}$N$_3$O$_2$: 300.17120).

Example 37

(1R*,2S*)-2-(3-Aminopropyl)-1-[1-(2-thienyl)-1H-imidazol-4-yl]cyclopropanecarboxylic acid dihydrochloride

[Step 1] Methyl (1R*,2S*)-2-{3-[bis(tert-butoxycarbonyl)amino]propyl}-1-[1-(2-thienyl)-1H-imidazol-4-yl]cyclopropanecarboxylic acid

[Formula 199]

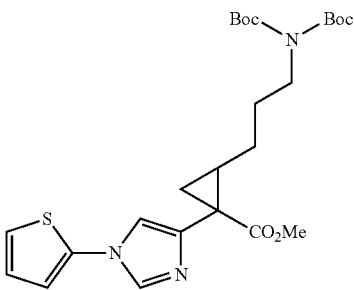

The compound (102 mg) obtained in Reference Example 8, copper (II) oxide (3.8 mg), and potassium carbonate (49.7 mg) were stirred at 100° C. for 3 hours in 2-iodothiophene (1.5 mL). Copper (II) oxide (3.8 mg) and 2-bromothiophene (1.5 mL) were further added thereto, and the mixture was stirred at 120° C. for 3 days. To the reaction solution, ethyl acetate and a saturated aqueous solution of sodium bicarbonate were added, and the mixture was filtered through celite. The organic layer was washed with saturated sodium chloride solution and then dried over anhydrous sodium sulfate. After filtration and concentration under reduced pressure, the obtained crude product was purified by silica gel column chromatography to obtain the title compound (4.1 mg).

¹H-NMR (CDCl₃) δ: 1.49 (18H, s), 1.53-1.74 (6H, m), 1.76-1.84 (1H, m), 3.59 (2H, t, J=7.2 Hz), 3.74 (3H, s), 6.95-7.00 (2H, m), 7.12 (1H, dd, J=5.1, 1.6 Hz), 7.34 (1H, br s), 7.60 (1H, br s).

[Step 2] (1R*,2S*)-2-(3-Aminopropyl)-1-[1-(2-thienyl)-1H-imidazol-4-yl]cyclopropanecarboxylic acid dihydrochloride

[Formula 200]

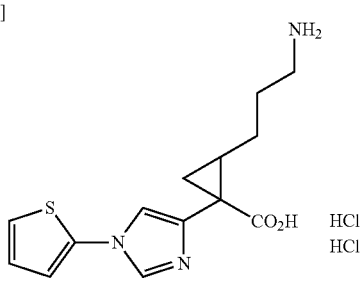

The compound (4.1 mg) obtained in Step 1 of this Example was heated to reflux for 3 hours in 5 N hydrochloric acid (3 mL). The reaction solution was concentrated under reduced pressure and then freeze-dried to obtain the title compound (2.6 mg).
¹H-NMR (CD₃OD) δ: 1.63-1.73 (2H, m), 1.77-1.92 (5H, m), 2.96-3.03 (2H, m), 7.14 (1H, dd, J=5.3, 3.7 Hz), 7.45-7.48 (1H, m), 7.55-7.57 (1H, m), 7.91 (1H, br s), 9.30 (1H, br s).
MS (ESI) m/z 292 (M+H)⁺, 314 (M+Na)⁺.
HRMS (ESI) m/z 292.11211 (M+H)⁺. (Calcd $C_{14}H_{18}N_3O_2S$: 292.11197).

Example 38

(1R*,2S*)-2-(3-Aminopropyl)-1-[1-(1,3-thiazol-2-yl)-1H-imidazol-4-yl]cyclopropanecarboxylic acid

[Step 1] Methyl (1R*,2S*)-2-{3-[bis(tert-butoxycarbonyl)amino]propyl}-1-[1-(1,3-thiazol-2-yl)-1H-imidazol-4-yl]cyclopropanecarboxylate

[Formula 201]

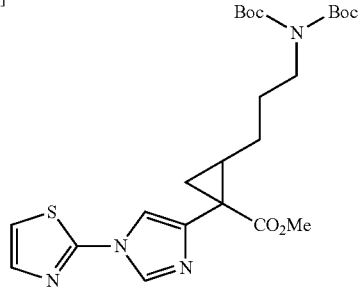

The compound (173 mg) obtained in Reference Example 8, 2-bromothiazole (0.11 mL), copper (II) oxide (NanoTek (registered trademark), 6.5 mg), and potassium carbonate (84.6 mg) were stirred at 110° C. for 8 hours in N,N-dimethylformamide (1.5 mL). To the reaction solution, ethyl acetate was added, and the mixture was filtered through celite. The organic layer was washed with a saturated aqueous solution of sodium bicarbonate and saturated sodium chloride solution and then dried over anhydrous sodium sulfate. After filtration and concentration under reduced pressure, the obtained crude product was purified by silica gel column chromatography to obtain the title compound (105 mg).
¹H-NMR (CDCl₃) δ: 1.49 (18H, s), 1.49-1.72 (6H, m), 1.78-1.86 (1H, m), 3.59 (2H, t, J=7.2 Hz), 3.76 (3H, s), 7.13 (1H, d, J=3.5 Hz), 7.56 (1H, d, J=3.5 Hz), 7.62 (1H, d, J=1.6 Hz), 8.06 (1H, d, J=1.6 Hz).

[Step 2] (1R*,2S*)-2-(3-Aminopropyl)-1-[1-(1,3-thiazol-2-yl)-1H-imidazol-4-yl]cyclopropanecarboxylic acid

[Formula 202]

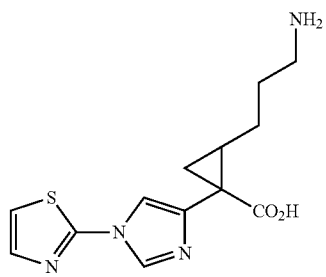

The title compound (56.7 mg) was obtained from the compound (105 mg) obtained in Step 1 of this Example in the same way as in Step 2 of Example 18.
¹H-NMR (CD₃OD) δ: 1.30 (1H, dd, J=8.2, 4.1 Hz), 1.41 (1H, dd, J=6.8, 4.1 Hz), 1.48-1.55 (1H, m), 1.63-1.84 (4H, m), 2.90-3.02 (2H, m), 7.42 (1H, d, J=3.5 Hz), 7.60 (1H, d, J=3.5 Hz), 7.71 (1H, d, J=1.6 Hz), 8.18 (1H, d, J=1.6 Hz).
MS (ESI) m/z 293 (M+H)⁺, 315 (M+Na)⁺.
HRMS (ESI) m/z 293.10736 (M+H)⁺. (Calcd $C_{13}H_{17}N_4O_2S$: 293.10722).

Example 39

(1R*,2S*)-2-(3-Aminopropyl)-1-(1-pyrimidin-2-yl-1H-imidazol-4-yl)cyclopropanecarboxylic acid

[Step 1] tert-Butyl (1R*,2S*)-2-{3-[bis(tert-butoxycarbonyl)amino]propyl}-1-(1-pyrimidin-2-yl-1H-imidazol-4-yl)cyclopropanecarboxylate

[Formula 203]

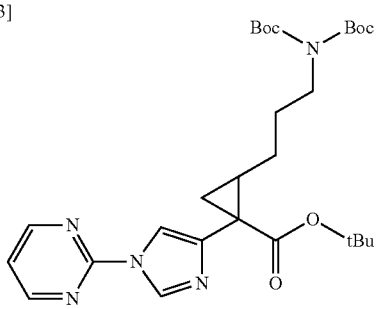

The title compound (199 mg) was obtained from the compound (191 mg) obtained in Reference Example 48 and 2-bromopyrimidine (103 mg) in the same way as in Step 1 of Example 38.
¹H-NMR (CDCl₃) δ: 1.48 (18H, s), 1.52 (9H, s), 1.53-1.63 (3H, m), 1.64-1.81 (4H, m), 3.59-3.63 (2H, m), 7.17 (1H, dd, J=5.1, 5.1 Hz), 7.99 (1H, br s), 8.45 (1H, br s), 8.67 (2H, d, J=5.1 Hz).

133

[Step 2] (1R*,2S*)-2-(3-Aminopropyl)-1-(1-pyrimidin-2-yl-1H-imidazol-4-yl)cyclopropanecarboxylic acid

[Formula 204]

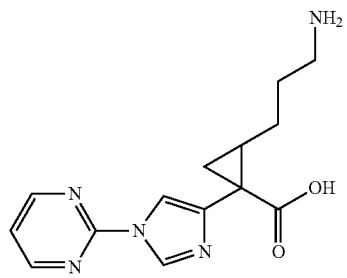

The compound (189 mg) obtained in Step 1 of this Example was stirred overnight at room temperature in a 4 M solution of hydrogen chloride in dioxane (10 mL). The reaction solution was concentrated, and the residue was then purified using a cation-exchange resin (PoraPak Rxn CX, eluting solvent: 28% ammonia water/methanol=10/46) to obtain the title compound (102 mg).

$^1$H-NMR (CD$_3$OD) δ: 1.28 (1H, dd, J=8.6, 4.3 Hz), 1.40 (1H, dd, J=6.7, 4.3 Hz), 1.48-1.55 (1H, m), 1.63-1.86 (4H, m), 2.91-3.03 (2H, m), 7.34 (1H, dd, J=4.7, 4.7 Hz), 8.01 (1H, d, J=1.6 Hz), 8.49 (1H, d, J=1.6 Hz), 8.76 (2H, d, J=4.7 Hz).

MS (ESI) m/z 288 (M+H)$^+$, 310 (M+Na)$^+$.

HRMS (ESI) m/z 288.14611 (M+H)$^+$. (Calcd C$_{14}$H$_{18}$N$_5$O$_2$: 288.14605).

Example 40

(1R*,2S*)-2-(3-Aminopropyl)-1-[1-(4-cyanophenyl)-1H-imidazol-4-yl]cyclopropanecarboxylic acid

[Step 1] tert-Butyl (1R*,2S*)-2-{3-[bis(tert-butoxycarbonyl)amino]propyl}-1-[1-(4-cyanophenyl)-1H-imidazol-4-yl]cyclopropanecarboxylate

[Formula 205]

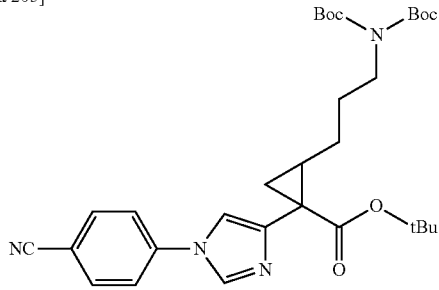

The title compound (85.9 mg) was obtained from the compound (193 mg) obtained in Reference Example 48 and 4-cyanophenylboronic acid (124 mg) in the same way as in Step 1 of Example 6.

$^1$H-NMR (CDCl$_3$) δ: 1.44-1.76 (7H, m), 1.49 (18H, s), 1.51 (9H, s), 3.61 (2H, t, J=7.0 Hz), 7.51-7.53 (2H, m), 7.62 (1H, d, J=1.6 Hz), 7.76-7.78 (3H, m).

134

[Step 2] (1R*,2S*)-2-(3-Aminopropyl)-1-[1-(4-cyanophenyl)-1H-imidazol-4-yl]cyclopropanecarboxylic acid

[Formula 206]

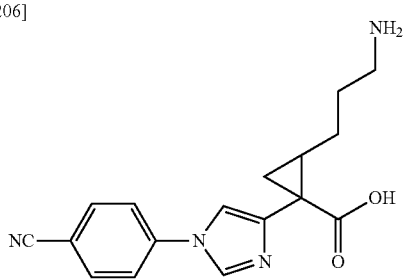

The title compound (42.5 mg) was obtained from the compound (81.9 mg) obtained in Step 1 of this Example in the same way as in Step 2 of Example 39.

$^1$H-NMR (CD$_3$OD) δ 1.28 (1H, dd, J=8.0, 3.9 Hz), 1.41 (1H, dd, J=6.6, 3.9 Hz), 1.48-1.55 (1H, m), 1.65-1.75 (2H, m), 1.76-1.85 (2H, m), 2.91-3.03 (2H, m), 7.66 (1H, d, J=1.2 Hz), 7.75-7.78 (2H, m), 7.86-7.89 (2H, m), 8.13 (1H, d, J=1.2 Hz). MS (ESI) m/z 311 (M+H)$^+$, 333 (M+Na)$^+$.

HRMS (ESI) m/z 311.15089 (M+H)$^+$. (Calcd C$_{17}$H$_{19}$N$_4$O$_2$: 311.15080).

Example 41

(1R*,2S*)-2-(3-Aminopropyl)-1-[1-(5-fluoropyridin-2-yl)-1H-imidazol-4-yl]cyclopropanecarboxylic acid

[Step 1] Ethyl (1R*,2S*)-2-{3-[bis(tert-butoxycarbonyl)amino]propyl}-1-[1-(5-fluoropyridin-2-yl)-1H-imidazol-4-yl]cyclopropanecarboxylate

[Formula 207]

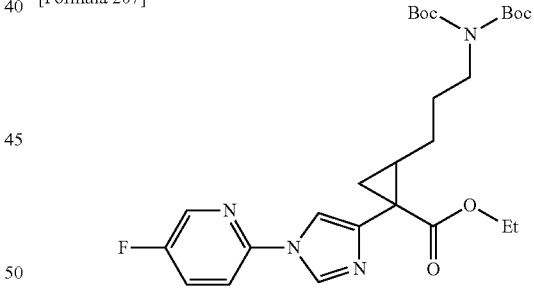

The compound (180 mg) obtained in Reference Example 16, copper (II) oxide (NanoTek (registered trademark), 6.6 mg), and potassium carbonate (114 mg) were stirred at 110° C. for 15 hours in a mixed solvent of 2,5-difluoropyridine (0.5 mL) and N,N-dimethylformamide (1.5 mL). To the reaction solution, ethyl acetate was added, and the mixture was filtered through celite. The organic layer was washed with a saturated aqueous solution of sodium bicarbonate and saturated sodium chloride solution and then dried over anhydrous sodium sulfate. After filtration and concentration under reduced pressure, the obtained crude product was purified by silica gel column chromatography to obtain the title compound (106 mg).

$^1$H-NMR (CDCl$_3$) δ: 1.29 (3H, t, J=7.2 Hz), 1.49 (18H, s), 1.50-1.73 (6H, m), 1.78-1.85 (1H, m), 3.60 (2H, t, J=7.4

Hz), 4.23 (2H, q, J=7.2 Hz), 7.33-7.36 (1H, m), 7.51-7.56 (1H, m), 7.73 (1H, d, J=1.6 Hz), 8.15 (1H, d, J=1.6 Hz), 8.31 (1H, d, J=2.7 Hz).

[Step 2] (1R*,2S*)-2-(3-Aminopropyl)-1-[1-(5-fluoropyridin-2-yl)-1H-imidazol-4-yl]cyclopropanecarboxylic acid

[Formula 208]

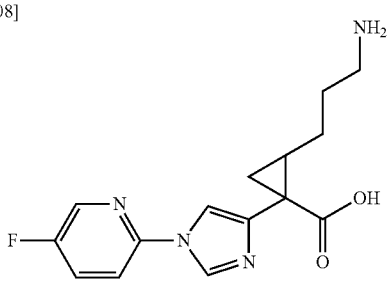

The title compound (58.0 mg) was obtained from the compound (106 mg) obtained in Step 1 of this Example in the same way as in Step 2 of Example 18.

$^1$H-NMR (CD$_3$OD) δ: 1.27 (1H, dd, J=8.8, 4.1 Hz), 1.39 (1H, dd, J=6.6, 4.1 Hz), 1.47-1.55 (1H, m), 1.63-1.85 (4H, m), 2.91-3.03 (2H, m), 7.66-7.69 (1H, m), 7.74-7.79 (1H, m), 7.81 (1H, d, J=1.6 Hz), 8.29 (1H, d, J=1.6 Hz), 8.36 (1H, d, J=2.7 Hz).

MS (ESI) m/z 305 (M+H)$^+$, 327 (M+Na)$^+$.

HRMS (ESI) m/z 305.14149 (M+H)$^+$ (Calcd C$_{15}$H$_{18}$N$_4$O$_2$: 305.14138).

Example 42

(1R*,2S*)-2-(3-Aminopropyl)-1-(1-quinolin-2-yl-1H-imidazol-4-yl)cyclopropanecarboxylic acid

[Step 1] tert-Butyl (1R*,2S*)-2-{3-[bis(tert-butoxycarbonyl)amino]propyl}-1-(1-quinolin-2-yl-1H-imidazol-4-yl)cyclopropanecarboxylate

[Formula 209]

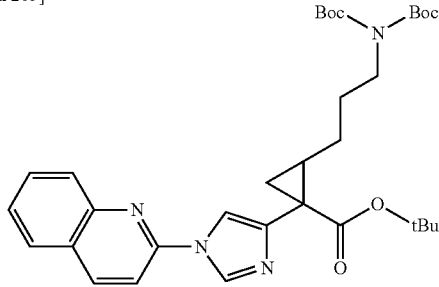

The title compound (108 mg) was obtained from the compound (175 mg) obtained in Reference Example 48 and 2-bromoquinoline (244 mg) in the same way as in Step 1 of Example 38.

$^1$H-NMR (CDCl$_3$) δ: 1.49 (18H, s), 1.49-1.82 (7H, m), 1.53 (9H, s), 3.63 (2H, t, J=7.2 Hz), 7.51 (1H, d, J=8.6 Hz), 7.52-7.56 (1H, m), 7.73-7.77 (1H, m), 7.82-7.84 (1H, m), 8.00 (1H, d, J=1.6 Hz), 8.03 (1H, d, J=8.6 Hz), 8.27 (1H, d, J=8.6 Hz), 8.37 (1H, d, J=1.6 Hz).

[Step 2] (1R*,2S*)-2-(3-Aminopropyl)-1-(1-quinolin-2-yl-1H-imidazol-4-yl)cyclopropanecarboxylic acid

[Formula 210]

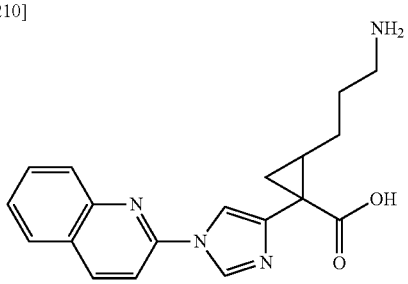

The compound (108 mg) obtained in Step 1 of this Example was stirred at room temperature for 3 hours in a 4 M solution of hydrogen chloride in dioxane (5 mL). The reaction solution was concentrated, and the residue was then purified using a cation-exchange resin (PoraPak Rxn CX, eluting solvent: 28% ammonia water/methanol=10/46) and subsequently, further purified by preparative reverse-phase HPLC (YMC-Pack ODS-A 30×250 mm, eluting solvent: water/acetonitrile=70/30) to obtain the title compound (29.3 mg).

$^1$H-NMR (CD$_3$OD) δ: 1.35 (1H, dd, J=8.8, 4.1 Hz), 1.44 (1H, dd, J=6.8, 4.1 Hz), 1.54-1.87 (5H, m), 2.93-3.05 (2H, m), 7.56-7.60 (1H, m), 7.76-7.81 (2H, m), 7.93-8.00 (2H, m), 8.06 (1H, d, J=1.6 Hz), 8.45 (1H, d, J=8.6 Hz), 8.54 (1H, d, J=1.6 Hz).

MS (ESI) m/z 337 (M+H)$^+$, 359 (M+Na)$^+$.

HRMS (ESI) m/z 377.16563 (M+H)$^+$. (Calcd C$_{19}$H$_{21}$N$_4$O$_2$: 337.16645).

Example 43

(1R*,2S*)-2-(3-Aminopropyl)-1-[1-(1-benzofuran-5-yl)-1H-imidazol-4-yl]cyclopropanecarboxylic acid

[Step 1] Methyl (1R*,2S*)-1-[1-(1-benzofuran-5-yl)-1H-imidazol-4-yl]-2-{3-[bis(tert-butoxycarbonyl)amino]propyl}cyclopropanecarboxylate

[Formula 211]

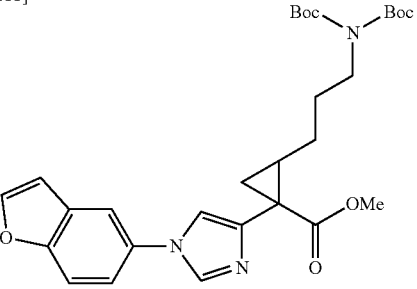

The title compound (88.0 mg) was obtained from the compound (115 mg) obtained in Reference Example 8 and benzofuran-5-boronic acid (87.9 mg) in the same way as in Step 1 of Example 6.

$^1$H-NMR (CDCl$_3$) δ: 1.50 (18H, s), 1.51-1.77 (6H, m), 1.80-1.87 (1H, m), 3.60 (2H, t, J=7.4 Hz), 3.75 (3H, s), 6.82-6.83 (1H, m), 7.32 (1H, dd, J=8.6, 2.2 Hz), 7.44 (1H, d, J=1.6 Hz), 7.57 (1H, d, J=8.6 Hz), 7.60 (1H, d, J=2.3 Hz), 7.69 (1H, d, J=1.6 Hz), 7.72 (1H, d, J=2.3 Hz).

[Step 2] (1R*,2S*)-2-(3-Aminopropyl)-1-[1-(1-benzofuran-5-yl)-1H-imidazol-4-yl]cyclopropanecarboxylic acid

[Formula 212]

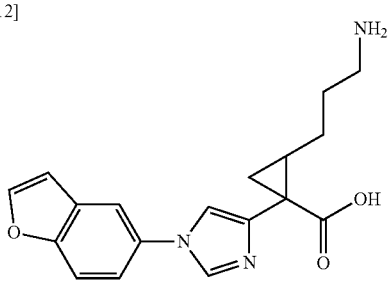

The title compound (21.0 mg) was obtained from the compound (83.0 mg) obtained in Step 1 of this Example in the same way as in Step 2 of Example 18.

$^1$H-NMR (CD$_3$OD) δ: 1.30 (1H, dd, J=9.0, 4.1 Hz), 1.40 (1H, dd, J=6.8, 4.1 Hz), 1.49-1.61 (1H, m), 1.64-1.87 (4H, m), 2.92-3.04 (2H, m), 6.92-6.93 (1H, m), 7.45 (1H, dd, J=8.8, 2.2 Hz), 7.52 (1H, d, J=1.2 Hz), 7.62 (1H, d, J=8.8 Hz), 7.77 (1H, d, J=2.3 Hz), 7.86 (1H, d, J=2.3 Hz), 7.90 (1H, d, J=1.2 Hz).

MS (ESI) m/z 326 (M+H)$^+$, 348 (M+Na)$^+$.

HRMS (ESI) m/z 326.14979 (M+H)$^+$. (Calcd C$_{18}$H$_{20}$N$_3$O$_3$: 326.15047).

Example 44

(1R*,2S*)-2-(3-Aminopropyl)-1-[1-(5-methoxypyridin-2-yl)-1H-imidazol-4-yl]cyclopropanecarboxylic acid

[Step 1] tert-Butyl (3-{(1R*,2S*)-2-cyano-2-[1-(5-methoxypyridin-2-yl)-1H-imidazol-4-yl]cyclopropyl}propyl)carbamate

[Formula 213]

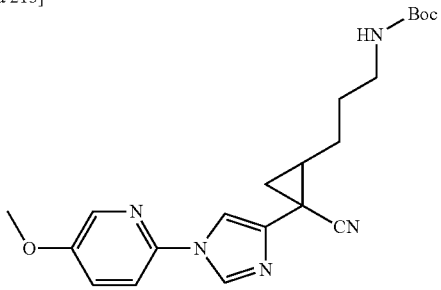

The compound (200 mg) obtained in Reference Example 51, copper (II) oxide (11 mg), potassium carbonate (190 mg), and 2-bromo-5-methoxypyridine (389 mg) were suspended in N,N-dimethylformamide (2 mL), and the suspension was stirred at 120° C. for 10 hours. The reaction mixture was separated into aqueous and organic layers by the addition of ethyl acetate and water. The organic layer was washed with saturated sodium chloride solution and then dried over anhydrous sodium sulfate. The obtained residue was purified by NH silica gel chromatography (eluting solvent: methylene chloride→methylene chloride/ethyl acetate=95/5) to obtain the title compound (124 mg).

$^1$H-NMR (CDCl$_3$) δ: 1.35-1.38 (1H, m), 1.44 (9H, s), 1.69-1.76 (4H, m), 1.77-1.90 (2H, m), 3.19-3.24 (2H, m), 3.91 (3H, s), 4.63 (1H, brs), 7.29 (1H, s), 7.35 (1H, dd, J=9.0, 3.1 Hz), 7.62 (1H, d, J=1.6 Hz), 8.10 (1H, d, J=1.6 Hz), 8.15 (1H, d, J=3.1 Hz).

[Step 2] (1R*,2S*)-2-(3-Aminopropyl)-1-[1-(5-methoxypyridin-2-yl)-1H-imidazol-4-yl]cyclopropanecarboxylic acid

[Formula 214]

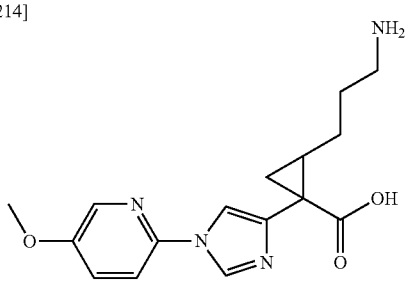

The compound (124 mg) obtained in Step 1 of this Example was dissolved in ethanol (5 mL) and a 2 N aqueous potassium hydroxide solution (5 mL), and the solution was heated to reflux at 110° C. for 3 hours. The reaction solution was concentrated, and the residue was then dissolved in a 5 N aqueous hydrochloric acid solution (10 mL). The solution was heated to reflux at 110° C. for 2 hours. The reaction solution was concentrated, and the residue was then purified by reverse-phase HPLC (eluting solvent: 10% acetonitrile-0.1% hydrochloric acid in water). The obtained residue was adsorbed onto an ion-exchange resin (PoraPak Rxn.CX), followed by elution with a 2.8% solution of ammonia in methanol. The obtained residue was freeze-dried to obtain the title compound (57 mg).

$^1$H-NMR (CD$_3$OD) δ: 1.25-1.28 (1H, m), 1.36-1.39 (1H, m), 1.47-1.54 (1H, m), 1.64-1.86 (4H, m), 2.90-3.03 (2H, m), 3.90 (3H, s), 7.52-7.54 (2H, m), 7.75 (1H, d, J=1.6 Hz), 8.13-8.14 (1H, m), 8.20 (1H, d, J=1.6 Hz).

HRMS (ESI) m/z 317.16067 (M+H)$^+$. (Calcd C$_{16}$H$_{21}$N$_4$O$_3$: 317.16136).

Example 45

(1R*,2S*)-2-(3-Aminopropyl)-1-[1-(5-chloropyridin-2-yl)-1H-imidazol-4-yl]cyclopropanecarboxylic acid

[Step 1] tert-Butyl (3-{(1R*,2S*)-2-[1-(5-chloropyridin-2-yl)-1H-imidazol-4-yl]-2-cyanocyclopropyl}propyl)carbamate

[Formula 215]

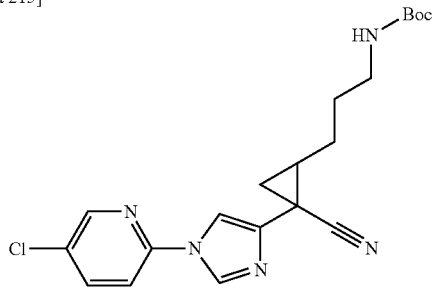

The compound (200 mg) obtained in Reference Example 51 was dissolved in N,N-dimethylformamide (5 mL). To the solution, sodium hydride (30 mg) was added under ice cooling, and the mixture was stirred at room temperature for 10 minutes. Then, 5-chloro-2-fluoropyridine (80 μL) was added thereto, and the mixture was stirred at 100° C. for 7 hours. The reaction mixture was separated into aqueous and organic layers by the addition of water and ethyl acetate. The organic layer was washed with saturated sodium chloride solution and then dried over anhydrous sodium sulfate. The obtained residue was purified by silica gel column chromatography (eluting solvent: methylene chloride→methylene chloride/ethyl acetate=75/25) to obtain the title compound (243 mg).

$^1$H-NMR (CDCl$_3$) δ: 1.38 (1H, dd, J=6.7, 4.3 Hz), 1.44 (9H, s), 1.70-1.77 (4H, m), 1.80-1.90 (2H, m), 3.19-3.23 (2H, m), 4.63 (1H, brs), 7.31 (1H, d, J=8.6 Hz), 7.67 (1H, d, J=1.2 Hz), 7.81 (1H, dd, J=8.6, 2.7 Hz), 8.19 (1H, d, J=1.2 Hz), 8.42-8.43 (1H, m).

[Step 2] (1R*,2S*)-2-(3-Aminopropyl)-1-[1-(5-chloropyridin-2-yl)-1H-imidazol-4-yl]cyclopropanecarboxylic acid

[Formula 216]

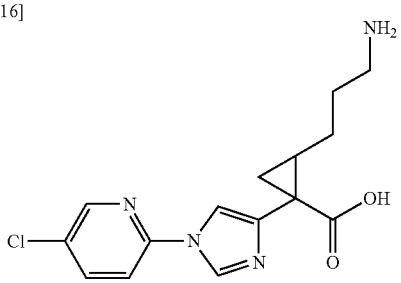

The title compound (31 mg) was obtained from the compound (243 mg) obtained in Step 1 of this Example in the same way as in Step 2 of Example 44.

$^1$H-NMR (CD$_3$OD) δ: 1.66-1.75 (2H, m), 1.82-1.95 (5H, m), 2.99-3.02 (2H, m), 7.95 (1H, d, J=8.6 Hz), 8.17-8.20 (1H, m), 8.32 (1H, s), 8.62 (1H, d, J=2.0 Hz), 9.72-9.74 (1H, m).

HRMS (ESI) m/z 321.11105 (M+H)$^+$. (Calcd C$_{15}$H$_{18}$ClN$_4$O$_2$: 321.11183).

Example 46

(1R*,2S*)-2-(3-Aminopropyl)-1-(1-isoquinolin-3-yl-1H-imidazol-4-yl)cyclopropanecarboxylic acid

[Step 1] tert-Butyl {3-[(1R*,2S*)-2-cyano-2-(1-isoquinolin-3-yl-1H-imidazol-4-yl)cyclopropyl]propyl}carbamate

[Formula 217]

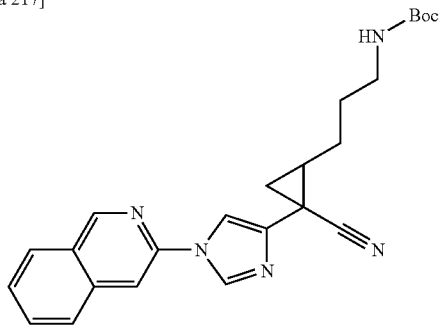

The title compound (137 mg) was obtained from the compound (300 mg) obtained in Reference Example 51 and 3-bromoisoquinoline (645 mg) in the same way as in Step 1 of Example 44.

$^1$H-NMR (CDCl$_3$) δ: 1.40 (1H, dd, J=6.7, 4.3 Hz), 1.45 (9H, s), 1.72-1.79 (4H, m), 1.83-1.92 (2H, m), 3.21-3.25 (2H, m), 4.64 (1H, brs), 7.60-7.65 (2H, m), 7.74-7.80 (2H, m), 7.89 (1H, d, J=8.4 Hz), 8.03 (1H, d, J=8.4 Hz), 8.36 (1H, d, J=1.2 Hz).

[Step 2] (1R*,2S*)-2-(3-Aminopropyl)-1-(1-isoquinolin-3-yl-1H-imidazol-4-yl)cyclopropanecarboxylic acid

[Formula 218]

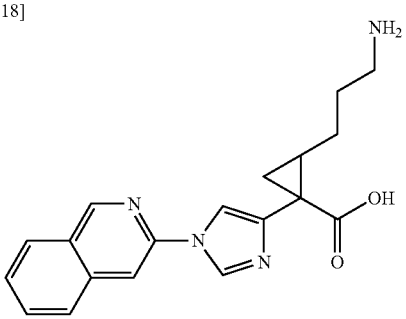

The title compound (89 mg) was obtained from the compound (136 mg) obtained in Step 1 of this Example in the same way as in Step 2 of Example 44.

$^1$H-NMR (CD$_3$OD) δ: 1.28-1.32 (1H, m), 1.41 (1H, dd, J=6.7, 4.3 Hz), 1.51-1.59 (1H, m), 1.67-1.86 (4H, m), 2.92-3.05 (2H, m), 7.64 (1H, dt, J=7.0, 1.2 Hz), 7.79 (1H, dt, J=7.0, 1.2 Hz), 7.95 (1H, d, J=1.6 Hz), 7.99 (1H, d, J=8.2 Hz), 8.11 (1H, d, J=8.2 Hz), 8.45 (1H, d, J=1.6 Hz).

HRMS (ESI) m/z 337.16583 (M+H)$^+$. (Calcd C$_{19}$H$_{21}$N$_4$O$_2$: 337.16645).

Example 47

(1R*,2S*)-2-(3-Aminopropyl)-1-[1-(1-naphthyl)-1H-imidazol-4-yl]cyclopropanecarboxylic acid

[Formula 219]

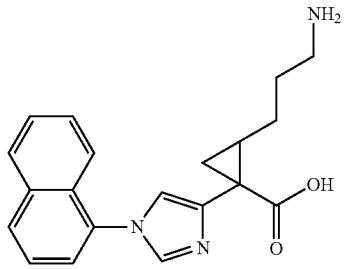

The compound (210 mg) obtained in Reference Example 54 was dissolved in 5 N hydrochloric acid, and the solution was heated to reflux for 89 hours. The reaction solution was concentrated, and the residue was then purified by reverse-phase HPLC (15% acetonitrile-0.1% hydrochloric acid in water). The obtained residue was adsorbed onto an ion-exchange resin (PoraPak Rxn.CX), followed by elution with a 2.8% solution of ammonia in methanol. The obtained residue was concentrated under reduced pressure to obtain the title compound (58 mg).

¹H-NMR (CD₃OD) δ: 1.38-1.41 (1H, m), 1.46-1.48 (1H, m), 1.59-1.66 (1H, m), 1.72-1.89 (4H, m), 2.94-3.06 (2H, m), 7.42 (1H, d, J=1.6 Hz), 7.52-7.62 (4H, m), 7.67-7.69 (1H, m), 7.79 (1H, d, J=1.6 Hz), 8.00-8.03 (2H, m).

HRMS (ESI) m/z 336.17128 (M+H)⁺. (Calcd C₂₀H₂₂N₃O₂: 336.17120).

Example 48

(1R,2S)-2-(3-Aminopropyl)-1-(1-pyridin-2-yl-1H-imidazol-4-yl)cyclopropanecarboxylic acid

[Formula 220]

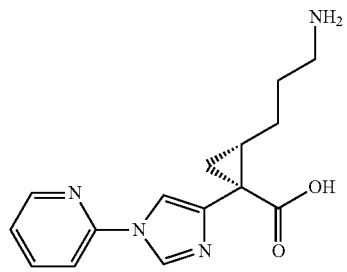

The compound (2.90 g) obtained in Reference Example 60 was dissolved in 5 N hydrochloric acid (80 mL), and the solution was heated to reflux at 100° C. for 3 hours. Hydrochloric acid was removed under reduced pressure. Then, 150 mL of water and an ion-exchange resin (PoraPak Rxn.CX, 21 g) were added to the residue, and the mixture was stirred at room temperature for 2 hours. The reaction solution was transferred to a glass filter to remove a liquid. The residue was washed with 450 mL of water, and the desired compound was then eluted with a 2.8% solution of ammonia/water in methanol. The obtained compound was dried under reduced pressure to obtain the title compound (1.82 g).

¹H-NMR (CD₃OD) δ: 1.27-1.32 (1H, m), 1.38-1.41 (1H, m), 1.48-1.56 (1H, m), 1.64-1.88 (4H, m), 2.92-3.04 (2H, m), 7.30-7.35 (1H, m), 7.60-7.64 (1H, m), 7.92-7.97 (1H, m), 8.37 (1H, s), 8.43-8.48 (1H, m).

MS (ESI) m/z 287 (M+H)⁺.

HRMS (ESI) m/z 287.15117 (M+H)⁺. (Calcd C₁₅H₁₉N₄O₂: 287.15080).

Example 49

(1R*,2S*)-2-(3-Aminopropyl)-1-[1-(5-methylpyridin-2-yl)-1H-imidazol-4-yl]cyclopropanecarboxylic acid

[Formula 221]

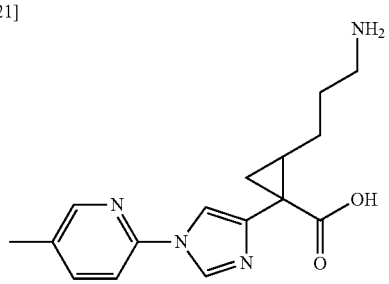

The title compound (0.16 g) was obtained from the compound (1.1 g) obtained in Reference Example 63 in the same way as in Step 2 of Example 44.

¹H-NMR (CD₃OD) δ: 1.26 (1H, dd, J=9.0, 3.9 Hz), 1.38 (1H, dd, J=6.7, 4.3 Hz), 1.47-1.54 (1H, m), 1.62-1.85 (4H, m), 2.37 (3H, s), 2.90-3.03 (2H, m), 7.50 (1H, d, J=8.2 Hz), 7.75-7.78 (1H, m), 7.80 (1H, d, J=1.6 Hz), 8.28-8.30 (2H, m).

HRMS (ESI) m/z 323.14866 (M+H)⁺. (Calcd C₁₆H₂₀N₄NaO₂: 323.14839).

Example 50

(1R,2S)-2-[(2R)-3-Amino-2-methylpropyl]-1-(1-phenyl-1H-imidazol-4-yl)cyclopropanecarboxylic acid

[Step 1] Methyl (1R,2S)-2-{(2R)-3-[(tert-butoxycarbonyl)amino]-2-methylpropyl}-1-(1-phenyl-1H-imidazol-4-yl)cyclopropanecarboxylate and methyl (1R,2S)-2-{(2S)-3-[(tert-butoxycarbonyl)amino]-2-methylpropyl}-1-(1-phenyl-1H-imidazol-4-yl)cyclopropanecarboxylate

[Formula 222]

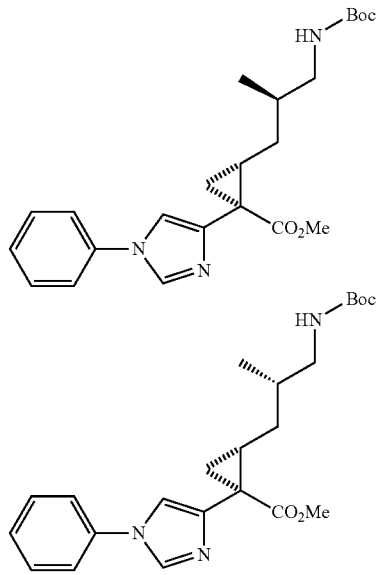

The compound (126 mg) obtained in Reference Example 68 was diastereomerically resolved in several portions by preparative HPLC (Daicel CHIRALPAK AD-H, 20×250 mm, eluting solvent: hexane/ethanol=70/30, 12 mL/min, 210 nm) to obtain methyl (1R,2S)-2-{(2R)-3-[(tert-butoxycarbonyl)amino]-2-methylpropyl}-1-(1-phenyl-1H-imidazol-4-yl)cyclopropanecarboxylate (40.4 mg) as the first peak and methyl (1R,2S)-2-{(2S)-3-[(tert-butoxycarbonyl)amino]-2-methylpropyl}-1-(1-phenyl-1H-imidazol-4-yl)cyclopropanecarboxylate (41.6 mg) as the second peak. Their purities were confirmed by analytical HPLC (Daicel CHIRALPAK AD-H, 4.6×250 mm, eluting solvent: hexane/ethanol=70/30, 1.0 mL/min, 210 nm, $t_R$=6.9 minutes (first peak), $t_R$=8.2 minutes (second peak)).

[Step 2] (1R,2S)-2-[(2R)-3-Amino-2-methylpropyl]-1-(1-phenyl-1H-imidazol-4-yl)cyclopropanecarboxylic acid

[Formula 223]

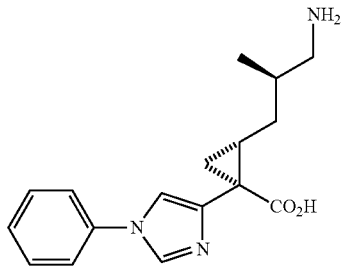

The title compound (28.4 mg) was obtained from methyl (1R,2S)-2-{(2R)-3-[(tert-butoxycarbonyl)amino]-2-methylpropyl}-1-(1-phenyl-1H-imidazol-4-yl)cyclopropanecarboxylate (40.4 mg) obtained in Step 1 of this Example in the same way as in Step 2 of Example 18.

$^1$H-NMR (CD$_3$OD) δ: 1.08 (3H, d, J=7.0 Hz), 1.32 (1H, dd, J=8.8, 4.2 Hz), 1.37 (1H, dd, J=6.6, 4.2 Hz), 1.52-1.65 (2H, m), 1.71-1.78 (1H, m), 1.96-2.05 (1H, m), 2.78 (1H, dd, J=12.7, 6.5 Hz), 2.98 (1H, dd, J=12.7, 7.6 Hz), 7.34-7.39 (1H, m), 7.48-7.55 (5H, m), 7.95 (1H, br s).

MS (ESI) m/z 300 (M+H)$^+$, 322 (M+Na)$^+$.

HRMS (ESI) m/z 300.17145 (M+H)$^+$. (Calcd C$_{17}$H$_{22}$N$_3$O$_2$: 300.17120).

Example 51

(1R,2S)-2-[(2S)-3-Amino-2-methylpropyl]-1-(1-phenyl-1H-imidazol-4-yl)cyclopropanecarboxylic acid

[Formula 224]

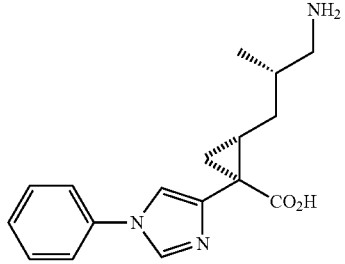

The title compound (30.1 mg) was obtained from methyl (1R,2S)-2-{(2S)-3-[(tert-butoxycarbonyl)amino]-2-methylpropyl}-1-(1-phenyl-1H-imidazol-4-yl)cyclopropanecarboxylate (41.6) obtained in Step 1 of Example 50 in the same way as in Step 2 of Example 18.

$^1$H-NMR (CD$_3$OD) δ: 1.07 (3H, d, J=6.6 Hz), 1.33 (1H, dd, J=8.6, 4.0 Hz), 1.38 (1H, dd, J=6.5, 4.0 Hz), 1.51-1.70 (3H, m), 1.94-2.02 (1H, m), 2.85 (2H, d, J=6.6 Hz), 7.34-7.39 (1H, m), 7.48-7.54 (5H, m), 7.95 (1H, br s).

MS (ESI) m/z 300 (M+H)$^+$, 322 (M+Na)$^+$.

HRMS (ESI) m/z 300.17080 (M+H)$^+$. (Calcd C$_{17}$H$_{22}$N$_3$O$_2$: 300.17120).

Example 52

(1R*,2R*)-2-(3-Amino-2,2-dimethylpropyl)-1-(1-phenyl-1H-imidazol-4-yl]cyclopropanecarboxylic acid

[Formula 225]

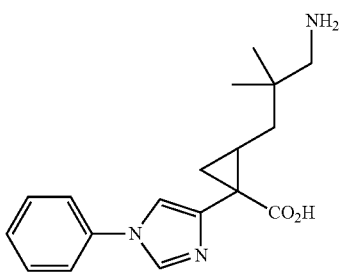

The title compound (53.3 mg) was obtained from the compound (77.6 mg) obtained in Reference Example 76 in the same way as in Step 2 of Example 18.

$^1$H-NMR (CD$_3$OD) δ: 1.08 (3H, s), 1.09 (3H, s), 1.30 (1H, dd, J=6.6, 3.9 Hz), 1.38 (1H, dd, J=9.0, 3.9 Hz), 1.43-1.50 (1H, m), 1.59 (1H, dd, J=14.7, 5.1 Hz), 1.72 (1H, dd, J=14.7, 7.6 Hz), 2.76 (1H, d, J=12.9 Hz), 2.91 (1H, d, J=12.9 Hz), 7.35-7.39 (1H, m), 7.48-7.54 (5H, m), 7.96 (1H, br s).

MS (ESI) m/z 314 (M+H)$^+$, 336 (M+Na)$^+$.

HRMS (ESI) m/z 314.18709 (M+H)$^+$. (Calcd for C$_{18}$H$_{24}$N$_3$O$_2$: 314.18685).

Example 53

(1R,2S)-2-[(2-Aminomethyl)butyl]-1-(1-phenyl-1H-imidazol-4-yl]cyclopropanecarboxylic acid

[Formula 226]

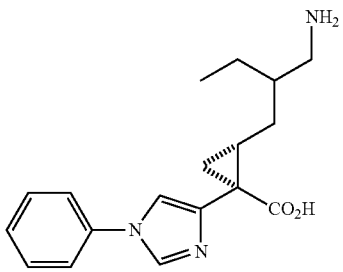

The title compound (98.6 mg) was obtained from the compound (159 mg) obtained in Reference Example 79 in the same way as in Step 2 of Example 18.

$^1$H-NMR (CD$_3$OD) δ: 0.97 (1.5H, t, J=7.4 Hz), 0.99 (1.5H, t, J=7.4 Hz), 1.31-1.37 (2H, m), 1.40-1.56 (3.5H, m), 1.67-1.88 (2.5H, m), 2.86 (0.5H, dd, J=12.9, 7.4 Hz), 2.90-3.00 (1H, m), 2.99 (0.5H, dd, J=12.9, 5.1 Hz), 7.34-7.39 (1H, m), 7.47-7.54 (5H, m), 7.94-7.95 (1H, m).

MS (ESI) m/z 314 (M+H)$^+$, 336 (M+Na)$^+$.

HRMS (ESI) m/z 314.18629 (M+H)$^+$. (Calcd C$_{18}$H$_{24}$N$_3$O$_2$: 314.18685).

Example 54

(1R,2S)-2-[(2R)-3-Amino-2-methylpropyl]-1-(1-pyridin-2-yl-1H-imidazol-4-yl]cyclopropanecarboxylic acid

[Formula 227]

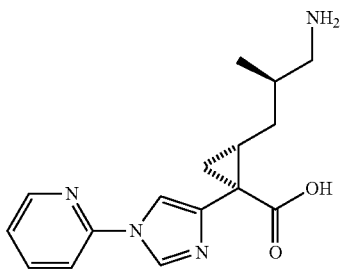

The title compound (133 mg) was obtained from methyl (1R,2S)-2-{(2R)-3-[bis(tert-butoxycarbonyl)amino]-2-methylpropyl}-1-(1-pyridin-2-yl-1H-imidazol-4-yl)cyclopropanecarboxylate (236 mg) obtained in Reference Example 86 in the same way as in Step 2 of Example 18.

$^1$H-NMR (CD$_3$OD) δ: 1.08 (3H, d, J=7.0 Hz), 1.31 (1H, dd, J=8.6, 3.9 Hz), 1.37 (1H, dd, J=6.6, 3.9 Hz), 1.53-1.66 (2H, m), 1.72-1.79 (1H, m), 1.97-2.05 (1H, m), 2.79 (1H, dd, J=12.7, 6.6 Hz), 2.98 (1H, dd, J=12.7, 7.6 Hz), 7.30-7.33 (1H, m), 7.62 (1H, d, J=8.2 Hz), 7.85 (1H, d, J=1.6 Hz), 7.91-7.96 (1H, m), 8.35 (1H, d, J=1.2 Hz), 8.44-8.46 (1H, m).

MS (ESI) m/z 301 (M+H)$^+$, 323 (M+Na)$^+$.

HRMS (ESI) m/z 301.16620 (M+H)$^+$. (Calcd C$_{16}$H$_{21}$N$_4$O$_2$: 301.16645).

Example 55

(1S,2R)-2-[(2R)-3-Amino-2-methylpropyl]-1-(1-pyridin-2-yl-1H-imidazol-4-yl]cyclopropanecarboxylic acid

[Formula 228]

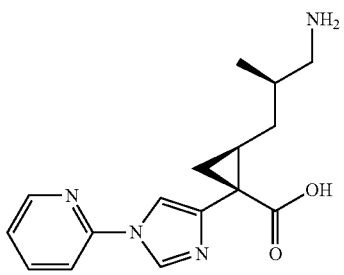

The title compound (318 mg) was obtained from methyl (1S,2R)-2-{(2R)-3-[bis(tert-butoxycarbonyl)amino]-2-methylpropyl}-1-(1-pyridin-2-yl-1H-imidazol-4-yl)cyclopropanecarboxylate (491 mg) obtained in Reference Example 86 in the same way as in Step 2 of Example 18.

$^1$H-NMR (CD$_3$OD) δ: 1.08 (3H, d, J=7.0 Hz), 1.33 (1H, dd, J=8.6, 3.9 Hz), 1.38 (1H, dd, J=6.5, 3.9 Hz), 1.51-1.71 (3H, m), 1.94-2.03 (1H, m), 2.85 (2H, d, J=6.6 Hz), 7.30-7.33 (1H, m), 7.62 (1H, d, J=8.2 Hz), 7.84 (1H, d, J=1.6 Hz), 7.91-7.96 (1H, m), 8.35 (1H, d, J=1.6 Hz), 8.44-8.46 (1H, m).

MS (ESI) m/z 301 (M+H)$^+$, 323 (M+Na)$^+$.

HRMS (ESI) m/z 301.16673 (M+H)$^+$. (Calcd C$_{16}$H$_{21}$N$_4$O$_2$: 301.16645).

Example 56

(1R,2S)-2-[(2S)-3-Amino-2-methylpropyl]-1-(1-pyridin-2-yl-1H-imidazol-4-yl]cyclopropanecarboxylic acid

[Formula 229]

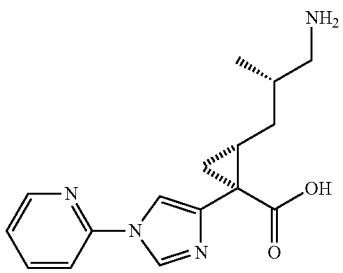

The title compound (294 mg) was obtained from methyl (1R,2S)-2-{(2S)-3-[bis(tert-butoxycarbonyl)amino]-2-methylpropyl}-1-(1-pyridin-2-yl-1H-imidazol-4-yl)cyclopropanecarboxylate (532 mg) obtained in Reference Example 89 in the same way as in Step 2 of Example 18.

$^1$H-NMR (CD$_3$OD) δ: 1.07 (3H, d, J=7.0 Hz), 1.33 (1H, dd, J=8.8, 3.9 Hz), 1.38 (1H, dd, J=6.7, 3.9 Hz), 1.51-1.71 (3H, m), 1.94-2.02 (1H, m), 2.85 (2H, d, J=6.7 Hz), 7.30-7.34 (1H, m), 7.62 (1H, d, J=8.2 Hz), 7.85 (1H, d, J=1.6 Hz), 7.92-7.96 (1H, m), 8.35 (1H, d, J=1.6 Hz), 8.44-8.46 (1H, m).

MS (ESI) m/z 301 (M+H)$^+$, 323 (M+Na)$^+$.

HRMS (ESI) m/z 301.16720 (M+H)$^+$. (Calcd C$_{16}$H$_{21}$N$_4$O$_2$: 301.16645).

Example 57

(1S,2R)-2-[(2S)-3-Amino-2-methylpropyl]-1-(1-pyridin-2-yl-1H-imidazol-4-yl]cyclopropanecarboxylic acid

[Formula 230]

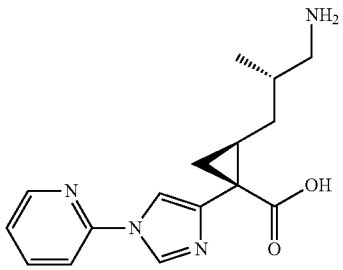

The title compound (123 mg) was obtained from methyl (1S,2R)-2-{(2S)-3-[bis(tert-butoxycarbonyl)amino]-2-methylpropyl}-1-(1-pyridin-2-yl-1H-imidazol-4-yl)cyclopropanecarboxylate (221 mg) obtained in Reference Example 89 in the same way as in Step 2 of Example 18.

$^1$H-NMR (CD$_3$OD) δ: 1.08 (3H, d, J=7.0 Hz), 1.31 (1H, dd, J=8.8, 3.9 Hz), 1.37 (1H, dd, J=6.7, 3.9 Hz), 1.53-1.65 (2H, m), 1.72-1.78 (1H, m), 1.97-2.05 (1H, m), 2.78 (1H, dd, J=12.7, 6.5 Hz), 2.98 (1H, dd, J=12.7, 7.6 Hz), 7.30-7.34 (1H, m), 7.62 (1H, d, J=8.2 Hz), 7.85 (1H, d, J=1.6 Hz), 7.92-7.96 (1H, m), 8.35 (1H, d, J=1.6 Hz), 8.44-8.46 (1H, m).

MS (ESI) m/z 301 (M+H)$^+$, 323 (M+Na)$^+$.

HRMS (ESI) m/z 301.16711 (M+H)$^+$. (Calcd for C$_{16}$H$_{21}$N$_4$O$_2$: 301.16645).

Example 58

(1R,2S)-2-[(2R)-3-Amino-2-methylpropyl]-1-[1-(5-methylpyridin-2-yl)-1H-imidazol-4-yl]cyclopropanecarboxylic acid

[Formula 231]

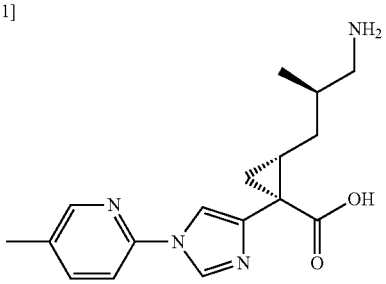

The title compound (84 mg) was obtained from methyl (1R,2S)-2-{(2R)-3-[bis(tert-butoxycarbonyl)amino]-2-methylpropyl}-1-[1-(5-methylpyridin-2-yl)-1H-imidazol-4-yl]cyclopropanecarboxylate (145 mg) obtained in Reference Example 92 in the same way as in Step 2 of Example 18.

$^1$H-NMR (CD$_3$OD) δ: 1.08 (3H, d, J=6.7 Hz), 1.28-1.38 (2H, m), 1.52-1.65 (3H, m), 1.71-1.78 (1H, m), 1.96-2.05 (1H, m), 2.37 (3H, s), 2.78 (1H, dd, J=12.9, 6.3 Hz), 2.97 (1H, dd, J=12.9, 6.3 Hz), 3.31 (3H, s), 7.51 (1H, d, J=8.5 Hz), 7.75-7.78 (1H, m), 7.80-7.81 (1H, m), 8.29-8.30 (2H, m).

HRMS (ESI) m/z 337.16410 (M+H)$^+$. (Calcd C$_{17}$H$_{22}$N$_4$NaO$_2$: 337.16404).

Example 59

(1S,2R)-2-[(2R)-3-Amino-2-methylpropyl]-1-[1-(5-methylpyridin-2-yl)-1H-imidazol-4-yl]cyclopropanecarboxylic acid

[Formula 232]

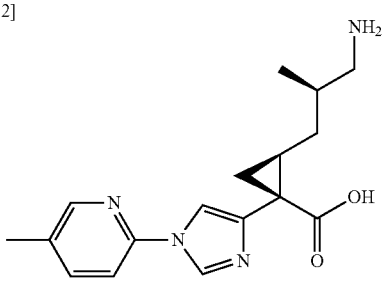

The title compound (174 mg) was obtained from methyl (1S,2R)-2-{(2R)-3-[bis(tert-butoxycarbonyl)amino]-2-methylpropyl}-1-[1-(5-methylpyridin-2-yl)-1H-imidazol-4-yl]cyclopropanecarboxylate (316 mg) obtained in Reference Example 92 in the same way as in Step 2 of Example 18.

$^1$H-NMR (CD$_3$OD) δ: 1.07 (3H, d, J=6.7 Hz), 1.28-1.39 (2H, m), 1.51-1.70 (3H, m), 1.93-2.02 (1H, m), 2.37 (3H, s), 2.84 (2H, d, J=6.7 Hz), 7.51 (1H, d, J=8.2 Hz), 7.75-7.78 (1H, m), 7.79-7.81 (1H, m), 8.28-8.30 (2H, m).

HRMS (ESI) m/z 337.16317 (M+H)$^+$. (Calcd C$_{17}$H$_{22}$N$_4$NaO$_2$: 337.16404).

Example 60

(1R,2S)-2-[(2R)-2-(Aminomethyl)butyl]-1-(1-pyridin-2-yl-1H-imidazol-4-yl)cyclopropanecarboxylic acid

[Formula 233]

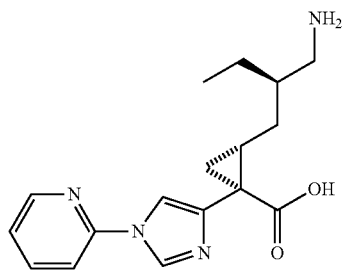

The title compound (135 mg) was obtained from methyl (1R,2S)-2-[(2R)-2-{[bis(tert-butoxycarbonyl)amino]methyl}butyl]-1-(1-pyridin-2-yl-1H-imidazol-4-yl)cyclopropanecarboxylate (249 mg) obtained in Reference Example 98 in the same way as in Step 2 of Example 18.

$^1$H-NMR (CD$_3$OD) δ: 0.99 (3H, t, J=7.4 Hz), 1.31-1.38 (2H, m), 1.44-1.54 (3H, m), 1.66-1.74 (1H, m), 1.76-1.86 (2H, m), 2.88-2.99 (2H, m), 7.31-7.34 (1H, m), 7.62 (1H, d, J=8.2 Hz), 7.84 (1H, br s), 7.92-7.96 (1H, m), 8.35 (1H, br s), 8.45 (1H, d, J=4.3 Hz).

MS (ESI) m/z 315 (M+H)$^+$, 337 (M+Na)$^+$.

HRMS (ESI) m/z 315.18189 (M+H)$^+$. (Calcd C$_{17}$H$_{23}$N$_4$O$_2$: 315.18210).

Example 61

(1S,2R)-2-[(2R)-2-(Aminomethyl)butyl]-1-(1-pyridin-2-yl-1H-imidazol-4-yl)cyclopropanecarboxylic acid

[Formula 234]

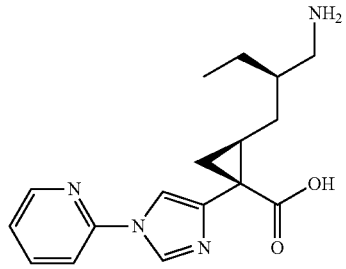

The title compound (211 mg) was obtained from methyl (1S,2R)-2-[(2R)-2-{[bis(tert-butoxycarbonyl)amino]methyl}butyl]-1-(1-pyridin-2-yl-1H-imidazol-4-yl)cyclopropanecarboxylate (387 mg) obtained in Reference Example 98 in the same way as in Step 2 of Example 18.

$^1$H-NMR (CD$_3$OD) δ: 0.97 (3H, t, J=7.6 Hz), 1.33-1.36 (2H, m), 1.42-1.56 (4H, m), 1.75-1.88 (2H, m), 2.86 (1H, dd, J=12.8, 7.6 Hz), 2.99 (1H, dd, J=12.8, 4.7 Hz), 7.30-7.34 (1H, m), 7.62 (1H, d, J=8.2 Hz), 7.84 (1H, d, J=1.6 Hz), 7.92-7.96 (1H, m), 8.36 (1H, d, J=1.6 Hz), 8.44-8.46 (1H, m).

MS (ESI) m/z 315 (M+H)$^+$, 337 (M+Na)$^+$.

HRMS (ESI) m/z 315.18196 (M+H)$^+$. (Calcd for C$_{17}$H$_{23}$N$_4$O$_2$: 315.18210).

Example 62

(1R,2S)-2-[(2R)-2-(Aminomethyl)butyl]-1-(1-phenyl-1H-imidazol-4-yl)cyclopropanecarboxylic acid

[Step 1] Methyl (1R,2S)-2-[(2R)-2-{[(tert-butoxycarbonyl)amino]methyl}butyl]-1-(1-phenyl-1H-imidazol-4-yl)cyclopropanecarboxylate and methyl (1R,2S)-2-[(2S)-2-{[(tert-butoxycarbonyl)amino]methyl}butyl]-1-(1-phenyl-1H-imidazol-4-yl)cyclopropanecarboxylate

[Formula 235]

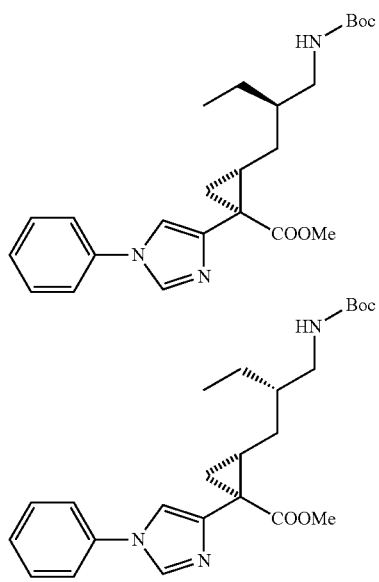

The diastereomeric mixture of the compounds (127.2 mg) obtained in Reference Example 79 was purified in several portions by HPLC (Chiral Pak IA, 2.0×25 cm, eluting solvent: hexane/ethanol=70/30, 10 mL/min) to respectively obtain methyl (1R,2S)-2-[(2R)-2-{[(tert-butoxycarbonyl)amino]methyl}butyl]-1-(1-phenyl-1H-imidazol-4-yl)cyclopropanecarboxylate (32.8 mg, 1st peak) and methyl (1R,2S)-2-[(2S)-2-{[(tert-butoxycarbonyl)amino]methyl}butyl]-1-(1-phenyl-1H-imidazol-4-yl)cyclopropanecarboxylate (70.3 mg, 2nd peak). The compounds were analyzed using Chiral Pak IA (4.6×150 mm, eluting solvent: hexane/ethanol=70/30, 1.0 mL/min). Retention time: isomer 1: 3.6 minutes, isomer 2: 5.1 minutes.

1st Peak:

$^1$H-NMR (CDCl$_3$) δ: 0.90 (3H, t, J=7.4 Hz), 1.25-1.59 (2H, m), 1.43 (9H, s), 1.61-1.73 (5H, m), 1.83-1.91 (1H, m), 3.15-3.22 (2H, m), 3.75 (3H, s), 4.75-4.79 (1H, m), 7.33-7.49 (6H, m), 7.72 (1H, d, J=1.2 Hz). 2nd peak:

$^1$H-NMR (CDCl$_3$) δ: 0.92 (3H, t, J=7.4 Hz), 1.43 (9H, s), 1.52-1.69 (7H, m), 1.79-1.86 (1H, m), 3.09-3.13 (2H, m), 3.76 (3H, s), 4.68-4.72 (1H, m), 7.35-7.50 (6H, m), 7.72 (1H, d, J=1.6 Hz).

[Step 2] (1R,2S)-2-[(2R)-2-{[(tert-Butoxycarbonyl)amino]methyl}butyl]-1-(1-phenyl-1H-imidazol-4-yl)cyclopropanecarboxylic acid

[Formula 236]

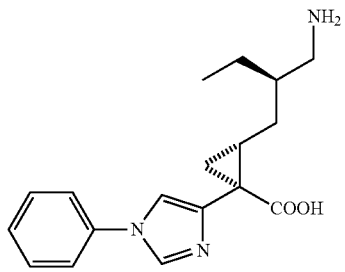

The title compound (21.1 mg) was obtained from the compound (32.8 mg) obtained first in Step 1 of this Example in the same way as in Step 2 of Example 18.

$^1$H-NMR (CD$_3$OD) δ: 0.99 (3H, t, J=7.4 Hz), 1.29-1.37 (2H, m), 1.44-1.54 (3H, m), 1.66-1.73 (1H, m), 1.77-1.85 (2H, m), 2.88-2.99 (2H, m), 7.34-7.39 (1H, m), 7.48-7.54 (5H, m), 7.95 (1H, d, J=1.6 Hz).

HRMS (ESI) m/z 314.18710 (M+H)$^+$. (Calcd C$_{18}$H$_{24}$N$_3$O$_2$: 314.18685).

Example 63

(1R,2S)-2-[(2S)-2-(Aminomethyl)butyl]-1-(1-phenyl-1H-imidazol-4-yl)cyclopropanecarboxylic acid

[Formula 237]

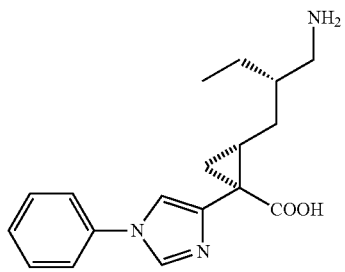

A crude product was obtained from the compound (70.3 mg) obtained second in Step 1 of Example 62 in the same way as in Step 2 of Example 18 and then purified by HPLC (eluting solvent: 15% acetonitrile/0.1% hydrochloric acid in water) to obtain the title compound (9.1 mg).

$^1$H-NMR (CD$_3$OD) δ: 0.97 (3H, t, J=7.4 Hz), 1.35 (2H, d, J=7.4 Hz), 1.41-1.56 (4H, m), 1.76-1.88 (2H, m), 2.86 (1H, dd, J=12.9, 7.4 Hz), 2.96 (1H, dd, J=12.9, 4.7 Hz), 7.35-7.90 (1H, m), 7.48-7.55 (5H, m), 7.96 (1H, d, J=1.6 Hz).

HRMS (ESI) m/z 314.18696 (M+H)$^+$. (Calcd C$_{18}$H$_{24}$N$_3$O$_2$: 314.18685).

Example 64

(1R*,2S*)-2-(3-Aminopropyl)-1-[1-(4-methylpyridin-2-yl)-1H-imidazol-4-yl]cyclopropanecarboxylic acid

[Formula 238]

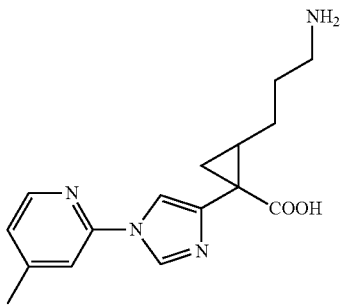

The title compound (34.9 mg) was obtained from the compound (97.5 mg) obtained in Reference Example 102 in the same way as in Step 2 of Example 18.

$^1$H-NMR (CD$_3$OD) δ: 1.34 (1H, dd, J=8.6, 4.2 Hz), 1.46 (1H, dd, J=6.8, 4.2 Hz), 1.58-1.66 (1H, m), 1.72-1.90 (4H, m), 2.46 (3H, s), 2.94-3.04 (2H, m), 7.19 (1H, dt, J=5.1, 0.8 Hz), 7.53 (1H, t, J=0.8 Hz), 7.84 (1H, d, J=1.6 Hz), 8.30 (1H, d, J=5.1 Hz), 8.38 (1H, d, J=1.6 Hz).

HRMS (ESI) m/z 301.16663 (M+H)$^+$. (Calcd C$_{16}$H$_{21}$N$_4$O$_2$: 301.16645).

Example 65

(1R*,2S*)-2-(3-Aminopropyl)-1-[1-(6-methylpyridin-2-yl)-1H-imidazol-4-yl]cyclopropanecarboxylic acid

[Formula 239]

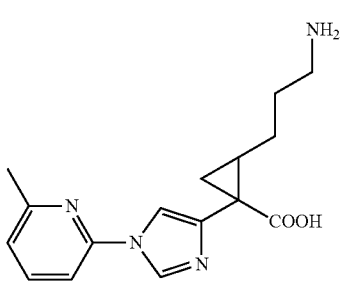

The title compound (41.9 mg) was obtained from the compound (123 mg) obtained in Reference Example 106 in the same way as in Step 2 of Example 18.

$^1$H-NMR (CD$_3$OD) δ: 1.35 (1H, dd, J=8.6, 4.2 Hz), 1.45 (1H, dd, J=6.8, 4.2 Hz), 1.55-1.63 (1H, m), 1.71-1.87 (4H, m), 2.54 (3H, s), 2.92-3.03 (2H, m), 7.20 (1H, d, J=7.8 Hz), 7.42 (1H, d, J=8.2 Hz), 7.80 (1H, d, J=7.8 Hz), 7.83 (1H, d, J=1.6 Hz), 8.38 (1H, d, J=1.2 Hz).

HRMS (ESI) m/z 301.16571 (M+H)$^+$. (Calcd C$_{16}$H$_{21}$N$_4$O$_2$: 301.16645).

Example 66

(1R,2S)-2-[(2R)-2-(Aminomethyl)pentyl]-1-(1-pyridin-2-yl-1H-imidazol-4-yl)cyclopropanecarboxylic acid

[Formula 240]

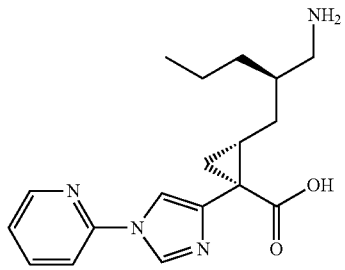

The title compound (93.9 mg) was obtained from (1R)-1-phenylethyl (1R,2S)-2-[(2R)-2-{[bis(tert-butoxycarbonyl)amino]methyl}pentyl]-1-(1-pyridin-2-yl-1H-imidazol-4-yl)cyclopropanecarboxylate (189 mg) obtained in Reference Example 112 in the same way as in Step 2 of Example 18.

$^1$H-NMR (CD$_3$OD) δ: 0.96 (3H, t, J=7.0 Hz), 1.31-1.54 (7H, m), 1.70 (1H, ddd, J=14.7, 5.5, 5.9 Hz), 1.81 (1H, ddd, J=14.7, 7.8, 5.5 Hz), 1.86-1.93 (1H, m), 2.89 (1H, dd, J=12.9, 5.1 Hz), 2.96 (1H, dd, J=12.9, 8.6 Hz), 7.31-7.34 (1H, m), 7.61-7.63 (1H, m), 7.84-7.84 (1H, m), 7.92-7.96 (1H, m), 8.35-8.36 (1H, m), 8.44-8.46 (1H, m).

LRMS (ESI) m/z 329 (M+H)$^+$, 351 (M+Na)$^+$.

HRMS (ESI) m/z 329.19743 [M+H]$^+$. (Calcd for C$_{18}$H$_{25}$N$_4$O$_2$: 329.19775).

Example 67

(1S,2R)-2-[(2R)-2-(Aminomethyl)pentyl]-1-(1-pyridin-2-yl-1H-imidazol-4-yl)cyclopropanecarboxylic acid

[Formula 241]

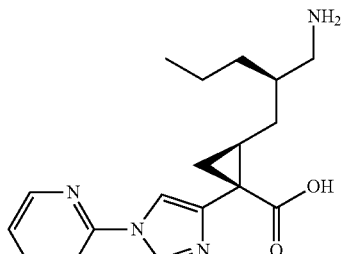

The title compound (99.4 mg) was obtained from (1R)-1-phenylethyl(1S,2R)-2-[(2R)-2-{[bis(tert-butoxycarbonyl)amino]methyl}pentyl]-1-(1-pyridin-2-yl-1H-imidazol-4-yl)cyclopropanecarboxylate (227 mg) obtained in Reference Example 112 in the same way as in Step 2 of Example 18.

$^1$H-NMR (CD$_3$OD) δ: 0.95 (3H, t, J=6.6 Hz), 1.34-1.57 (8H, m), 1.82-1.88 (2H, m), 2.85 (1H, dd, J=12.9, 7.0 Hz), 2.98 (1H, dd, J=12.9, 4.3 Hz), 7.30-7.34 (1H, m), 7.62 (1H, d, J=8.2 Hz), 7.84 (1H, d, J=1.6 Hz), 7.91-7.96 (1H, m), 8.36 (1H, d, J=1.6 Hz), 8.44-8.46 (1H, m).

LRMS (ESI) m/z 329 (M+H)$^+$, 351 (M+Na)$^+$.

HRMS (ESI) m/z 329.19712 (M+H)$^+$. (Calcd for C$_{18}$H$_{25}$N$_4$O$_2$: 329.19775).

Example 68

2-[(2R)-4-Aminobutane-2-yl]-1-[1-(pyridin-2-yl)-1H-imidazol-4-yl)cyclopropanecarboxylic acid

[Formula 242]

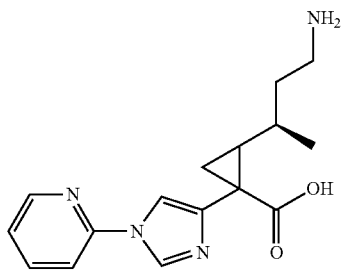

A mixture of the compound (35 mg) obtained in Reference Example 119 and a 5 N aqueous hydrochloric acid solution (5 mL) was heated to reflux for 8 hours, and the solvent was distilled off under reduced pressure. The obtained residue was dissolved in deionized water. To the solution, an ion-exchange resin (Waters Corp., PoraPak Rxn CX, bulk, 400 mg) was added, and the mixture was stirred for a while. The reaction mixture was transferred to a syringe with a filter (Shoko Scientific Co., Ltd.) to remove water. The resin was washed with deionized water until the washings became neutral to a pH test paper. The resin was further washed several times with methanol. A solution of 28% ammonia water diluted 10-fold with methanol (40 ml) was added to the resin, and the eluate was concentrated under reduced pressure. The obtained residue was dissolved by the addition of deionized water, and the solution was concentrated under reduced pressure. This procedure was repeated several times, and the residue was then dried under reduced pressure to obtain the title compound (17.2 mg).

$^1$H-NMR (CD$_3$OD) δ: 1.09 (1.5H, d, J=6.3 Hz), 1.11 (1.5H, d, J=6.3 Hz), 1.28-1.84 (6.0H, m), 2.94-3.08 (2.0H, m), 7.30-7.34 (1.0H, m), 7.61 (0.5H, s), 7.63 (0.5H, s), 7.83 (0.5H, d, J=1.6 Hz), 7.88 (0.5H, s), 7.92-7.96 (1.0H, m), 8.35-8.36 (1.0H, m), 8.44-8.46 (1.0H, m).

LRMS (ESI) m/z 301 (M+H)$^+$.

Test Example 1

Determination of TAFIa Enzyme Inhibitory Activity (1) Activation of TAFI

HEPES buffered saline (20 mM HEPES, 150 mM NaCl, pH 7.4; hereinafter, referred to as HBS) was used in the preparation of a reaction solution. To 12 μL of a 250 μg/mL TAFI solution, 30 μL of an HBS solution containing 4 U/mL human thrombin, 12 U/mL rabbit lung thrombomodulin, and 12 mM CaCl$_2$ was added, and the mixture was gently stirred. Then, TAFI was activated at room temperature. Ten minutes later, thrombin was neutralized by the addition of 10 μL of 100 μM PPACK (thrombin inhibitor) to terminate the activation of TAFI. The formed TAFIa was stored in ice and diluted immediately before use in determination with 2050 μL of an HBS solution containing BSA (bovine serum albumin) adjusted to 0.1% in terms of the final concentration.

(2) Determination of TAFIa Inhibitory Activity

A test substance was dissolved in HBS to prepare a 10-fold dilution series of evaluation concentrations. 80 μL of the TAFIa solution and 10 μL of the test substance were added to each well of a 96-well plate and mixed by shaking for 10 minutes. 10 μL of furylacryloyl-alanyl-lysine (FAAK) adjusted to 5 mg/mL was added to each well, and the change in the absorbance of this mixed solution at 330 nm was read for 30 minutes to determine the degradation rate of the substrate.

(3) Calculation of Inhibitory Activity IC$_{50}$

The degradation rate of the substrate in each well was applied to a standard curve prepared using the dilution series of the TAFIa solution to calculate TAFIa activity. The 50% inhibitory concentration (IC$_{50}$) was calculated based on the correlation between the concentration of the test compound and the TAFIa activity. The results are shown in Table 1.

TABLE 1

| TAFIa enzyme inhibitory activity | |
|---|---|
| Example No. | TAFIa IC$_{50}$ (μM) |
| 1 | 0.0087 |
| 2 | 0.42 |
| 3 | 0.097 |
| 4 | 0.029 |
| 5 | 0.014 |
| 6 | 0.027 |
| 7 | 0.016 |
| 8 | 0.037 |
| 9 | >0.30 |
| 10 | 0.042 |
| 11 | 0.031 |
| 12 | 0.036 |
| 13 | 0.14 |
| 14 | 0.099 |
| 15 | 0.021 |
| 16 | 0.052 |
| 17 | 0.061 |
| 18 | 0.025 |
| 19 | 0.070 |
| 20 | 0.14 |
| 21 | 0.027 |
| 22 | 0.040 |
| 23 | 0.17 |
| 24 | 0.098 |
| 25 | 0.029 |
| 26 | 10 |
| 27 | >0.10 |
| 28 | 0.0045 |
| 29 | >10 |
| 30 | 0.013 |
| 31 | 0.015 |
| 32 | 0.035 |
| 33 | 0.039 |
| 34 | 0.93 |
| 35 | 0.34 |
| 36 | 0.036 |
| 37 | 0.10 |
| 38 | 0.058 |
| 39 | 0.030 |
| 40 | 0.029 |
| 41 | 0.019 |
| 42 | 0.058 |
| 43 | 0.026 |
| 44 | 0.016 |
| 45 | 0.063 |
| 46 | 0.016 |
| 47 | 0.054 |
| 48 | 0.011 |
| 49 | 0.018 |
| 50 | 0.014 |
| 51 | 0.035 |
| 52 | >0.30 |
| 53 | 0.013 |
| 54 | 0.011 |
| 55 | >3.0 |
| 56 | 0.033 |
| 57 | 0.49 |

TABLE 1-continued

TAFIa enzyme inhibitory activity

| Example No. | TAFIa $IC_{50}$ (μM) |
|---|---|
| 58 | 0.0087 |
| 59 | 0.50 |
| 60 | 0.0083 |
| 61 | 0.36 |
| 62 | 0.0079 |
| 63 | 0.012 |
| 64 | 0.019 |
| 65 | 0.073 |
| 66 | 0.041 |
| 67 | >0.10 |
| 68 | 0.012 |

The compound of the present invention exhibits excellent TAFIa inhibitory activity and is useful as a pharmaceutical drug for the treatment of myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis.

Test Example 2

Evaluation of Fibrinolysis Enhancing Activity by Measurement of Time of Plasma Clot Lysis To a 96-well plate, 20 μL/well HBS, 50 μL/well normal human plasma, 10 μL/well compound solution (the compound solution was prepared by dissolving the compound in HBS, followed by serial dilution with this buffer), and 10 μL/well tPA (Activacin (Kyowa Hakko Kirin Co., Ltd.) was adjusted to 600,000 U/mL with a lysis solution included therein, followed by dilution with HBS) were added, and the mixture was stirred. Then, 10 μL/well reaction solution A (13.8 U/mL human thrombin, 170 mM $CaCl_2$, and 0.9 U/mL thrombomodulin) was added thereto, and the mixture was stirred again. The absorbance at 405 nm was measured using a plate reader at 30-second intervals, with the temperature kept at 37° C. to measure the extent of coagulation. In change in absorbance, a point in time when each well exhibited absorbance closest to an average (ABS-ave: [(ABS-max)−(ABS-min)]/2) of the maximum absorbance (ABS-max) and the minimum absorbance (ABS-min) in the fibrinolysis process was defined as ½ lysis time (½ LT) and used as an index for the fibrinolytic activity of each well. A concentration that achieves 50% of ½ LT was calculated as $EC_{50}$ from the relationship between the concentration of the test substance and ½ LT.

The compound of the present invention exhibits excellent fibrinolysis enhancing activity and is useful as a pharmaceutical drug for the treatment of myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis.

Test Example 3

Evaluation of Fibrinolysis Enhancing Activity in Rat Models of Thromboembolism

Wistar rats were used. At any point in time, a test substance prepared with a 0.5% methylcellulose solution was orally administered thereto or a test substance prepared with saline was intravenously administered thereto. Forty minutes or four hours later, a PT reagent (Thromboplastin C plus, Sysmex Corp.) adjusted to 2.25 U/mL with saline was continuously injected (16.8 mL/kg/hr×20 min) from the jugular veins under thiopental anesthesia. An excessive-dose TAFIa inhibitor-administered group was selected as a positive control group. Forty five minutes after the beginning of the PT reagent, blood was collected from the jugular veins using citric acid to obtain plasma. The amount of D-dimer contained in the plasma was measured using a fully automated coagulation analyzer ACL-9000 or ACL-TOP500CTS. Its ratio to the average value of the positive control group was calculated, and $ED_{50}$ was calculated as a dose increasing D-dimer by 50%.

The compound of the present invention exhibits excellent fibrinolysis enhancing activity in vivo and is useful as a pharmaceutical drug for the treatment of myocardial infarction, angina pectoris, acute coronary syndrome, cerebral infarction, deep vein thrombosis, pulmonary embolism, peripheral arterial occlusion, sepsis, disseminated intravascular coagulation syndrome, or pulmonary fibrosis.

Preparation Example 1

Hard Capsule

Each of standard hard gelatin capsule shells separable to two parts is filled with 100 mg of the compound of Example 1 in a powder form, 150 mg of lactose, 50 mg of cellulose, and 6 mg of magnesium stearate to prepare unit capsules, which are then washed and then dried.

Preparation Example 2

Soft Capsule

A mixture of the compound of Example 2 contained in a digestible oil substance, for example, soybean oil, cottonseed oil, or olive oil, is prepared and injected into gelatin using a positive displacement pump to obtain soft capsules containing 100 mg of the active ingredient. These soft capsules are washed and then dried.

Preparation Example 3

Tablet

Each tablet is prepared according to a conventional method using 100 mg of the compound of Example 3, 0.2 mg of colloidal silicon dioxide, 5 mg of magnesium stearate, 275 mg of microcrystalline cellulose, 11 mg of starch, and 98.8 mg of lactose.

If desired, a coating is applied to the tablet.

Preparation Example 4

Suspension 5 mL of a suspension is produced to contain 100 mg of the compound of Example 4 in a fine powder form, 100 mg of sodium carboxy methylcellulose, 5 mg of sodium benzoate, 1.0 g of a sorbitol solution (Japanese Pharmacopoeia), and 0.025 mL of vanillin.

Preparation Example 5

Cream 100 mg of the compound of Example 5 in a fine powder form is mixed into 5 g of a cream containing 40% white petrolatum, 3% microcrystalline wax, 10% lanoline, 5% Span-20, 0.3% Tween-20, and 41.7% water to produce a cream.

Preparation Example 6

Injection 1.5% by weight of the compound of Example 6 is stirred in 10% by weight of propylene glycol, subsequently adjusted to a given volume with injectable water, and then sterilized to prepare an injection.

INDUSTRIAL APPLICABILITY

A cyclopropanecarboxylic acid derivative of the present invention represented by any of the general formulae (I) and (Ia) to (If) or a pharmacologically acceptable salt thereof has excellent TAFIa enzyme inhibitory activity and is useful as a therapeutic drug for myocardial infarction, angina pectoris, acute coronary syndrome, cerebral infarction, deep vein thrombosis, pulmonary embolism, peripheral arterial occlusion, sepsis, disseminated intravascular coagulation syndrome, pulmonary fibrosis, or the like, or as a therapeutic drug for a thromboembolism-derived disease.

The invention claimed is:
1. A method of treating a disease caused by inhibition of fibrinolysis comprising administering a compound of formula (I):

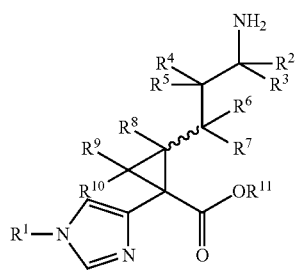

or a pharmacologically acceptable salt thereof, to a subject, wherein:
$R^1$ is selected from:
  a C1 to C6 alkyl group which may be substituted by one to three identical or different groups selected from substituent group A,
  a C2 to C6 alkenyl group which may be substituted by one to three identical or different groups selected from substituent group A,
  a C3 to C8 cycloalkyl group which may be substituted by one to three identical or different groups selected from substituent group A,
  an aryl group which may be substituted by one to three identical or different groups selected from substituent group A, provided that when the aryl group is a phenyl group having a substituent, the substituent is substituted at a meta or para position on the benzene ring,
  a saturated heterocyclyl group which may be substituted by one to three identical or different groups selected from substituent group A, and
  an unsaturated heterocyclyl group which may be substituted by one to three identical or different groups selected from substituent group A;

$R^2$, $R^3$, and $R^8$ are each independently selected from a hydrogen atom and a C1 to C3 alkyl group;
$R^4$, $R^5$, $R^6$, $R^7$, $R^9$, and $R^{10}$ are each independently selected from a hydrogen atom, a fluoro group, and a C1 to C3 alkyl group;
$R^{11}$ is selected from a hydrogen atom, a methyl group, and an ethyl group; and
substituent group A consists of a hydroxy group, a halogeno group, a cyano group, a nitro group, an amino group, a carboxy group, a C1 to C3 alkyl group, a halogeno-C1 to C3 alkyl group, a C3 to C8 cycloalkyl group, a C1 to C3 alkoxy group, a halogeno-C1 to C3 alkoxy group, a C1 to C3 alkylsulfonyl group, an aryl group, a saturated heterocyclyl group, an unsaturated heterocyclyl group, and an aryloxy group.

2. A method of enhancing fibrinolysis comprising administering a compound of formula (I):

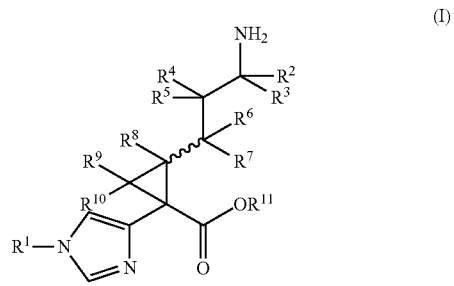

or a pharmacologically acceptable salt thereof, to a subject, wherein:
$R^1$ is selected from:
  a C1 to C6 alkyl group which may be substituted by one to three identical or different groups selected from substituent group A,
  a C2 to C6 alkenyl group which may be substituted by one to three identical or different groups selected from substituent group A,
  a C3 to C8 cycloalkyl group which may be substituted by one to three identical or different groups selected from substituent group A,
  an aryl group which may be substituted by one to three identical or different groups selected from substituent group A, provided that when the aryl group is a phenyl group having a substituent, the substituent is substituted at a meta or para position on the benzene ring,
  a saturated heterocyclyl group which may be substituted by one to three identical or different groups selected from substituent group A, and
  an unsaturated heterocyclyl group which may be substituted by one to three identical or different groups selected from substituent group A;

$R^2$, $R^3$, and $R^8$ are each independently selected from a hydrogen atom and a C1 to C3 alkyl group;
$R^4$, $R^5$, $R^6$, $R^7$, $R^9$, and $R^{10}$ are each independently selected from a hydrogen atom, a fluoro group, and a C1 to C3 alkyl group;
$R^{11}$ is selected from a hydrogen atom, a methyl group, and an ethyl group; and
substituent group A consists of a hydroxy group, a halogeno group, a cyano group, a nitro group, an amino group, a carboxy group, a C1 to C3 alkyl group, a halogeno-C1 to C3 alkyl group, a C3 to C8 cycloalkyl group, a C1 to C3 alkoxy group, a halogeno-C1 to C3 alkoxy group, a C1 to C3 alkylsulfonyl group, an aryl group, a saturated heterocyclyl group, an unsaturated heterocyclyl group, and an aryloxy group.

3. A method of inhibiting thrombin-activatable fibrinolysis inhibitor (TAFIa), comprising administering a compound of formula (I):

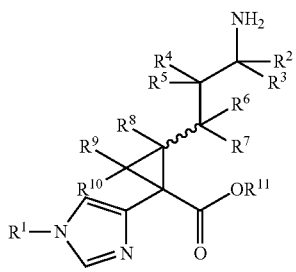
(I)

or a pharmacologically acceptable salt thereof, to a subject, wherein:

$R^1$ is selected from:
- a C1 to C6 alkyl group which may be substituted by one to three identical or different groups selected from substituent group A,
- a C2 to C6 alkenyl group which may be substituted by one to three identical or different groups selected from substituent group A,
- a C3 to C8 cycloalkyl group which may be substituted by one to three identical or different groups selected from substituent group A,
- an aryl group which may be substituted by one to three identical or different groups selected from substituent group A, provided that when the aryl group is a phenyl group having a substituent, the substituent is substituted at a meta or para position on the benzene ring,
- a saturated heterocyclyl group which may be substituted by one to three identical or different groups selected from substituent group A, and
- an unsaturated heterocyclyl group which may be substituted by one to three identical or different groups selected from substituent group A;

$R^2$, $R^3$, and $R^8$ are each independently selected from a hydrogen atom and a C1 to C3 alkyl group;

$R^4$, $R^5$, $R^6$, $R^7$, $R^9$, and $R^{10}$ are each independently selected from a hydrogen atom, a fluoro group, and a C1 to C3 alkyl group;

$R^{11}$ is selected from a hydrogen atom, a methyl group, and an ethyl group; and substituent group A consists of a hydroxy group, a halogeno group, a cyano group, a nitro group, an amino group, a carboxy group, a C1 to C3 alkyl group, a halogeno-C1 to C3 alkyl group, a C3 to C8 cycloalkyl group, a C1 to C3 alkoxy group, a halogeno-C1 to C3 alkoxy group, a C1 to C3 alkylsulfonyl group, an aryl group, a saturated heterocyclyl group, an unsaturated heterocyclyl group, and an aryloxy group.

4. The method of any one of claim 1, 2, or 3, wherein the compound or salt of formula (I) is a compound of formula (Ia):

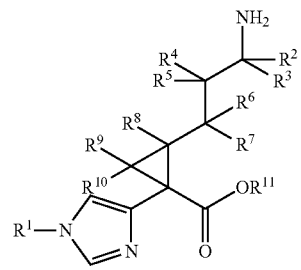
(Ia)

or a pharmacologically acceptable salt thereof.

5. The method of any one of claim 1, 2, or 3, wherein the compound or salt of formula (I) is a compound of formula (Ic):

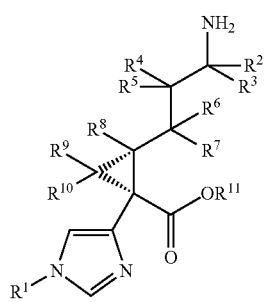
(Ic)

or a pharmacologically acceptable salt thereof.

6. The method of any one of claim 1, 2, or 3, wherein the compound or salt of formula (I) is a compound of formula (I-1):

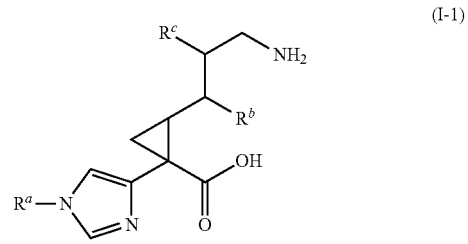
(I-1)

or a pharmacologically acceptable salt thereof, wherein:

$R^a$ is selected from:
- a C3 to C6 branched alkyl group;
- a C3 to C6 cycloalkyl group which may be substituted by one or two identical or different C1 to C3 alkyl groups;
- a phenyl group which may be substituted by one or two identical or different groups selected from the group consisting of a C1 to C3 alkyl group, a C1 to C3 alkoxy group, a phenoxy group, a halogeno group, and a cyano group, wherein the substituent is substituted at the 3- or 4-position, or both, of the phenyl group;
- a naphthyl group;
- a 5- or 6-membered heteroaryl group which may be substituted by one or two identical or different groups selected from the group consisting of a C1 to C3 alkyl group, a C1 to C3 alkoxy group, a phenoxy group, a halogeno group, and a cyano group, wherein the heteroaryl group has one or more nitrogen atoms in the ring and may be condensed with a benzene ring; and a benzofuranyl group; and $R^b$ and $R^c$ are each independently selected from a hydrogen atom or a C1 to C3 alkyl group.

7. The method of any one of claim 1, 2, or 3, wherein the subject is a human.

8. The method of claim 7, wherein the compound or salt of formula (I) is administered in an amount of 0.01 mg to 5000 mg in a single dose.

9. The method of claim 7, wherein the compound or salt of formula (I) is administered in an amount of 0.1 mg to 1000 mg in a single dose.

10. The method of claim 7, wherein the compound or salt of formula (I) is administered in an amount of 1 mg to 200 mg in a single dose.

11. The method of claim 7, wherein the compound or salt of formula (I) is administered in an amount of 0.001 mg to 100 mg per kg body weight of the subject.

12. The method of claim 7, wherein the compound or salt of formula (I) is administered in an amount of 0.005 mg to 20 mg per kg body weight of the subject.

13. The method of claim 7, wherein the compound or salt of formula (I) is administered in an amount of 0.01 mg to 5 mg per kg body weight of the subject.

14. The method of claim 2, wherein enhancing fibrinolysis treats thrombosis, embolism, or a sequela thereof, and the thrombosis, embolism or a sequela thereof is selected from: acute coronary syndrome such as myocardial infarction and angina pectoris (stable angina and unstable angina); venous thromboembolism such as deep vein thrombosis and pulmonary embolism; thrombosis or embolism occurring in the cardiovascular system after surgical operation such as vessel revascularization, angioplasty, stent placement, and bypass surgery; thrombosis; embolism after artificial joint replacement operation such as knee joint replacement operation and hip joint replacement operation; inflammation-related intravascular disease such as sepsis and disseminated intravascular coagulation syndrome (DIC); peripheral vascular disorder-derived or -related disease such as peripheral arterial occlusion (PAO), arteriosclerosis, and diabetes mellitus; tumor-related disease such as solid cancer and blood cancer; and organ disorder attributed to thrombus or embolus such as pulmonary embolus, cerebral infarction, and renal infarction.

15. The method of claim 2, wherein enhancing fibrinolysis treats a thrombosis or embolism selected from: a disease caused by contact with foreign matter in the body, the foreign matter including a medical device such as a joint prosthesis used in joint replacement, a vascular catheter, a blood prosthesis, a blood stent, and a prosthetic valve; and a disease caused by contact between blood and a medical device outside the body, the medical device including a pump oxygenator used in cardiac operation and a medical device used in hemodialysis.

16. The method of claim 3 wherein inhibiting thrombin-activatable fibrinolysis inhibitor (TAFIa) treats a disease selected from: pulmonary disease such as pulmonary hypertension, adult respiratory distress syndrome, pulmonary fibrosis, and chronic thromboembolic pulmonary hypertension; renal disease such as glomerulonephritis including acute glomerulonephritis, chronic glomerulonephritis, nephrotic nephritis, and rapidly progressive glomerulonephritis; renal disease such as renal infarction, and diabetic nephritis; hepatic disease such as hepatic fibrosis, hepatitis, and hepatic cirrhosis; eye disease associated with fibrin deposition in the eye; organ dysfunction after organ transplantation or resection; microcirculatory disorder caused by microthrombus, including thrombotic microangiopathy; and disease or symptoms associated with cancer cell migration or metastasis.

17. The method of any one of claim 1, 2, or 3, wherein the compound or salt of formula (I) is administered with a pharmacologically acceptable carrier as a pharmaceutical composition.

* * * * *